United States Patent
Yang et al.

(10) Patent No.: US 10,406,237 B2
(45) Date of Patent: Sep. 10, 2019

(54) AMINE-CONTAINING TRANSFECTION REAGENTS AND METHODS FOR MAKING AND USING SAME

(71) Applicant: LIFE TECHNOLOGIES CORPORATION, Carlsbad, CA (US)

(72) Inventors: Zhiwei Yang, San Diego, CA (US); Parul Angrish, San Diego, CA (US); Xavier de Mollerat du Jeu, Encinitas, CA (US); Kristin Wiederholt, Vista, CA (US)

(73) Assignee: LIFE TECHNOLOLGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/844,380

(22) Filed: Dec. 15, 2017

(65) Prior Publication Data

US 2018/0200374 A1    Jul. 19, 2018

Related U.S. Application Data

(62) Division of application No. 14/340,395, filed on Jul. 24, 2014, now Pat. No. 9,901,642, which is a division of application No. 13/297,231, filed on Nov. 15, 2011, now abandoned.

(60) Provisional application No. 61/543,242, filed on Oct. 4, 2011, provisional application No. 61/438,903, filed on Feb. 2, 2011, provisional application No. 61/437,503, filed on Jan. 28, 2011, provisional application No. 61/413,905, filed on Nov. 15, 2010.

(51) Int. Cl.

| | |
|---|---|
| *A61K 47/54* | (2017.01) |
| *C07C 227/06* | (2006.01) |
| *C07D 211/28* | (2006.01) |
| *C07D 211/58* | (2006.01) |
| *C12N 15/88* | (2006.01) |
| *A61K 48/00* | (2006.01) |
| *C07C 229/08* | (2006.01) |
| *C12N 15/113* | (2010.01) |

(52) U.S. Cl.
CPC ............ *A61K 47/54* (2017.08); *A61K 47/543* (2017.08); *A61K 48/0008* (2013.01); *C07C 227/06* (2013.01); *C07C 229/08* (2013.01); *C07D 211/28* (2013.01); *C07D 211/58* (2013.01); *C12N 15/1137* (2013.01); *C12N 15/88* (2013.01); *C12N 2310/11* (2013.01); *C12N 2310/141* (2013.01)

(58) Field of Classification Search
CPC .. A61K 47/54; A61K 47/543; A61K 48/0008; C07C 227/06; C07C 229/08; C07D 211/28; C07D 211/58; C12N 15/1137; C12N 15/88; C12N 2310/11; C12N 2310/141
See application file for complete search history.

(56) References Cited

U.S. PATENT DOCUMENTS

| | | | |
|---|---|---|---|
| 2,580,922 | A | 1/1952 | Jacoby et al. |
| 2,844,629 | A | 7/1958 | Bruce et al. |
| 3,223,700 | A | 12/1965 | Wilfrid et al. |
| 3,979,442 | A | 9/1976 | Schafer et al. |
| 6,291,423 | B1 | 9/2001 | Bischoff et al. |
| 7,145,039 | B2 | 12/2006 | Chu et al. |
| 7,166,745 | B1 | 1/2007 | Chu et al. |
| 7,173,154 | B2 | 2/2007 | Chu et al. |
| 7,199,267 | B1 | 4/2007 | Burns et al. |
| 7,323,594 | B2 | 1/2008 | Chu et al. |
| 7,470,817 | B2 | 12/2008 | Chu et al. |
| 7,479,573 | B2 | 1/2009 | Chu et al. |
| 7,601,872 | B2 | 10/2009 | Chu et al. |
| 7,915,450 | B2 | 3/2011 | Chu et al. |
| 8,158,827 | B2 | 4/2012 | Chu et al. |
| 8,466,122 | B2 | 6/2013 | Heyes et al. |
| 8,569,256 | B2 | 10/2013 | Heyes et al. |
| 8,785,200 | B2 | 7/2014 | Chu et al. |
| 9,011,903 | B2 | 4/2015 | Niitsu et al. |
| 9,358,300 | B2 | 6/2016 | Chu et al. |
| 2009/0023215 | A1 | 1/2009 | Jessee et al. |

(Continued)

FOREIGN PATENT DOCUMENTS

| | | |
|---|---|---|
| AU | 772847 | 5/2004 |
| CA | 780214 A | 3/1968 |

(Continued)

OTHER PUBLICATIONS

Akinc, Akin et al., "A combinatorial library of lipid-like materials for delivery of RNAi therapeutics", *Nature Biotechnology*, vol. 26, No. 5, May 2008, pp. 561-569.

(Continued)

*Primary Examiner* — Pancham Bakshi
*Assistant Examiner* — Mark R Luderer

(57) ABSTRACT

There are provided for herein novel amine-containing transfection compounds and methods for making and using same. The compounds are generally obtained by reacting a primary amine with an unsaturated compound. Transfection complexes made using the amine-containing transfection compounds in combination with additional compounds to encapsulate biologically active agents such as nucleic acids are also provided for herein. Methods of using the transfection complexes for the in vivo or in vitro delivery of biologically active agents are also described. The transfection complexes of the present invention are highly potent, thereby allowing effective modulation of a biological activity at relatively low doses compared to analogous transfection compounds known in the art.

24 Claims, 8 Drawing Sheets

Specification includes a Sequence Listing.

(56) References Cited

U.S. PATENT DOCUMENTS

| | | |
|---|---|---|
| 2010/0260817 A1 | 10/2010 | Slobodkin et al. |
| 2010/0331234 A1 | 12/2010 | Mahon et al. |
| 2011/0009641 A1 | 1/2011 | Anderson et al. |
| 2011/0015252 A1 | 1/2011 | Fitzgerald et al. |
| 2013/0022665 A1 | 1/2013 | Niitsu et al. |
| 2015/0174260 A1 | 6/2015 | Yang et al. |

FOREIGN PATENT DOCUMENTS

| | | |
|---|---|---|
| CA | 2206550 A1 | 11/1997 |
| DE | 1162380 B | 2/1964 |
| DE | 1165038 B | 3/1964 |
| EP | 0846680 A1 | 6/1998 |
| JP | S4957196 A | 6/1974 |
| JP | H1072423 A | 3/1998 |
| JP | H10152461 A | 6/1998 |
| JP | H10510813 A | 10/1998 |
| JP | H11510489 A | 9/1999 |
| JP | 2001522827 A | 11/2001 |
| JP | 2004520316 A | 7/2004 |
| JP | 2009-525259 | 7/2009 |
| JP | 2010-505873 | 2/2010 |
| WO | WO-9618372 A2 | 6/1996 |
| WO | WO-9703939 A1 | 2/1997 |
| WO | WO-1998/056423 | 12/1998 |
| WO | WO-9924392 A1 | 5/1999 |
| WO | WO-0250100 A2 | 6/2002 |
| WO | WO-2004026811 A2 | 4/2004 |
| WO | WO-2006/082088 | 8/2006 |
| WO | WO-2006/138380 | 12/2006 |
| WO | WO2006138380 * | 12/2006 |
| WO | WO-2007/107304 | 9/2007 |
| WO | WO-2008/042973 | 4/2008 |
| WO | WO-2009/086558 | 7/2009 |
| WO | WO-2009/148955 | 12/2009 |
| WO | WO-2010/062322 | 6/2010 |

OTHER PUBLICATIONS

Federal Register, "Supplemental Examination Guidelines for Determining Compliance with 35 U.S.C. 112 and for Treatment of Related Issues in Patent Applications; Supplementary Section 112 Examination Guidelines (Apr. 8, 2011)—Markush Claims", *Improper Markush*, vol. 76, No. 27, training slides 64-67, Feb. 9, 2011, pp. 7162-7175.

Fujita, M. et al., "Synthesis and Bioactivities of Novel 4,5,6,7-Tetrahydrothieno [2,3-c] pyridines as Inhibitors of Tumor Necrosis Factor-a (TNF-a) Production", *Bioorganic & Medicinal Chemistry Letters*, vol. 12, 1607-1611, 2002.

Guillot-Nieckowski, et al., "Dendritic vectors for gene transfection", *New Journal of Chemistry*, vol. 31, 2007, 1111-1127.

Hann, et al., "On the Double Bond Isostere of the Peptide Bond: Preparation of an Enkephalin Analogue", *Journal of the Chemical Society, Perkin Transactions 1*, 1982, 307-314.

Jeffs, Lloyd B. et al., "A Scalable, Extrusion-Free Method for Efficient Liposomal Encapsulation of Plasmid DNA", *Pharmaceutical Research*, vol. 22, No. 3, Mar. 2005, pp. 362-372

Love, Kevin T. et al., "Lipid-like materials for low-dose, in vivo gene silencing", *PNAS Early Edition*, www.pnas.org/cgi/doi/10.1073/pnas.0910603106, Sep. 17, 2009, pp. 1-6.

MacLachlan, Ian , "Liposomal Formulations for Nucleic Acid Delivery", Chapter 9, Antisense Drug Technologies, 2nd Edition, 2007, pp. 237-270.

Maurer, Norbert et al., "Spontaneous Entrapment of Polynucleotides upon Electrostatic Interaction with Ehtanol-Destabilized Cationic Liposomes", *Biophysical Journal*, vol. 80, No. 5, May 2001, 99. 2310-2326.

Patani, G. et al., "Bioisoterism: A Rational Approach to Drug Design", *Chemical Reviews*, vol. 96, No. 8, 1996, pp. 3147-3176.

PCT/US2011/060877, International Search Report and Written Opinion dated Mar. 27, 2012, 19 Pages.

Perrine, T. , "Symmetrical 1,3-Bis-Dialkylamino-2-Propanols", National Institute of Arthritis and Metabolic Diseases, National Institues of Health, Public Health Service Department of Health, Education, and Welfare, 1954, pp. 1137-1141.

Rajesh, M. et al., "Dramatic Influence of the Orientation of Linker Between Hydrophilic and Hydrophobic Lipid Moiety in Liposomal Gene Delivery", *J. Am Chem. Soc.*, vol. 127, Aug. 25, 2007, 11408-11420.

Rubini, E. et al., "Synthesis of Isosteric Methylene-Oxy Pseudodipeptide Analogues as Novel Amide Bond Surrogate Units", *Tetrahedron*, vol. 42(21), 1986, pp. 6039-6045.

Semple, Sean C. et al., "Rational design of cationic lipids for siRNA delivery", *Nature Biotechnology Letters*, Advance Online Publication, doi:10.1038/nbt.1602, Jan 17, 2010, pp. 1-7.

Yaroshenko, et al., "Synthesis of aminopolycarboxylic esters", *Journal of Organic Chemistry of the USSR*, vol. 10, No. 3, Jan. 1, 1974, 462-464.

Extended European Search Report for Application No. 18202571.8, dated Mar. 1, 2019, 8 pages.

* cited by examiner

AMINE-CONTAINING TRANSFECTION REAGENTS AND METHODS FOR MAKING AND USING SAME

CROSS-REFERENCE TO RELATED APPLICATIONS

This application is a divisional of U.S. application Ser. No. 14/340,395 filed Jul. 24, 2014, now U.S. Pat. No. 9,901,642, issued Feb. 27, 2018, which is a divisional of U.S. application Ser. No. 13/297,231, filed Nov. 15, 2011, now abandoned, which application claims the right of priority under 35 U.S.C. § 119 to U.S. Provisional Application Ser. No. 61/543,242, filed Oct. 4, 2011, and to U.S. Provisional Application Ser. No. 61/438,903, filed Feb. 2, 2011, and to U.S. Provisional Application Ser. No. 61/437,503, filed Jan 28, 2011, and to U.S. Provisional Application Ser. No. 61/413,905, filed Nov. 15, 2010. The aforementioned patents and patent applications are commonly owned with the present application and the entire contents thereof are hereby expressly incorporated by reference in their entirety as though fully set forth herein.

REFERENCE TO BIOLOGICAL SEQUENCE DISCLOSURE

This application contains nucleotide sequence and/or amino acid sequence disclosure in computer readable form and a written sequence listing, the entire contents of both of which are expressly incorporated by reference in their entirety as though fully set forth herein.

FIELD OF THE INVENTION

This invention relates generally to the field of transfection reagents for the in vitro and in vivo delivery of biologically active agents. More specifically, this invention relates to biodegradable and biocompatible lipids, and transfection complexes made using same, that may be used to introduce nucleic acids or other biologically active agents into cells in vitro or in vivo.

BACKGROUND

Gene therapy, such as the treatment of diseases through the application of nucleotide based drugs has become an important medical field. Typically, modified viruses as gene transfer vectors have been used in recent years. However, concerns over possible undesirable side effects, such as unsolicited immune responses, when viral vectors are used have resulted in efforts to develop non-viral alternatives (e.g., polymeric delivery systems, liposomal formulations and "naked" DNA injections). While these alternative approaches have not yet achieved the clinical effectiveness of viral vectors, the potential safety, processing, and economic benefits offered by these methods are promising.

Accordingly, better non-toxic, biodegradable, biocompatible lipids are needed that is easily and economically efficiently prepared to be used to transfect nucleic acids. Such lipids would have several uses, including the delivery of nucleic acids in gene therapy as well as in the packaging and/or delivery of diagnostic, therapeutic, and prophylactic agents. The instant specification describes such new transfection reagents and methods for synthesizing thereof.

SUMMARY

The present invention is directed towards amine-containing transfection reagents and methods for synthesizing the same. Additional embodiments of the present invention relate to the use of the amine-containing transfection reagents to make transfection complexes suitable for use in the intracellular delivery of one or more biologically active agents to a cell in vitro or a tissue in a human or an animal in vivo.

According to some embodiments of the invention, amine-containing transfection compounds having the general structure I, or pharmaceutically acceptable salts or derivatives thereof are provided:

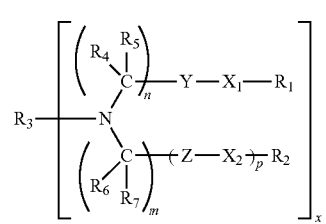

wherein each of $X_1$ and $X_2$ is a moiety independently selected from the group consisting of O, S, N—A and C—A, wherein A is selected from the group consisting of hydrogen and a $C_1$-$C_{20}$ hydrocarbon chain; each of Y and Z is a moiety independently selected from the group consisting of CH—OH, C=O, C=S, S=O and $SO_2$; each of $R_1$, $R_2$, $R_3$, $R_4$, $R_5$, $R_6$ and $R_7$ is a moiety independently selected from the group consisting of hydrogen, a cyclic or an acyclic, substituted or unsubstituted, branched or unbranched aliphatic group, a cyclic or acyclic, substituted or unsubstituted, branched or unbranched heteroaliphatic group, a substituted or unsubstituted, branched or unbranched acyl group, a substituted or unsubstituted, branched or unbranched aryl group, a substituted or unsubstituted, branched or unbranched heteroaryl group, x is an integer independently having the value between 1 and 10, inclusively, n is an integer independently having the value between 1 and 3, inclusively, m is an integer independently having the value between 0 and 20, inclusively, p is an integer independently having the value of 0 or 1, wherein if m=p=0, then $R_2$ is hydrogen, with the further proviso that if at least one of n or m has the value of 2, then $R_3$ and nitrogen in structure I form a moiety selected from the group consisting of:

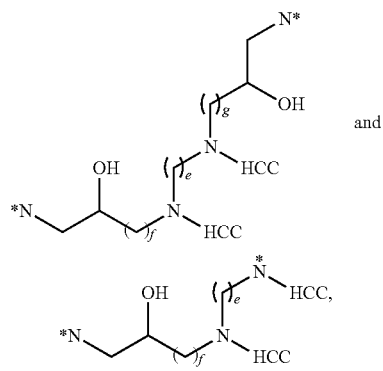

wherein each of g, e and f is an integer independently having the value between 1 and 6, inclusively, "HCC" symbolizes a hydrocarbon chain, and each * indicates the nitrogen atom in structure I.

According to other embodiments of the invention, there are provided amine-containing transfection compounds having the general structure II or pharmaceutically acceptable salts thereof:

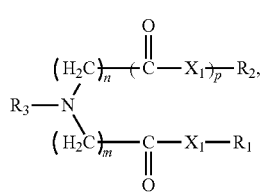

wherein when n=p=0, $R_2$ is H.

According to other embodiments of the invention, there are provided methods for synthesizing amine-containing transfection compounds having the structure I, or pharmaceutically acceptable salts thereof, the method comprising reacting one or more equivalents of an unsaturated component comprising at least two compounds selected from the group consisting of the first intermediate having the structure $R_1$—$X_1$—Y—$(CR_4R_5)_n$—Br and the second intermediate having the structure $R_2$—$X_2$—Z—$(CR_6R_7)_m$—Br, wherein in $(CR_4R_5)_n$ and $(CR_6R_7)_m$ portions of the structures, each $R_4$ is the same or different, each $R_5$ is the same or different, each $R_6$ is the same or different, and each $R_7$ is the same or different, wherein the first and the second intermediates are the same or different, with one equivalent of an amino component comprising a primary amine $NH_2$—$R_3$, a diamine, a polyamine or a combination thereof.

The amine-containing transfection compounds of the present invention may exist in neutral form or as a cation. In some embodiments, at a pH at or near physiologically neutral (e.g. pH from about 5 to about 8), the predominant form of an amine-containing transfection compound according to the presently described embodiments is a cation. In other embodiments, a pH at or near physiologically neutral (e.g., pH from about 5 to about 8), the predominant form of the amine-containing transfection compound according to the presently described embodiments is neutral.

In a further set of non-limiting embodiments, transfection complexes suitable for the delivery of one or more biologically active agents to a cell or a tissue in vitro or in vivo are provided for herein. The transfection complexes may include one or more of the amine-containing transfection compounds described herein. In some embodiments, the transfection complexes may optionally be made in combination with one or more helper lipids, optionally in combination with one or more pegylated lipids, optionally in combination with one or more cationic lipids, and optionally in combination with one or more targeting moieties. In some embodiments, transfection may be made with peptide or non-peptide transfection enhancers, fusogenic peptide or non-peptide agents, peptide or non-peptide endosomal release agents, or nuclear targeting agents (such as, e.g., a peptide containing one or more nuclear localization sequences, such as will be readily apparent to one skilled in the art without undue experimentation.

Helper lipids suitable for use in the preparation and formation of transfection complexes disclosed herein may include, though are not limited to a cholesterol, a cholesterol derivative, one or more sterols, including phytosterols, zoosterols and hopanoids, or any of the neutral or cationic lipids that are known to allow or to facilitate the introduction of exogenous bioactive molecules to the interior of a cell or of a tissue. In some embodiments, more than one helper lipid may be used in the formulation of the transfection complexes described herein.

Illustrative though non-limiting neutral or cationic lipids suitable for use as helper lipids in accordance with the embodiments set forth herein may include saturated and unsaturated alkyl and alicyclic ethers and esters of amines, amides or derivatives thereof. Straight-chain and branched alkyl and alkene groups of cationic lipids can contain from 1 to about 25 carbon atoms. In some embodiments, straight-chain or branched alkyl or alkene groups have six or more carbon atoms. In some embodiments, straight-chain or branched alkyl or alkene groups have eight to about twenty carbon atoms. Alicyclic groups can contain from about 6 to 30 carbon atoms, or, in some embodiments eight to twenty carbon atoms. In some embodiments, the alicyclic groups include cholesterol and other steroid groups. Cationic lipids can be prepared with a variety of counter ions (anions) including among others: Cl—, Br—, I—, F—, acetate, trifluoroacetate, sulfate, nitrite, triflate, and nitrate Exemplary though non-limiting neutral or cationic lipids contemplated for use in the preparation of the presently disclosed transfection complexes may include one or lipids selected from the following: BMOP (N-(2-bromoethyl)-N, N-dimethyl-2,3-bis(9-octadecenyloxy)-propana minimun bromide), DDPES (Dipalmitoylphosphatidylethanolamine 5-carboxyspermylamide), DSPC, CTAB:DOPE (formulation of cetyltrimethylammonium bromide (CATB) and DOPE), POPC (1-palmitoyl -2-oleoyl-sn-glycero-3-phosphocholine), DOPE (dioleoylphosphatidylethanolamine), DMG, DMAP (4-dimethylaminopyridine), DMPE (Dimyristoylphospatidylethanolamine), DOMG, DMA, DOPC (Dioleoylphosphatidylcholine), DMPC (dimyristoylphosphatidylcholine), DPEPC (Dipalmitoylethylphosphatidylcholine), DODAC (dioleoydimethylammonium chloride), DOSPER (1,3-Di-Oleoyloxy-2-(6-Carboxyspermyl)-Propylamid), DOTMA (N-[1-(2,3-dioleyloxy)propyl]-n,n,n-trimethylammoniumchloride), DDAB (didoceyl methylammonium bromide), DOTAP (N-[1-(2,3-dioleoyloxy)propyl]-N,N,N-trimethyl-ammonium methylsulfate), DOTAP.Cl, DC-chol (3,β-N,(N',N'-dimethylaminoethane)-carbamoyl]cholesterol), DOSPA (2-(sperminecarboxamido) ethyl)-N,N-dimethy-lammonium trifluoroacetate), DC-6-14 (O,O'-Ditetradecanoyl-N-(alphatrimethylammonioacetyl) diethanolamine chloride), DCPE (Dicaproylphosphtidylethanolamine), DLRIE (dilauryl oxypropyl-3-dimethylhydroxy ethylammonium bromide), DODAP (1,2-Dioleoyl-3-dimethylammonium-propane), Ethyl-PC, DOSPA (2,3-dioleoyloxy-N-[2-(sperminecarboxamidoethyl]-N,N-dimet-hyl-1-propanaminium trifluoroacetate), DOGS (dioctadecylamidoglycyl carboxyspermine), DMRIE (N-[1-(2,3 dimyristyloxy)propyl]-N,N-dimethyl-N-(2-hydroxyethyl) ammonium bromide), DOEPC (Dioleoylethyl-phosphocholine), DOHME (N-[1-(2,3-dioleoyloxy)propyl]-N-[11-(2-hydroxyethyl)]-N,Ndimethylammonium iodide), GAP-DLRIE:DOPE (N-(3-aminopropyl)-N, N-dimethyl-2, 3-bis(dodecyloxy)-1-propaniminium bromide/dioleyl phosphatidylethanolamine), DPPC (Dipalmitoylphosphatidylcholine), DOPG (1,2-dioleoyl-sn-glycero-3-[phospho-rac-(3-lysyl(1-glycerol)).Cl), N-lauroylsarcosine, (R)-(+)-limonene, lecithins (and derivatives thereof); phosphotidylethanolamine (and derivatives thereof); phosphatidylethanolamines, dioleoylphosphatidylethanolamine), DPhPE (diphytanoylphosphatidylethanolamine), DPPE dipalmitoylphosphatidylethanolamine), dipalmiteoylphosphatidylethanolamine, O-Chol (3 beta[1-ornithinamidecarbamoyl] cholesterol), POPE (palmitoyloleoylphosphatidylethanolamine) and distearoylphosphatidylethanolamine; phosphotidylcholine; phosphatidylcholines, DPPC (dipalmitoylphosphatidylcholine) POPC (palmitoyloleoylphosphatidylcholine) and distearoylphosphatidylcholine; phosphatidylglycerol; piperazine-based cationic lipids, phosphatidylglycerols, such as DOPG (dioleoylphosphatidylglycerol), DPPG (dipalmitoylphosphatidylglycerol), and distearoylphosphatidylglycerol; phosphatidylserine (and derivatives thereof); phosphatidylserines, such as dioleoyl- or dipalmitoylphosphatidylserine; diquaternary ammonium salts such as N,N'-dioleyl-N,N,N',N'-tetramethyl-1,2-ethanediamine (TmedEce), N,N'-dioleyl-N,N,N',N'-tetramethyl-1,3-propanediamine (PropEce), N,N'-dioleyl-N,N,N',N'-tetramethyl-1,6-hexanediamine (HexEce), and their corresponding N,N'-dicetyl saturated analogues (TmedAce, PropAce and HexAce), diphosphatidylglycerols; fatty acid esters; monocationic transfection lipids such as 1-deoxy-1-[dihexadecyl(methyl)ammonio]-D-xylitol; 1-deoxy-1-[methyl(ditetradecyl)ammonio]-Darabinitol; 1-deoxy-1-[dihexadecyl(methyl)ammonio]-D-arabinitol; 1-deoxy-1-[methyl(dioctadecyl)ammonio]-Darabinitol, glycerol esters; sphingolipids; cardolipin; cerebrosides; and ceramides; and mixtures thereof. Neutral lipids also include cholesterol and other 3βOH-sterols as well as derivatives thereof phosphatidyl choline or commercially available cationic lipid mixtures such as, for example, LIPOFECTIN® CELLFECTIN® (1:1.5 (M/M) formulation of N, NI,NII, NIII-tetramethyl-N, NI, NII, NIII-tetrapalmitylspermine (TMTPS) and dioleoyl phosphatidylethanolamine (DOPE), LIPOFECTACE®, GS 2888 CYTOFECTIN®, FUGENE 6®, EFFECTENE®, and LIPOFECTAMINE®, LIPOFECTAMINE 2000®, LIPOFECTAMINE PLUS®, LIPOTAXI®, POLYECT®, SUPERFECT®, TFXN™, TRANSFAST™, TRANSFECTAM®, TRANSMESSENGER®, vectamidine (3-tetradecylamino-N-tert-butyl-N'-tetradecyl-propionamidine (a.k.a. diC14-amidine), OLIGOFECTAMINE®, among others. Also contemplated are any mixtures of combination of the above listed helper lipids.

Pegylated lipids suitable for use in the preparation and formation of transfection complexes disclosed herein can be any lipid or mixture of lipids that are compatible with the formation of transfection complexes described herein, and with the administration thereof to an animal or to a human in vivo, or to tissues or cells in vitro. The pegylated lipids used in the present invention include a PEG polymer having a molecular weight between about 250 daltons and about 12,000, or in some embodiments, about 350 daltons and about 6,000 daltons, or, in some embodiments, between about 500 daltons and about 1,000 daltons, or, in some embodiments, between about 1,000 daltons and about 2,000 daltons, or, in some embodiments, between about 2,000 daltons and 5,000 daltons.

In some embodiments, the transfection complexes may include one or more biologically active agents to be delivered to a cell or to a target tissue in vitro or in vivo. Suitable biologically active agents may include any molecule that is capable of forming a transfection complex with the presently described amine-containing transfection reagents and that elicits a biological response when delivered to the interior of a cell or cells or to a tissue in vivo or in vitro. Biologically active agents contemplated for use in the presently described embodiments may be cationic, neutral or anionic agents. By way of non-limiting example, exemplary biologically active agents suitable for formulation in a transfection complex may include, though are not limited to; nucleic acids (including but not limited to single or double stranded linear or circular DNA molecules including cDNA molecules, single or double stranded RNA molecules, small interfereing RNA (siRNA) molecules, small hairpin RNA (shRNA) molecules, microRNA (miRNA) molecules, oligonucleotides, anti-sense oligonucleotides, sense oligonucleotides), polypeptides, antibodies, oligopeptides, therapeutic peptides or protein molecules, peptide nucleic acids (PNAs), cationic, anionic or neutral organic molecules or drugs, in addition to pharmaceutically acceptable salts thereof.

In certain non-limiting illustrative embodiments of the invention, transfection complexes and methods are provided that use the compounds of the present invention to deliver nucleic acid molecules into cells or tissues in vitro or in vivo, including the delivery of RNA interference molecules (RNAi) or small interfering RNA molecules (siRNA, shRNA or miRNA) into cells for inhibition of gene expression.

In certain non-limiting illustrative embodiments, transfection complexes and methods are provided that use the compounds of the present invention to deliver mRNA molecules into a cell or a tissue in vivo or in vitro to promote the expression of a specific protein or proteins are also provided.

In other non-limiting illustrative embodiments of the invention, transfection complexes and methods are provided that use the compounds of the present invention to deliver DNA molecules (including cDNA molecules) into a cell or a tissue in vivo or in vitro to promote the expression of a specific protein or proteins or to synthesize specific RNA molecules, including but not limited to mRNA molecules or RNAi or miRNA or shRNA molecules are also provided.

In some embodiments, the transfection complexes described herein may optionally include one or more fusogenic or cell-penetrating peptides. A fusogenic or cell-penetrating peptide is any peptide molecule that is capable of promoting the fusion of a lipid-containing complex to a cell membrane (either a plasma membrane or an endosomal membrane). A variety of fusogenic or cell-penetrating peptides are known in the art and it is well within the skill level of a practitioner to identify suitable fusogenic or cell-penetrating peptides and condition for the use thereof in the present invention without undue experimentation.

In some embodiments, the transfection complexes described herein may optionally include one or more transfection helpers or targeting moieties. A targeting moiety may be a peptide, a modified peptide, an antibody, a modified antibody, a receptor molecule, a modified receptor molecule, a single or a double stranded nucleic acid molecule, a modified single or double stranded nucleic acid molecule, a peptide or nucleic acid aptamer, a modified peptide or nucleic acid aptamer, an organic molecule, a polysaccharide, or any other molecule that is capable of targeting a transfection complex to specific tissue or cell type for targeted delivery of a biologically agent thereto, such as will be readily apparent to have having ordinary skill level in the art. In some embodiments, modification of a peptide, an antibody, a nucleic acid, an aptamer, and the like may include conjugating the peptide, antibody, nucleic acid, aptamer, and the like to a PEG moiety. Alternatively, modification of a peptide, an antibody, a nucleic acid, an aptamer, and the like may include conjugating the peptide, antibody, nucleic acid, aptamer, and the like to a PEG-lipid moiety A variety of targeting moieties are widely known to those skilled in the art, and all are contemplated for use with the presently described embodiments, without limitation.

In some embodiments, the transfection complexes provided for herein may be stable for up to 1 year and may either be contacted with the cells or tissues to be transfected, or be administered to an animal or to a human immediately or shortly after being formed, or optionally may be stored for a period of time prior to being contacted with the cells or tissues, or being administered to an animal or a human. The transfection complexes are stable and may be stored for a time period of at least 30 minutes, at least 45 minutes, at least 1 hour, at least 2 hours, at least 3 hours, at least 4 hours, at least 5 hours, at least 10 hours, at least 15 hours, at least 20 hours, at least 24 hours, at least 48 hours, at least 72 hours, at least 5 days, at least 7 days, at least 14 days, at least 28 days, at least 1 month, at least 2 months, at least 3 months, at least 4 months, at least 5 months, at least 6 months or at least 1 year at room temperature, or at a temperature greater than freezing, up to about room temperature. It is to be understood that the formulation described herein may include one or more stabilizing agents, preservatives, buffers, etc, that aid in the long-term stabilization and storage of bioactive formulation, such as will be readily understood by the skilled practitioner of the biological and pharmaceutical arts, and without requiring undue experimentation to achieve. It is also understood, that the storage period can be between any of these time periods, for example between 31 minutes and 1 hour or between 1 hour and 24 hours.

In some embodiments, methods for the preparation of functional transfection complexes are provided. The methods generally include forming a lipid-aggregate by encapsulating a biologically active agent in a composition containing one or more of the amine-containing transfection compounds described herein, optionally in combination with one or more helper lipids, stabilizing lipids, transfection helpers, pegylated lipids or targeting moieties. Such methods may include a1) mixing one or more amine-containing transfection compounds, at least one helper lipid, optionally more than one helper lipid and one or more pegylated lipids, or a salt thereof, in an alcohol/aqueous solution wherein the alcohol concentration is <50%; a2) mixing one or more amine-containing transfection compounds, at least one helper, optionally more than one helper lipid and one or more pegylated lipids, or a salt thereof, in a molar percentage such that the one or more amine-containing transfection compounds are present at 15%-50%; a3) mixing one or more amine-containing transfection compounds, at least one helper lipid, optionally more than one helper lipid and one or more pegylated lipids, or a salt thereof, in a molar percentage such that the Pegylated lipids are present at <50%; and a4) mixing one or more amine-containing transfection compounds, at least one helper lipid, optionally more than one helper lipid and one or more pegylated lipids, or a salt thereof, wherein the pegylated lipid has a polyethylene glycol molecular weight of about 2000-12000 and a fatty acid chain length of $C_6$-$C_{20}$ alkyl, or $C_{10}$-$C_{20}$ alkenyl; and complexing the lipid aggregate in an alcohol/aqueous solution with the bioactive agent to form a transfection complex, wherein the alcohol concentration is <50%, preferably less than 40%. In some embodiments, the method includes a1) and a2), a2) and a3), a1) and a3), a2) and a4), a3) and a4), a1) and a4), or a1)-a)4, for example. In some embodiments, the alcohol is a $C_1$-$C_4$ alcohol. In some embodiments, the alcohol is ethanol. In some embodiments, the alcohol is a pharmaceutically acceptable alcohol such as an alcohol that is liquid at about room temperature, for example, ethanol, propylene glycol, 2-(2-ethoxyethoxy)ethanol (Transcutol™), benzyl alcohol, glycerol, polyethylene glycol 200, polyethylene glycol 300, polyethylene glycol 400 or a mixture thereof. In some embodiments, the alcohol for mixing is different than the alcohol for complexing.

Further embodiments described herein provide for methods to screen large numbers of transfection compounds for tissue-biased delivery in vivo. Such methods may include preparing a plurality of transfection complexes containing a compound that readily facilitates the detection of a marker in combination with a test transfection compound, delivering each of the plurality of transfection complexes to a test animal, and detecting the marker.

In some embodiments, a method for screening tissue-biased delivery of a transfection complex may include preparing a plurality of transfection complexes, each transfection complex having at least one test transfection compound in combination with at least one nucleic acid that facilitates detection of delivery to a tissue. The nucleic acid may be an RNA molecule or a DNA molecule that encodes a protein that can be directly detected (such as, e.g., Green Fluorescent Protein (GFP), red Fluorescent Protein, Luciferase, or the like), or encode a protein that effects expression of a protein that can be directly detected.

In an embodiment, a method for screening tissue-biased delivery of a transfection complex may include preparing a plurality of unique transfection complexes, each transfection complex having at least one test transfection compound in combination with an mRNA or a cDNA that encodes Green Fluorescent Protein. Each unique transfection complex may be delivered either intravenously, subcutaneously, or to a tissue to a test animal, such as a mouse. After a predetermined amount of time, tissues from the mouse may be harvested and the expression of GFP in various tissues may be detected by gross examination, histological examination or by molecular detection (PCR, Western blotting, or the like) to determine which to tissue or tissues transfection complexes containing specific transfection compounds are delivered to.

In an embodiment, a method for screening tissue-biased delivery of a transfection complex may include preparing a plurality of unique transfection complexes, each transfection complex having at least one test transfection compound in combination with an mRNA or a cDNA that encodes Luciferase. Each unique transfection complex may be delivered either intravenously, subcutaneously, or to a tissue to a test animal, such as a mouse. After a predetermined amount of time, tissues from the mouse may be harvested and the expression of Luciferase in various tissues may be detected by gross examination, histological examination or by molecular detection (PCR, Western blotting, or the like), or imaged in-vivo using the IVIS® Imaging System (Caliper).

In an embodiment, a method for screening tissue-biased delivery of a transfection complex may include preparing a plurality of unique transfection complexes, each transfection complex having at least one test transfection compound in combination with an mRNA or a cDNA that encodes a specific transcription factor. Each unique transfection complex may be delivered either intravenously, subcutaneously, or to a tissue to a transgenic animal that expresses a reporter gene (such as, e.g., luciferase) under the control of the specific transcription factor. After a predetermined amount of time, tissues from the transgenic animal may be harvested and the expression of reporter gene in various tissues may be detected by gross examination, histological examination or by molecular detection (PCR, Western blotting, or the like). If the reporter gene is luciferase, detection may be accomplished in-vivo using the IVIS® Imaging System (Caliper).

These and other features of the present invention will become better understood with reference to the following description, drawings, and appended claims.

DETAILED DESCRIPTION

Figure 1:
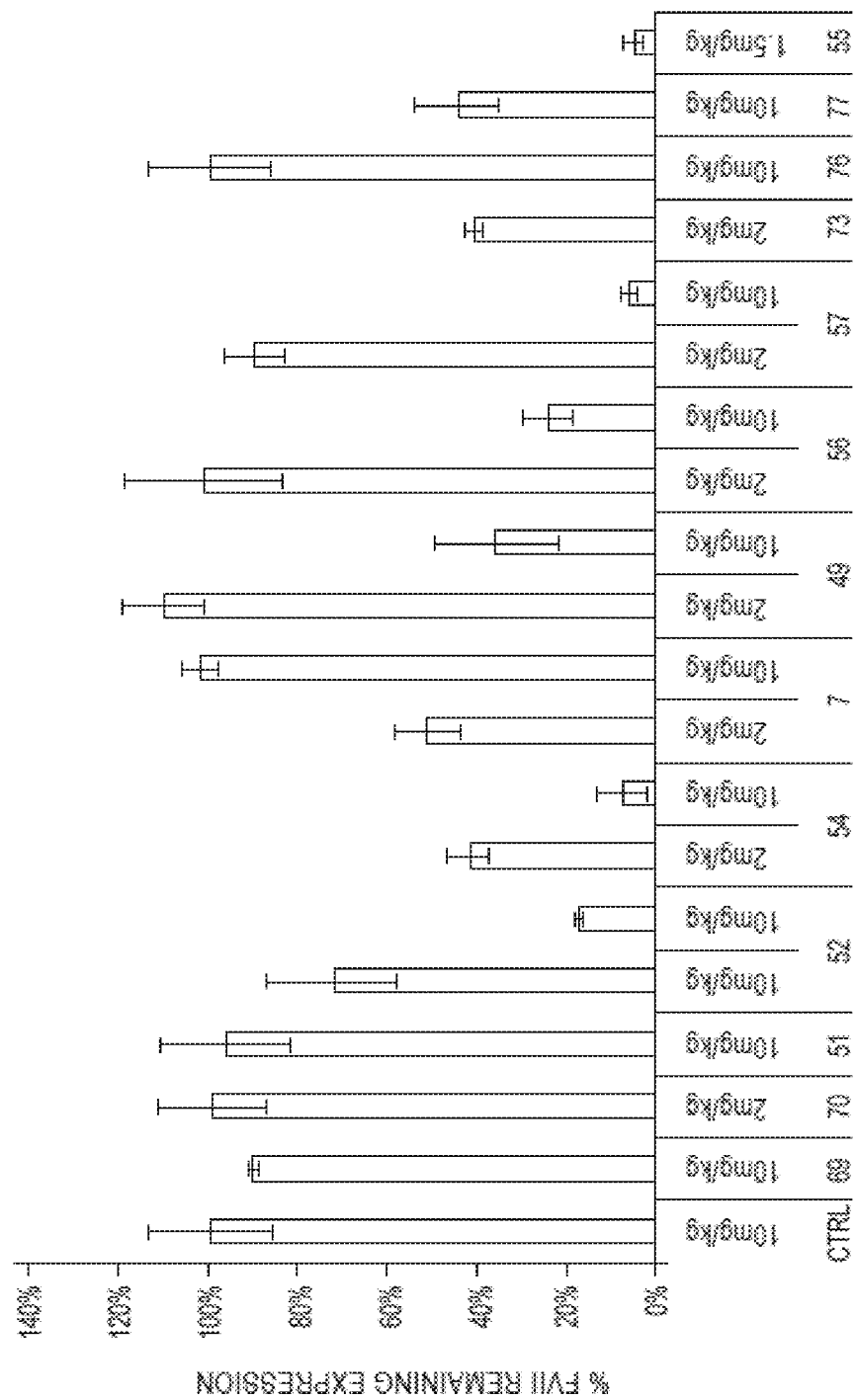
FIG. 1 shows a graph depicting some properties of a lipid composition prepared using compounds according to some embodiments of the present invention.

Reference will now be made in detail to some embodiments of the invention. While the invention will be described in conjunction with the embodiments discussed below, it will be understood that they are not intended to limit the invention to those embodiments. On the contrary, the invention is intended to cover alternatives, modifications, and equivalents, which is included within the invention as defined by the appended claims.

I. DEFINITIONS AND ABBREVIATIONS

It is to be understood that the present invention is not limited to particular devices or biological systems, which may, of course, vary. It is also to be understood that, as used in this specification and the appended claims, the singular forms "a", "an", and "the" include singular and plural referents unless the content clearly dictates otherwise. Thus, for example, reference to "a lipid" includes one or more lipids. It is to be yet further understood that any terminology used herein is for the purpose of describing particular embodiments only, and is not intended to be limiting.

The terms used throughout this specification generally have their ordinary meanings in the art, within the context of the invention, and in the specific context where each term is used. Certain terms are discussed below, or elsewhere in the specification, to provide additional guidance to the practitioner in describing the general embodiments of the invention, as well as how to make and use them. It will be readily appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

Compounds of the present invention may exist in particular geometric or stereoisomeric forms. The present invention contemplates all such compounds, including cis- and toms-isomers, R- and S-enantiomers, diastereomers, (D)-isomers, (L)-isomers, the racemic mixtures thereof, and other mixtures thereof, as falling within the scope of the invention. Additional asymmetric carbon atoms is present in a substituent such as an alkyl group. All such isomers, as well as mixtures thereof, are intended to be included in this invention.

Isomeric mixtures containing any of a variety of isomer ratios is utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures. If, for instance, a particular enantiomer of a compound of the present invention is desired, it is prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless stated otherwise, the following terms, definitions, and abbreviations as used herein are intended to have the following meanings:

The term "protecting group," as used herein, refers to a group that temporarily blocks a particular functional moiety, e.g., O, S, or N, is so that a reaction is carried out selectively at another reactive site in a multifunctional compound. A protecting group reacts selectively in good yield to give a protected substrate that is stable to the projected reactions, and the protecting group is selectively removable in good yield by readily available reagents that do not attack the other functional groups; the protecting group forms an easily separable derivative; and the protecting group has a minimum of additional functionality to avoid further sites of reaction.

As detailed herein, oxygen, sulfur, nitrogen, and carbon protecting groups is utilized. Non-limiting examples of exemplary hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl iV-oxido, diphenylmethyl, p,p'-dinitrobenzhydryl, 5-dibenzosuberyl, triphenylmethyl, α-naphthyldiphenylmethyl,p-methoxyphenyldiphenylmethyl, di(p-niethoxyphenyl)phenylmethyl, tri(p-methoxyphenyl)methyl, 4-(4'-bromophenacyloxyphenyl)diphenylmethyl, 4,4',4' '-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxy acetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

For protecting 1,2- or 1,3-diols, non-limiting examples of exemplary protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Non-limiting examples of exemplary amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-f-butyl-[9-(10, 10-dioxo-10, 10, 10, 10-tetrahydrothtoxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocimiamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfmylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1, 4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl] amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1, 1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, NN'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), α-trimethylsilylethanesulfonamide (SES), 9-anthracenesulfonamide, 4-(4',8'-dimethoxynaphthylmethyl)benzenesulfonamide (DNMB S), benzylsulfonamide, trifluoromethylsulfonamide, and phenacylsulfonamide.

The term "substituted" whether used alone or is preceded by the term "optionally," and substituents contained in formulae of this invention, refer to the replacement of hydrogen radicals in a given structure with the radical of a specified substituent. When more than one position in any given structure is substituted with more than one substituent selected from a specified group, the substituent is either the same or different at every position. The term "substituted" is inclusive of all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables are those that result in the formation of stable compounds.

The term "stable," as used herein, refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. The term "aliphatic" is inclusive of, but is not limited to, alkyl, alkenyl, alkynyl, cycloalkyl, cycloalkenyl, and cycloalkynyl moieties.

The term "alkyl" includes straight, branched and cyclic alkyl groups. An analogous convention applies to other generic terms such as "alkenyl" or "alkynyl." The terms "alkyl," "alkenyl" and "alkynyl" encompass both substituted and unsubstituted groups. The alkyl, alkenyl, and alkynyl groups employed in the invention contain 1-20 aliphatic carbon atoms. "Lower alkyl" is used to indicate those alkyl groups (cyclic, acyclic, substituted, unsubstituted, branched or unbranched) having 1-6 carbon atoms.

Exemplary aliphatic groups include, but are not limited to, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, and —CH$_2$-cyclohexyl moieties which is one or more substituents. Exemplary alkenyl groups include, but are not limited to, ethenyl, propenyl, butenyl and 1-methyl-2-buten-1-yl. Representative alkynyl groups include, but are not limited to, ethynyl, 2-propynyl (propargyl) and 1-propynyl.

The term "alkyl," as used herein, refers to saturated, straight- or branched-chain hydrocarbon radicals derived from a hydrocarbon moiety containing between one and twenty carbon atoms by removal of a single hydrogen atom. Exemplary alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

The term "alkenyl," as used herein, refers to a monovalent group derived from a hydrocarbon moiety having at least one carbon-carbon double bond by the removal of a single hydrogen atom. Exemplary alkenyl groups include, but are not limited to, ethenyl, propenyl, butenyl and 1-methyl-2-buten-1-yl.

The term "alkynyl," as used herein refers to a monovalent group derived from a hydrocarbon having at least one carbon-carbon triple bond by the removal of a single hydrogen atom. Exemplary alkynyl groups include, but are not limited to, ethynyl, 2-propynyl (propargyl) and 1-propynyl, and the like.

The terms "alkoxy" and "thioalkyl," as used herein refer to an alkyl group, as previously defined, attached to the parent molecule through an oxygen atom or through a sulfur atom, respectively. In certain embodiments, the alkyl, alkenyl, and alkynyl groups contain 1-20 alipahtic carbon atoms. Exemplary alkoxy groups, include but are not limited to, methoxy, ethoxy, propoxy, isopropoxy, n-butoxy, tert-butoxy, neopentoxy and n-hexoxy. Exemplary thioalkyl groups include, but are not limited to, methylthio, ethylthio, propylthio, isopropylthio and n-butylthio.

The term "alkylamino," as used herein, refers to a group having the structure —NHR', wherein R' is aliphatic, as defined above, containing 1-20 aliphatic carbon atoms. Exemplary alkylamino groups include, but are not limited to, methylamino, ethylamino, n-propylamino, iso-propylamino, cyclopropylamino, n-butylamino, tert-butylamino, neopentylamino, n-pentylamino, hexylamino and cyclohexylamino.

The term "dialkylamino," as used herein, refers to a group having the structure —NRR$_1$, wherein R and R$_1$ are each an aliphatic group, as defined herein, containing 1-20 aliphatic carbon atoms. R and R$_1$ is the same or different or is linked to form an aromatic or non-aromatic cyclic structure. Exemplary dialkylamino groups include, but are not limited to, dimethylamino, methyl ethylamino, diethylamino, methylpropylamino, di(n-propyl)amino, di(iso-propyi)amino, di(cyclopropyl)amino, di(n-butyl)amino, di(tert-butyl) amino, di(neopentyl)amino5 di(n-pentyl)amino, di(hexyl) amino and di(cyclohexyl)amino. Exemplary cyclic diaminoalkyl groups include, but are not limited to, aziridinyl, pyrrolidinyl, piperidinyl, morpholinyl, pyrrolyl, imidazolyl, 1,3,4-trianolyl and tetrazolyl.

The term "carboxylic acid," as used herein, refers to a compound comprising a group of formula —COOH.

Some examples of substituents of the above-described aliphatic and other moieties of compounds of the invention include, but are not limited to to aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, —F, —Cl, —Br, —I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R$_x$, —OCON(R$_x$)$_2$, —N(R$_x$)$_2$, —S(O)$_2$R$_x$ and —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein is substituted or unsubstituted, branched or unbranched, cyclic or acyclic, and wherein any of the aryl or heteroaryl substituents described above and herein is substituted or unsubstituted.

The terms "aryl" and "heteroaryl," as used herein, refer to stable mono- or polycyclic, heterocyclic, polycyclic, and polyheterocyclic unsaturated moieties having 3-14 carbon atoms, each of which is substituted or unsubstituted. Substituents include, but are not limited to, any of the substituents recited above for aliphatic moieties. The term "aryl" is inclusive of mono- or bicyclic carbocyclic ring systems having one or two aromatic rings including, but not limited to, phenyl, naphthyl, tetrahydronaphthyl, indanyl and The term "heteroaryl" is inclusive of cyclic aromatic radicals having from five to ten ring atoms, of which 1-3 ring atoms is selected from S, O, and N, and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl,oxadiazolyl, thiophenyl, furanyl, quinolinyl or isoquinolinyl.

Aryl and heteroaryl groups is unsubstituted or substituted, wherein substitution includes replacement of one, two, three, or more of the hydrogen atoms thereon independently with any one or more of the following moieties including, but not limited to aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, —F, —Cl, —Br, —I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R$_x$, —OCON(R$_x$)$_2$, —N(R$_x$)$_2$, —S(O)$_2$R$_x$ and —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein is substituted or unsubstituted, branched or unbranched, cyclic or acyclic, and wherein any of the aryl or heteroaryl substituents described above and herein is substituted or unsubstituted.

The term "cycloalkyl," as used herein, refers specifically to groups having three to seven, preferably three to ten carbon atoms. Suitable cycloalkyls include, but are not limited to cyclopropyl, cyclobutyl, cyclopentyl, cyclohexyl and cycloheptyl, which may optionally be substituted with substituents including, but not limited to aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, —F, —Cl, —Br, —I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R$_x$, —OCON(R$_x$)$_2$, —N(R$_x$)$_2$, —S(O)$_2$R$_x$ and —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and is substituted or unsubstituted, branched or unbranched, cyclic or acyclic, and wherein any of the aryl or heteroaryl substituents described above and herein is substituted or unsubstituted.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties is branched, unbranched, cyclic or acyclic and include saturated and unsaturated heterocycles such as morpholino, pyrrolidinyl, etc. Heteroaliphatic moieties are substituted by independent replacement of one or more of the hydrogen atoms thereon with one or more moieties including, but not limited to aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, —F, —Cl, —Br, —I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R$_x$, —OCON(R$_x$)$_2$, —N(R$_x$)$_2$, —S(O)$_2$R$_x$ and —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein is substituted or unsubstituted, branched or unbranched, cyclic or acyclic, and wherein any of the aryl or heteroaryl substituents described above and herein is substituted or unsubstituted.

The terms "halo" and "halogen," as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl and trifluoromethyl.

The term "heterocycloalkyl" or "heterocycle," as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms is optionally be oxidized, (iii) the nitrogen heteroatom may optionally be quaternized, and (iv) any of the above heterocyclic rings is fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl and tetrahydrofuryl. The term a "substituted" heterocycloalkyl or heterocycle group is utilized and as used herein, refers to a heterocycloalkyl or heterocycle group, as defined above, substituted by the independent replacement of one, two or three of the hydrogen atoms thereon with but are not to aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, —F, —Cl, —Br, —I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$), —OC(O)R$_x$, —OCO$_2$R$_x$, —OCON(R$_x$)$_2$, —N(R$_x$)$_2$, —S(O)$_2$R$_x$ and —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein is substituted or unsubstituted, branched or unbranched, cyclic or acyclic, and wherein any of the aryl or heteroaryl substituents described above and herein is substituted or unsubstituted.

Exemplary non-limiting heterocyclic and aromatic heterocyclic groups that is included in the compounds of the invention include 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, A-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, A-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4-(2-nitrophenyl)piperazine, 4-(2-nitrophenyl)piperazine, 4-(2-phenylethyl)piperazine, A-(2-pyridyl)piperazine, 4-(2-pyrimidinyl)piperazine, 4-(2,3-dimethylphenyl)piperazine, 4-(2,4-difluorophenyl) piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term "carbocycle," as used herein, refers to an aromatic or non-aromatic ring in which each atom of the ring is a carbon atom.

The term "independently selected" is used herein to indicate that the groups is identical or different.

As used herein, the term "labeled" is intended to mean that a compound has at least one element, isotope, or chemical compound attached to enable the detection of the compound by using a radioactive or heavy isotope label, or an immune label such as an antibody or antigen or a label derived from a colored, luminescent, phosphorescent, or fluorescent dye. Photoaffinity labeling employing, for example, o-, m- and p-azidobenzoyls, substituted with one or more halogen moieties, including, but not limited to 4-azido-2,3,5,6-tetrafluorobenzoic acid, is utilized for the direct elucidation of intermolecular interactions in biological systems.

The term "animal," as used herein, may refer to humans as well as non-human animals, including, for example, mammals (e.g., a rodent, a mouse, a rat, a rabbit, a monkey, a dog, a cat, a primate, or a pig), birds, reptiles, amphibians, and fish.

The term "cell" generally refers to eukaryotic cells of any type and from any source. Types of eukaryotic cells include epithelial, fibroblastic, neuronal, hematopoietic cells and the like from primary cells, tumor cells or immortalized cell lines. Sources of such cells include any animal such as human, canine, mouse, hamster, cat, bovine, porcine, monkey, ape, sheep, fish, insect, fungus, and any plant including crop plants, algae, ornamentals and trees.

"Delivery" is used to denote a process by which a desired compound is transferred to a target cell such that the desired compound is ultimately located inside the target cell or in, or on, the target cell membrane. In many uses of the compounds of the invention, the desired compound is not readily taken up by the target cell and delivery via lipid aggregates or transfection complexes a means for delivering the desired compound to the appropriate cellular compartment within a cell. In certain uses, especially under in vivo conditions, delivery to a specific target cell type is preferable and can be facilitated by compounds of the invention.

Drug refers to any therapeutic or prophylactic agent other than food which is used in the prevention, diagnosis, alleviation, treatment, or cure of disease in man or animal.

"Kit" refers to transfection or protein expression kits which include one or more of the compounds of the present invention or mixtures thereof. Such kits may comprise a carrying means being compartmentalized to receive in close confinement one or more container means such as vials, test tubes and the like. Each of such container means comprises components or a mixture of components needed to perform transfection. Such kits may include one or more components selected from nucleic acids (preferably one or more vectors), cells, one or more compounds of the present invention, lipid-aggregate forming compounds, transfection enhancers, biologically active substances, etc.

The term "associated with", when used in the context of molecular interactions, refers to two entities linked by a direct or indirect covalent or non-covalent interaction, such as hydrogen bonding, van der Waals interactions, hydrophobic interactions, magnetic interactions, electrostatic interactions, etc.

The term "biocompatible," as used herein refers to compounds that are not toxic to cells. Compounds are biocompatible if their addition to cells in vitro results in less than or equal to 20% cell death, and their administration in vivo does not induce inflammation or other such adverse effects.

The term "biodegradable," as used herein, refers to compounds that, when introduced into cells, are broken down into components that the cells can either reuse or dispose of without significant toxic effect on the cells (i.e., fewer than about 20% of the cells are killed when the components are added to cells in vitro). The components do not induce inflammation or other adverse effects in vivo. The chemical reactions relied upon to break down the biodegradable compounds are typically uncatalyzed. The term "effective amount," as used herein with respect to an active agent, refers to the amount necessary to elicit the desired biological response. The effective amount of an agent or device may vary depending on such factors as the desired biological endpoint, the agent to be delivered, the composition of the encapsulating matrix, the target tissue, etc. Delivery of an "effective amount of a molecule" is the delivery of the molecule into a cell in sufficient amounts so that the molecule elicits a biological response, for example, modulating the expression of one or more genes in the cell. In specific embodiments, an effective amount of a molecule is delivered to a cell such that an amelioration or improvement in a disease, condition, or disorder related to the cell can be obtained. Delivery of an "effective amount of siRNA" or an "effective amount or RNAi" is the delivery of siRNA or other RNAi into a cell in sufficient amounts to cause a reduction in expression of the target gene in the cell.

The terms "biologically active agent", "bioactive agents" or the like, generally refers to a composition, complex, compound or molecule which has a biological effect or that modifies, causes, promotes, enhances, blocks or reduces a biological effect, or that enhances or limits the production or activity of, reacts with and/or binds to a second molecules which has a biological effect. The second molecule can, but need not be, an endogenous molecule (e.g., a molecule, such as a protein or nucleic acid, normally present in the target cell). A biological effect may be, but is not limited to, one that stimulates or causes an immunoreactive response; one that impacts a biological process in a cell, tissue or organism (e.g., in an animal); one that imparts a biological process in a pathogen or parasite; one that generated or causes to be generated a detectable signal; one that regulates the expression of a protein or polypeptide; one that stops or inhibits the expression of a protein or polypeptide; or one that causes or enhances the expression of a protein or polypeptide. Biologically active compositions, complexes, compounds or molecules may be used in investigative, therapeutic, prophylactic and diagnostic methods and compositions and generally act to cause.

The term "cationic lipid" refers to any cationic lipids which may be used for transfection and which under physiological conditions possess at least one positive charge. While it is to be understood that certain of the amine-containing transfection agents that form the basis of the present disclosure also exist as cations under physiological conditions, the term is also extended without limitation to any cationic helper lipids that may be used to co-formulate transfection complexes as described herein. Additional cationic lipids other than the novel amine-containing transfection agents described herein may include, but not limited to, e.g., DOSPA, DOTMA, DMRIE, DOT AP, DOGS and TMTPS, as well as any of the cationic lipids described herein as "helper lipid".

"Target cell" or "target tissue" refers to any cell or tissue to which a desired compound is delivered, using a lipid aggregate or transfection complex as carrier for the desired compound.

Transfection is used herein to mean the delivery of any nucleic acid, protein or other macromolecule to a target cell or tissue in vitro or in vivo (i.e., in an animal, a plant or a human), such that the nucleic acid, protein or other macromolecule is expressed in, confers a phenotype to, or has a biological function in the cell.

The term "expressible nucleic acid" includes both DNA and RNA without regard to molecular weight, and the term "expression" means any manifestation of the functional presence of the nucleic acid within the cell including, without limitation, both transient expression and stable expression.

The term "transfection complex", as used herein generally refers to a composition formulated for the delivery of a biologically active agent, such as a nucleic acid, a protein, a macromolecule, or the like, to a cell or to a tissue in vivo or in vitro. Transfection complexes as used herein may include at least one or more of the amine-containing transfection compounds in combination with the biologically active compound to be delivered, optionally in combination with one or more helper lipids, one or more pegylated lipids, one or more targeting moieties, in addition to the bioactive agent that is to be delivered. For the purposes described herein, the term "transfection complex" may be thought of as a lipoplex or a lipid aggregate contacted with a bioactive agent. Thus, in some instances in the following disclosure, terms such as lipoplex, lipid aggregate and the like may be used to make reference a transfection complex that lacks the one or more bioactive agents or "payloads".

The term "helper lipid", as used herein, generally refers to a lipid that is suitable for use in the preparation and formation of transfection complexes disclosed herein. Suitable helper lipids may include, though are not limited to cholesterols, cholesterol derivatives, sterols, including phytosterols, zoosterols and hopanoids, or any of the neutral or cationic lipids that are known to allow or to facilitate the introduction of exogenous bioactive molecules to the interior of a cell or of a tissue. In some embodiments, more than one helper lipid may be used in the formulation of the transfection complxes described herein. Exemplary though non-limiting neutral or cationic lipids contemplated for use in the preparation of the presently disclosed transfection complexes may include one or lipids selected from the following: BMOP (N-(2-bromoethyl)-N,N-dimethyl-2,3-bis (9-octadecenyloxy)-propana minimun bromide), DDPES (Dipalmitoylphosphatidylethanolamine 5-carboxyspermylamide), DSPC, CTAB:DOPE (formulation of cetyltrimethylammonium bromide (CATB) and DOPE), POPC (1-palmitoyl-2-oleoyl-sn-glycero-3-phosphocholine), DOPE (dioleoylphosphatidylethanolamine), DMG, DMAP (4-dimethylaminopyridine), DMPE (Dimyristoylphospatidylethanolamine), DOMG, DMA, DOPC (Dioleoylphosphatidylcholine), DMPC (dimyristoylphosphatidylcholine), DPEPC (Dipalmitoylethylphosphatidylcholine), DODAC (dioleoy-dimethylammonium chloride), DOSPER (1,3-Di-Oleoy-loxy-2-(6-Carboxyspermyl)-Propylamid), DOTMA (N-[1-(2,3-dioleyloxy)propyl]-n,n,n-trimethylammoniumchloride), DDAB (didoceyl methylammonium bromide), DOTAP (N-[1-(2,3-dioleoy-loxy)propyl]-N,N,N-trimethyl-ammonium methylsulfate), DOTAP.Cl, DC-chol (3,β-N,(N',N'-dimethylaminoethane)-carbamoyl]cholesterol), DOSPA (2-(sperminecarboxamido) ethyl)-N,N-dimethy-lammonium trifluoroacetate), DC-6-14 (O,O'-Ditetradecanoyl-N-(alphatrimethylammonioacetyl) diethanolamine chloride), DCPE (Dicaproylphosphtidyle-thanolamine), DLRIE (dilauryl oxypropyl-3-dimethylhy-droxy ethylammonium bromide), DODAP (1,2-Dioleoyl-3-dimethylammonium-propane), Ethyl-PC, DOSPA (2,3-dioleoyloxy-N-[2-(sperminecarboxamidoethyl]-N,N-di-met-hyl-1-propanaminium trifluoroacetate), DOGS (dioctadecylamidoglycyl carboxyspermine), DMRIE (N-[1-(2,3 dimyristyloxy)propyl]-N,N-dimethyl-N-(2-hydroxy-ethyl) ammonium bromide), DOEPC (Dioleoylethyl-phos-phocholine), DOHME (N-[1-(2,3-dioleoyloxy)propyl]-N-[1-(2-hydroxyethyl)]-N,Ndimethylammonium iodide), GAP-DLRIE:DOPE (N-(3-aminopropyl)-N, N-dimethyl-2, 3-bis(dodecyloxy)-1-propaniminium bromide/dioleyl phos-phatidylethanolamine), DPPC (Dipalmitoylphosphatidyl-choline), DOPG (1,2-dioleoyl-sn-glycero-3-[phospho-rac-(3-lysyl(1-glycerol)).Cl), N-lauroylsarcosine, (R)-(+)-limonene, lecithins (and derivatives thereof); phosphotidylethanolamine (and derivatives thereof); phos-phatidylethanolamines, dioleoylphosphatidylethanolamine), DPhPE (diphytanoylphosphatidylethanolamine), DPPE dipalmitoylphosphatidylethanolamine), dipalmiteoylphos-phatidylethanolamine, O-Chol (3 beta[1-ornithinamidecar-bamoyl] cholesterol), POPE (palmitoyloleoylphosphatidyle-thanolamine) and distearoylphosphatidylethanolamine; phosphotidylcholine; phosphatidylcholines, DPPC (di-palmitoylphosphatidylcholine) POPC (palmitoyloleoyl-phosphatidylcholine) and distearoylphosphatidylcholine; phosphatidylglycerol; piperazine-based cationic lipids, phosphatidylglycerols, such as DOPG (dioleoylphosphati-dylglycerol), DPPG (dipalmitoylphosphatidylglycerol), and distearoylphosphatidylglycerol; phosphatidylserine (and derivatives thereof); phosphatidylserines, such as dioleoyl- or dipalmitoylphosphatidylserine; diquaternary ammonium salts such as N,N'-dioleyl-N,N,N',N'-tetramethyl-1,2-eth-anediamine (TmedEce), N,N'-dioleyl-N,N,N',N'-tetram-ethyl-1,3-propanediamine (PropEce), N,N'-dioleyl-N,N,N', N'-tetramethyl-1,6-hexanediamine (HexEce), and their corresponding N,N'-dicetyl saturated analogues (TmedAce, PropAce and HexAce), diphosphatidylglycerols; fatty acid esters; monocationic transfection lipids such as 1-deoxy-1-[dihexadecyl(methyl)ammonio]-D-xylitol; 1-deoxy-1-[methyl(ditetradecyl)ammonio]-Darabinitol; 1-deoxy-1-[di-hexadecyl(methyl)ammonio]-D-arabinitol; 1-deoxy-1-[methyl(dioctadecyl)ammonio]-Darabinitol, glycerol esters; sphingolipids; cardolipin; cerebrosides; and ceramides; and mixtures thereof. Neutral lipids also include cholesterol and other 3βOH-sterols as well as derivatives thereof phospha-tidyl choline or commercially available cationic lipid mix-tures such as, for example, LIPOFECTIN® CELLFEC-TIN® (1:1.5 (M/M) formulation of N, NI,NII, NIII-tetramethyl-N, NI, NII, NIII-tetrapalmitylspermine (TMTPS) and dioleoyl phosphatidylethanolamine (DOPE), LIPOFECTACE®, GS 2888 CYTOFECTIN®, FUGENE 6®, EFFECTENE®, and LIPOFECTAMINE®, LIPO-FECTAMINE 2000®, LIPOFECTAMINE PLUS®, LIPO-TAXI®, POLYECT®, SUPERFECT®, TFXN™ TRANS-FAST™, TRANSFECTAM®, TRANSMESSENGER®, vectamidine (3-tetradecylamino-N-tert-butyl-N'-tetradecyl-propionamidine (a.k.a. diC14-amidine), OLIGO-FECTAMINE®, among others. Also contemplated are any mixtures of combination of the above listed helper lipids. The following patent documents, patent applications, or references are incorporated by reference herein in their entirety and in particular for their disclosure of transfection agents containing cationic and neutral helper lipids which may be used to comprise the transfection complexes of the present invention: U.S. Pat. Nos. 6,075,012; 6,020,202; 5,578,475; 5,736,392; 6,051,429; 6,376,248; 5,334,761; 5,316,948; 5,674,908; 5,834,439; 6,110,916; 6,399,663; 6,716,882; 5,627,159; PCT/US/2004/000430, published as WO 04063342 A2; PCT/US/9926825, published as WO 0027795 A1; PCT/US/04016406, published as WO 04105697; and PCT/US2006/019356, published as WO 07130073 A2.

The term "pegylated lipid" as used herein generally refers to a lipid that is covalently conjugated to one or more polyethylene glycol moieties. Pegylated lipids for lipoplex embodiments herein include phosphatidylethanolamine (PE) based pegylated lipids such as, for example, 1,2-dimyristoyl-sn-glycero-3-phosphoethanolamine-N-[methoxy(polyethylene glycol)-MW] where MW refers to average MW of the polyethylene glycol moiety. Such dimyristoyl-PEG-PE lipids are commonly designated 14:0 PEG (MW) PE. The average MW of the polyethylene glycol moiety can be 25, 350, 550, 750, 1000, 2000, 3000, 5000, 6000, 8000 or 12000, for example. The fatty acid chains of the phosphatidylethanolamine based pegylated lipids may include, for example, a 1,2-dioleoyl group such as for 18:1 PEG (MW) PE, a 1,2-dipalmitoyl group such as for 16:0 PEG (MW) PE, or a 1,2-distearoyl-group such as for 18:0 PEG (MW) PE. Further phosphatidylethanolamine (PE) based pegylated lipids include, for example, 1,2-distearoyl-sn-glycero-3-phosphoethanolamine-N-[MOD(polyethylene glycol)-MW], also referred to as DSPE-MOD PEG(MW) wherein MOD refers to a functional moiety such as an amine, biotin, carboxylic acid, folate, maleimide, PDP, or carboxyfluorescein moiety. The MW may be 2000 or 5000, for example. Pegylated lipids for the embodiments described herein also include ceramide based pegylated lipids such as, for example, N-octanoyl-sphingosine-1-{succinyl[methoxy (polyethylene glycol)MW]}, designated C8 PEG (MW) ceramide, where MW is 750, 2000, or 5000, for example. Alternatively, the fatty acid moiety may have an N-palmitoyl (C16) group such as for C16 PEG (MW) ceramide.

A "liposomal composition" generally is a formulation that includes one or more liposomes. In some instances, the term "liposomal composition" may be used interchangeably with the term "transfection complex". These formulations are typically colloids, but can be dried formulations as well. A liposome is a vesicular colloidal particle composed of self assembled amphiphilic molecules. Liposomal compositions of the present invention typically include at least one or more cationic lipids either alone or optionally in combina-tion with one or more helper lipids (i.e., a neutral lipid, a cholesterol or cholesterol derivative, a cationic lipid) that are processed using standard methods to form a liposome-containing colloid suspension. Liposomal compositions of the present invention are those containing one or more amine-containing transfection lipids, one or more helper lipids, one or more pegylated lipids, optionally, in combi-nation with one or more neutral and/or helper lipids or targeting moieties which are treated by any of the standard methods known in the art without limitation to form liposomes. Liposomal compositions can be distinguished one from another by particle size measurements. Different compositions will exhibit differences in particle size and uniformity of particle size, e.g., average particle size, and polydispersity. Different compositions will exhibit differences in the extent of the composition that is in the form of liposomes. In some non-limiting embodiments, liposomal compositions will exhibit particle size in the range 120 nm and 800 nm and will exhibit generally lower polydispersity. Lipoplex particle size (with siRNA or other cargo) may range from about 40 nm to 135 nm. In some embodiments, lipoplex particle size is 50 nm to 120 nm, 50 nm to 100 nm, 60 nm to 90 nm, 70 nm to 90 nm, or about 85 nm.

The term "Lipid aggregate" or "lipoplex" is a generic term that includes liposomes of all types, both unilamellar and multilamellar, as well as vesicles, micelles and more amorphous aggregates. A cationic lipid aggregate is a lipid aggregate comprising a combination of one or more cationic compounds, optionally in combination with non-cationic lipids (including neutral lipids), such that the lipid aggregate has a net positive charge. Amine-containing transfection compounds of the present invention can form a lipid aggregate, optionally with a helper lipid and further optionally with one or more pegylated lipids and/or one or more targeting moieties, which can then form a lipid-bioactive agent complex when contacted with a suitable bioactive agent. The terms "lipid aggregate" or "lipoplex" are generally used herein to refer to a "naked" transfection complex, i.e., a transfection complex that generally lacks a payload of bioactive agent to be delivered to a cell or to a tissue in vitro or in vivo.

The term "lipid-bioactive agent" generally refers to the noncovalent association between a lipid or lipid aggregate and a bioactive agent, such as a nucleic acid, a polypeptide, and the like.

As used herein "nucleic acid" and its grammatical equivalents will include the full range of polymers of single or double stranded nucleotides and includes nucleic acids (including DNA, RNA, and DNA-RNA hybrid molecules) that are isolated from a natural source; that are prepared in vitro, using techniques such as PCR amplification or chemical synthesis; that are prepared in vivo, e.g., via recombinant DNA technology; or that are prepared or obtained by any known method. A nucleic acid typically refers to a polynucleotide molecule comprised of a linear strand of two or more nucleotides (deoxyribonucleotides and/or ribonucleotides) or variants, derivatives and/or analogs thereof. The exact size will depend on many factors, which in turn depends on the ultimate conditions of use, as is well known in the art. The nucleic acids of the present invention include without limitation primers, probes, oligonucleotides, vectors, constructs, plasmids, genes, transgenes, genomic DNA, cDNA, RNA, RNAi, siRNA, shRNA, stRNA, PCR products, restriction fragments, oligonucleotides and the like.

As used herein, the term "nucleotide" includes any monomeric unit of DNA or RNA containing a sugar moiety (pentose), a phosphate, and a nitrogenous heterocyclic base and may also include mono-, di- and triphosphate forms of such nucleotides. The base is usually linked to the sugar moiety via the glycosidic carbon (at the 1' carbon of pentose) and that combination of base and sugar is called a "nucleoside." The base characterizes the nucleotide with the four customary bases of DNA being adenine (A), guanine (G), cytosine (C) and thymine (T). Inosine (I) is an example of a synthetic base that can be used to substitute for any of the four, naturally occurring bases (A, C, G, or T). The four RNA bases are A, G, C, and uracil (U). Accordingly, a nucleic acid may be a nucleotide sequence comprising a linear array of nucleotides connected by phosphodiester bonds between the 3' and 5' carbons of adjacent pentoses. Other modified nucleotides are known and may be sued in the practice of the invention. The term nucleotide includes ribonucleoside triphosphates ATP, UTP, ITP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels. Various labeling methods known in the art can be employed in the practice of this invention.

"RNA" or "RNA molecule" refers to any RNA molecule or functional portion thereof, of any size and having any sequence, from any source, including RNA from viral, prokaryotic, and eukaryotic organisms. The RNA molecule may be chemically modified and in any form, including, but not limited to, linear or circular, and single or double stranded. Non-limiting examples of RNA molecules include rRNA, tRNA, mRNA, mtRNA, tmRNA, RNAi, siRNA, shRNA, and stRNA. In some embodiments, siRNA molecules useful in the practice of the invention include, for example, those described in U.S. Patent Application No's. 10/357,529 published as U.S. 2004/0014956, 10/357,826 published as U.S. 2004/0054155, 11/049,636 published as U.S. 2006/0009409, 11/776,313 published as U.S. 2009/0023216, and 12/062,380 filed Apr. 3, 2008; and as described in PCT published applications PCT/US03/03223 published as WO 2003/064626, and PCT/US03/03208 published as WO 03/064625, which U.S. and PCT applications are incorporated by reference herein. Further siRNA molecules useful in the practice of the invention include, for example, those described in PCT patent application PCT/US2008/076675 published as WO 2009/039173 on Mar. 26, 2009; which application is incorporated by reference herein.

The terms "peptide", "polypeptide", or "protein," as used herein refer to a string of at least three amino acids linked together by peptide bonds. The terms "protein" and "peptide" may be used interchangeably, though it is generally understood that a "polypeptide" or "protein" is larger than a peptide. "Peptide" may refer to an individual peptide or a collection of peptides.

The terms "polynucleotide" or "oligonucleotide," as used herein, refer to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

The term "lipid" refers to hydrophobic or amphiphilic organic compounds inclusive of fats, oils and triglyderides.

II. EMBODIMENTS OF THE INVENTION

Amine-Containing Transfection Compounds

The present invention describes various amine-containing compounds useful as transfection reagents and methods of synthesizing thereof. More particularly, according to some embodiments of the invention, there are provided compounds having the general structure I, or pharmaceutically acceptable salts thereof:

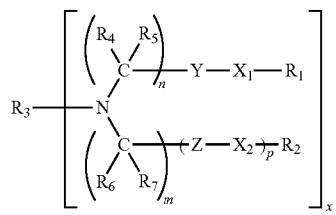

I wherein each of $X_1$ and $X_2$ is a moiety independently selected from the group consisting of O, S, N—A and C—A, wherein A is selected from the group consisting of hydrogen and a $C_1$-$C_{20}$ hydrocarbon chain; each of Y and Z is a moiety independently selected from the group consisting of CH—OH, C=O, C=S, S=O and $SO_2$; each of $R_1$, $R_2$, $R_3$, $R_4$, $R_5$, $R_6$ and $R_7$ is a moiety independently selected from the group consisting of hydrogen, a cyclic or an acyclic, substituted or unsubstituted, branched or unbranched aliphatic group, a cyclic or acyclic, substituted or unsubstituted, branched or unbranched heteroaliphatic group, a substituted or unsubstituted, branched or unbranched acyl group, a substituted or unsubstituted, branched or unbranched aryl group, a substituted or unsubstituted, branched or unbranched heteroaryl group, x is an integer independently having the value between 1 and 10, inclusively, n is an integer independently having the value between 1 and 3, inclusively, m is an integer independently having the value between 0 and 20, inclusively, p is an integer independently having the value of 0 or 1, wherein if m=p=0, then $R_2$ is hydrogen, with the further proviso that if at least one of n or m has the value of 2, then $R_3$ and nitrogen in structure I form a moiety selected from the group consisting of:

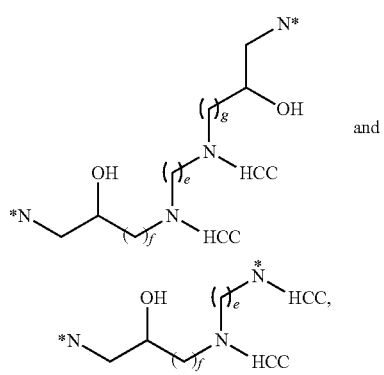

wherein each of g, e and f is an integer independently having the value between 1 and 6, inclusively, "HCC" symbolizes a hydrocarbon chain, and each * indicates the nitrogen atom in structure I.

In some embodiments, $R_3$ is a polyamine. In other embodiments, $R_3$ is a ketal. In some embodiments, each of $R_1$ and $R_2$ in the general structure I is independently any of substituted or unsubstituted, branched or unbranched alkyl or alkenyl groups having between 3 and about 20 carbon atoms, such as between 8 and about 18 carbon atoms, and between 0 and 4 double bonds, such as between 0 and 2 double bonds.

In some embodiments, if each of n and m independently has the value of 1 or 3, $R_3$ is any of the following moieties:

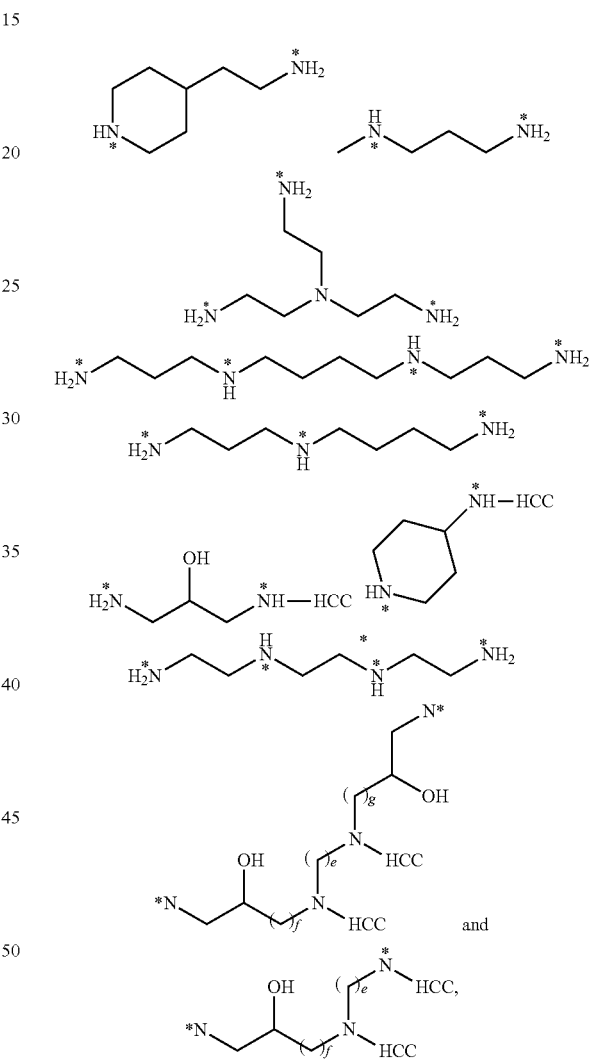

wherein each "HCC" symbolizes a hydrocarbon chain, and each * shows a potential point of attachment of $R_3$ to the nitrogen atom in structure I, where each H on any * position can be replaced to achieve the attachment to the nitrogen atom in structure I.

According to some embodiments, compounds the general structure I may have each of $R_4$, $R_5$, $R_6$ and $R_7$ being hydrogen, each of Y and Z being C=O, each of $R_1$ and $R_2$ being the same and each of $X_1$ and $X_2$ also being the same. Such compounds are represented by the general structure II (which is a sub-genus of the compound the general structure I):

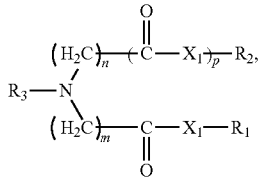

wherein when n=p=0, $R_2$ is H.

In compounds of the general structure II, at least one $X_1$ is NH, or at least one $X_1$ is O. Furthermore, in some embodiments, in compounds of the general structure II, each $R_1$ is independently any of substituted or unsubstituted, branched or unbranched alkyl or alkenyl groups having between 3 and about 20 carbon atoms, e.g., between 8 and about 18 carbon atoms, and between 0 and 4 double bonds, e.g., between 0 and 2 double bonds. Furthermore, in some embodiments, if each of n and m independently has the value of 1 or 3, $R_3$ is any of the following moieties:

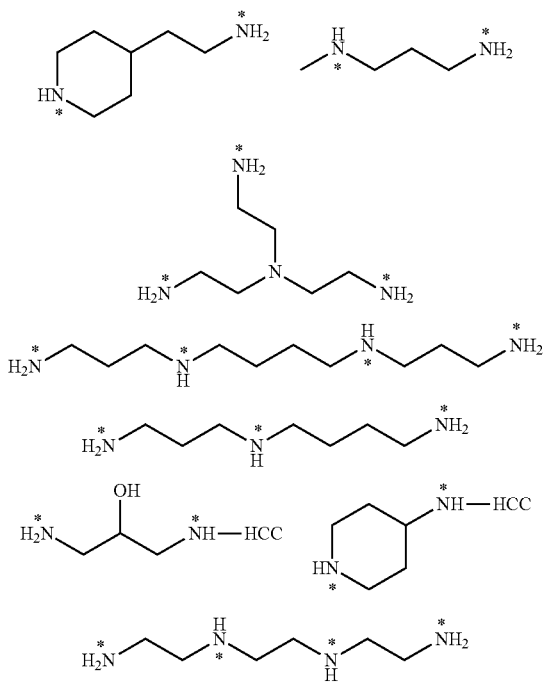

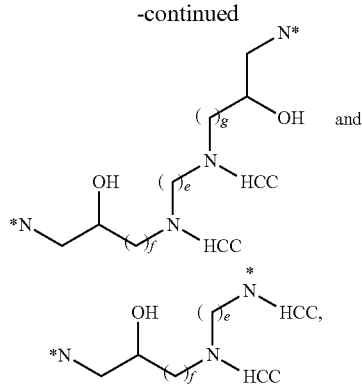

wherein each "HCC" symbolizes a hydrocarbon chain, and each * shows a potential point of attachment of $R_3$ to the nitrogen atom in structure II, where each H on any * position can be replaced to achieve the attachment to the nitrogen atom in structure II.

In some embodiments, if at least one of n or m in the general structure II has the value of 2, then $R_3$ is either of the following moieties:

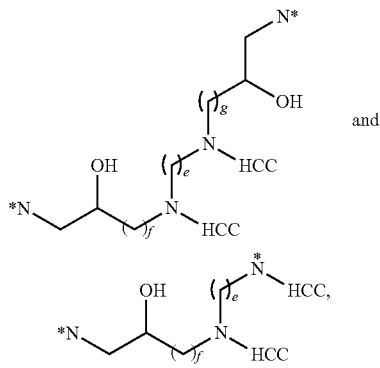

wherein each of g, e and f is an integer independently having the value between 1 and 6, inclusively, each "HCC" symbolizes a hydrocarbon chain, and each * shows a point of attachment of $R_3$ to the nitrogen atom in structure II.

According to embodiments of the invention, there are provided some specific compounds that are species within either the general structure I or the general structure II, or both. Non-limiting examples of such specific compounds are any of the following lipids 1-87, or any isomer of each of compounds 1-87, or any combination of isomers for each of compounds 1-87:

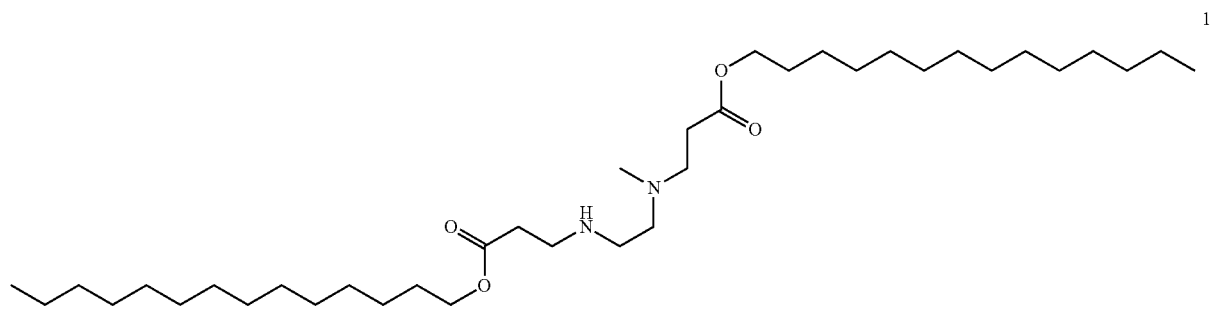

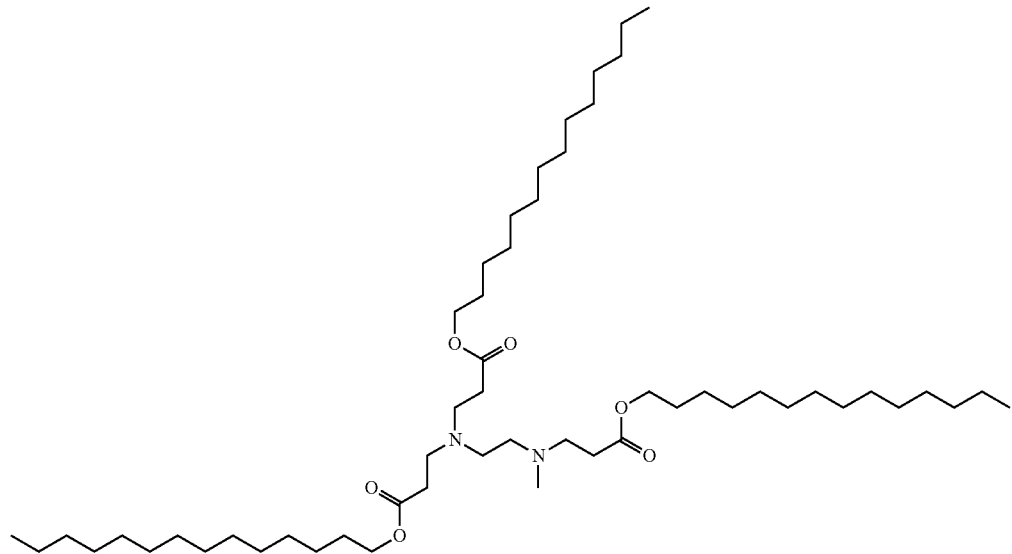
2
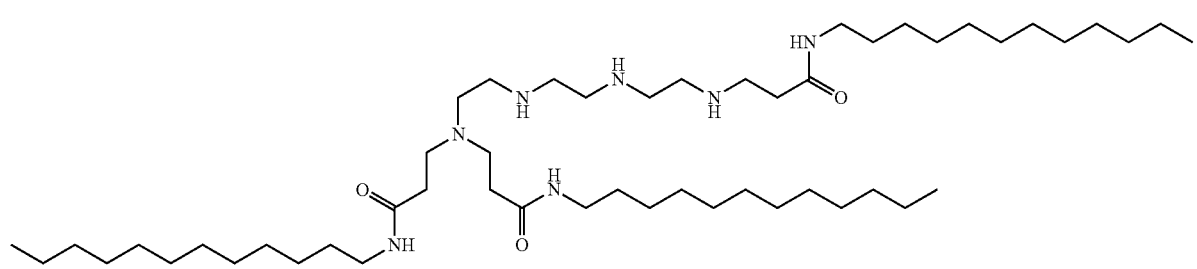
3
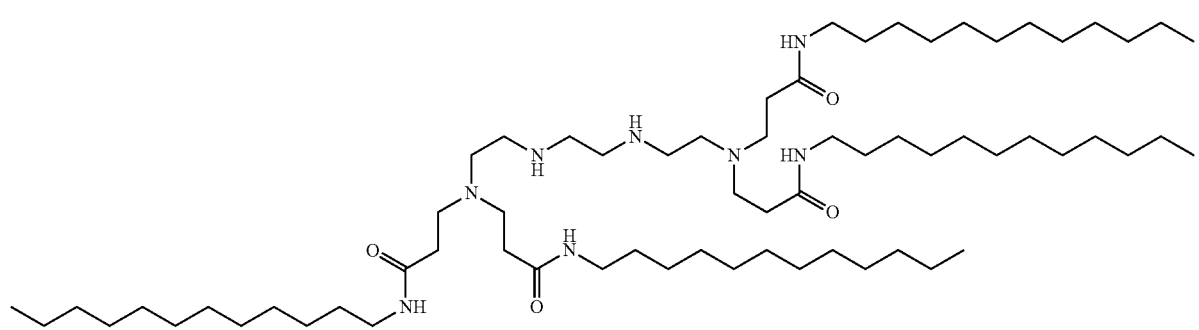
4
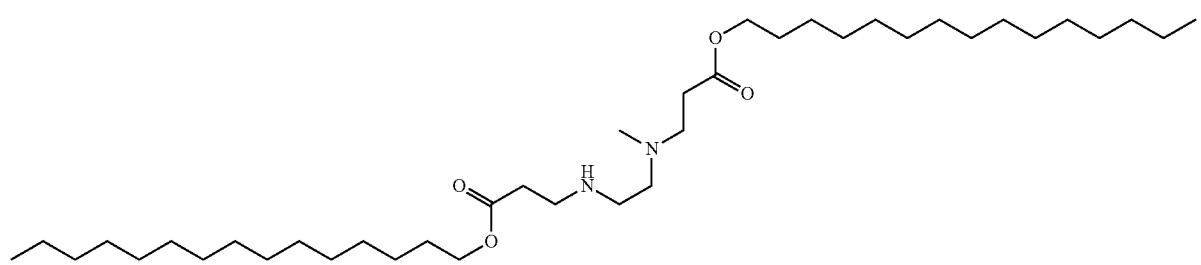
5

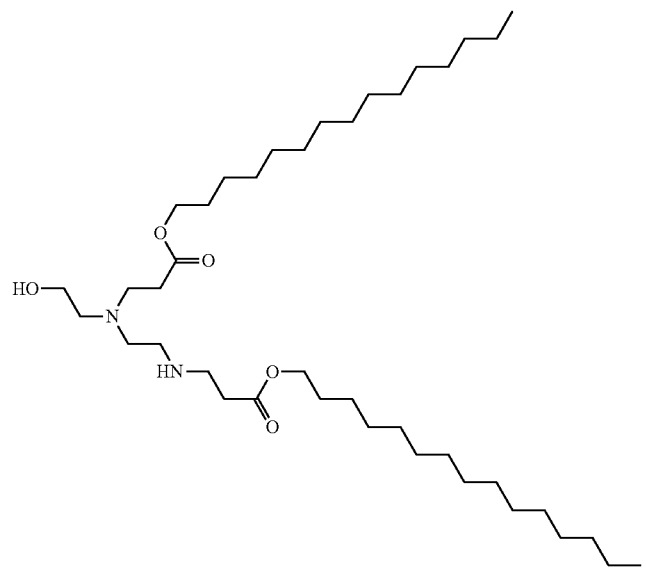
6
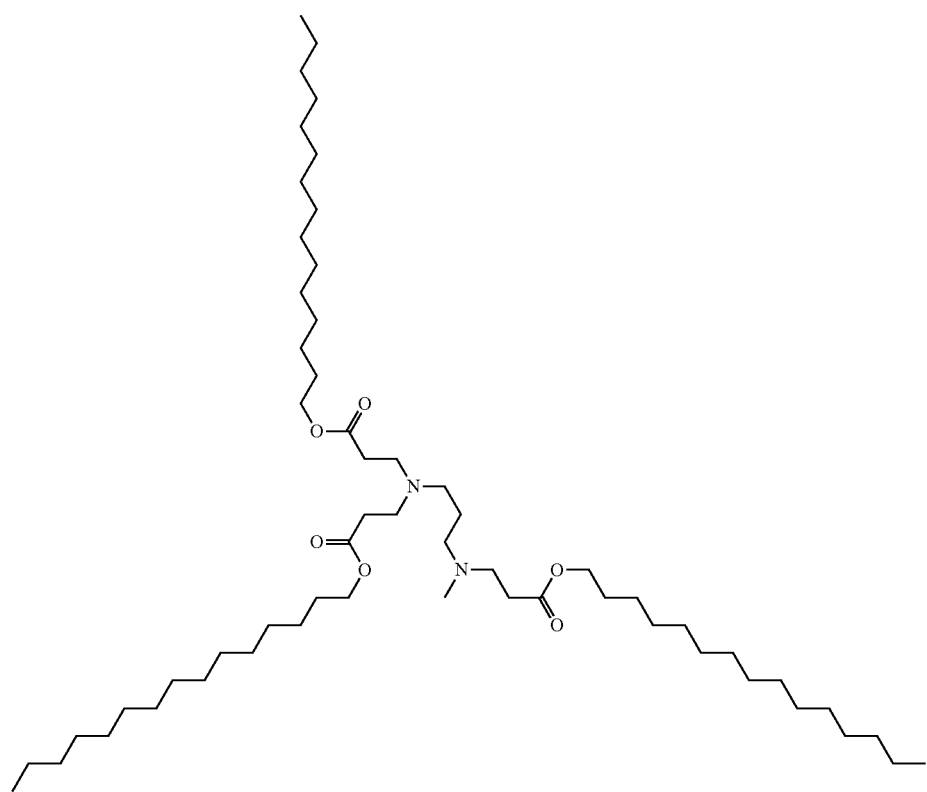
7

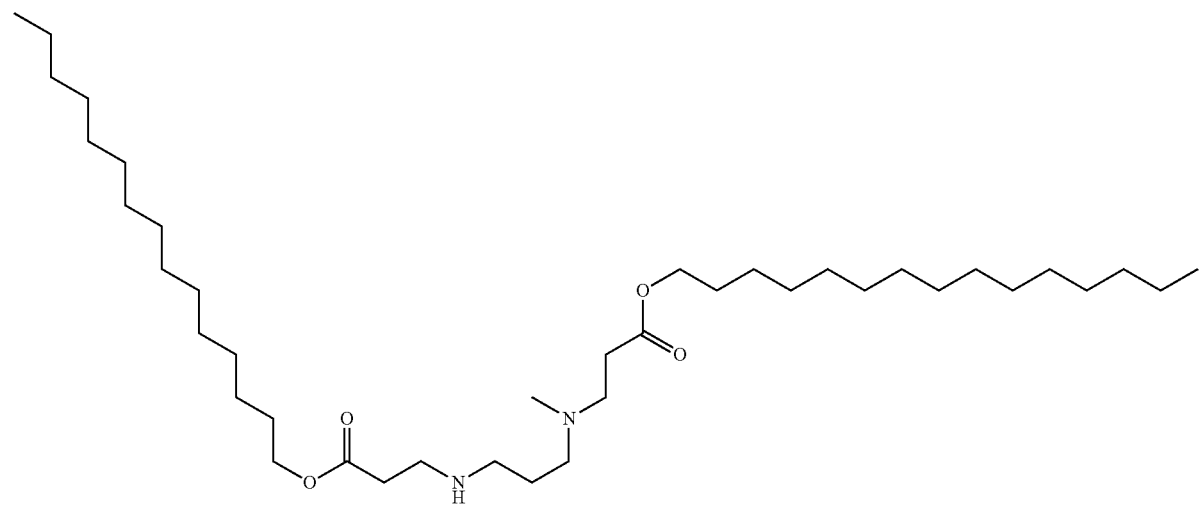
8
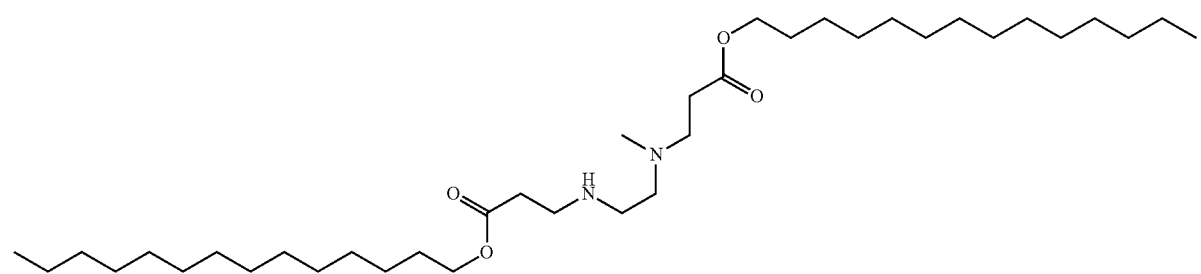
9
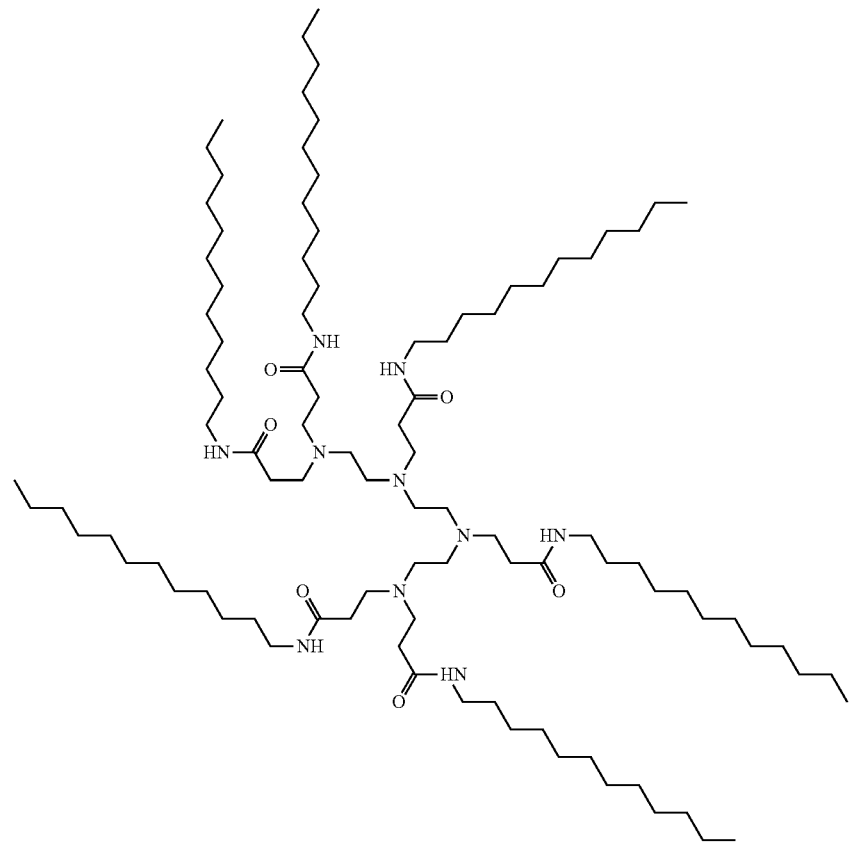
10

-continued
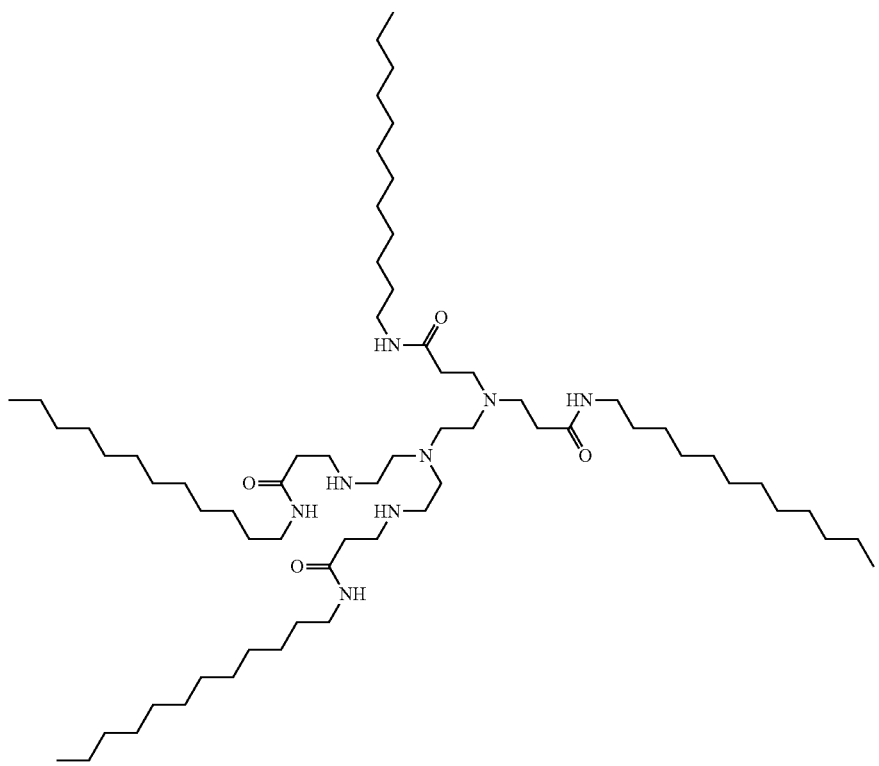
11
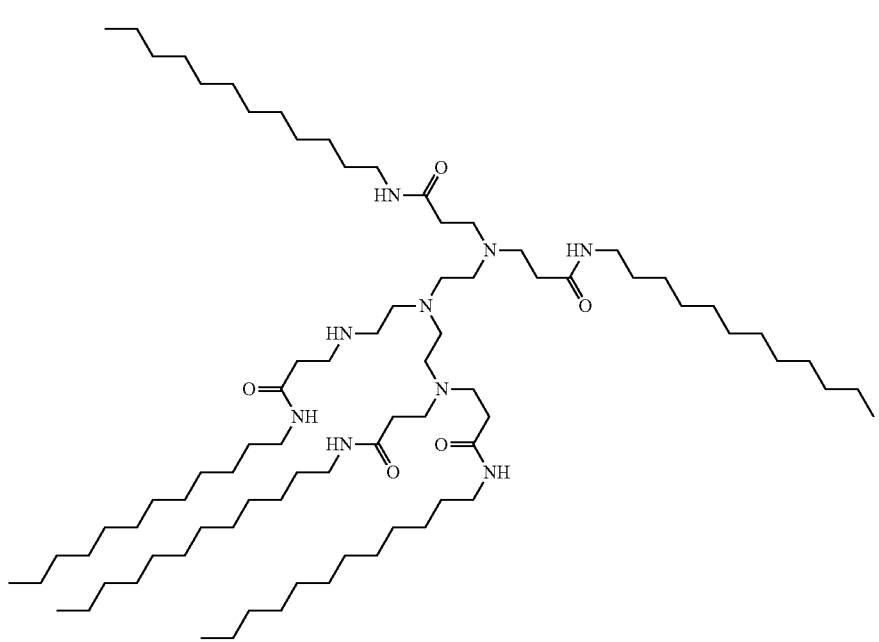
12

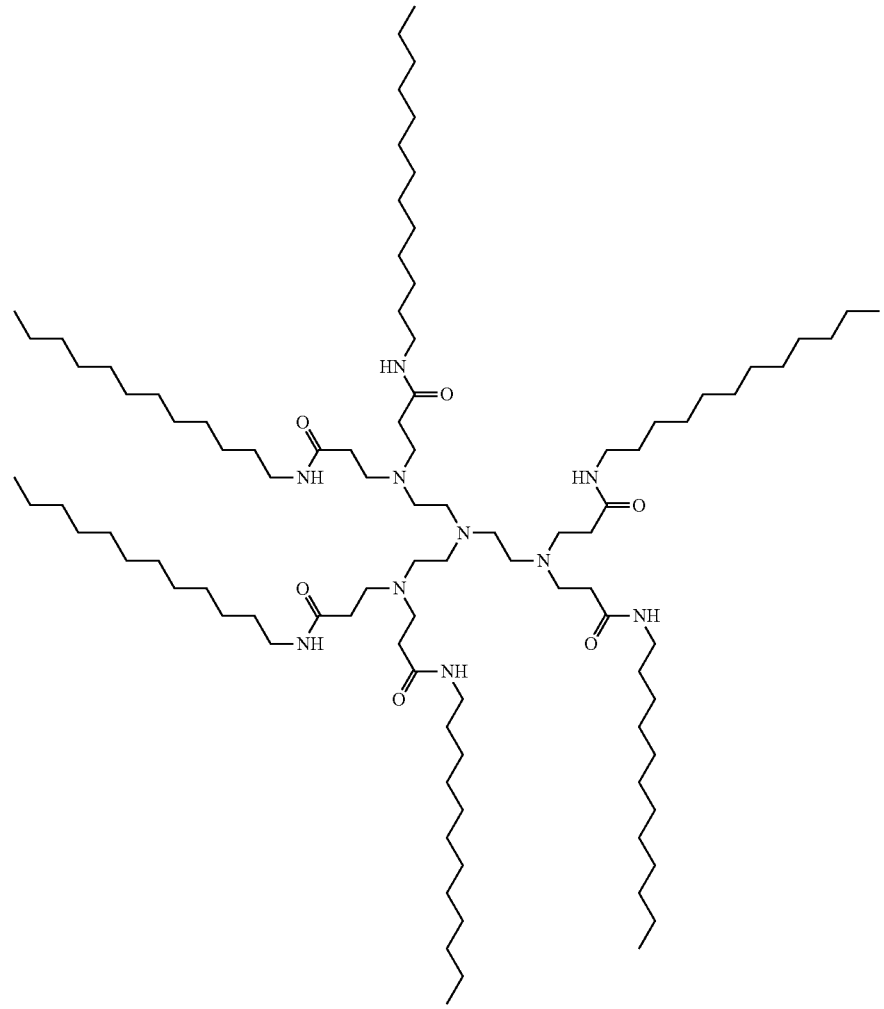
13
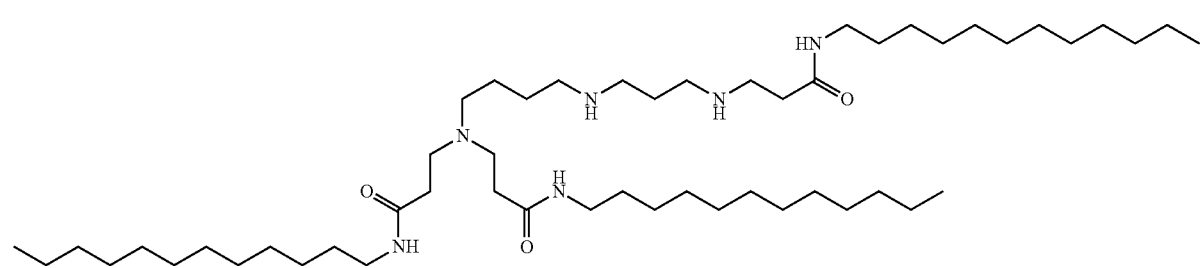
14

-continued
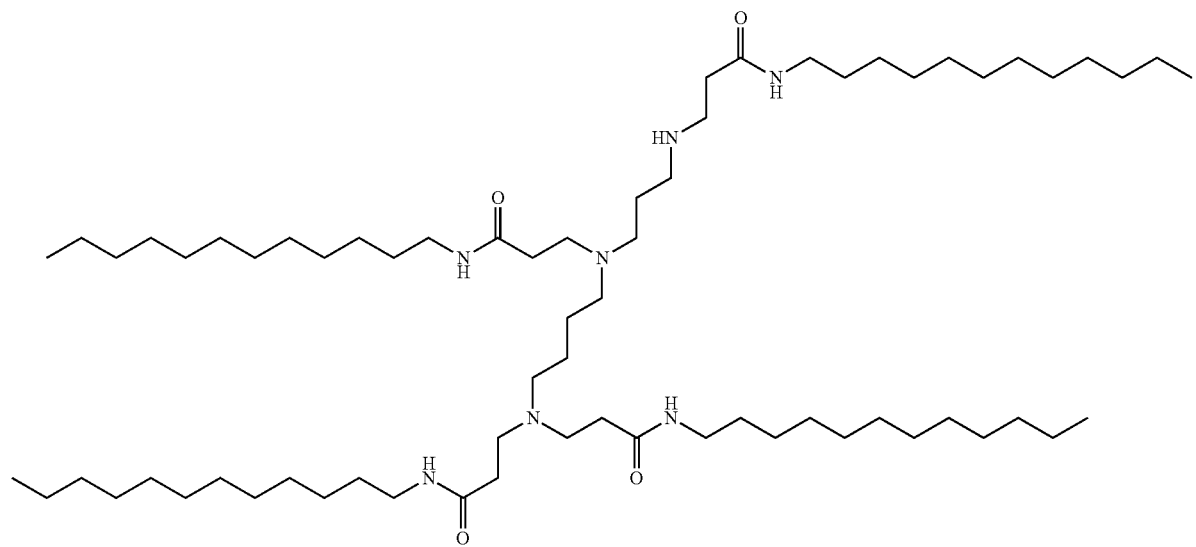
15
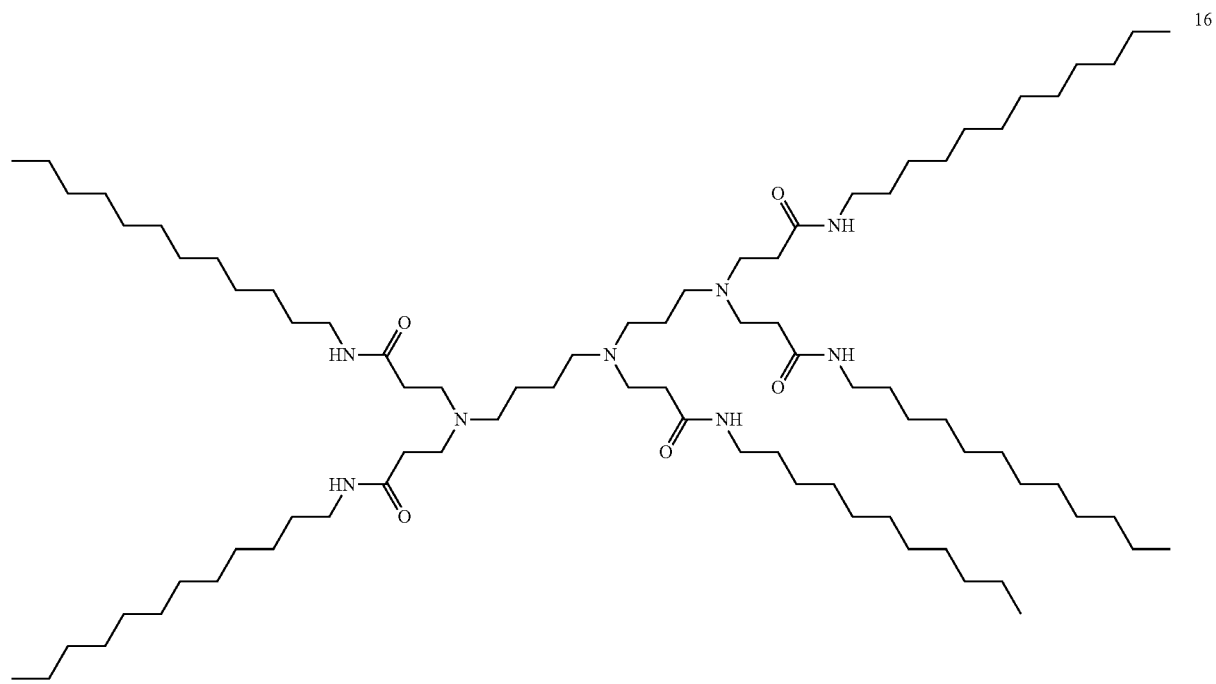
16

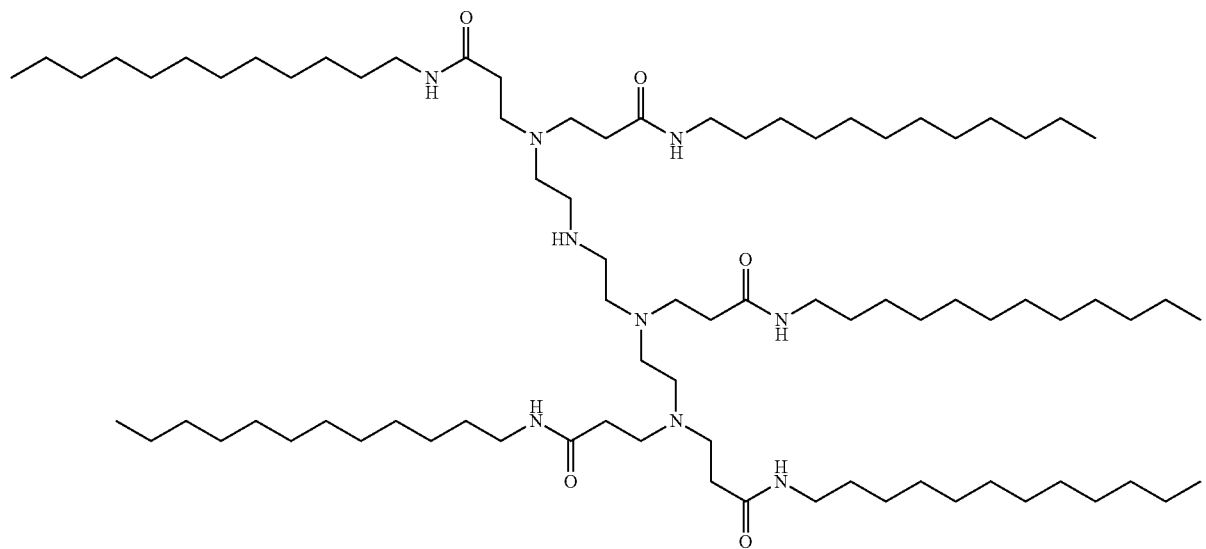
17
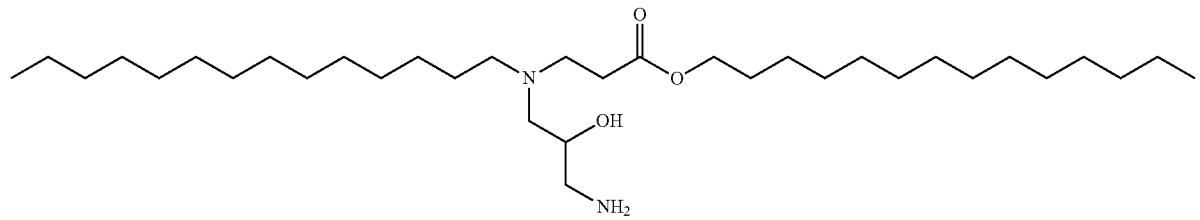
18
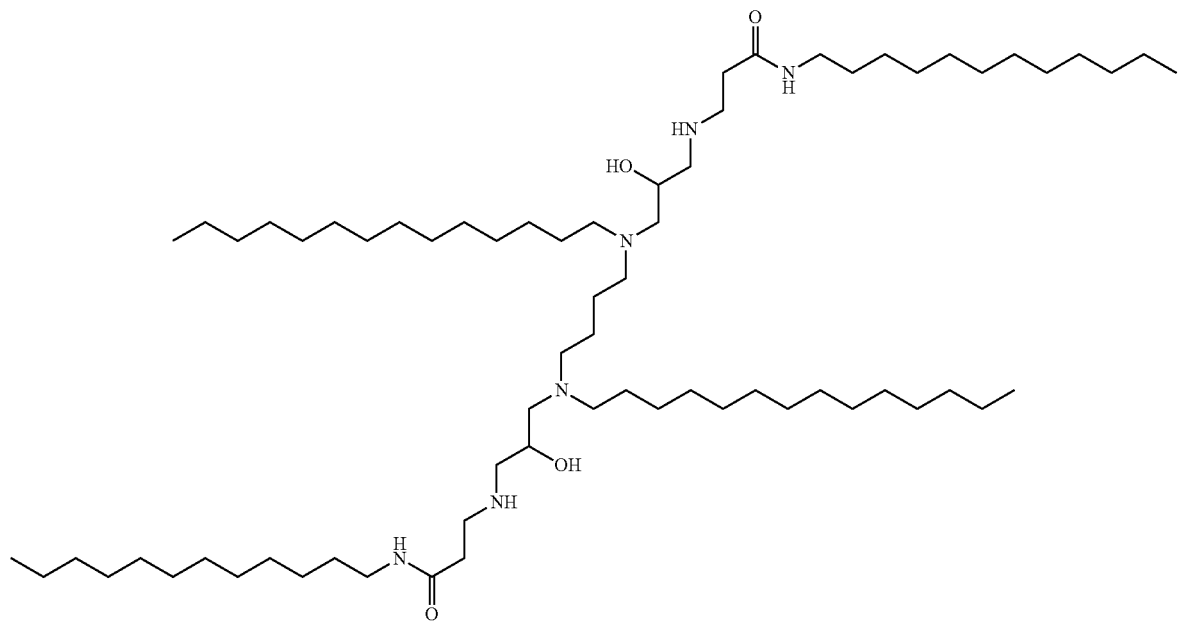
19

-continued
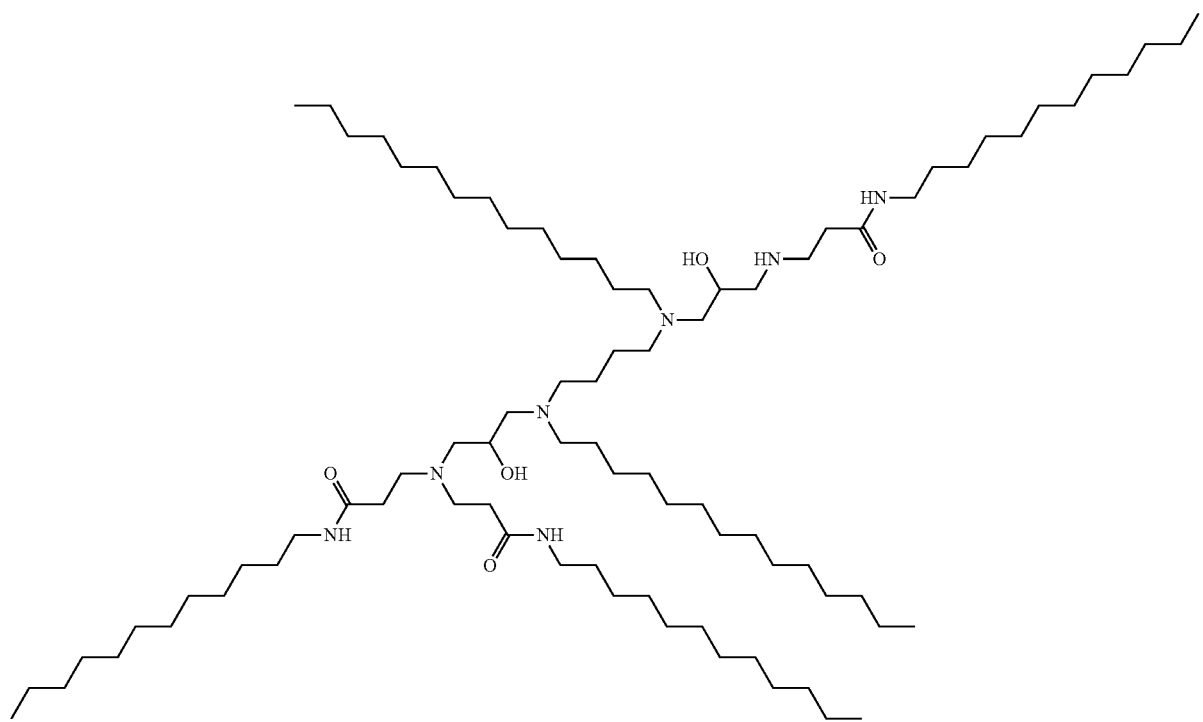
20
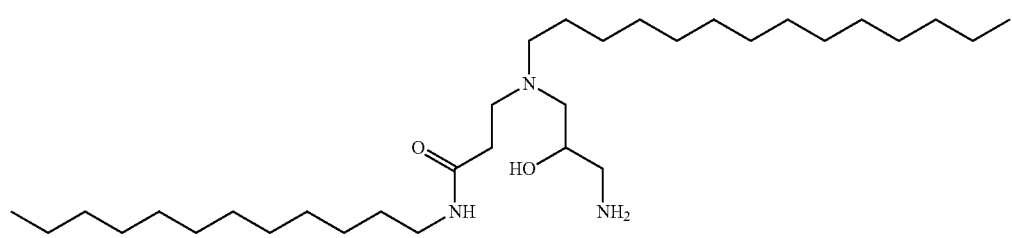
21
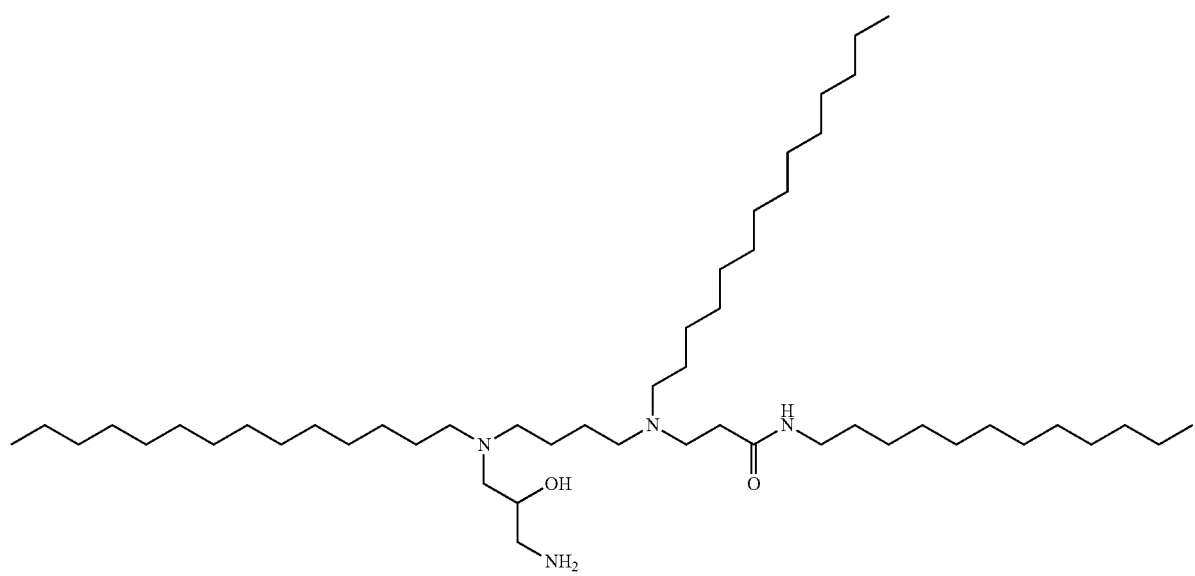
22

-continued
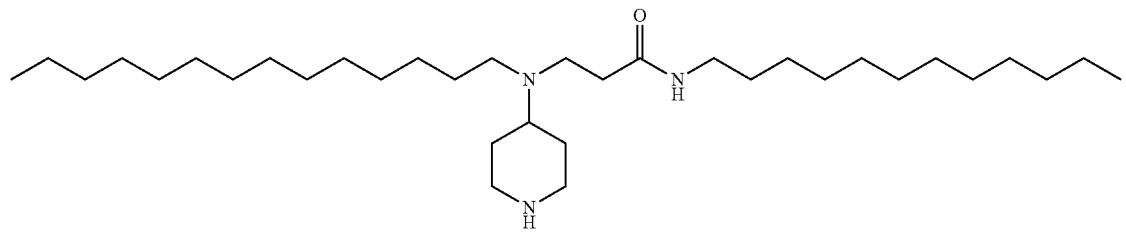
23
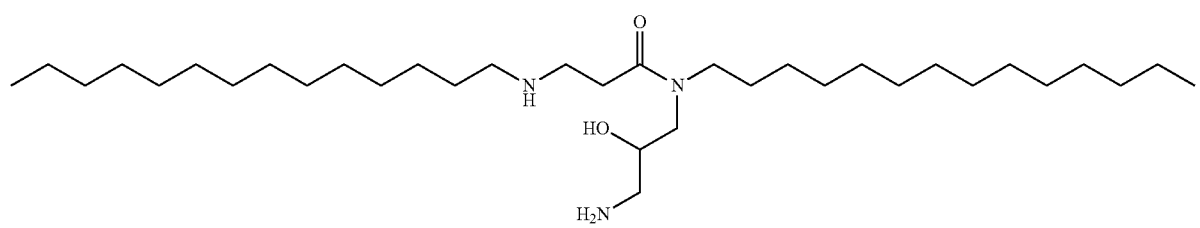
24
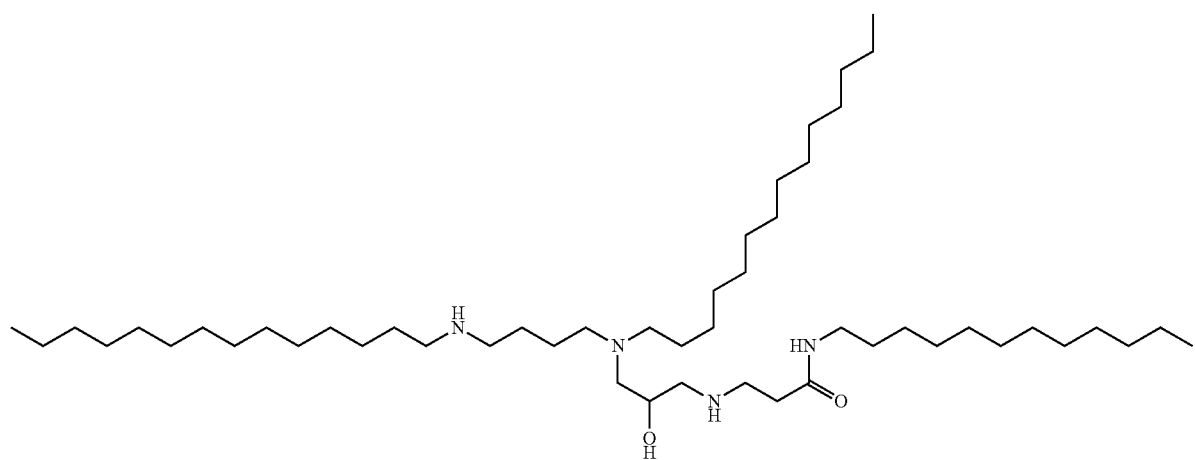
25
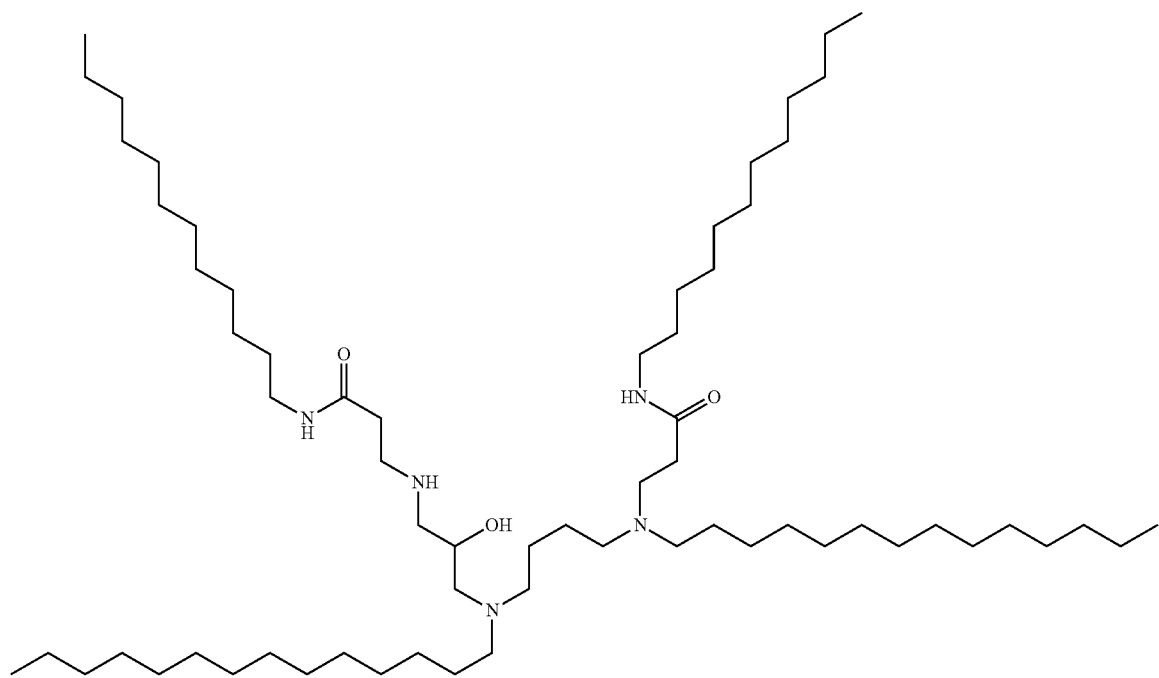
26

27
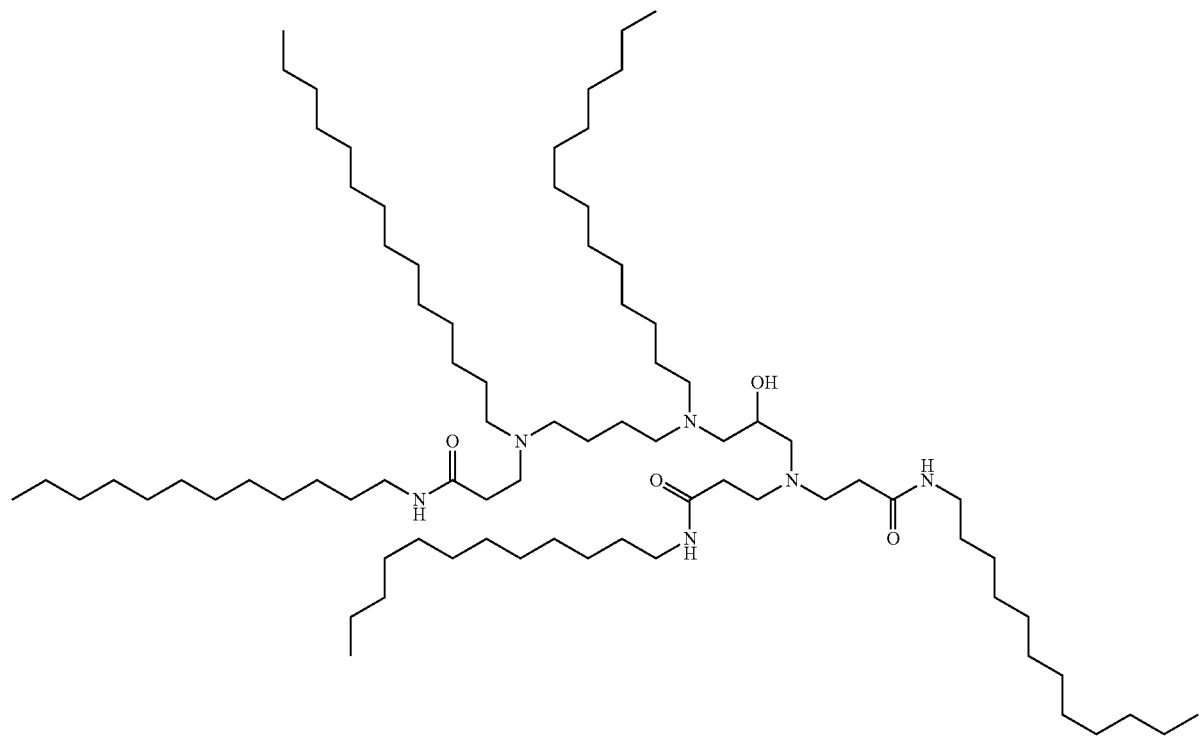
28
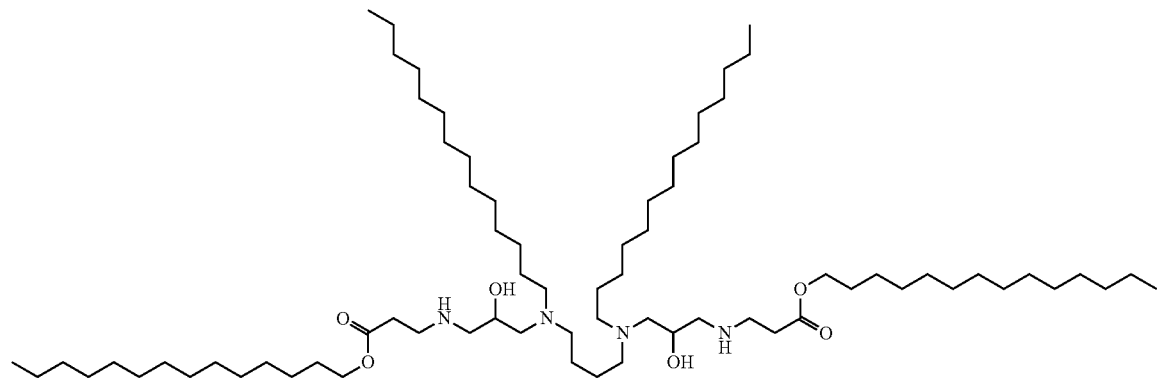
29
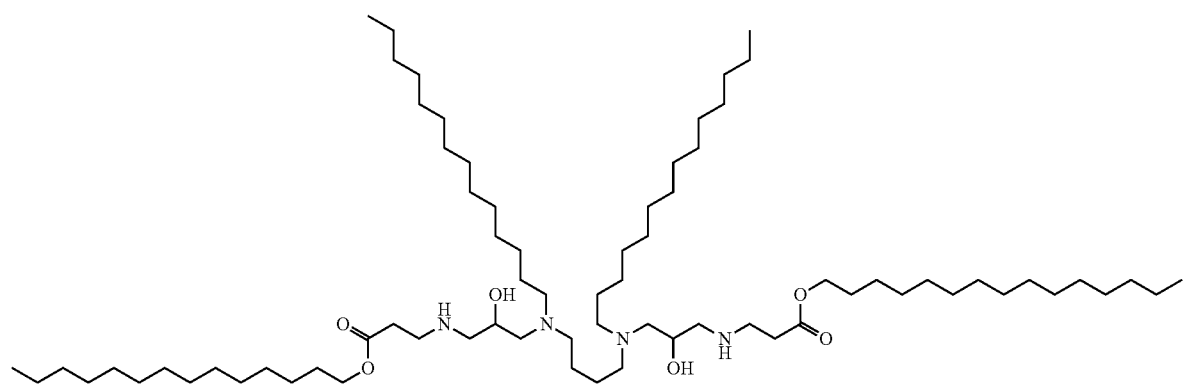

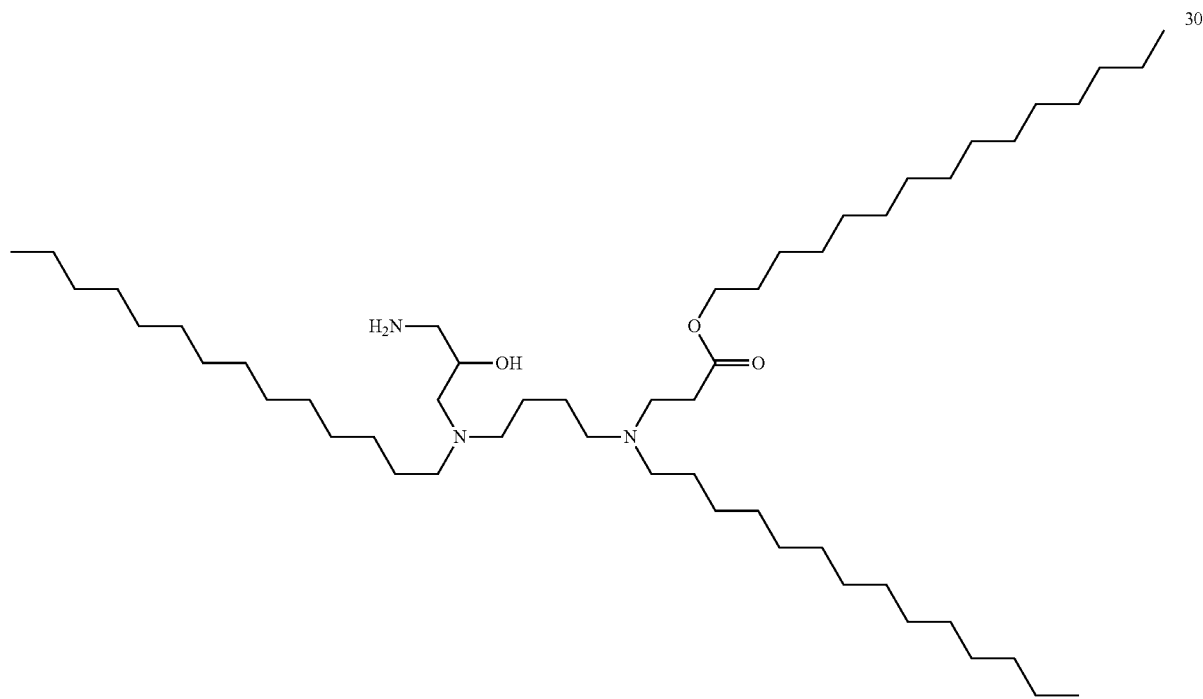
30
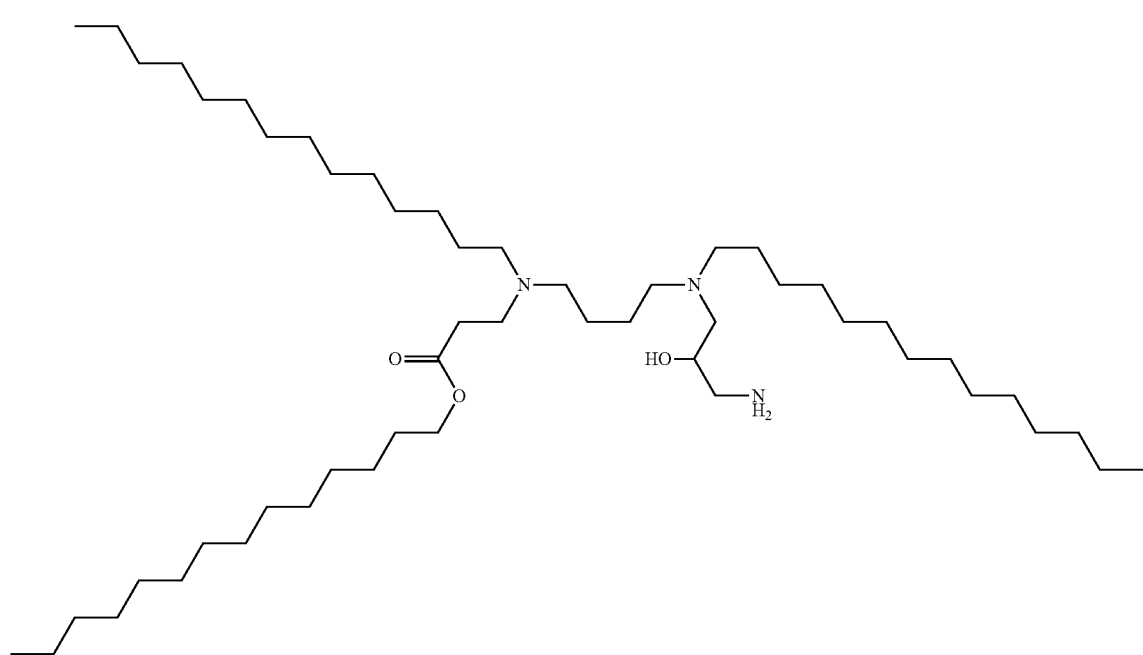
31

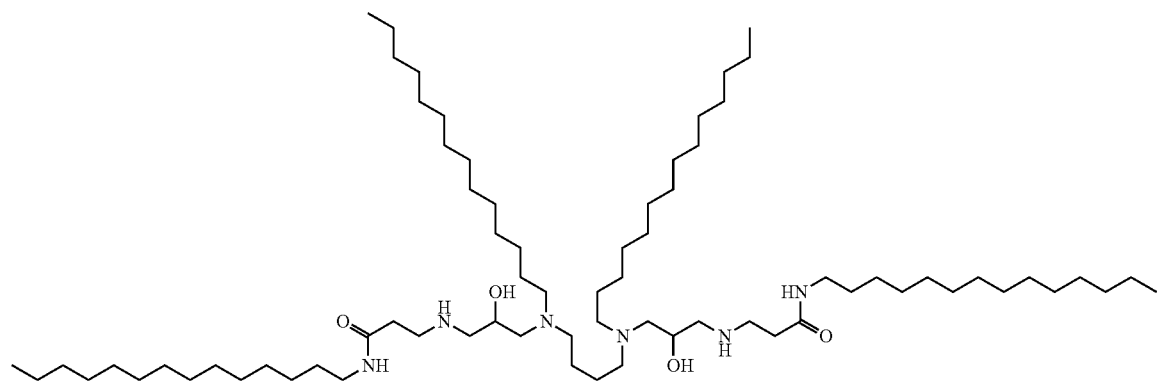
32
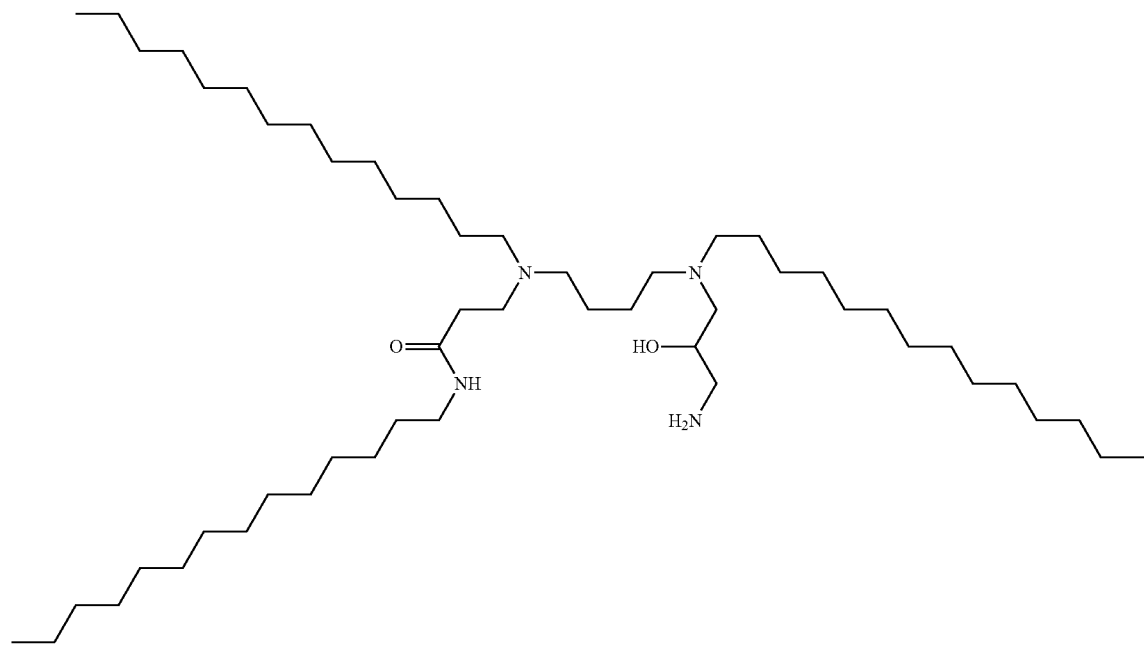
33
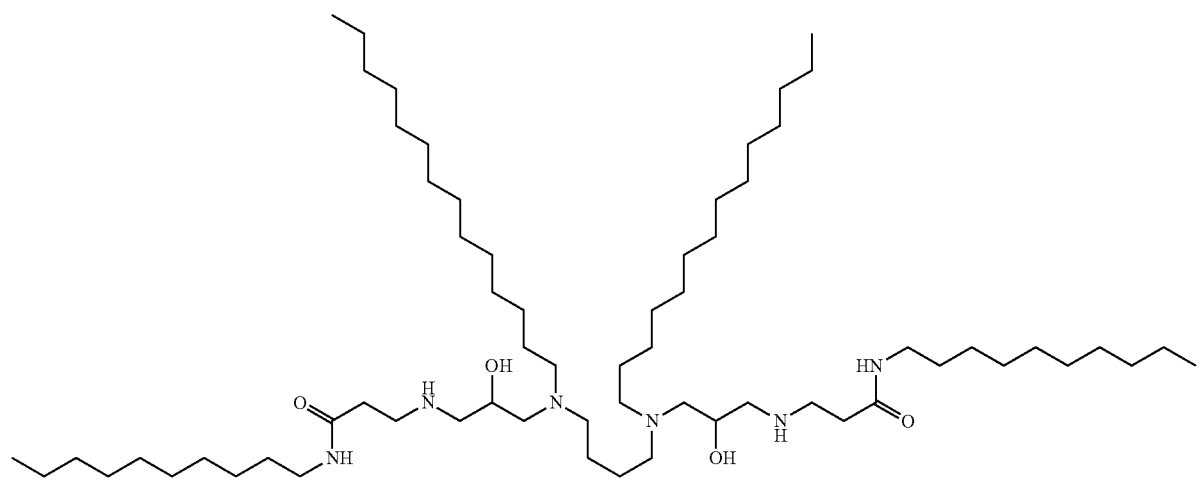
34

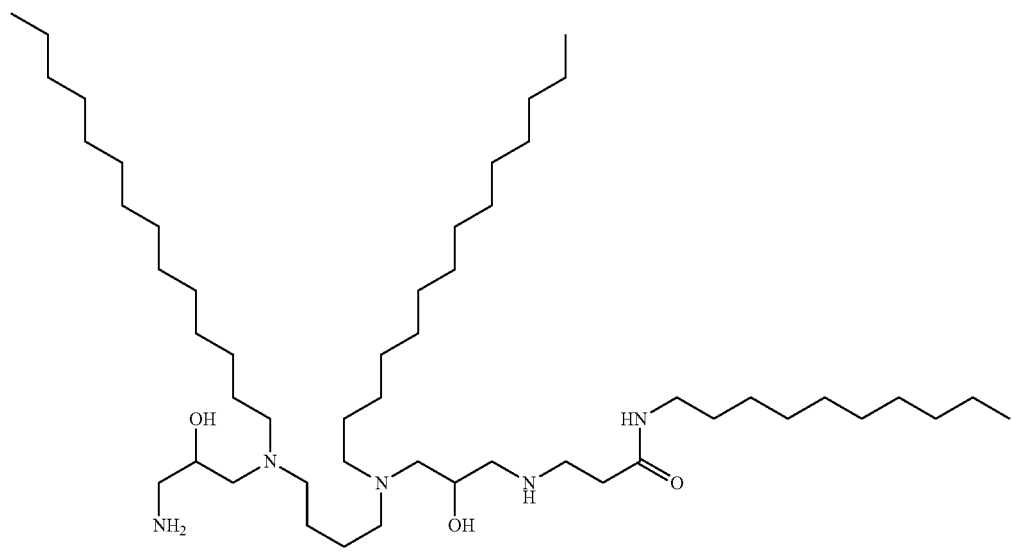
35
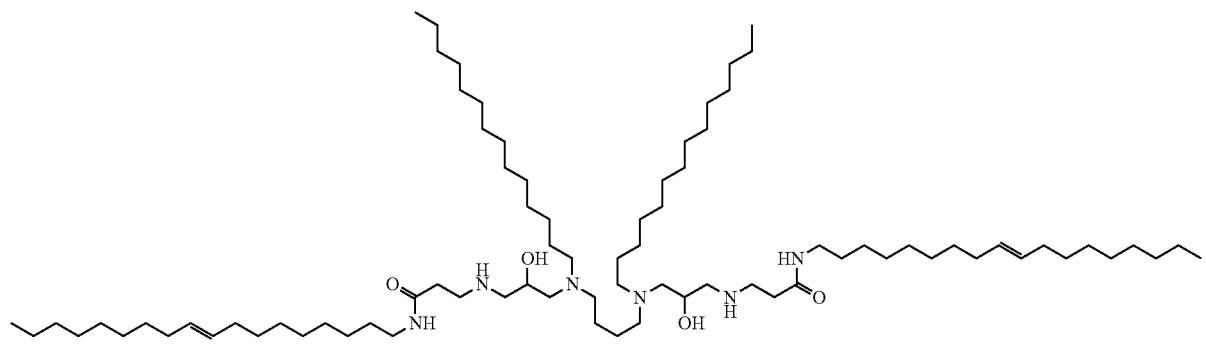
36
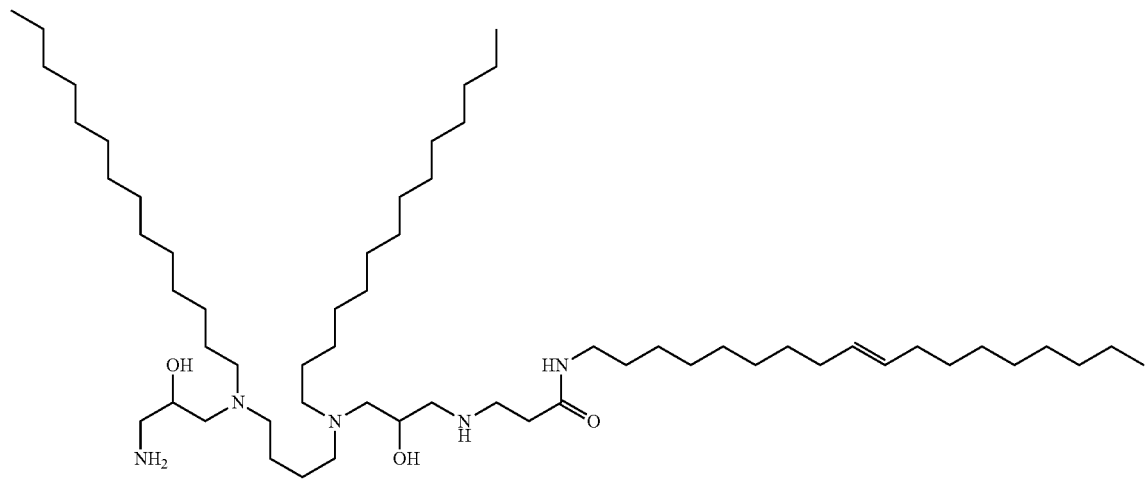
37

38
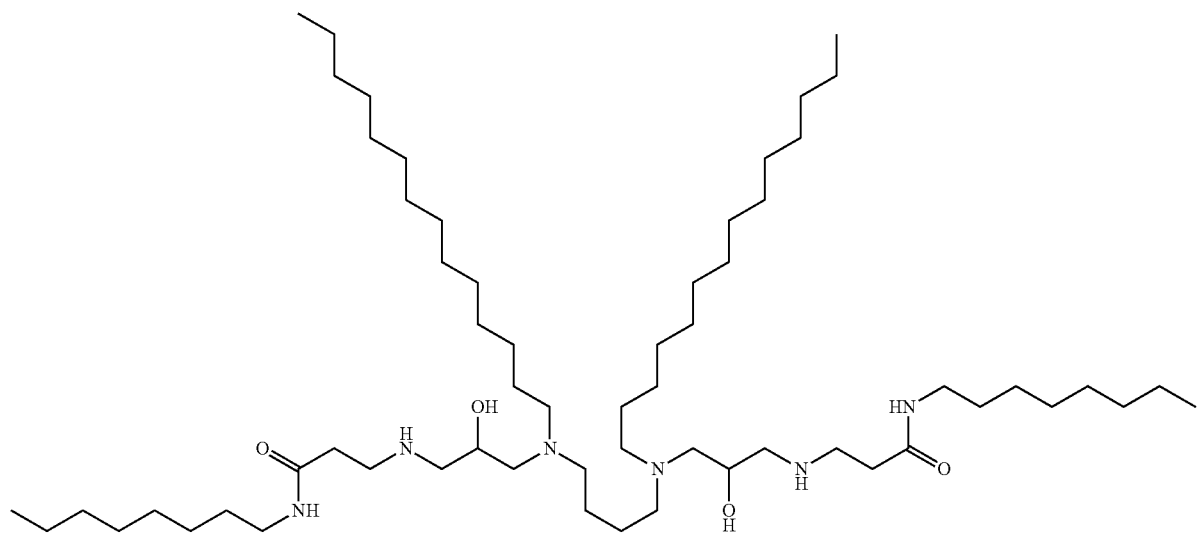
39
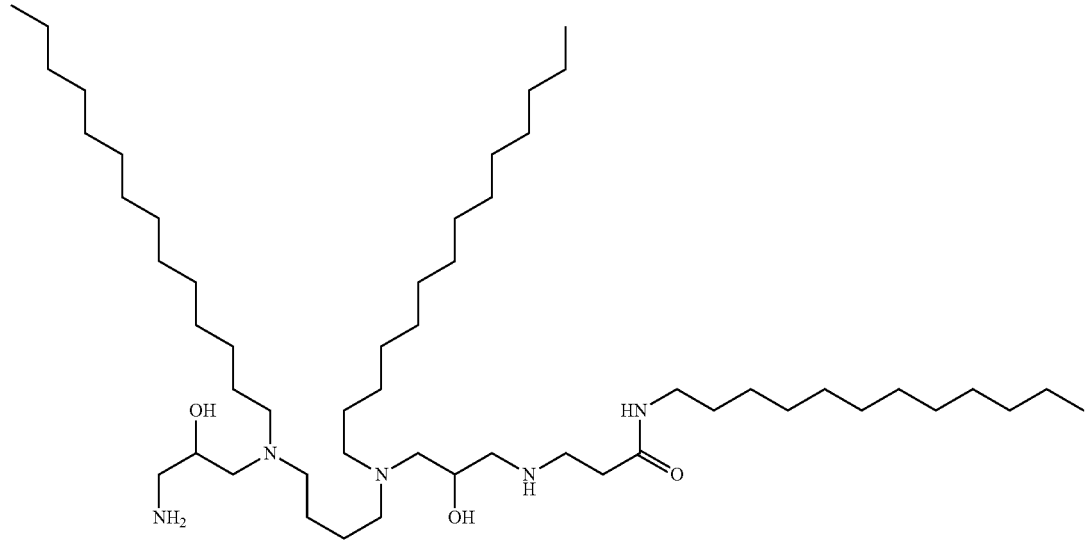
40
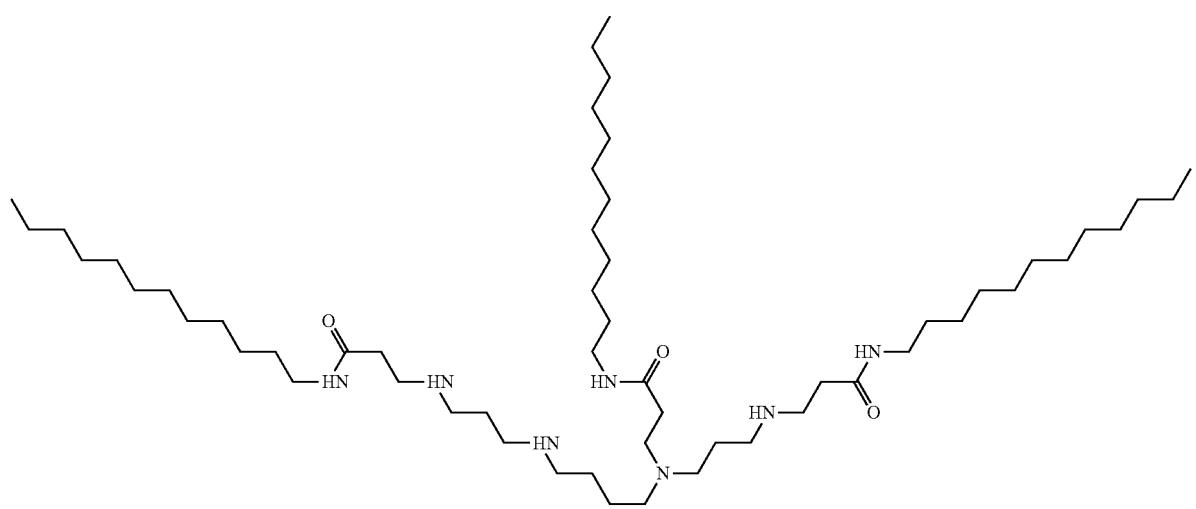

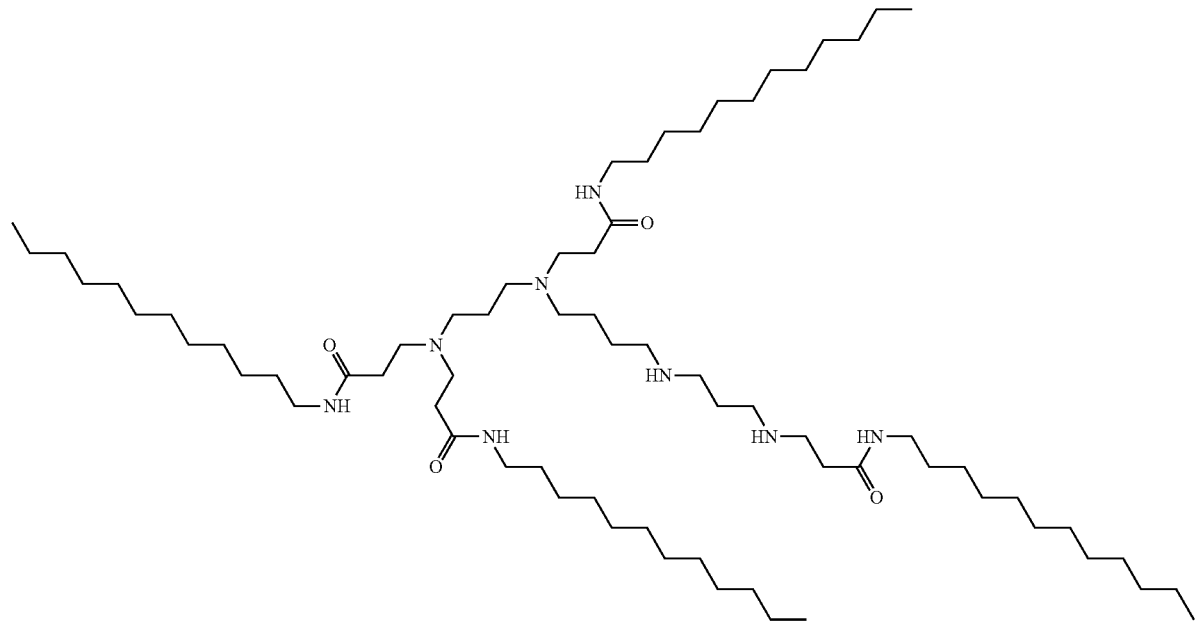
41
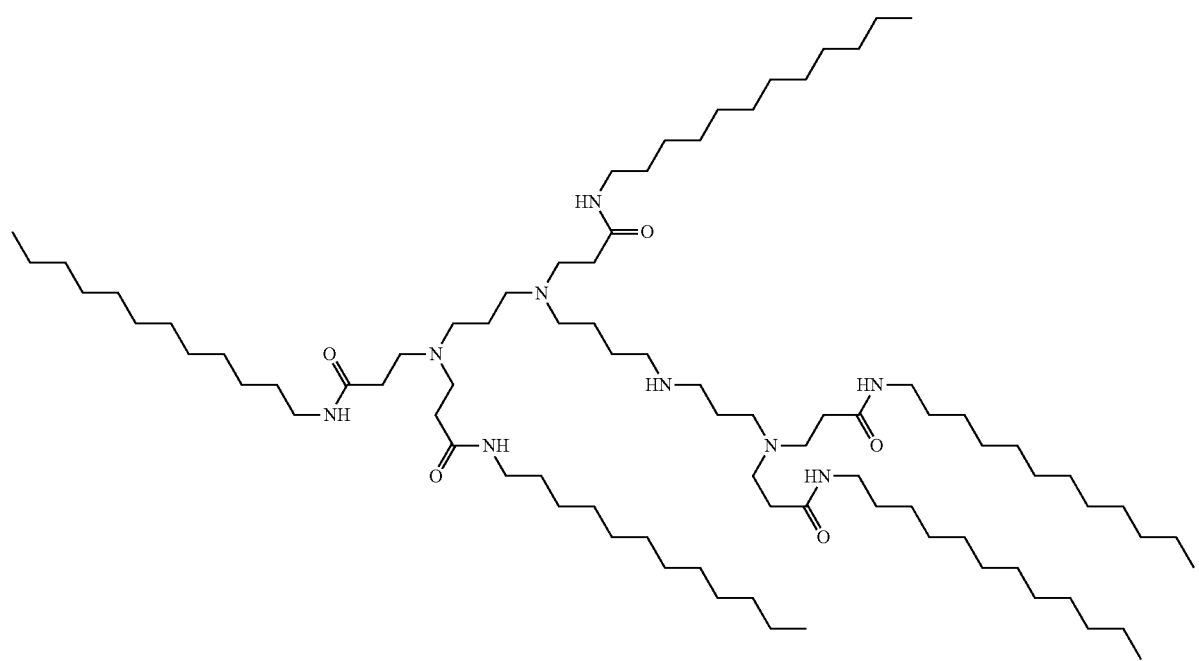
42

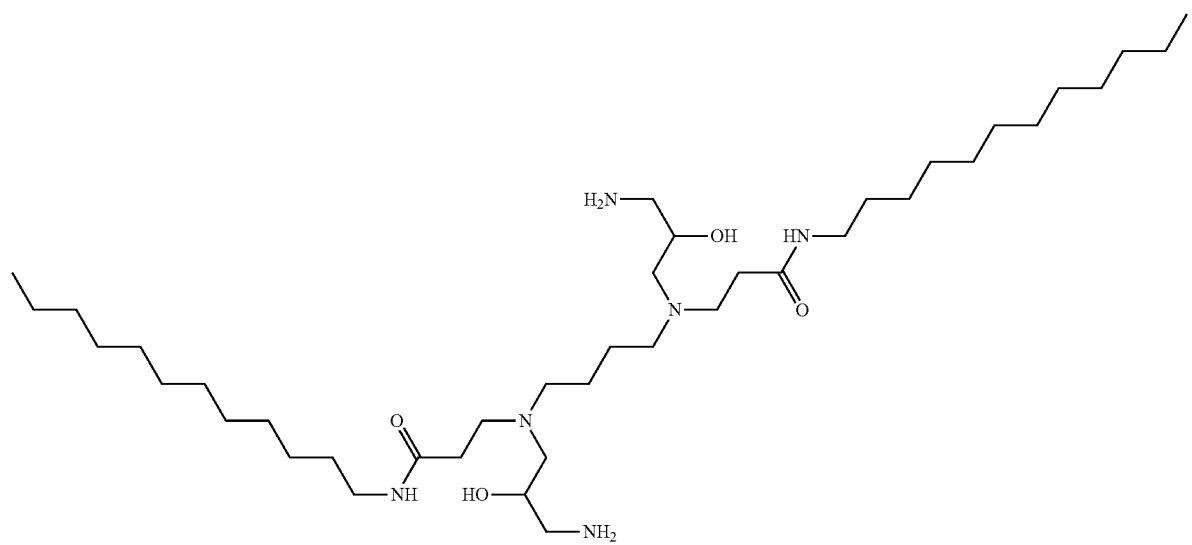
43
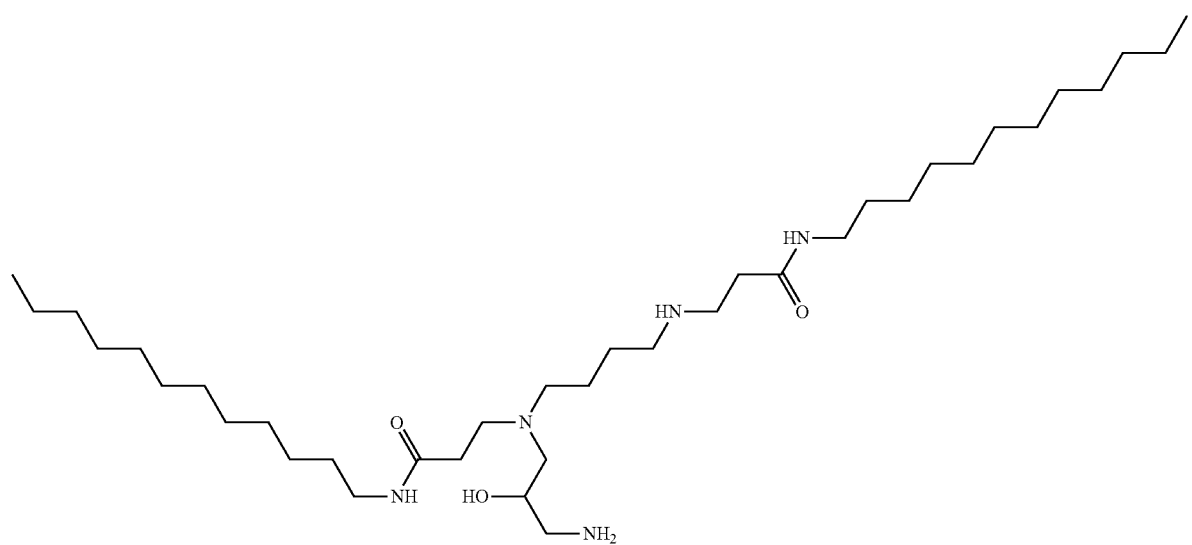
44
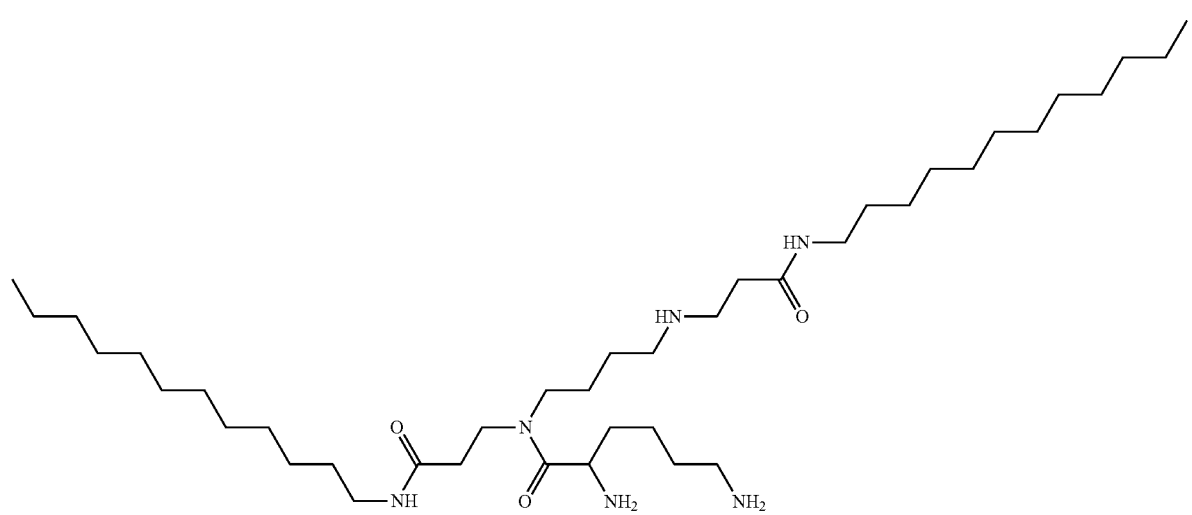
45

-continued
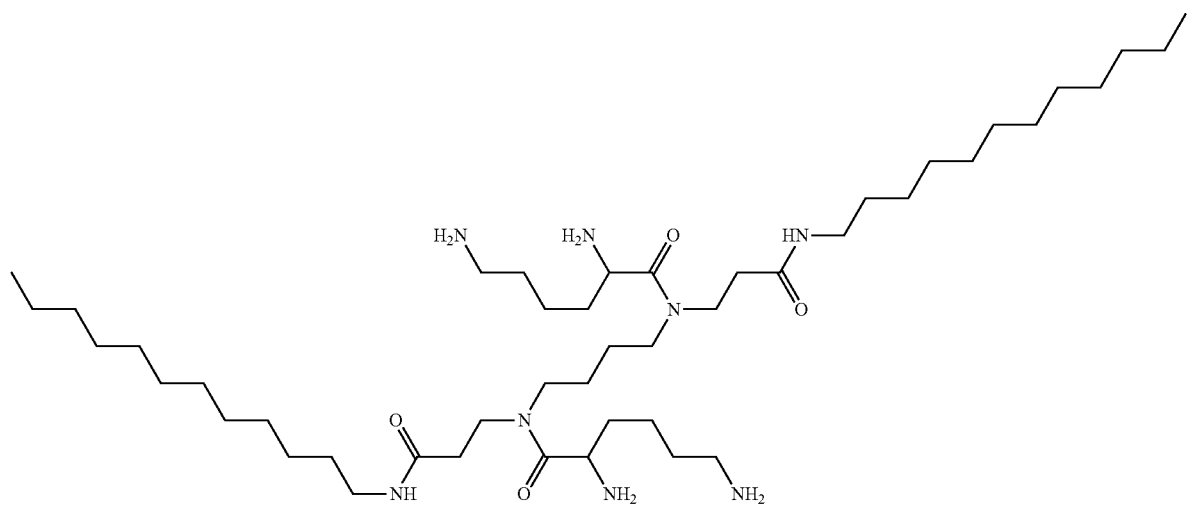
46
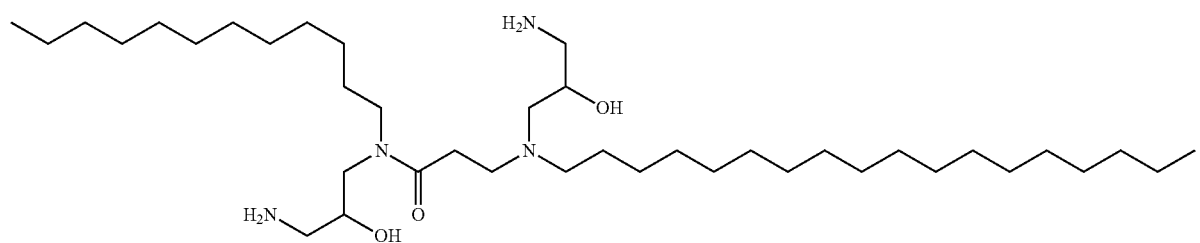
47
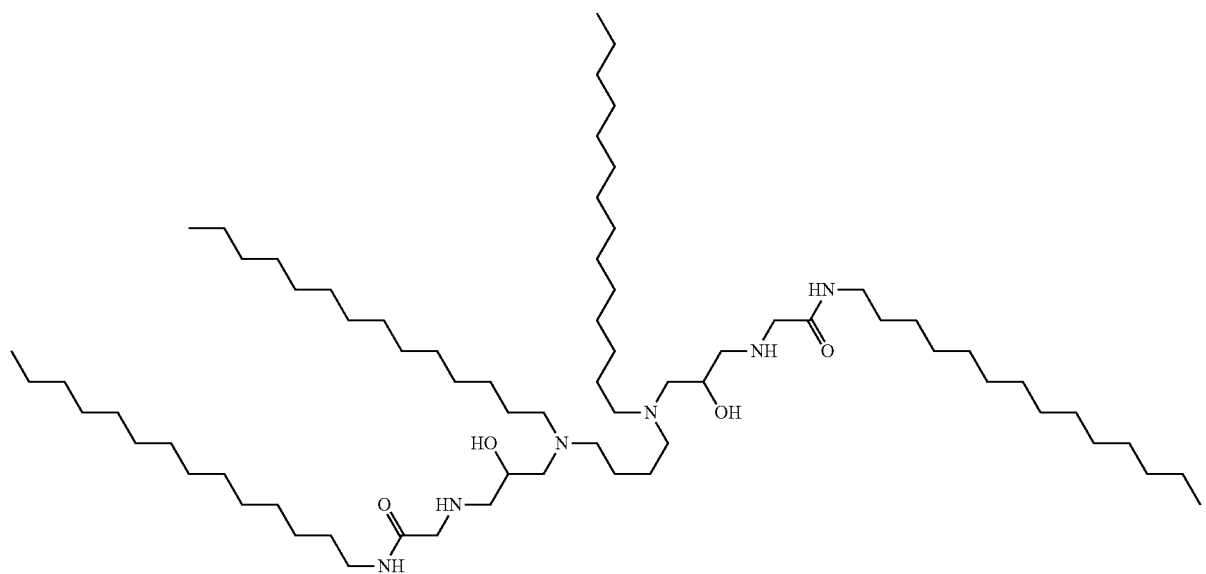
48

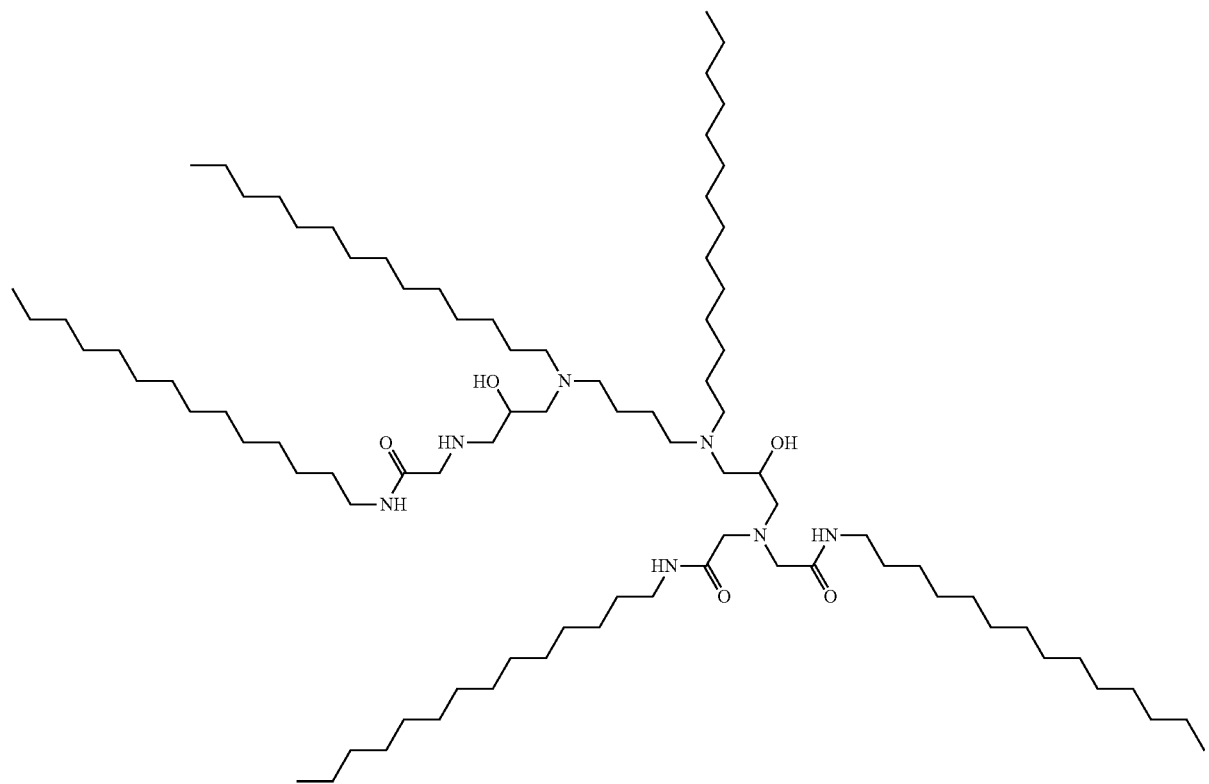
49
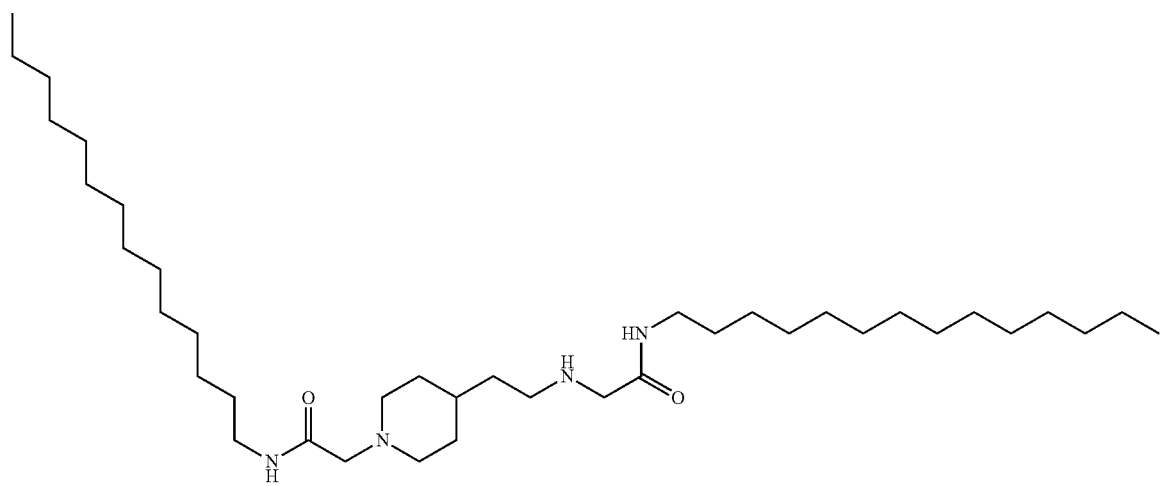
50

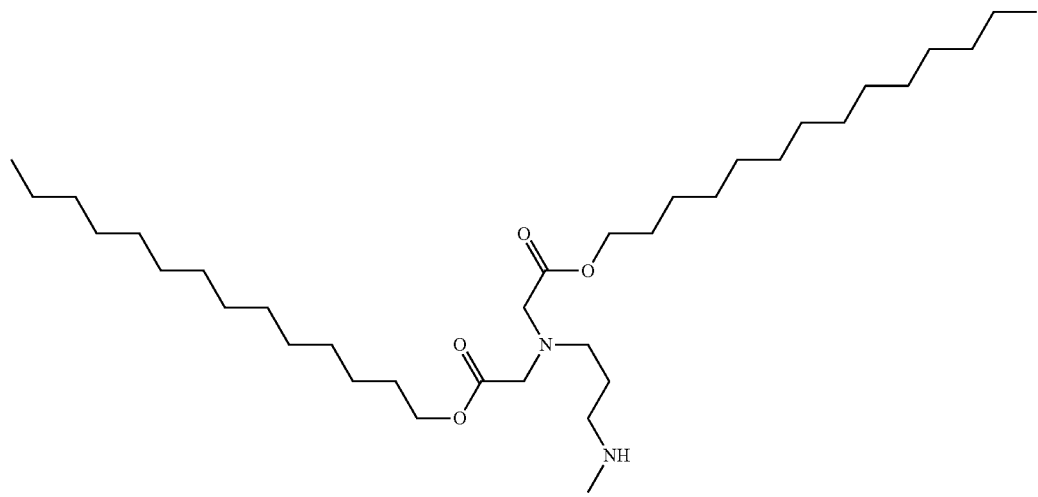
51
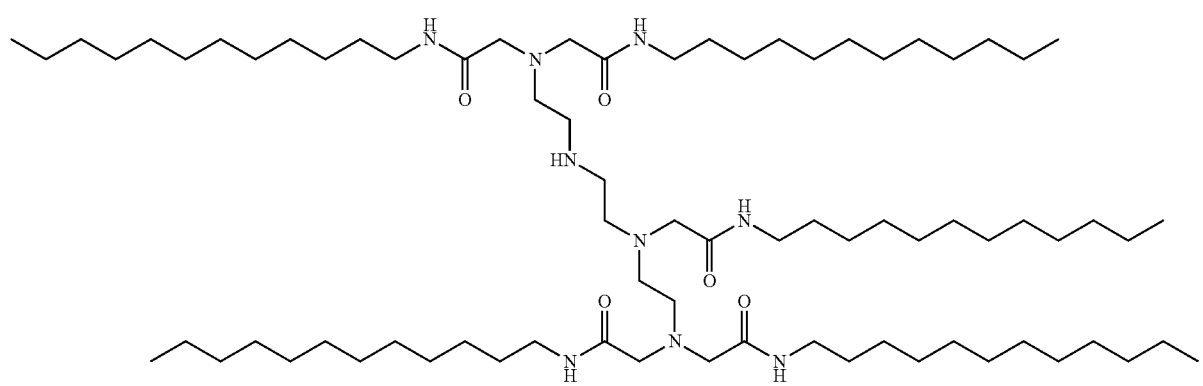
52
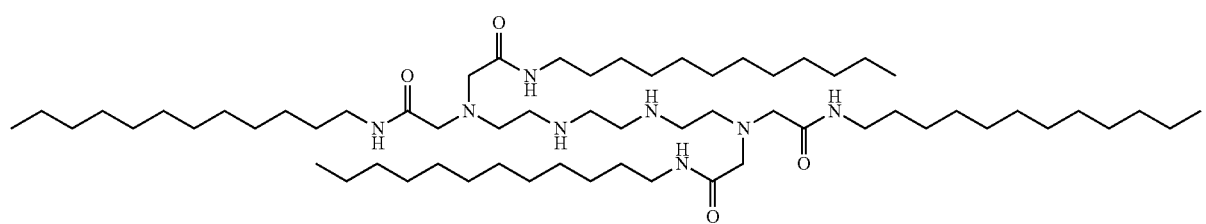
53

54
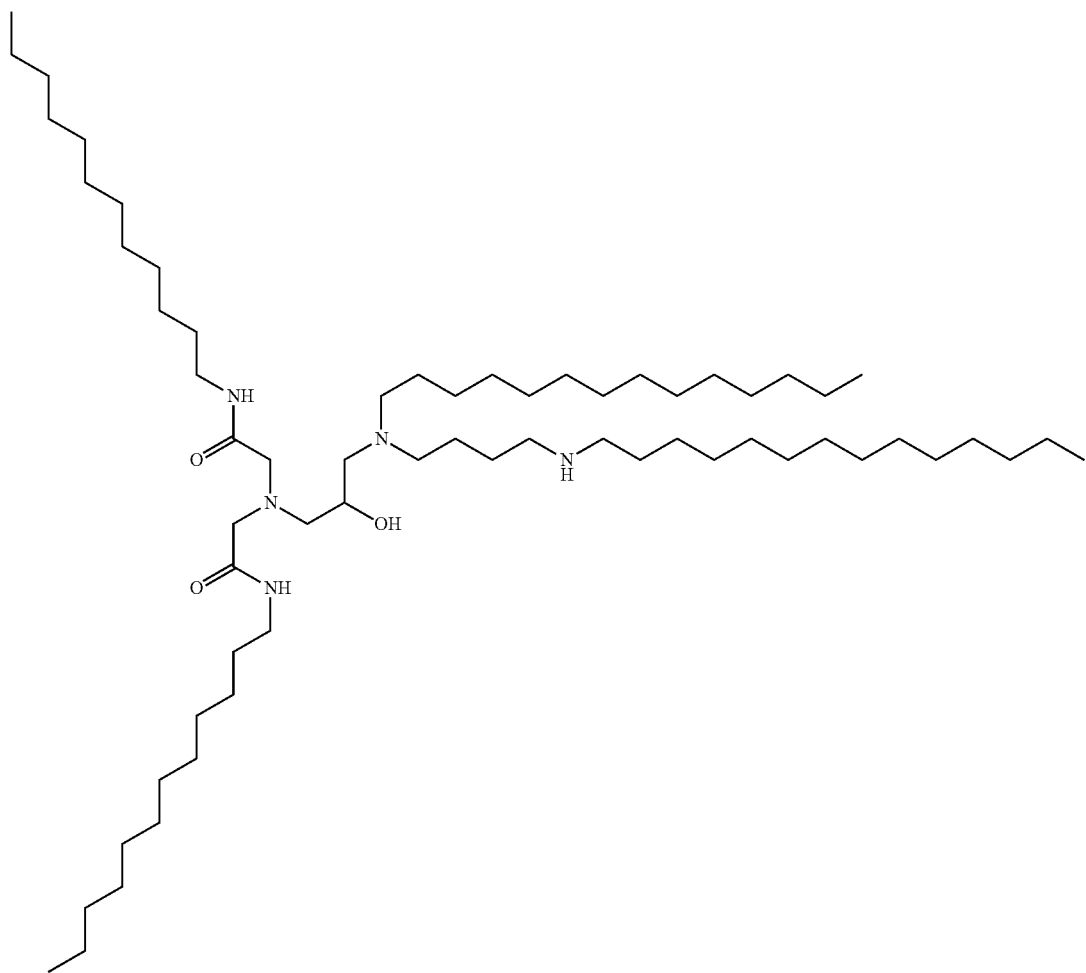
55
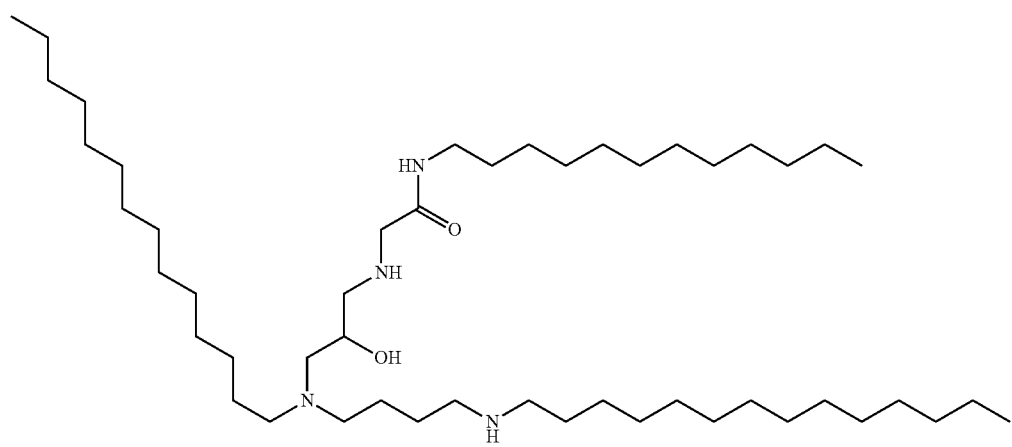

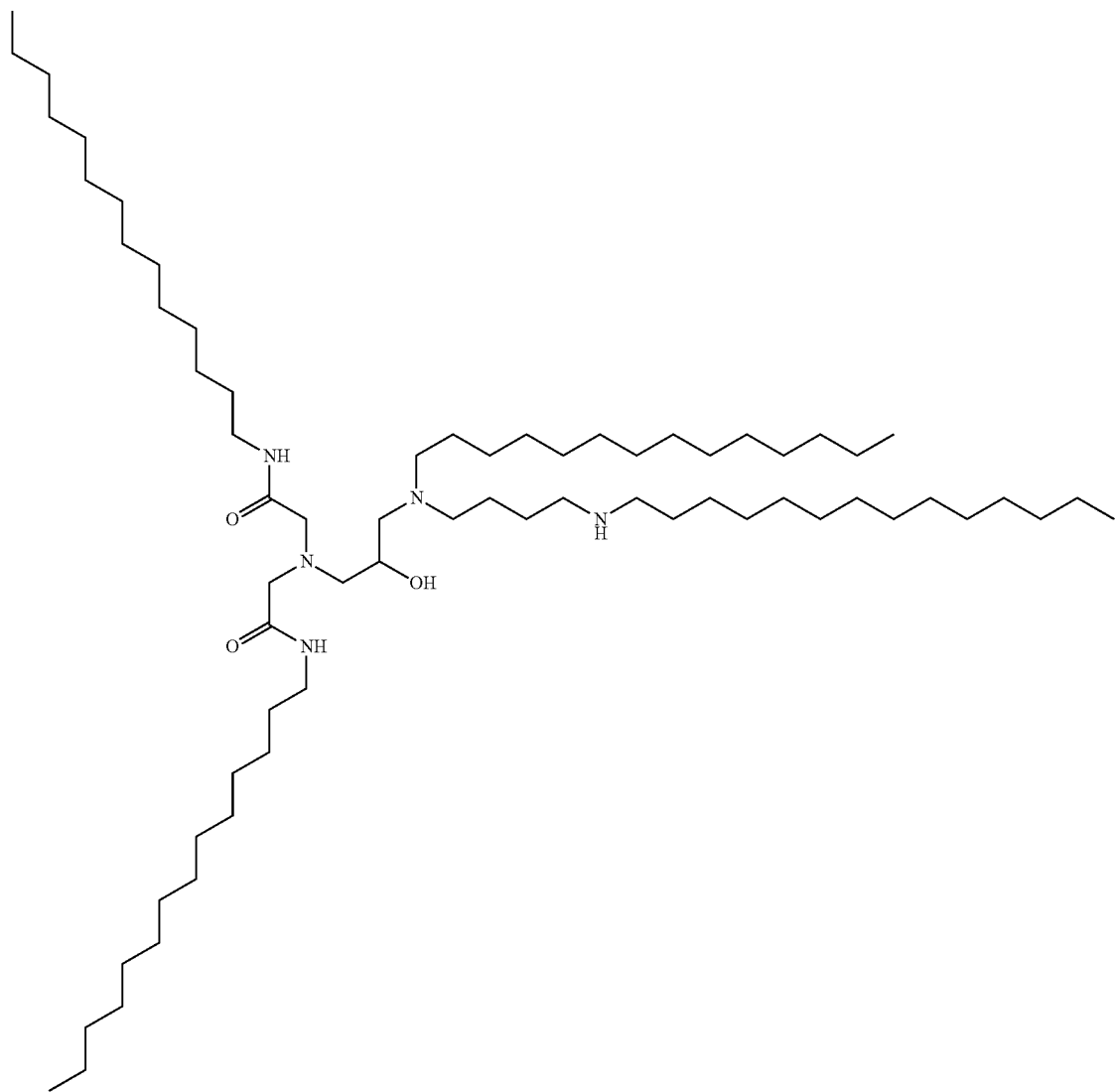
56

57
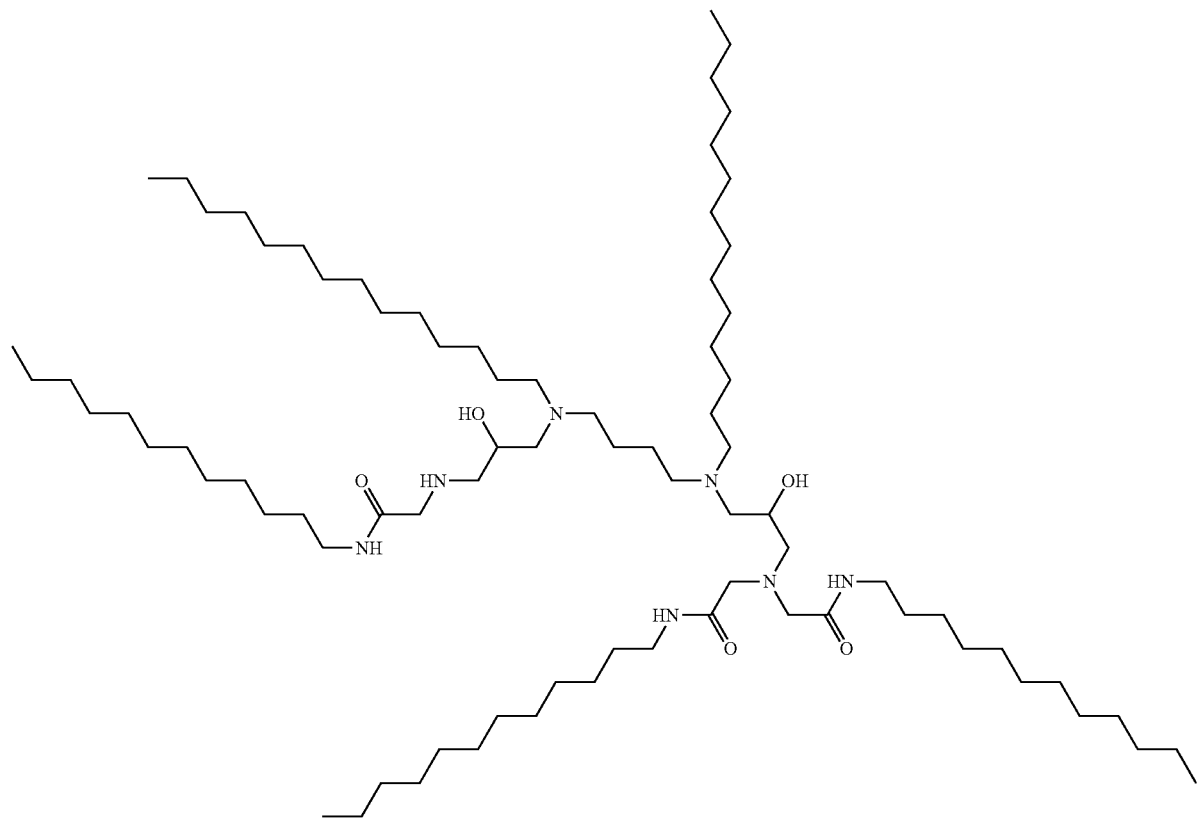
58
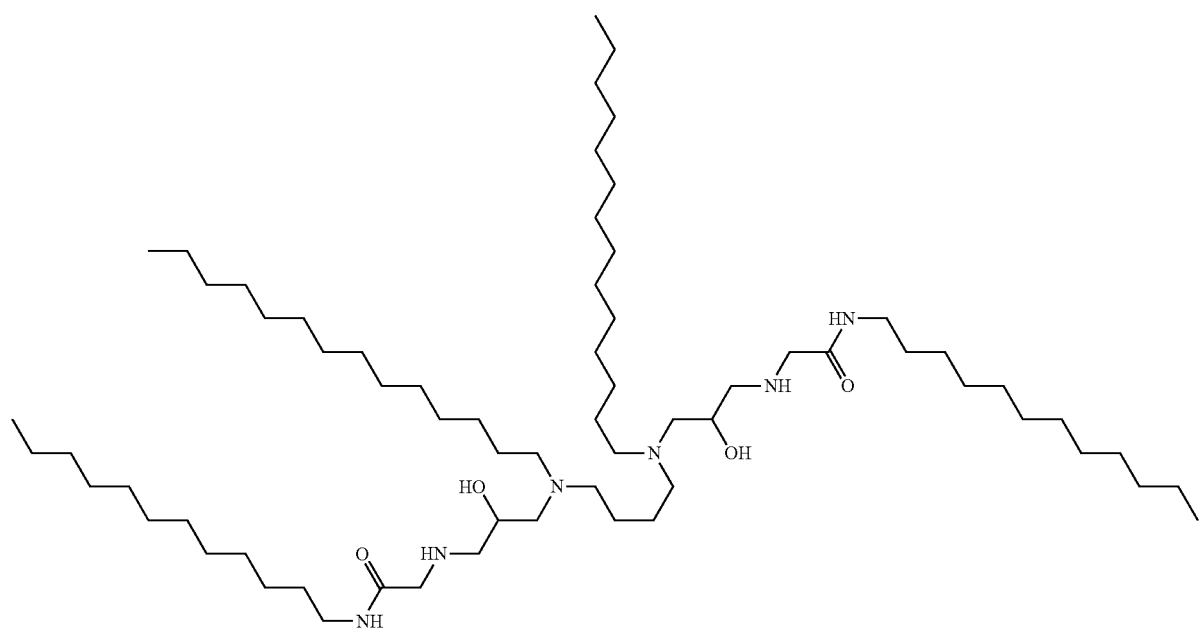

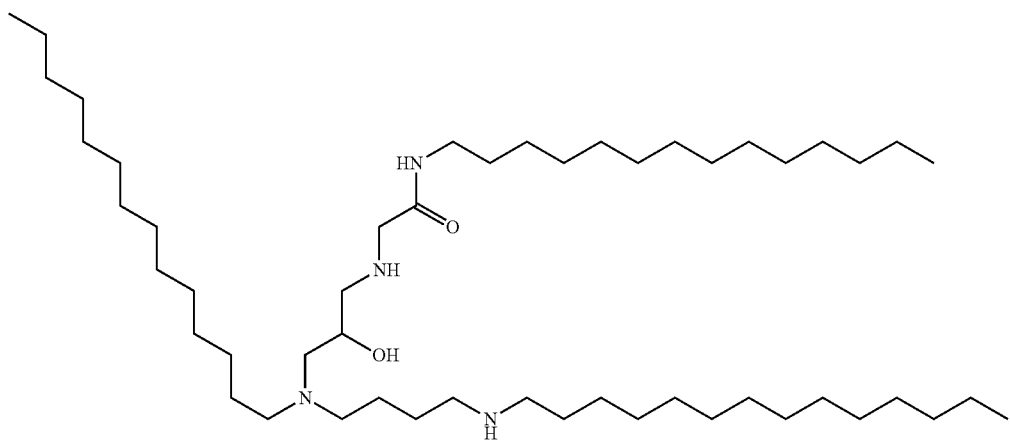
59
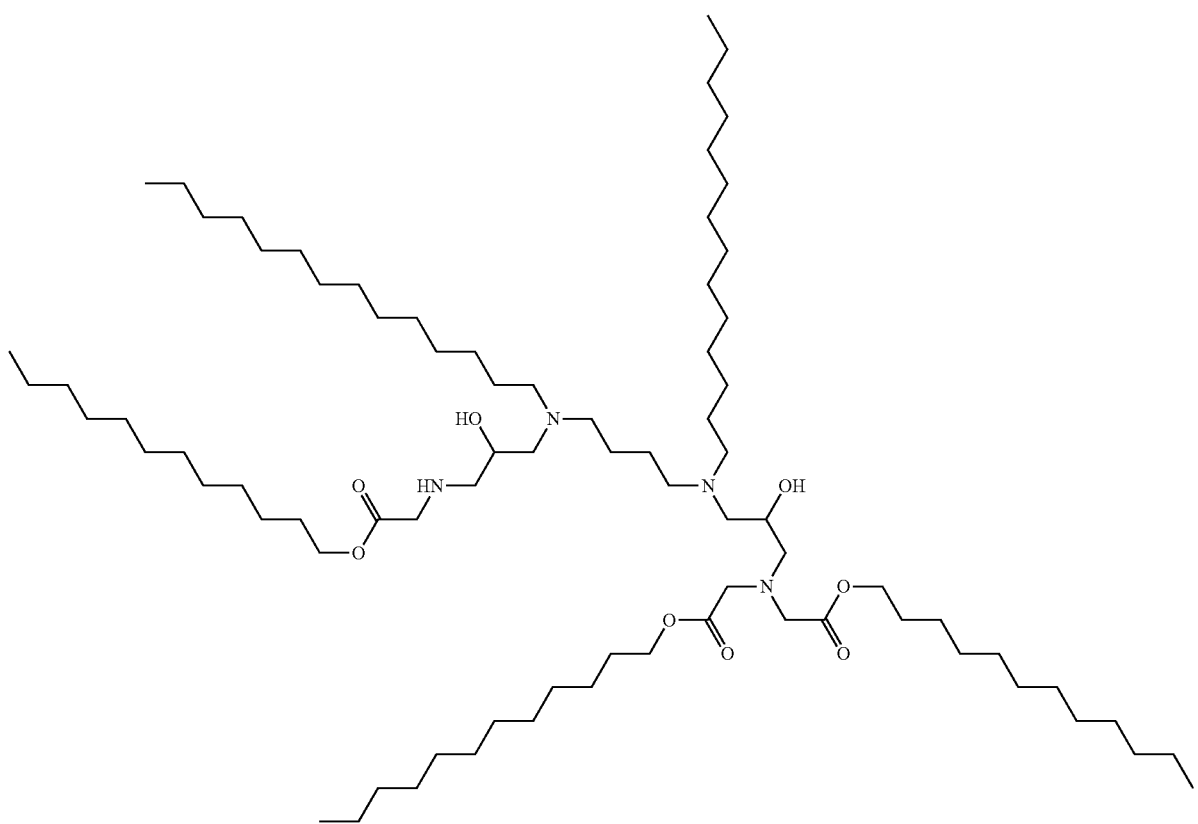
60

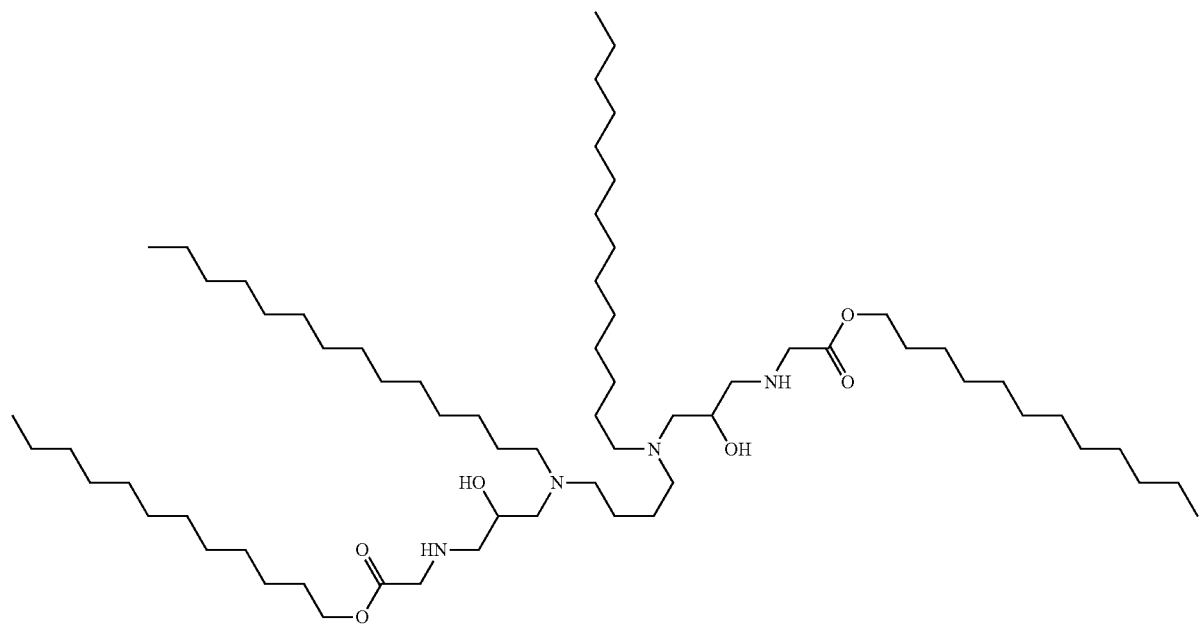
61
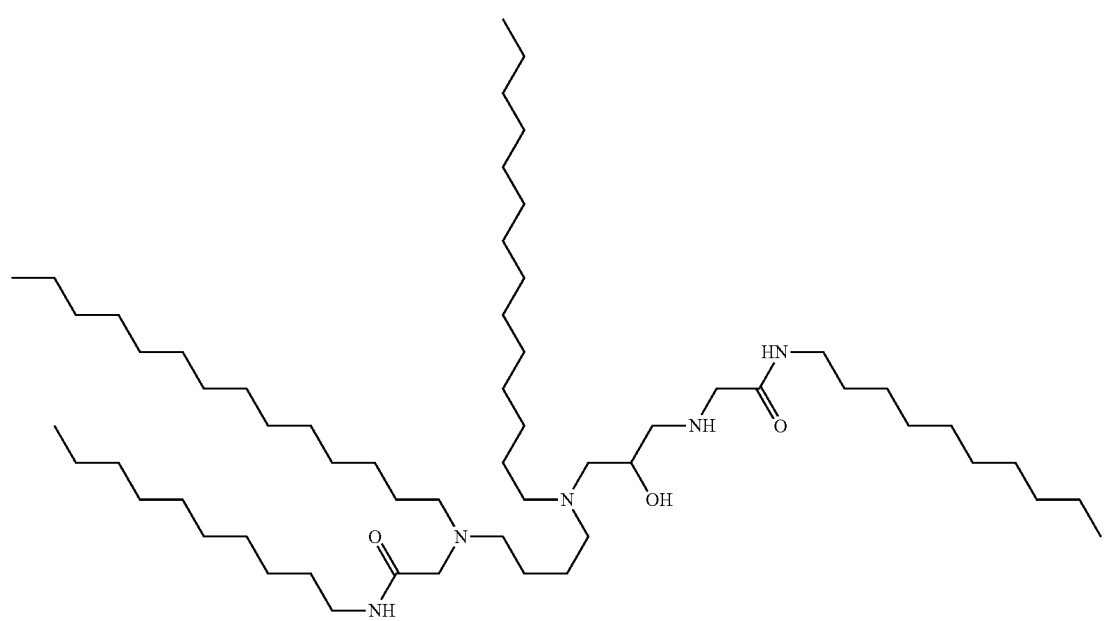
62

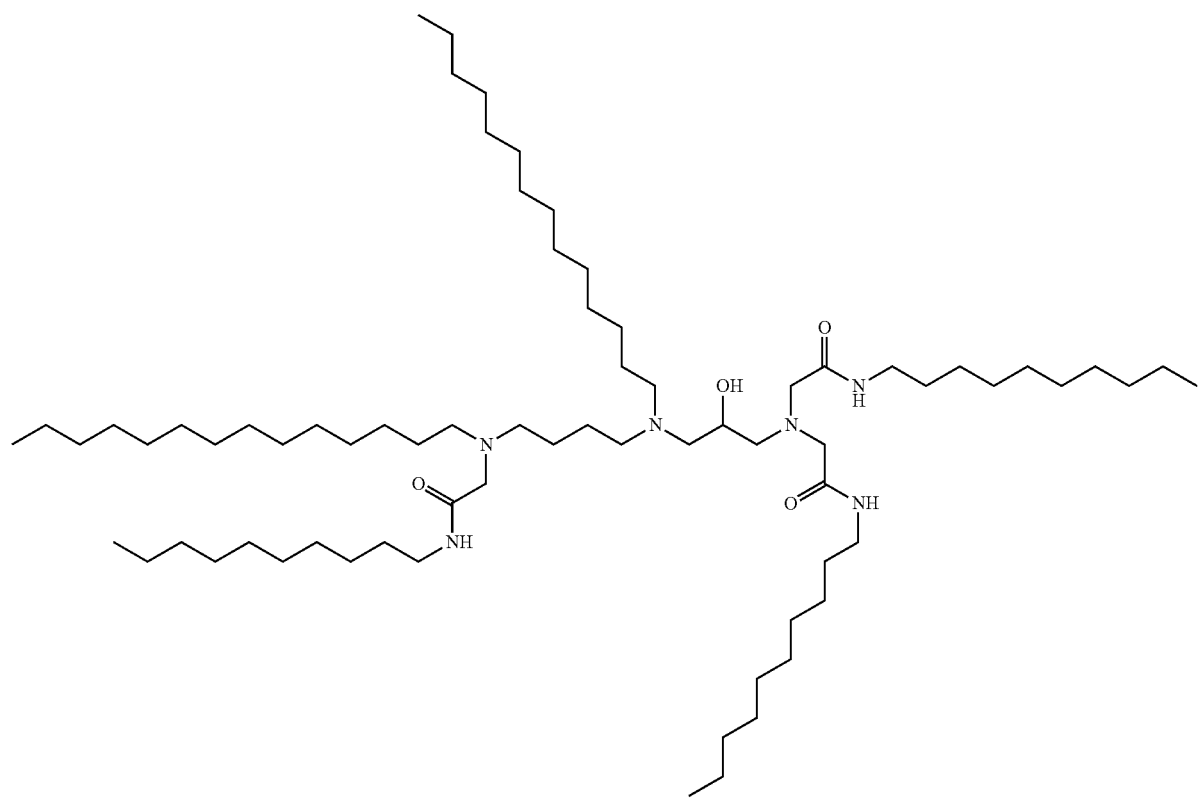
63
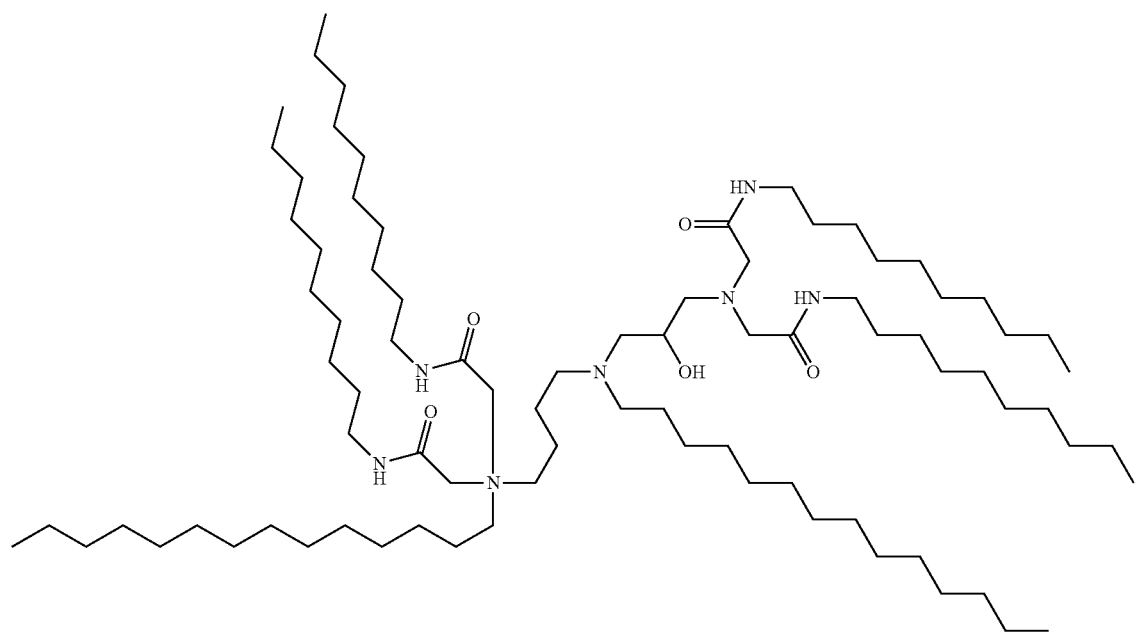
64

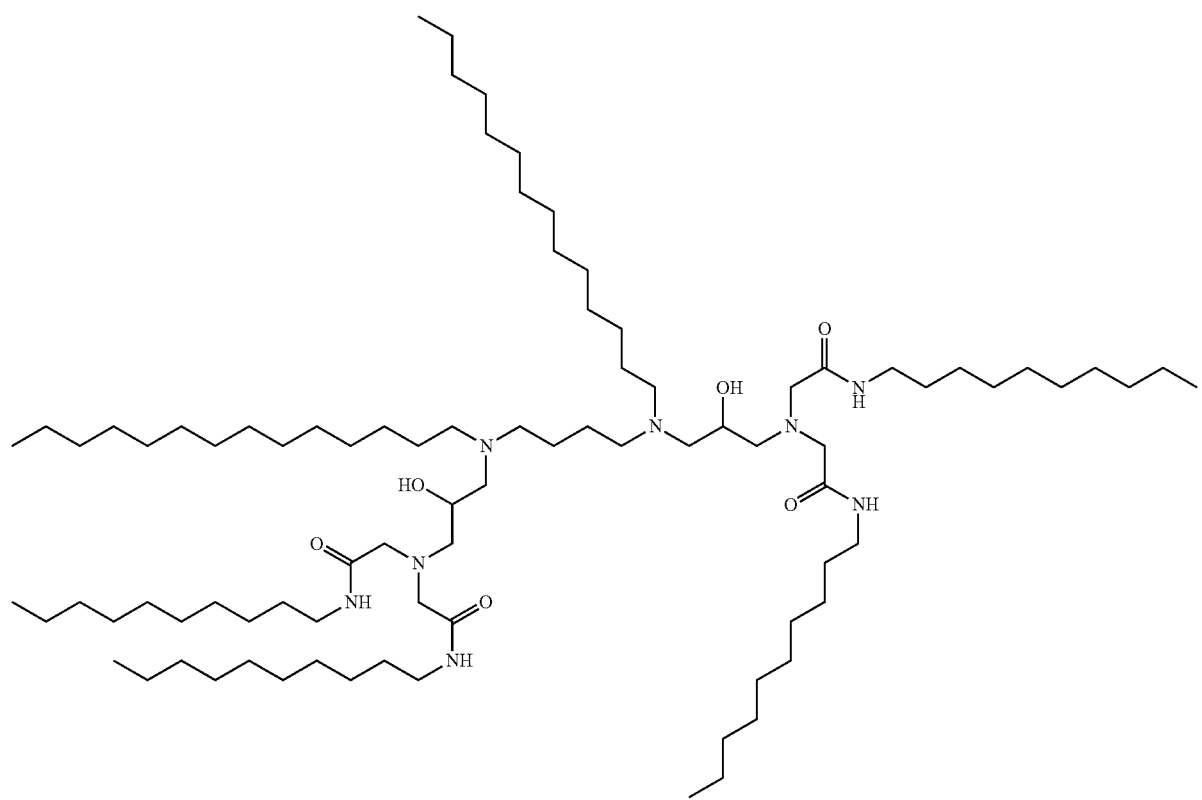
65
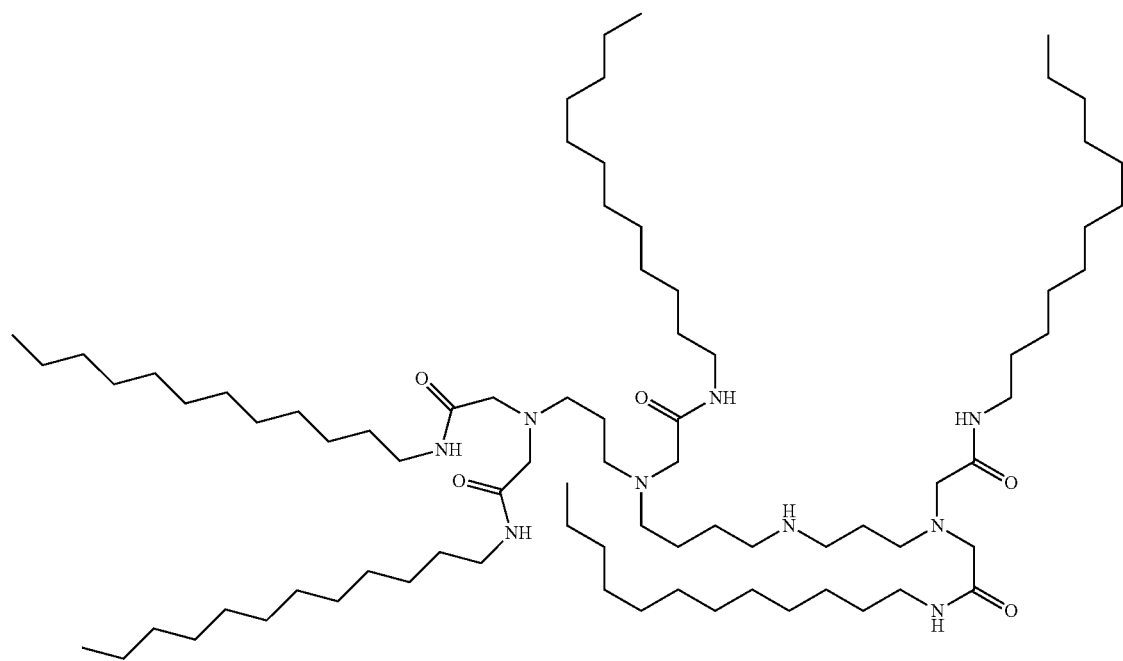
66

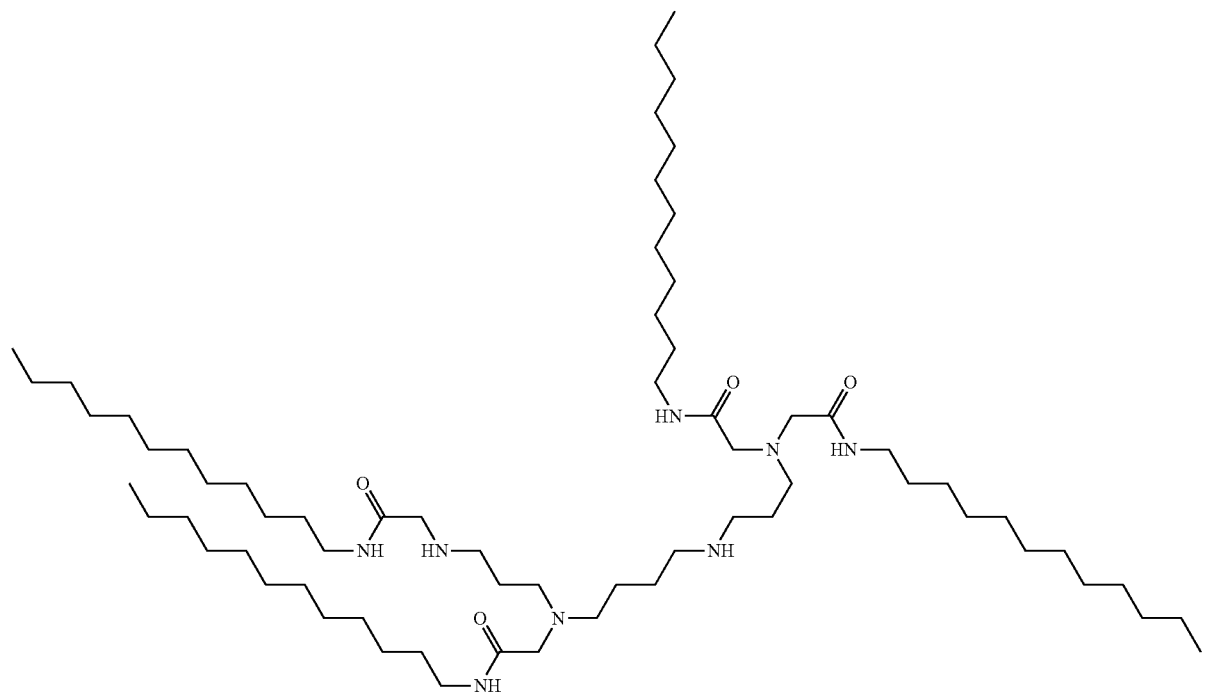
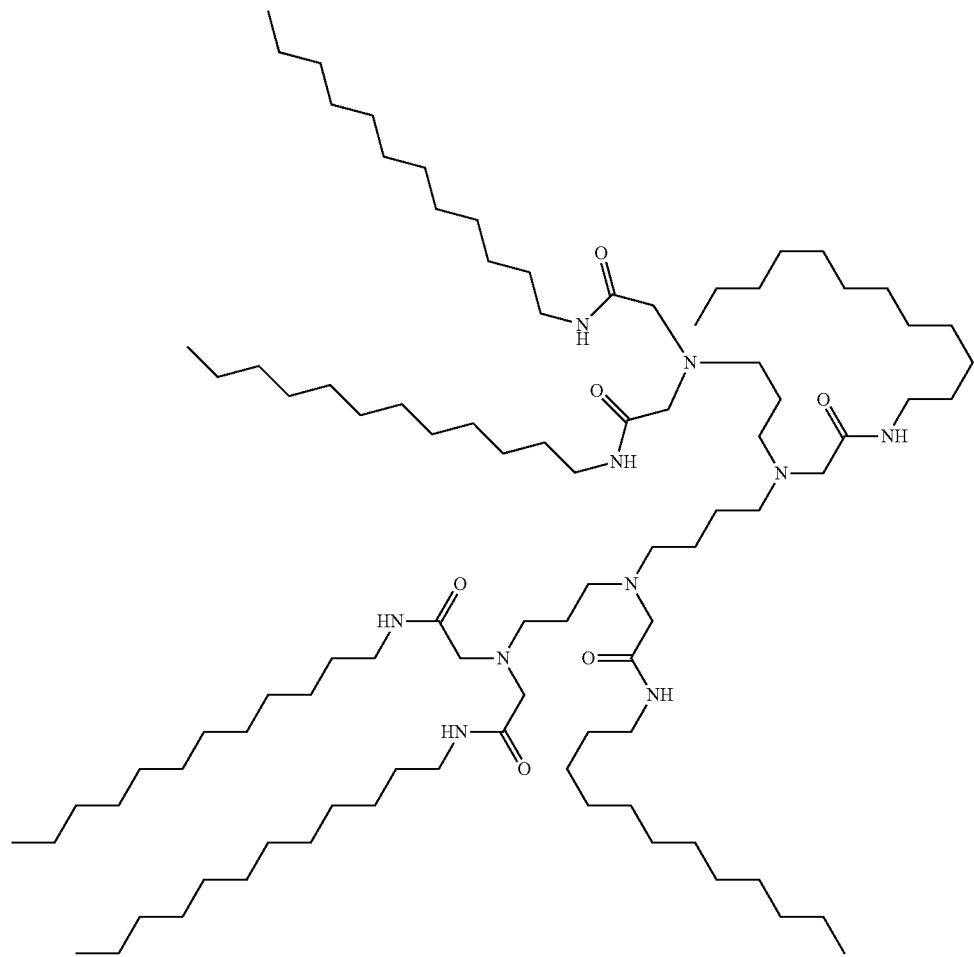

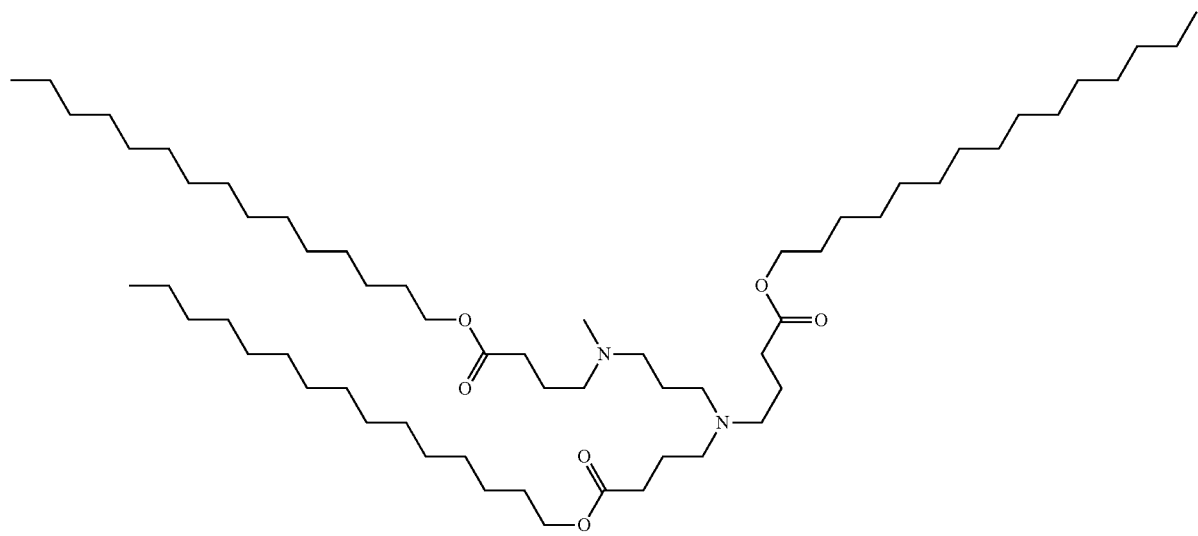
69
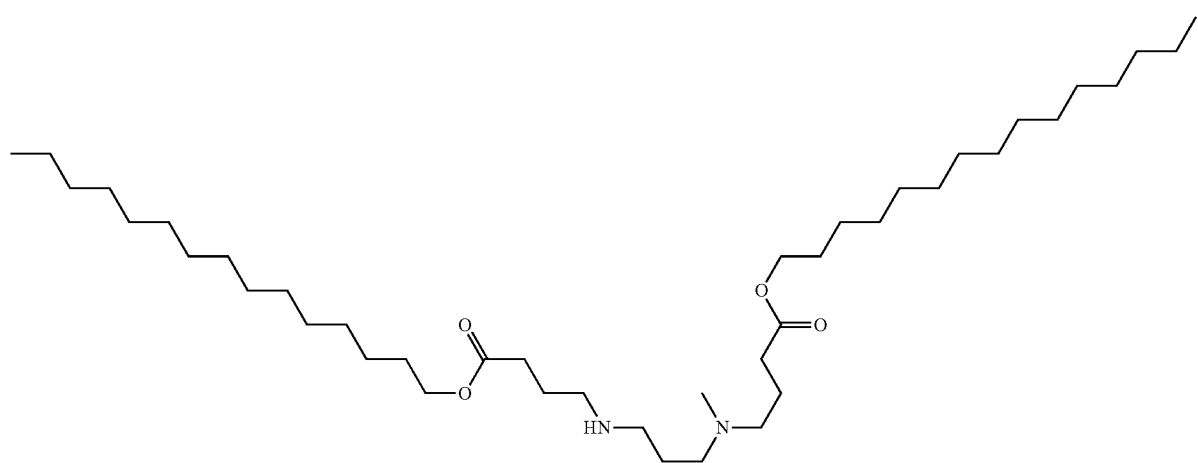
70
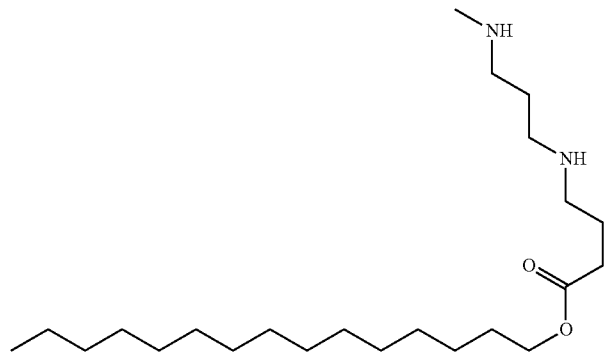
71

72
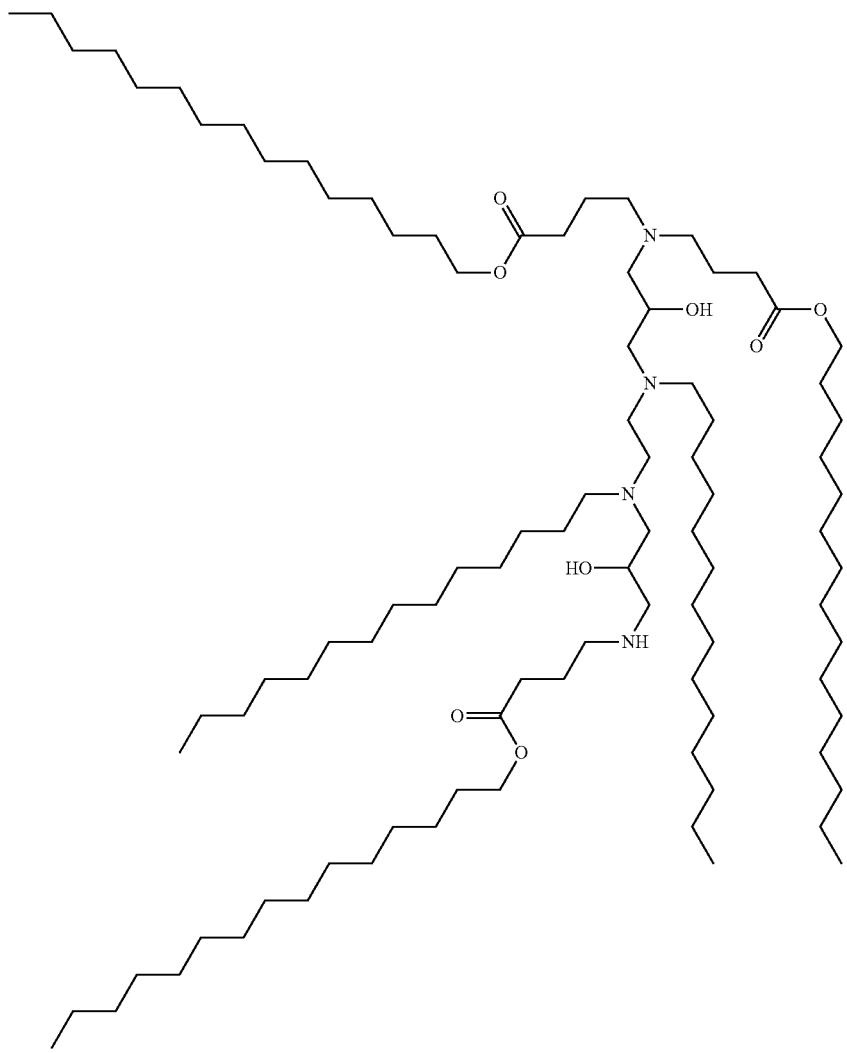
73
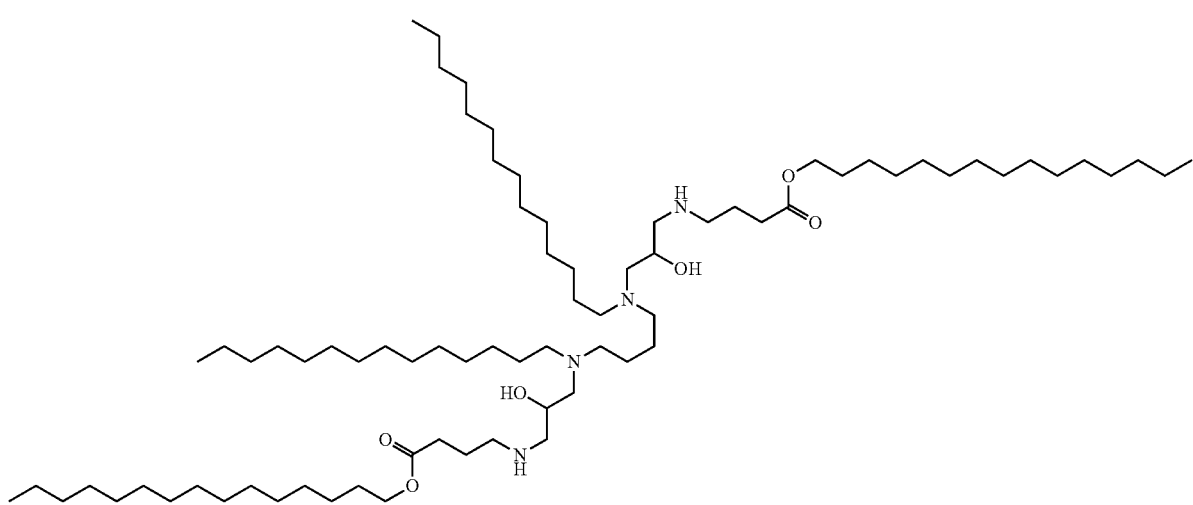

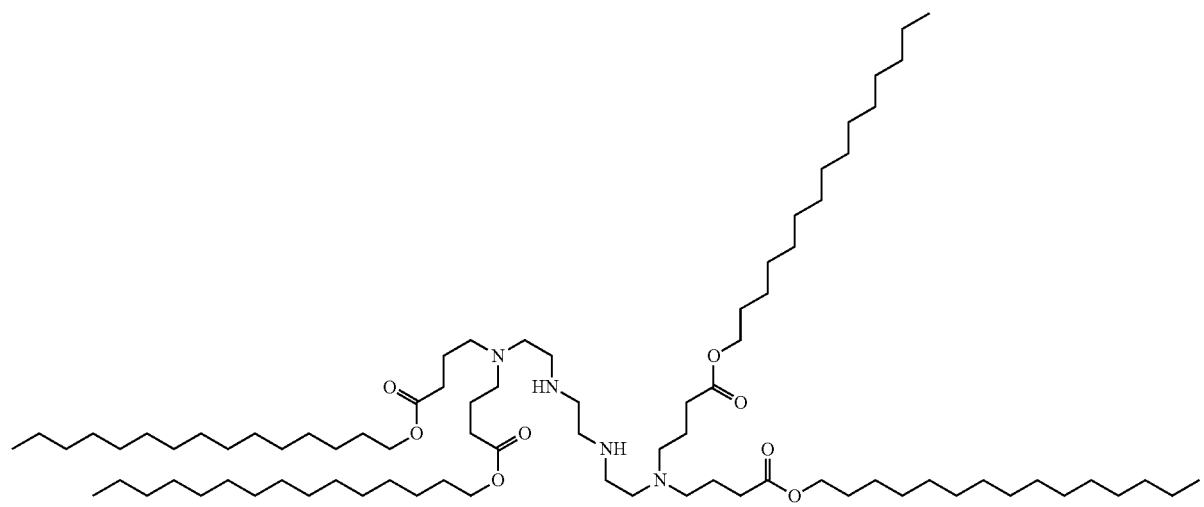
74
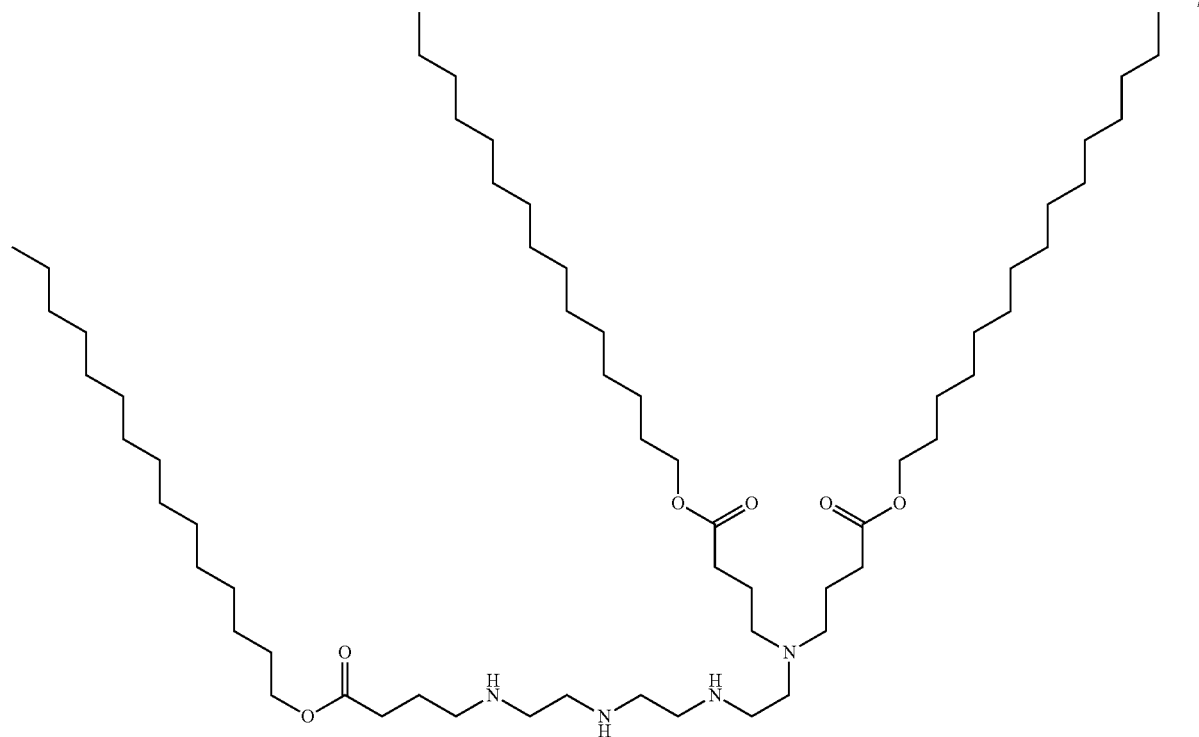
75

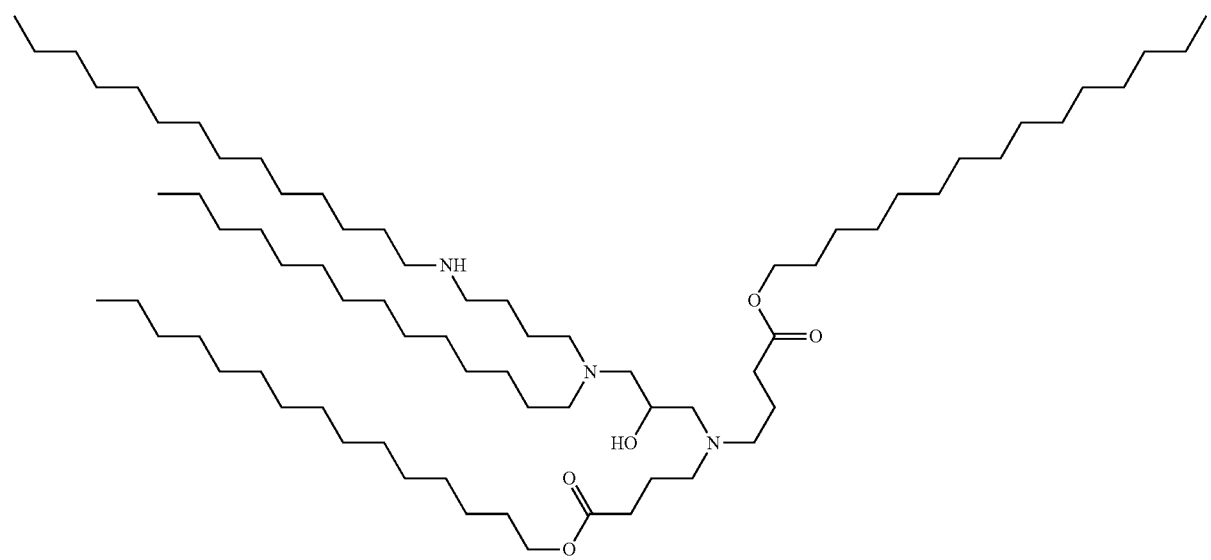
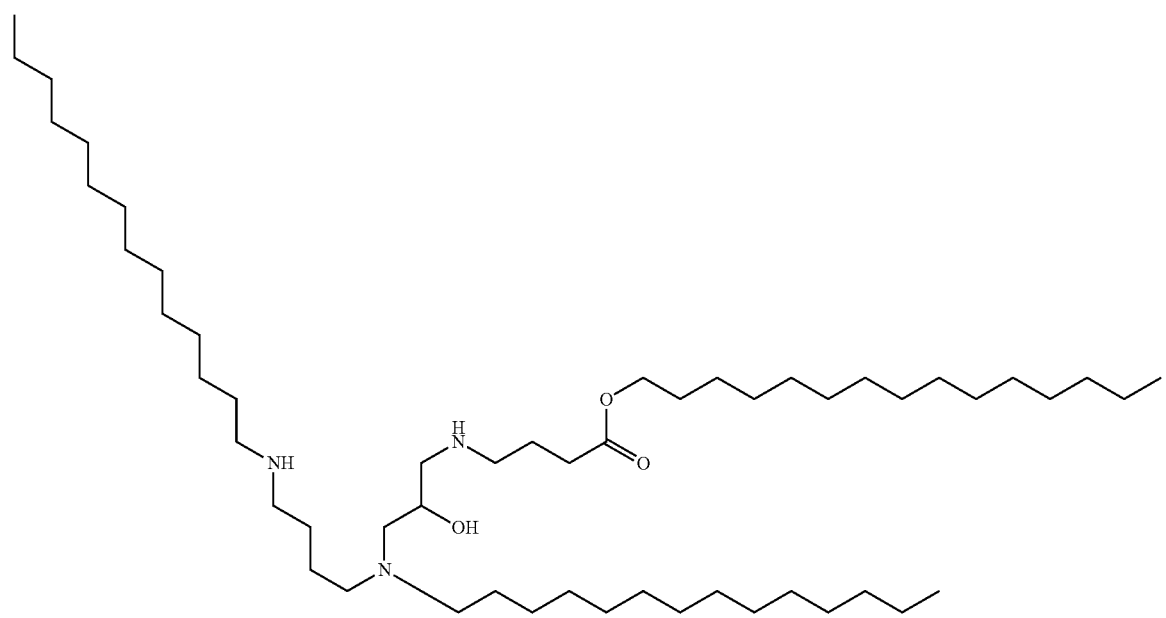

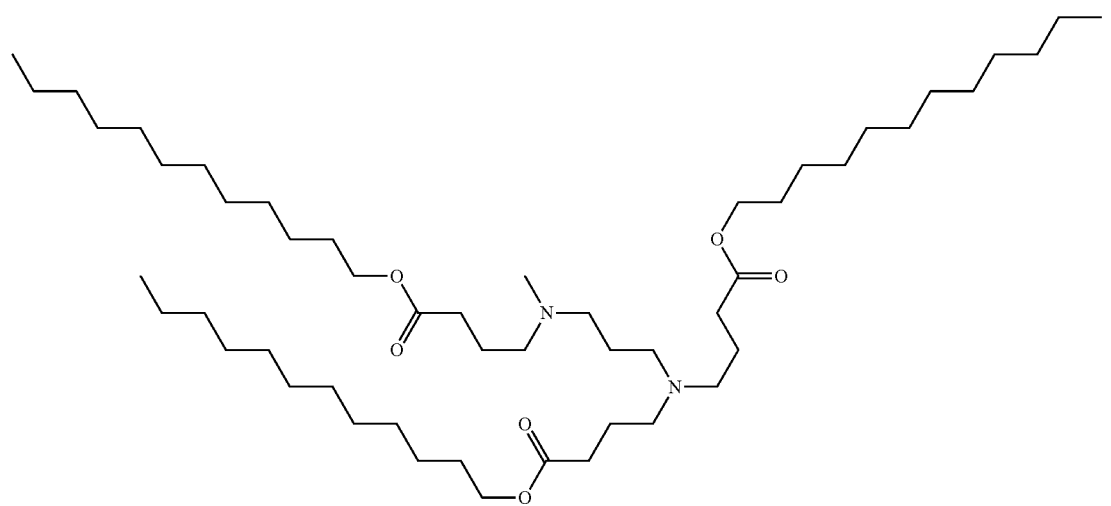
78
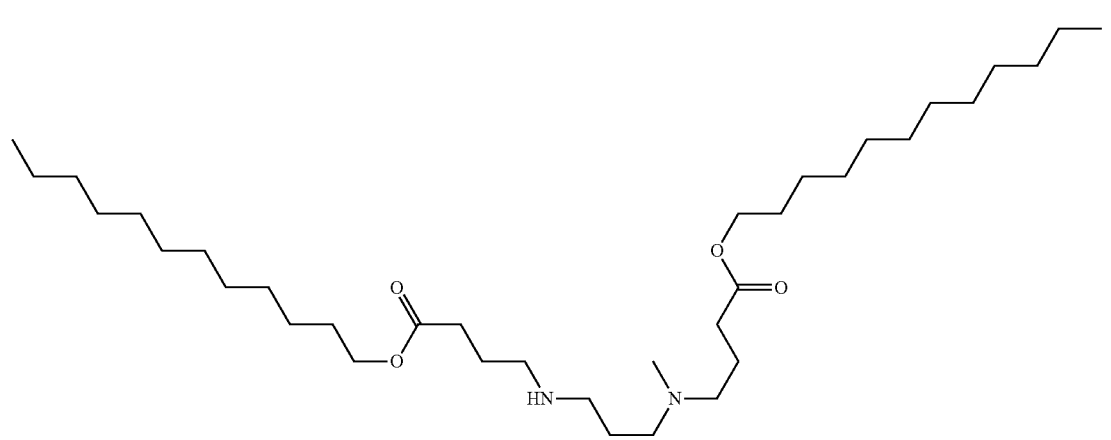
79
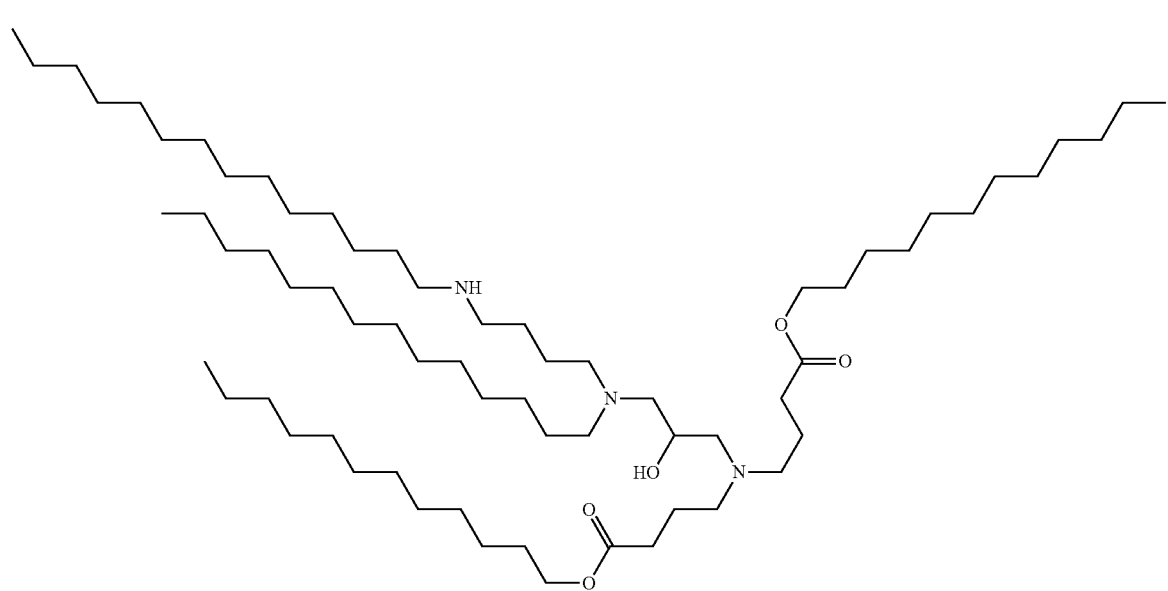
80

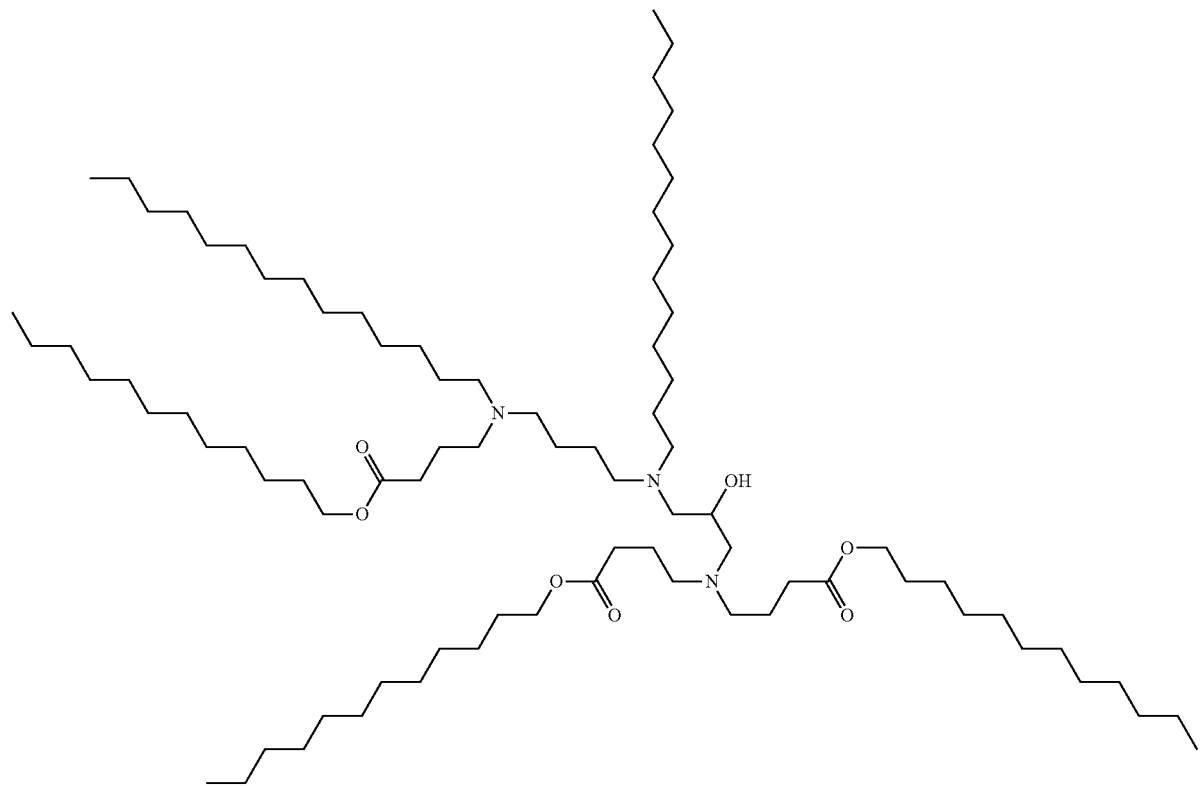
81
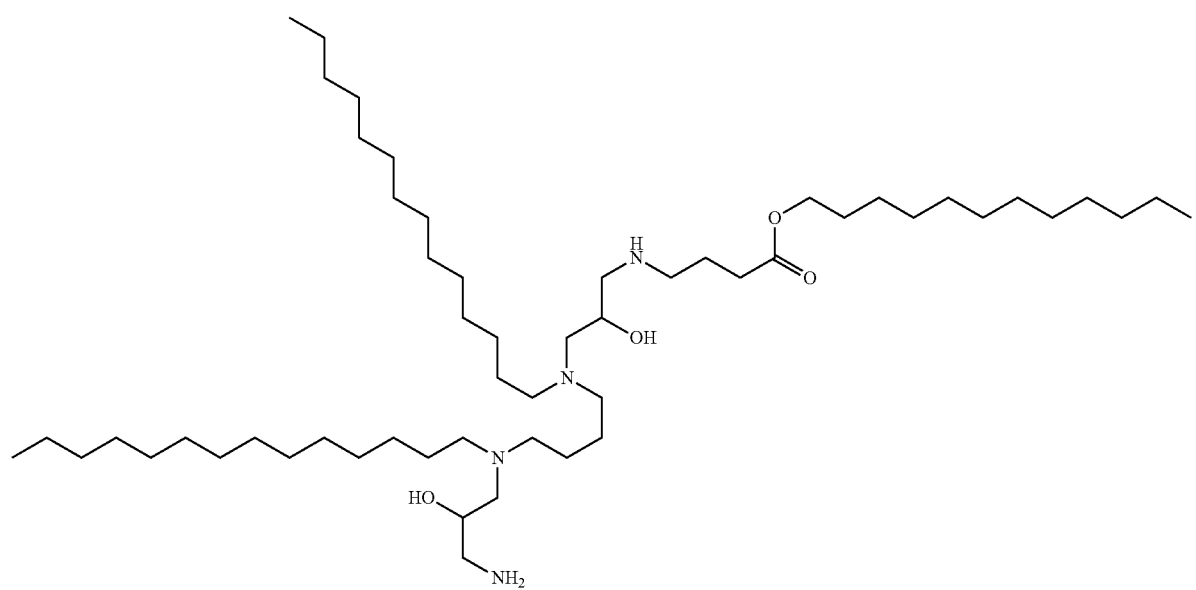
82

83
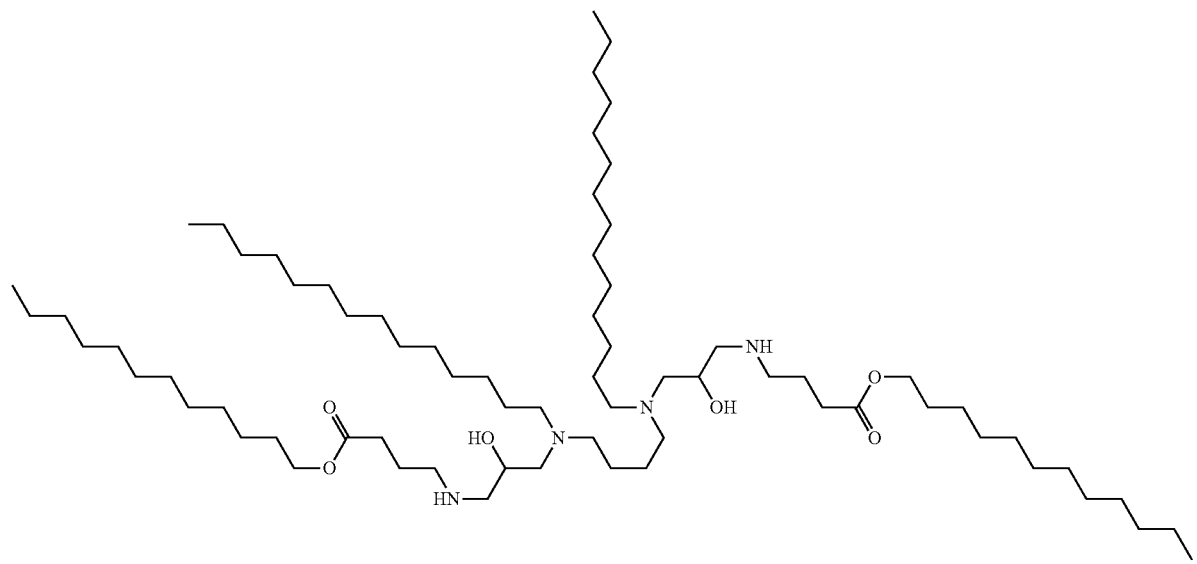
84
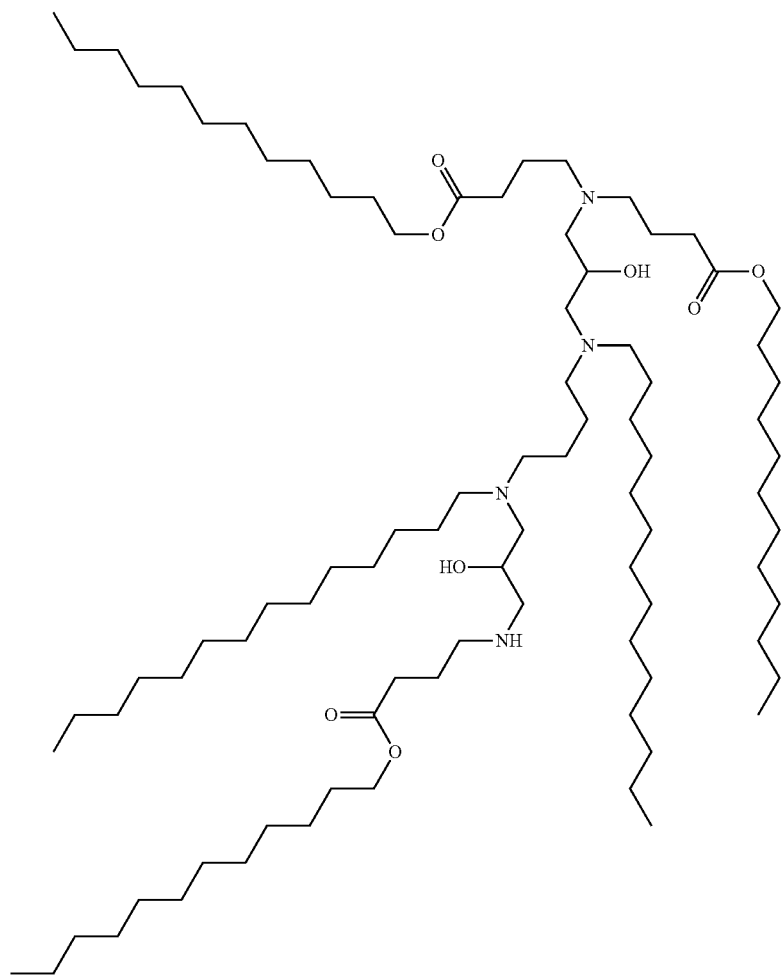

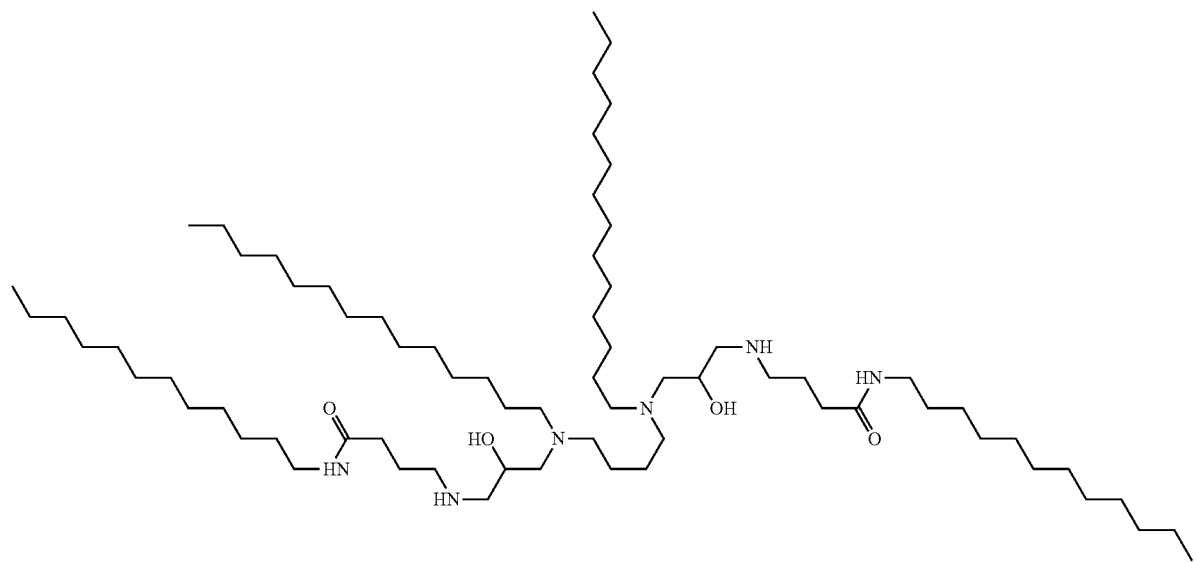
85
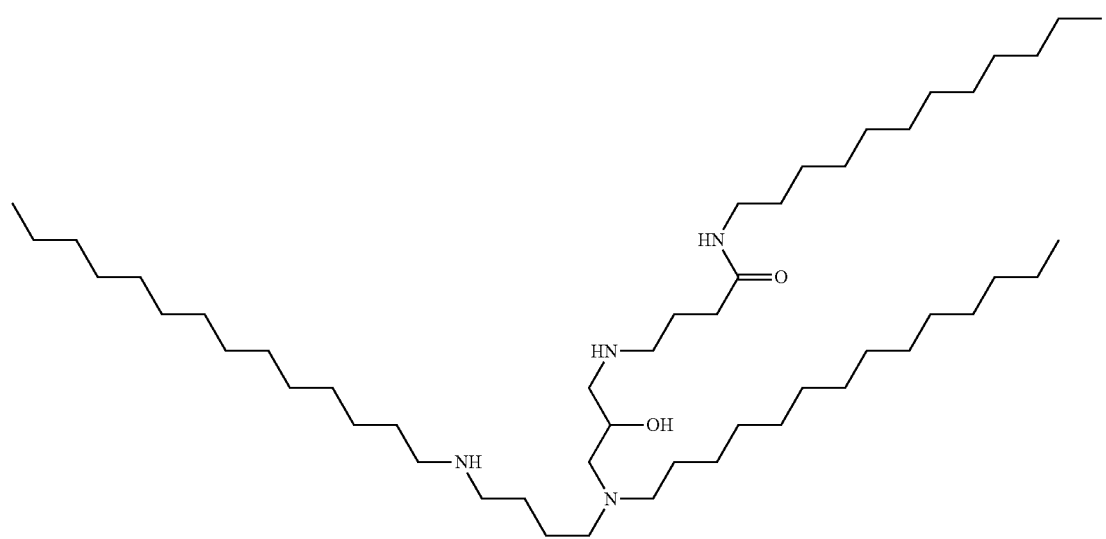
86

-continued

87

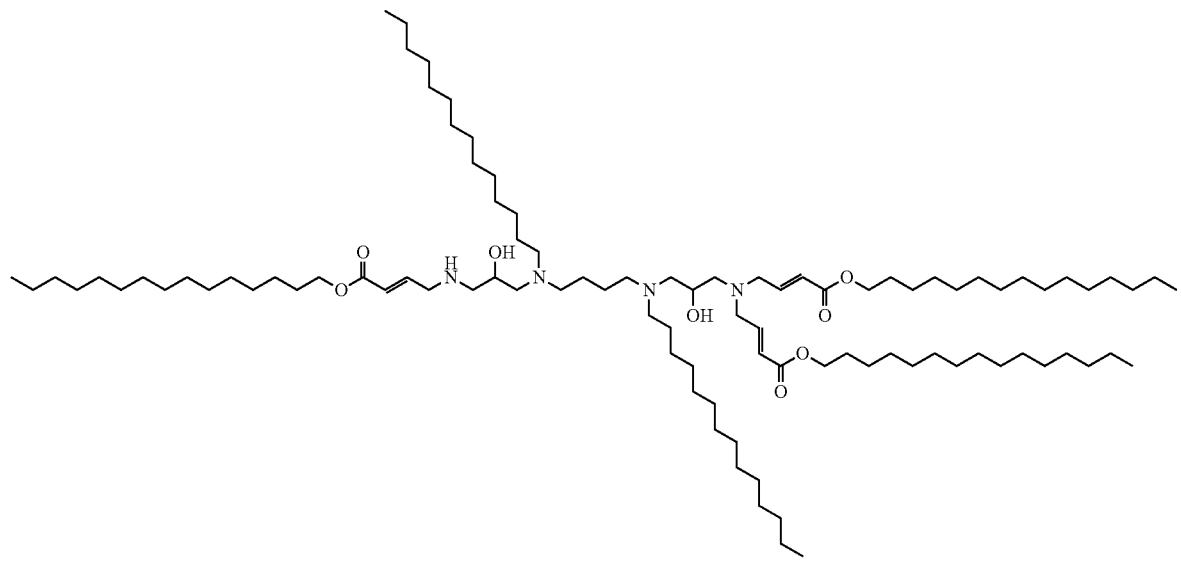

Some of compounds 1-87 shown above were used to prepare some lipid compositions. These compositions are described in detail in Example 9 below, and are shown in Table 1 in Example 9. The numbers of the compounds in the first column of Table 1 correspond to the numbers of compounds shown above.

According to other embodiments of the invention, the above-described compounds of the invention may be synthesized by reacting an amino component with an unsaturated component, e.g., by the addition of the primary amino group of the amino component to a double bond of the unsaturated component where the double is conjugated with an electrophlic group such as, e.g., carbonyl. In general, the synthetic method includes reacting one equivalent of the amino component with one or more equivalents of the unsaturated component. The amino component comprises a primary amine $NH_2$—$R_3$, a diamine, a polyamine or a combination thereof. The unsaturated component comprises of at least one first intermediate having the structure $R_1$—$X_1$—Y—$(CR_4R_5)_n$—Br and the second intermediate having the structure $R_2$—$X_2$—Z—$(CR_6R_7)_m$—Br, wherein in $(CR_4R_5)_n$ and $(CR_6R_7)_m$ portions of the structures, each $R_4$ is the same or different, each $R_5$ is the same or different, each $R_6$ is the same or different, and each $R_7$ is the same or different, wherein the first and the second intermediates are the same or different. In some embodiments, the first and/or the second intermediate(s) of the unsaturated component can be an acrylate or acrylamide.

In certain embodiments, all the amino groups of the amine $NH_2$—$R_3$, a diamine or a polyamine are fully reacted with the unsaturated component to form tertiary amines. In other embodiments, not all the amino groups are so reacted to form tertiary amines thereby resulting in primary or secondary amines in the lipid molecule.

The synthesis of the compounds of the invention may be performed with or without solvent, and the synthesis may be performed at temperatures ranging between room temperature and about 100° C., for example, at about 95° C. The reaction may be optionally catalyzed by adding an acid, a base or a metal. Those having ordinary skill in the art can select the optimal conditions under which the synthesis is carried out, to choose an appropriate catalyst, if necessary, and to select the molar ratio between the amino component and the unsaturated component. For example, when the amino component is the primary amine $NH_2$—$R_3$, the molar ratio between the unsaturated component and the primary amine $NH_2$—$R_3$ can be between about 1:1 and about 6:1. The prepared lipids may be optionally purified. The lipids may also be alkylated using an alkyl halide (e.g., methyl iodide) or other alkylating agent.

In one exemplary non-limiting, embodiment the synthetic process can be illustrated by the following reaction scheme:

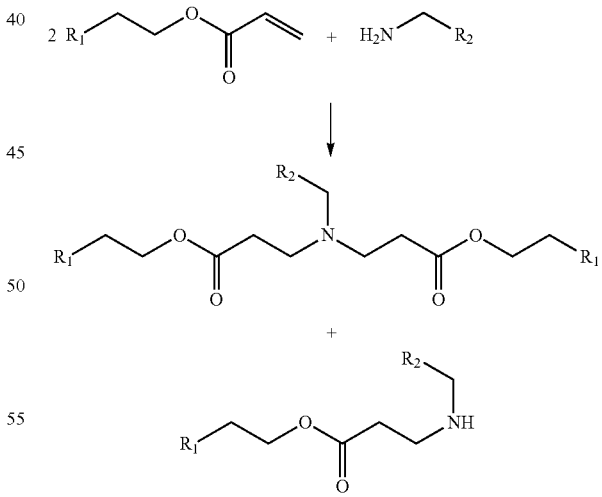

In the above-provided structures of the first and the second intermediates comprising the unsaturated component, each of $X_1$ and $X_2$ is a moiety independently selected from the group consisting of O, S, N—A and C—A, wherein A is selected from the group consisting of hydrogen and a $C_1$-$C_{20}$ hydrocarbon chain; each of Y and Z is a moiety independently selected from the group consisting of CH—OH, C=O, C=S, S=O and $SO_2$; each of $R_1$, $R_2$, $R_4$, $R_5$, $R_6$ and $R_7$ is a moiety independently selected from the group consisting of hydrogen, a cyclic or an acyclic, substituted or unsubstituted, branched or unbranched aliphatic group, a cyclic or acyclic, substituted or unsubstituted, branched or unbranched heteroaliphatic group, a substituted or unsubstituted, branched or unbranched acyl group, a substituted or unsubstituted, branched or unbranched aryl group, a substituted or unsubstituted, branched or unbranched heteroaryl group, and each of n and m is an integer independently having the value between 1 and 3, inclusively.

In some embodiments, if at least one of n or m in the above-provided structures of the first and the second intermediates of the unsaturated component has the value of 2, and the primary amine $NH_2$—$R_3$ is used as the amino component, then $R_3$ in the above-provided structure of the primary amine is either of the following moieties:

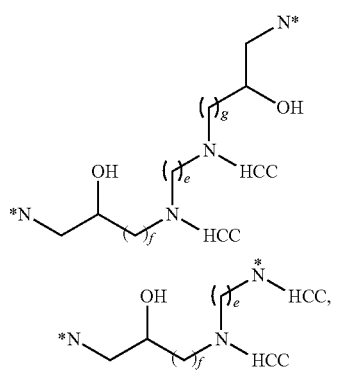

wherein each of g, e and f is an integer independently having the value between 1 and 6, inclusively, each "HCC" symbolizes a hydrocarbon chain, and each * shows a point of attachment of $R_3$ to the amino group in the primary amine $NH_2$—$R_3$.

In some embodiments, each of $R_1$ and $R_2$ in the above-provided structures of the first and the second intermediates of the unsaturated component is independently any of substituted or unsubstituted, branched or unbranched alkyl or alkenyl groups having between 3 and about 20 carbon atoms, such as between 8 and about 18 carbon atoms, and between 0 and 4 double bonds, such as between 0 and 2 double bonds.

In some embodiments, if in the above-provided structures of the first and the second intermediates of the unsaturated component each of n and m independently has the value of 1 or 3, and the primary amine $NH_2$—$R_3$ is used as the amino component, $R_3$ in the above-provided structure of the primary amine can be any of the following moieties:

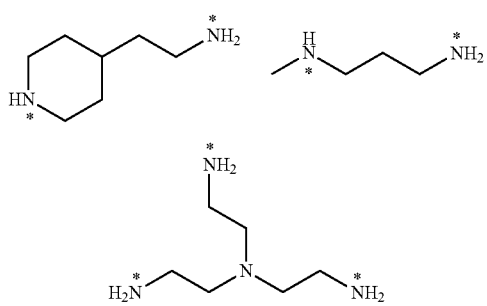

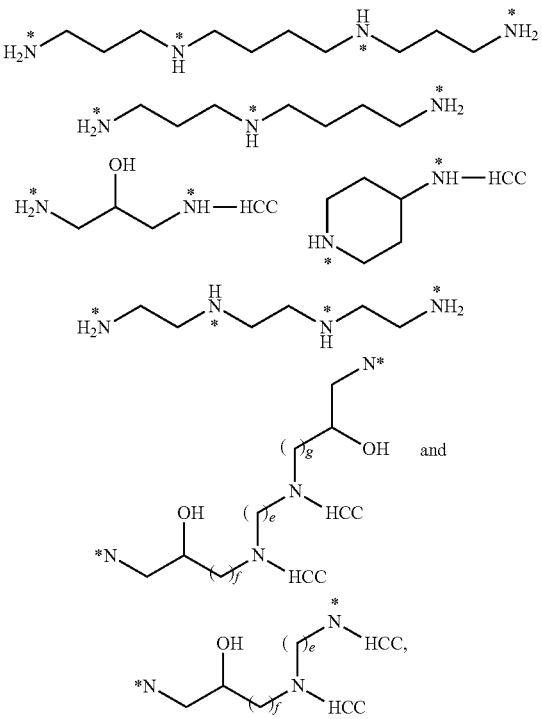

wherein each "HCC" symbolizes a hydrocarbon chain, and each * shows a potential point of attachment of $R_3$ to the amino group in the primary amine $NH_2$—$R_3$, where each H on any * position can be replaced to achieve the attachment to the nitrogen atom in the primary amine $NH_2$—$R_3$.

The above described compounds of the invention may be used in the delivery of biologically active or therapeutic agents to a subject, to an animal, or to a cell or a tissue in vitro or in vivo. In certain illustrative though non-limiting embodiments, the compounds may be particularly suited to delivering negatively charged bioactive agents. For example, the amin-containing transfection compounds of the present invention may be used to delivery DNA, RNA, other polynucleotides, other anions or polyanions to a subject or to a cell.

In some embodiments, the inventive lipids are combined with an agent to form transfection complexes, such as microparticles, liposomes or micelles. The bioactive agent to be delivered (e.g., a polynucleotide, a protein, a peptide or a small molecule) by these delivery vehicles may be in the solid or liquid or disolved form. The inventive lipids may be combined with other lipids, polymers, surfactants, cholesterol, carbohydrates, proteins, etc. to form the particles. These particles may be combined with a pharmaceutically excipient to form pharmaceutical compositions.

The lipid synthesized as described above may be further purified by any known technique, such as by crystallization, chromatography, precipitation (e.g. repeated precipitations in diethyl ether, hexane or another organic solvent) or distillation. The lipid may be also isolated as a salt that can be formed when the lipid is reacted with an organic acid or inorganic acid. In some embodiments, if the lipid comprises the tertiary amine moiety, it can be alkylated with any alkylating agent, for example, alkyl halides such as methyl iodide to form a quaternary ammonium salt of the lipid. The anion associated with the quaternary amine may be any pharmaceutically acceptable organic or inorganic anion.

In some embodiments, the synthetic process results in a mixture of isomers having acrylic tails, with varying numbers and positions of the acrylate tails. Such mixtures can be used with or without further purification, as desired. When an amine is not exhaustively alkylated, the resulting products may be further reacted with another electrophile, such as an acrylate or acrylamide optionally followed by further purification.

In some embodiments, a library of different lipids can be prepared in parallel. To that end, a different amine and/or unsaturated component can be added to each vial in a set of vials or to each well of a multi-well plate. The array of reaction mixtures is incubated at a temperature and length of time sufficient to allow formation of the lipids to occur. The lipids may then be isolated and purified using known techniques followed by screening using high-throughput techniques to identify lipids with a desired characteristic (e.g., solubility, ability to bind polynucleotides, ability to bind heparin, ability to bind small molecules, ability to form microparticles, ability to increase transfection efficiency and the like).

Transfection Complexes

It is a further object of the presently disclosed embodiments to provide novel transfection complexes that are formulated to deliver a biologically active compound to a cell or a tissue in vitro, or to a cell or tissue in an animal in vivo. The delivery of a biologically active agent to cells or tissue as contemplated herein may be for the provision of a therapeutic modality for the treatment of a disorder, or may alternatively be provided during the course of conducting scientific research (e.g., as a research tool).

In some embodiments, a transfection complex as provided for herein may include one or more amine-containing transfection agents formulated as a lipid aggregate such that the biologically active agent can be delivered to a cell or a tissue to affect a desired biological response. In some embodiments, a transfection complex may optionally include one or more helper lipids. In an embodiment, a transfection complex may optionally include one or more pegylated lipids. In an embodiment, a transfection complex may optionally include one or more targeting moieties or transfection enhancers.

In an embodiment, an a transfection complex may include an amine-containing transfection compound having the general structure I, or pharmaceutically acceptable salts thereof:

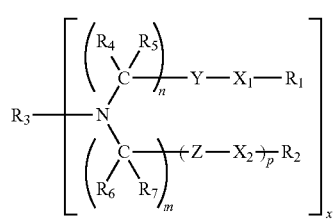
I wherein each of $X_1$ and $X_2$ is a moiety independently selected from the group consisting of O, S, N—A and C—A, wherein A is selected from the group consisting of hydrogen and a $C_1$-$C_{20}$ hydrocarbon chain; each of Y and Z is a moiety independently selected from the group consisting of CH—OH, C=O, C=S, S=O and $SO_2$; each of $R_1$, $R_2$, $R_3$, $R_4$, $R_5$, $R_6$ and $R_7$ is a moiety independently selected from the group consisting of hydrogen, a cyclic or an acyclic, substituted or unsubstituted, branched or unbranched aliphatic group, a cyclic or acyclic, substituted or unsubstituted, branched or unbranched heteroaliphatic group, a substituted or unsubstituted, branched or unbranched acyl group, a substituted or unsubstituted, branched or unbranched aryl group, a substituted or unsubstituted, branched or unbranched heteroaryl group, x is an integer independently having the value between 1 and 10, inclusively, n is an integer independently having the value between 1 and 3, inclusively, m is an integer independently having the value between 0 and 20, inclusively, p is an integer independently having the value of 0 or 1, wherein if m=p=0, then $R_2$ is hydrogen, with the further proviso that if at least one of n or m has the value of 2, then $R_3$ and nitrogen in structure I form a moiety selected from the group consisting of:

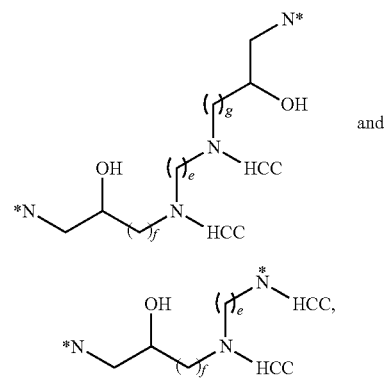

wherein each of g, e and f is an integer independently having the value between 1 and 6, inclusively, "HCC" symbolizes a hydrocarbon chain, and each * indicates the nitrogen atom in structure I.

In some embodiments, $R_3$ is a polyamine. In other embodiments, $R_3$ is a ketal. In some embodiments, each of $R_1$ and $R_2$ in the general structure I is independently any of substituted or unsubstituted, branched or unbranched alkyl or alkenyl groups having between 3 and about 20 carbon atoms, such as between 8 and about 18 carbon atoms, and between 0 and 4 double bonds, such as between 0 and 2 double bonds.

In some embodiments, if each of n and m independently has the value of 1 or 3, $R_3$ is any of the following moieties:

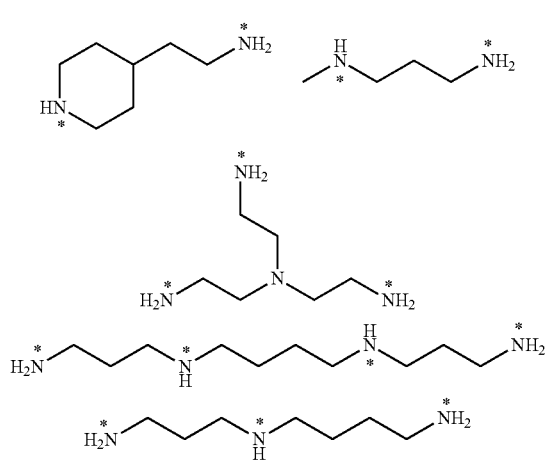

-continued

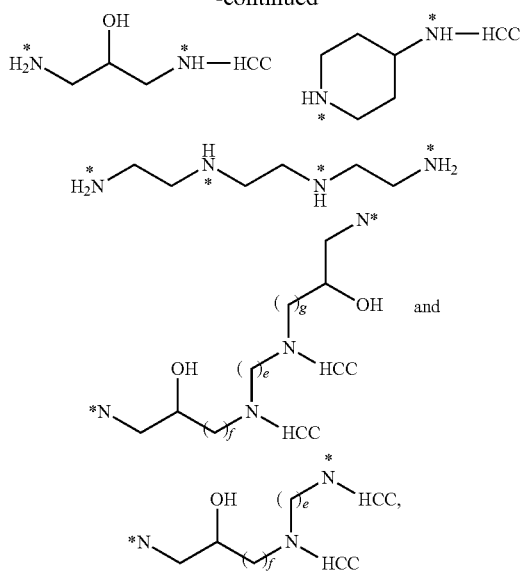

wherein each "HCC" symbolizes a hydrocarbon chain, and each * shows a potential point of attachment of $R_3$ to the nitrogen atom in structure I, where each H on any * position can be replaced to achieve the attachment to the nitrogen atom in structure I.

According to some embodiments, transfection complexes containing amine-containing transfection compounds having the general structure I may have each of $R_4$, $R_5$, $R_6$ and $R_7$ being hydrogen, each of Y and Z being C=O, each of $R_1$ and $R_2$ being the same and each of $X_1$ and $X_2$ also being the same. Such compounds are represented by the general structure II (which is a sub-genus of the compound the general structure I):

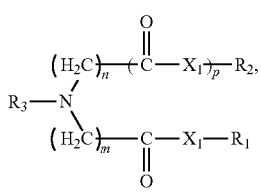
II wherein when n=p=0, $R_2$ is H.

In compounds of the general structure II, at least one $X_1$ is NH, or at least one $X_1$ is O. Furthermore, in some embodiments, in compounds of the general structure II, each $R_1$ is independently any of substituted or unsubstituted, branched or unbranched alkyl or alkenyl groups having between 3 and about 20 carbon atoms, e.g., between 8 and about 18 carbon atoms, and between 0 and 4 double bonds, e.g., between 0 and 2 double bonds. Furthermore, in some embodiments, if each of n and m independently has the value of 1 or 3, $R_3$ is any of the following moieties:

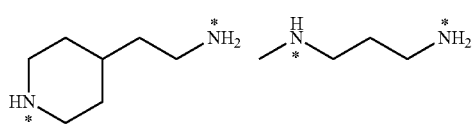

-continued

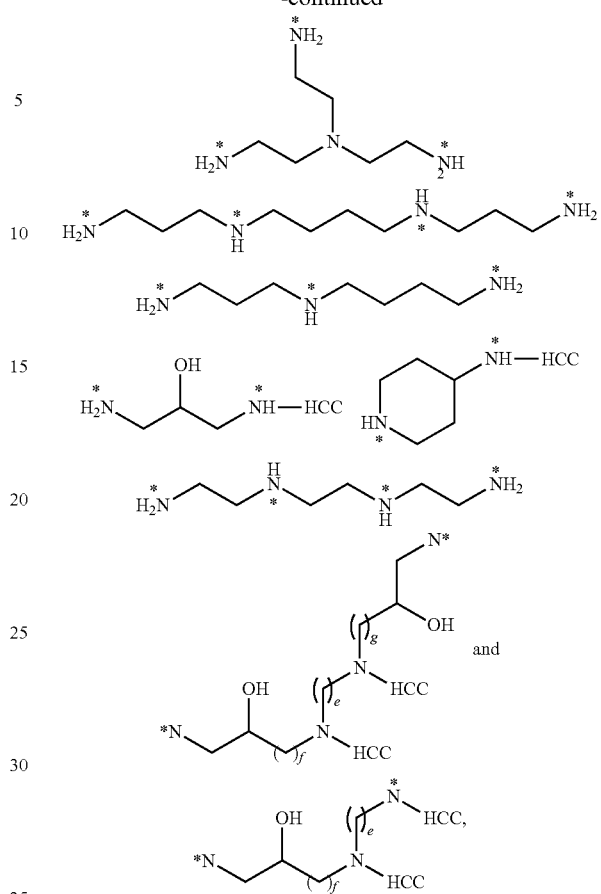

wherein each "HCC" symbolizes a hydrocarbon chain, and each * shows a potential point of attachment of $R_3$ to the nitrogen atom in structure II, where each H on any * position can be replaced to achieve the attachment to the nitrogen atom in structure II.

In some embodiments, if at least one of n or m in the general structure II has the value of 2, then $R_3$ is either of the following moieties:

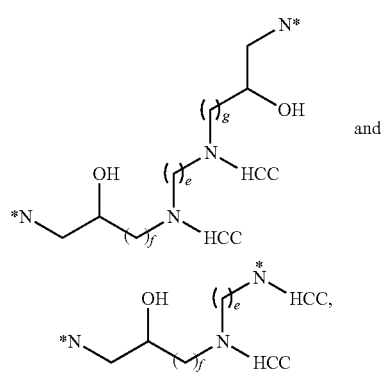

wherein each of g, e and f is an integer independently having the value between 1 and 6, inclusively, each "HCC" symbolizes a hydrocarbon chain, and each * shows a point of attachment of $R_3$ to the nitrogen atom in structure II.

According to embodiments of the invention, transfection complexes may include one or more amine-containing transfection compounds that are species within either the general structure I or the general structure II, or both. Non-limiting examples of such specific compounds are any of the following lipids 1-87 indicated above, or any isomer of each of compounds 1-87, or any combination of isomers for each of compounds 1-87:

In some embodiments, the molar percentage of the amine-containing transfection compound is from about 15% to about 50% of the lipid aggregate; in other embodiments, the molar percentage of the cationic lipid is from about 20% to about 40% of the transfection complex; in some embodiments, the molar percentage of the amine-containing transfection compound is from about 25% to about 35% of the lipid aggregate; or, in some embodiments, the molar percentage of the amine-containing transfection compound is about 33% of the lipid aggregate. In some embodiments, the molar percentage of the amine-containing transfection compound is between about 15% and about 35% of the lipid aggregate; in other embodiments, the molar percentage of the amine-containing transfection compound is between about 20% and about 30% of the lipid aggregate; or in some embodiments, the molar percentage of the amine-containing transfection compound is approximately 25% of the lipid aggregate.

In some embodiments, a transfection complex may optionally include one or more helper lipids. Illustrative though non-limiting examples of helper lipids suitable for use in the formulation of the presently described transfection complexes include cholesterols, cholesterol derivatives, sterols, including phytosterols, zoosterols and hopanoids, or any of the neutral or cationic lipids that are known to allow or to facilitate the introduction of exogenous bioactive molecules to the interior of a cell or of a tissue. In some embodiments, more than one helper lipid may be used in the formulation of the transfection complxes described herein. Exemplary though non-limiting neutral or cationic lipids contemplated for use in the preparation of the presently disclosed transfection complexes may include one or lipids selected from the following: BMOP (N-(2-bromoethyl)-N, N-dimethyl-2,3-bis(9-octadecenyloxy)-propana minimun bromide), DDPES (Dipalmitoylphosphatidylethanolamine 5-carboxyspermylamide), DSPC, CTAB:DOPE (formulation of cetyltrimethylammonium bromide (CATB) and DOPE), POPC (1-palmitoyl-2-oleoyl-sn-glycero-3-phosphocholine), DOPE (dioleoylphosphatidylethanolamine), DMG, DMAP (4-dimethylaminopyridine), DMPE (Dimyristoylphospatidylethanolamine), DOMG, DMA, DOPC (Dioleoylphosphatidylcholine), DMPC (dimyristoyl-phosphatidylcholine), DPEPC (Dipalmitoylethylphosphatidylcholine), DODAC (dioleoydimethylammonium chloride), DOSPER (1,3-Di-Oleoyloxy-2-(6-Carboxyspermyl)-Propylamid), DOTMA (N-[1-(2,3-dioleyloxy)propyl]-n,n,n-trimethylammoniumchloride), DDAB (didoceyl methylammonium bromide), DOTAP (N-[1-(2,3-dioleoyloxy)propyl]-N,N,N-trimethyl-ammonium methylsulfate), DOTAP.Cl, DC-chol (3,β-N,(N',N'-dimethylaminoethane)-carbamoyl]cholesterol), DOSPA (2-(sperminecarboxamido) ethyl)-N,N-dimethy-lammonium trifluoroacetate), DC-6-14 (O,O'-Ditetradecanoyl-N-(alphatrimethylammonioacetyl) diethanolamine chloride), DCPE (Dicaproylphosphtidyle-thanolamine), DLRIE (dilauryl oxypropyl-3-dimethylhydroxy ethylammonium bromide), DODAP (1,2-Dioleoyl-3-dimethylammonium-propane), Ethyl-PC, DOSPA (2,3-dioleoyloxy-N-[2-(sperminecarboxamidoethyl]-N,N-di-met-hyl-1-propanaminium trifluoroacetate), DOGS (dioctadecylamidoglycyl carboxyspermine), DMRIE (N-[1-(2,3 dimyristyloxy)propyl]-N,N-dimethyl-N-(2-hydroxy-ethyl) ammonium bromide), DOEPC (Dioleoylethyl-phosphocholine), DOHME (N-[1-(2,3-dioleoyloxy)propyl]-N-[1-(2-hydroxyethyl)]-N,Ndimethylammonium iodide), GAP-DLRIE:DOPE (N-(3-aminopropyl)-N, N-dimethyl-2, 3-bis(dodecyloxy)-1-propaniminium bromide/dioleyl phosphatidylethanolamine), DPPC (Dipalmitoylphosphatidylcholine), DOPG (1,2-dioleoyl-sn-glycero-3-[phospho-rac-(3-lysyl(1-glycerol)).Cl), N-lauroylsarcosine, (R)-(+)-limonene, lecithins (and derivatives thereof); phosphotidylethanolamine (and derivatives thereof); phosphatidylethanolamines, dioleoylphosphatidylethanolamine), DPhPE (diphytanoylphosphatidylethanolamine), DPPE dipalmitoylphosphatidylethanolamine), dipalmiteoylphosphatidylethanolamine, O-Chol (3 beta[1-ornithinamidecarbamoyl] cholesterol), POPE (palmitoyloleoylphosphatidylethanolamine) and distearoylphosphatidylethanolamine; phosphotidylcholine; phosphatidylcholines, DPPC (dipalmitoylphosphatidylcholine) POPC (palmitoyloleoyl-phosphatidylcholine) and distearoylphosphatidylcholine; phosphatidylglycerol; piperazine-based cationic lipids, phosphatidylglycerols, such as DOPG (dioleoylphosphatidylglycerol), DPPG (dipalmitoylphosphatidylglycerol), and distearoylphosphatidylglycerol; phosphatidylserine (and derivatives thereof); phosphatidylserines, such as dioleoyl- or dipalmitoylphosphatidylserine; diquaternary ammonium salts such as N,N'-dioleyl-N,N,N',N'-tetramethyl-1,2-ethanediamine (TmedEce), N,N'-dioleyl-N,N,N',N'-tetramethyl-1,3-propanediamine (PropEce), N,N'-dioleyl-N,N,N', N'-tetramethyl-1,6-hexanediamine (HexEce), and their corresponding N,N'-dicetyl saturated analogues (TmedAce, PropAce and HexAce), diphosphatidylglycerols; fatty acid esters; monocationic transfection lipids such as 1-deoxy-1-[dihexadecyl(methyl)ammonio]-D-xylitol; 1-deoxy-1-[methyl(ditetradecyl)ammonio]-Darabinitol; 1-deoxy-1-[dihexadecyl(methyl)ammonio]-D-arabinitol; 1-deoxy-1-[methyl(dioctadecyl)ammonio]-Darabinitol, glycerol esters; sphingolipids; cardiolipin; cerebrosides; and ceramides; and mixtures thereof. Neutral lipids also include cholesterol and other 3βOH-sterols as well as derivatives thereof phosphatidyl choline or commercially available cationic lipid mixtures such as, for example, LIPOFECTIN® CELLFEC-TIN® (1:1.5 (M/M) formulation of N, NI, NII, NIII-tetramethyl-N, NI, NII, NIII-tetrapalmitylspermine (TMTPS) and dioleoyl phosphatidylethanolamine (DOPE), LIPOFECTACE®, GS 2888 CYTOFECTIN®, FUGENE 6®, EFFECTENE®, and LIPOFECTAMINE®, LIPOFECTAMINE 2000®, LIPOFECTAMINE PLUS®, LIPOTAXI®, POLYECT®, SUPERFECT®, TFXN™ TRANSFAST™, TRANSFECTAM®, TRANSMESSENGER®, vectamidine (3-tetradecylamino-N-tert-butyl-N'-tetradecyl-propionamidine (a.k.a. diC14-amidine), OLIGOFECTAMINE®, among others. Also contemplated are any mixtures of combination of the above listed helper lipids. The following patent documents, patent applications, or references are incorporated by reference herein in their entirety and in particular for their disclosure of transfection agents containing cationic and neutral helper lipids which may be used to comprise the transfection complexes of the present invention.

The molar percentage of the helper or neutral lipid is between about 60% and about 85% of the lipid aggregate; in some embodiments, the molar percentage of the helper or neutral lipid is between about 70% and about 80% of the lipid aggregate; or, in some embodiments, the molar percentage of the helper or neutral lipid is between about 70% and about 75% of the lipid aggregate.

In some embodiments, a transfection complex may include one or more Pegylated lipids. Pegylated lipids suitable for use in the preparation and formation of transfection complexes disclosed herein can be any lipid or mixture of lipids that are compatible with the formation of transfection complexes described herein, and with the administration thereof to an animal or to a human in vivo, or to tissues or cells in vitro. The pegylated lipids used in the present invention include a PEG polymer having a molecular weight between about 250 daltons and about 12,000, or in some embodiments, about 350 daltons and about 6,000 daltons, or, in some embodiments, between about 500 daltons and about 1,000 daltons, or, in some embodiments, between about 1,000 daltons and about 2,000 daltons, or, in some embodiments, between about 2,000 daltons and 5,000 daltons. More specifically, suitable Pegylated lipids include phosphatidylethanolamine (PE) based pegylated lipids such as, for example, 1,2-dimyristoyl-sn-glycero-3-phosphoethanolamine-N-[methoxy(polyethylene glycol)-MW] where MW refers to average MW of the polyethylene glycol moiety. Such dimyristoyl-PEG-PE lipids are commonly designated 14:0 PEG (MW) PE. The average MW of the polyethylene glycol moiety can be 25, 350, 550, 750, 1000, 2000, 3000, 5000, 6000, 8000 or 12000, for example. The fatty acid chains of the phosphatidylethanolamine based pegylated lipids may include, for example, a 1,2-dioleoyl group such as for 18:1 PEG (MW) PE, a 1,2-dipalmitoyl group such as for 16:0 PEG (MW) PE, or a 1,2-distearoyl-group such as for 18:0 PEG (MW) PE. Further phosphatidylethanolamine (PE) based pegylated lipids include, for example, 1,2-distearoyl-sn-glycero-3-phosphoethanolamine-N-[MOD(polyethylene glycol)-MW], also referred to as DSPE-MOD PEG(MW) wherein MOD refers to a functional moiety such as an amine, biotin, carboxylic acid, folate, maleimide, PDP, or carboxyfluorescein moiety. The MW may be 2000 or 5000, for example. Pegylated lipids for the embodiments described herein also include ceramide based pegylated lipids such as, for example, N-octanoyl-sphingosine-1-{succinyl[methoxy(polyethylene glycol)MW]}, designated C8 PEG (MW) ceramide, where MW is 750, 2000, or 5000, for example. Alternatively, the fatty acid moiety may have an N-palmitoyl (C16) group such as for C16 PEG (MW) ceramide.

In some embodiments, the molar percentage of the pegylated lipid is between about 0.5% and 15% of the transfection complex; in some embodiments, the molar percentage of the pegylated lipid is between about 1% and about 10% of the transfection complex; or in some embodiments, the molar percentage of the pegylated lipid is approximately 1% or 5% of the transfection complex.

In some embodiments, the molar percentage of amine-containing transfection compound:helper lipid:pegylated lipid of the transfection complex ranges from 15:84:1 to 15:75:10, from 20:79:1 to 20:70:10, from 25:74:1 to 25:65:10, from 30:69:1 to 30:60:10, from 40:59:1 to 40:50:10, or from 50:49:1 to 50:40:10. In some embodiments, the molar percentage of amine-containing transfection compound: helper lipid:pegylated lipid of the transfection complex ranges from 10-90:7-35:5-70, from 15-85:5-35:8-50, from 30-85:5-35:8-50, from 35-70; 10-30:15-45, from 40-65:15-25:20-40, from 50-60:18-22:25-35, from 50-55:19-21:27-30, or from 51-53:20-20.5:28-29. Of course, it will be readily appreciated by the skilled practitioner that alternative ratios may be employed, and optimizing the ratios of such formulations is well within the skill level of such a person, without requiring undue experimentation.

Further non-limiting embodiments of the present invention provide methods for delivering a bioactive agent, such as, e.g., a polyanion, a polynucleotide or a polypeptide into a cell or cells, or into a tissue, wherein the method includes forming a lipid aggregate, such as a liposome, comprising one or more of the amine-containing transfection compounds described above, optionally with one or more helper lipids and/or one or more pegylated lipids, and contacting the lipid aggregate with the bioactive agent to form a neutral or positively charged bioactive agent-lipid aggregate complex, and incubating the complex with a cell or a tissue in vitro, or administering the resulting transfection complex to an animal or to a human, optionally as a therapeutic composition. Useful bioactive agents contemplated for such administration include proteins, peptides and nucleic acids, such as DNA or RNA.

In some embodiments, the transfection complexes may include one or more biologically active agents to be delivered to a cell or to a target tissue in vitro or in vivo. Suitable biologically active agents may include any molecule that is capable of forming a transfection complex with the presently described amine-containing transfection reagents and that elicits a biological response when delivered to the interior of a cell or cells or to a tissue in vivo or in vitro. Biologically active agents contemplated for use in the presently described embodiments may be cationic, neutral or anionic agents. By way of non-limiting example, exemplary biologically active agents suitable for formulation in a transfection complex may include, though are not limited to; nucleic acids (including but not limited to single or double stranded linear or circular DNA molecules including cDNA molecules, single or double stranded RNA molecules, small interfereing RNA (siRNA) molecules, small hairpin RNA (shRNA) molecules, microRNA (miRNA) molecules, oligonucleotides, antisense oligonucleotides, sense oligonucleotides), polypeptides, antibodies, oligopeptides, therapeutic peptides or protein molecules, peptide nucleic acids (PNAs), cationic, anionic or neutral organic molecules or drugs, in addition to pharmaceutically acceptable salts thereof.

In certain non-limiting illustrative embodiments of the invention, transfection complexes and methods are provided that use the compounds of the present invention to deliver nucleic acid molecules into cells or tissues in vitro or in vivo, including the delivery of RNA interference molecules (RNAi) or small interfering RNA molecules (siRNA, shRNA or miRNA) into cells for inhibition of gene expression.

In certain non-limiting illustrative embodiments, transfection complexes and methods are provided that use the compounds of the present invention to deliver mRNA molecules into a cell or a tissue in vivo or in vitro to promote the expression of a specific protein or proteins are also provided.

In other non-limiting illustrative embodiments of the invention, transfection complexes and methods are provided that use the compounds of the present invention to deliver DNA molecules (including cDNA molecules) into a cell or a tissue in vivo or in vitro to promote the expression of a specific protein or proteins or to synthesize specific RNA molecules, including but not limited to mRNA molecules or RNAi or miRNA or shRNA molecules are also provided.

In some embodiments, the transfection complexes described herein may optionally include one or more fusogenic or cell-penetrating peptides. A fusogenic or cell-penetrating peptide is any peptide molecule that is capable of promoting the fusion of a lipid-containing complex to a cell membrane (either a plasma membrane or an endosomal membrane). A variety of fusogenic or cell-penetrating peptides are known in the art and it is well within the skill level of a practitioner to identify suitable fusogenic or cell-penetrating peptides and condition for the use thereof in the present invention without undue experimentation.

In some embodiments, the transfection complexes described herein may optionally include one or more transfection helpers or targeting moieties. A targeting moiety may be a peptide, a modified peptide, an antibody, a modified antibody, a receptor molecule, a modified receptor molecule, a single or a double stranded nucleic acid molecule, a modified single or double stranded nucleic acid molecule, a peptide or nucleic acid aptamer, a modified peptide or nucleic acid aptamer, an organic molecule, a polysaccharide, or any other molecule that is capable of targeting a transfection complex to specific tissue or cell type for targeted delivery of a biologically agent thereto, such as will be readily apparent to have having ordinary skill level in the art. In some embodiments, modification of a peptide, an antibody, a nucleic acid, an aptamer, and the like may include conjugating the peptide, antibody, nucleic acid, aptamer, and the like to a PEG moiety. Alternatively, modification of a peptide, an antibody, a nucleic acid, an aptamer, and the like may include conjugating the peptide, antibody, nucleic acid, aptamer, and the like to a PEG-lipid moiety A variety of targeting moieties are widely known to those skilled in the art, and all are contemplated for use with the presently described embodiments, without limitation.

In some embodiments, the transfection complexes provided for herein may be stable for up to 1 year and may either be contacted with the cells or tissues to be transfected, or be administered to an animal or to a human immediately or shortly after being formed, or optionally may stored for a period of time prior to being contacted with the cells or tissues, or being administered to an animal or a human. The transfection complexes are stable and may be stored for a time period of at least 30 minutes, at least 45 minutes, at least 1 hour, at least 2 hours, at least 3 hours, at least 4 hours, at least 5 hours, at least 10 hours, at least 15 hours, at least 20 hours, at least 24 hours, at least 48 hours, at least 72 hours, at least 5 days, at least 7 days, at least 14 days, at least 28 days, at least 1 month, at least 2 months, at least 3 months, at least 4 months, at least 5 months, at least 6 months or at least 1 year at room temperature, or at a temperature greater than freezing, up to about room temperature. It is to be understood that the formulation described herein may include one or more stabilizing agents, preservatives, buffers, etc, that aid in the long-term stabilization and storage of bioactive formulation, such as will be readily understood by the skilled practitioner of the biological and pharmaceutical arts, and without requiring undue experimentation to achieve. It is also understood, that the storage period can be between any of these time periods, for example between 31 minutes and 1 hour or between 1 hour and 24 hours.

Optionally, the bioactive agent-lipid aggregate complex is stored for a period prior to being contacted with the cell or cells. The polyanion-lipid aggregate complex is stable and can be stored for a time period of at least 45 minutes, at least 1 hour, at least 2 hours, at least 3 hours, at least 4 hours, at least 5 hours, at least 10 hours, at least 15 hours, at least 20 hours, at least 24 hours, at least 48 hours, at least 72 hours, at least 5 days, at least 7 days, at least 14 days, at least 28 days, at least 1 month, at least 2 months, at least 3 months, at least 4 months, at least 5 months, at least 6 months or at least 1 year, or for a time period between any of these time periods.

The present invention is particularly suited to deliver RNAi components, including siRNA, short hairpin RNA (shRNA), microRNAs (miRNA) and small temporally regulated RNA (stRNA), which optionally are chemically modified, to cells or to tissues in vitro or in vivo.

The delivery methods employing the transfection complexes of the present invention or mixtures thereof can be applied to cells in vitro, ex vivo, and in vivo, particularly for transfection of eukaryotic cells or tissues including animal cells, human cells, non-human animal cells, insect cells, plant cells (including algae), avian cells, fish cells, mammalian cells and the like.

In some embodiments, the bioactive agent that is to be delivered into the cell is contacted with lipid aggregates of this invention to form a transfection complex comprising a bioactive agent-lipid aggregate complex. The target cell or cells or the target tissues are then incubated with the complex, or, for in vivo applications, the complex is administered to the organism by an appropriate route (e.g., intravenous, intramuscular, subcutaneous, transdermal, transmucosal, etc) so that the complex contacts the target cells or tissue. Methods for the application of transfection complexes to cells or tissue in vitro or to tissues or an animal in vivo are widely known in the art, and the use of such methods is contemplated herein without limitation for the administration of the presently described lipid transfection complexes to cell, tissues or an animal. It is well within the ability of the practitioner having ordinary skill level in the art to adapt these methods for use with the presently described compositions without departing from the spirit and the scope of the invention described herein. The compounds of may also be conjugated to or mixed with or used in conjunction with a variety of useful molecules and substances, also referred to as transfection helpers or targeting moieties, such as proteins, peptides, growth factors, antibodies, nucleic acids, aptamers, or modified versions thereof (such as, e.g., conjugating said transfection helpers or targeting moieties to PEG or PEG-lipids) and the like to enhance cell-targeting, uptake, internalization, nuclear targeting and expression, all of which are likewise within the skill level of the skilled practitioner.

A further embodiment provides a method of transfecting a cell or tissue with a nucleic acid in vivo wherein the method comprises forming a lipid aggregate, such as a liposome, comprising one or more amine-containing transfection compounds, one or more pegylated lipids and optionally one or more helper lipids, contacting the lipid aggregate with the nucleic acid to form a neutral or positively charged lipid aggregate-nucleic acid complex, and administering the lipid aggregate-nucleic acid complex to the cells or tissues in vitro or to an organism so that the complex contacts the target cells or tissue. Administration of the lipid aggregate-nucleic acid complex can be achieved orally, intravenously, or by subcutaneous or intramuscular injection or applied topically to the tissue as further described below.

Optionally, the bioactive agent-lipid aggregate complex is stored for a period prior to being contacted with the cell or cells for transfection. The polyanion-lipid aggregate complex is stable and can be stored for a time period of at least 30 minutes, at least 45 minutes, at least 1 hour, at least 2 hours, at least 3 hours, at least 4 hours, at least 5 hours, at least 10 hours, at least 15 hours, at least 20 hours, at least 24 hours, at least 48 hours, at least 72 hours, at least 5 days, at least 7 days, at least 14 days, at least 28 days, at least 1 month, at least 2 months, at least 3 months, at least 4 months, at least 5 months, at least 6 months or at least 1 year, or for a time period between any of these time periods.

In another embodiment, transfection complexes of the present invention (approximately between 5 µl and 2000 µl) are provided in the wells of a multiwell plate. Bioactive molecules to be delivered into target cells are selected and added to the wells to form polyanion-lipid aggregate complexes, which are subsequently contacted with the target cells in vitro or in vivo. The lipid aggregates can have the same composition and concentration in each well, or the lipid aggregate composition and/or concentration can vary from well to well (for example, the amount of pegylation in the lipid aggregate can vary across the wells to determine the range for delivery and transfection). Where the bioactive agents are nucleic acids such as RNAi, the nucleic acids can be added to the wells and optionally stored before contacting with the target cells.

The methods of this invention optionally comprise the step of contacting the one or more amine-containing transfection compounds with one or more helper lipids and one or more pegylated lipids before or at the same time as contacting the bioactive agent with the one or more amine-containing transfection compounds to form lipid aggregates encapsulating the bioactive agent. The methods also optionally comprise forming the lipid aggregates into liposomes prior to contact with the bioactive agent. In further embodiments, the liposomes are formed by microfluidization, extrusion or other means known in the art. In some embodiments, the bioactive agents may include nucleic acid molecules such as DNA or RNA that inhibit or promote the expression of a target gene. In some embodiments, the bioactive agent associates with a transcript of the gene to effect inhibition thereof. In some embodiments, the bioactive agent is a nucleic acid, such as a DNA an mRNA, RNAi, siRNA, shRNA, miRNA or stRNA, and is optionally chemically modified.

In another embodiment, the invention also provides medicaments prepared by combining liposome comprising one or more amine-containing transfection compounds optionally with one or more helper lipids, optionally with one or more pegylated lipids and optionally with one or more targeting moieties or transfection helpers (as described above) or a salt thereof, with a bioactive agent such as, e.g., a nucleic acid, wherein introduction of the bioactive agent into a cell or tissue modulates expression of one or more target genes therein thereby effecting at least one biological response and/or at least one therapeutic benefit. Optionally the medicament further comprises an additional excipient or pharmaceutical carrier, such as will be readily apparent to the practitioner having ordinary skill level in the pharmaceutical and/or the medical arts. In some embodiments, the bioactive agent may be a nucleic acid, such as, e.g., a DNA or RNA. In some embodiments, the nucleic acid is mRNA, RNAi, siRNA, shRNA, miRNA or stRNA, and is optionally chemically modified. In some embodiments, medicaments or pharmaceutical preparations are provided for treatment of a disease, condition, or disorder that relates to the expression of one or more genes in a cell or a tissue. Formulation of pharmacologically acceptable medicaments is known in the art. Administration of the medicament delivers an effective amount of the polyanion, for example RNA or a DNA, to the cells or tissue associated with the disease, condition, or disorder to provide amelioration of the disease, condition or disorder. By way of non-limiting examples, such medicaments can be administered orally, intravenously, or by subcutaneous or intramuscular injection or applied topically to the tissue as further described below.

The invention also provides kits for the preparation of one or more transfection complexes of the presently described invention invention. Such kits may, for example, comprise one or more liposomal compositions of this invention. Such kits typically comprise a carrier, such as a box, carton, tube or the like, having in close confinement therein one or more containers, such as vials, tubes, ampules, bottles, and the like, wherein containers contain one or more amine-containing transfection compounds, optionally with one or more helper lipids, optionally with one or more pegylated or cationic lipids (or acceptable salts thereof) in accordance with the embodiments described above, or a liposomal compositions of the present invention. The kits encompassed by this aspect of the present invention may further comprise one or more additional components (e.g., reagents and compounds) necessary or beneficial for carrying out one or more particular applications of the compositions of the present invention. In some embodiments, the kit may optionally contain one or more multiwell plates suitable for holding the lipid aggregates or transfection complexes of the present invention. In further examples, the kits may also contain one or more components useful in carrying out a desired transfection of cells. In yet further examples, the kit may also contain one or more components useful in carrying out diagnosis, treatment or prevention of a particular disease or physical disorder (e.g., one or more additional therapeutic compounds or compositions, one or more diagnostic reagents). In general kits may also contain one or more buffers, positive or negative control samples, carriers or excipients, and the like, one or more additional compositions of the invention, one or more sets of instructions, and the like.

Methods of encapsulating a bioactive agent, such as a nucleic acid, a DNA, and RNA, or the like, in a transfection complex (i.e., a lipid aggregate-bioactive agent complex) are provided as some embodiments. Such methods may include forming a lipid aggregate comprising one or more amine-containing transfection compounds, such as those represented in structures I and II and in formulae 1-87, one or more helper lipids, one or more pegylated lipids, and optionally one or more transfection helpers or targeting moieties under any one or more of the following conditions:

a1) mixing one or more amine-containing transfection compounds, at least one helper lipid, optionally more than one helper lipid and one or more pegylated lipids, or a salt thereof, in an alcohol/aqueous solution wherein the alcohol concentration is <50%;

a2) mixing one or more amine-containing transfection compounds, at least one helper, optionally more than one helper lipid and one or more pegylated lipids, or a salt thereof, in a molar percentage such that the one or more amine-containing transfection compounds are present at 15%-50%;

a3) mixing one or more amine-containing transfection compounds, at least one helper lipid, optionally more than one helper lipid and one or more pegylated lipids, or a salt thereof, in a molar percentage such that the Pegylated lipids are present at <50%; and a4) mixing one or more amine-containing transfection compounds, at least one helper lipid, optionally more tha one helper lipid and one or more pegylated lipids, or a salt thereof, wherein the pegylated lipid has a polyethylene glycol molecular weight of about 2000-12000 and a fatty acid chain length of $C_6$-$C_{20}$ alkyl, or $C_{10}$-$C_{20}$ alkenyl; and complexing the lipid aggregate in an alcohol/aqueous solution with the bioactive agent to form a transfection complex, wherein the alcohol concentration is <50%, preferably less than 40%. In some embodiments, the method includes a1) and a2), a2) and a3), a1) and a3), a2) and a4), a3) and a4), a1) and a4), or a1)-a)4, for example. In some embodiments, the alcohol is a C1-C4 alcohol. In some embodiments, the alcohol is ethanol. In some embodiments, the alcohol is a pharmaceutically acceptable alcohol such as an alcohol that is liquid at about room temperature, for example, ethanol, propylene glycol, 2-(2-ethoxyethoxy)ethanol (Transcutol™), benzyl alcohol, glycerol, polyethylene glycol 200, polyethylene glycol 300, polyethylene glycol 400 or a mixture thereof. In some embodiments, the alcohol for mixing is different than the alcohol for complexing.

Transfection complexes of embodiments described herein may be administered via the following routes for in vivo administration, for example, intravenous, intradermal, intraarterial, intraperitoneal, intralesional, intracranial, intraarticular, intraventricular, intraprostatica, intrapleural, intratracheal, intranasal, intravitreal, intravaginal, intrauterine, intrarectal, topical, intratumoral, intrathecal, intramuscular, subcutaneous, subconjunctival, intravesicular, mucosal, intrapericardial, intraumbilical, intraocular, oral, topical, local, via inhalation (e.g. aerosol inhalation), injection, infusion, continuous infusion, localized perfusion bathing target cells directly, via a catheter, via a lavage, in cremes, or by other methods or any combination of the foregoing as would be known to one of ordinary skill in the art (Remington's Pharmaceutical Sciences, 18th Ed., Mack Publishing Co. 1990).

A dosage for ex vivo or in vivo use is from 0.01 µg to 1 g/kg of body weight, 0.1 µg to 0.1 g/kg of body weight, 1 µg to 0.01 g/kg of body weight, 10 µg to 0.01 g/kg of body weight, 0.1 mg to 10 mg/kg of body weight, or ranges between and including any of 0.1 mg, 0.25 mg, 0.5 mg, 1.0 mg, 1.5 mg, 2 mg, and 10 mg/kg of body weight. Administration may be once or more per day, week, month or year. Administration may be in bolus form. Generally, an effective amount of the lipoplexes of embodiments herein is an amount sufficient to reduce expression of the targeted gene and results in an extracellular concentration at the surface of the target cell of from 100 µM to 1 µM, or from 1 nM to 100 nM, or from 2 nM to about 25 nM, or to about 10 nM. The amount required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue.

In some embodiments for in vivo administration, transfection complexes are prepared at a final concentration of 0.5-1 mg/ml. The ratio of lipid aggregate to nucleic acid is between about 0.7:1 and 1.3:1 (v:w) depending upon the targeted organ. One of ordinary skill in the art, in light of the teachings herein, is able to test various ratios of lipid aggregate to nucleic acid for in vivo administration. For example, for a 1 mg/ml lipoplex in 5% glucose, administration may be intravenous thereby targeting the lung, kidney, liver, tumor, or spleen (using 50-200 µl), intraperitoneal thereby targeting a tumor or inflammation (using 100 □l), intranasal thereby targeting the lung (using 50 µl), intratumoral or retro-orbital (local) thereby targeting the eye, a tumor, knee-joint, or the ear (using 10-100 µl), intracerebral (local) thereby targeting the brain (using 0.5-5 µl), intrathecal thereby targeting the spinal cord (using 10 µl), or hydrodynamic thereby targeting the liver, kidney, or virus (using 0.8-2.5 ml), for example.

Methods for Screening Tissue-specific Delivery

Further embodiments described herein provide for methods to screen large numbers of transfection compounds for tissue-biased delivery in vivo. Such methods may include preparing a plurality of transfection complexes containing a compound that readily facilitates the detection of a marker in combination with a test transfection compound, delivering each of the plurality of transfection complexes to a test animal, and detecting the marker.

In some embodiments, a method for screening tissue-biased delivery of a transfection complex may include preparing a plurality of transfection complexes, each transfection complex having at least one test transfection compound in combination with at least one nucleic acid that facilitates detection of delivery to a tissue. The nucleic acid may be an RNA molecule or a DNA molecule that encodes a protein that can be directly detected (such as, e.g., Green Fluorescent Protein (GFP), red Fluorescent Protein, luciferase, or the like), or encode a protein that effects expression of a protein that can be directly detected.

In an embodiment, a method for screening tissue-biased delivery of a transfection complex may include preparing a plurality of unique transfection complexes, each transfection complex having at least one test transfection compound in combination with an mRNA or a cDNA that encodes Green Fluorescent Protein. Each unique transfection complex may be delivered either intravenously, subcutaneously, or to a tissue to a test animal, such as a mouse. After a predetermined amount of time, tissues from the mouse may be harvested and the expression of GFP in various tissues may be detected by gross examination, histological examination or by molecular detection (PCR, Western blotting, or the like) to determine which to tissue or tissues transfection complexes containing specific transfection compounds are delivered to.

In an embodiment, a method for screening tissue-biased delivery of a transfection complex may include preparing a plurality of unique transfection complexes, each transfection complex having at least one test transfection compound in combination with an mRNA or a cDNA that encodes Luciferase. Each unique transfection complex may be delivered either intravenously, subcutaneously, or to a tissue to a test animal, such as a mouse. After a predetermined amount of time, tissues from the mouse may be harvested and the expression of Luciferase in various tissues may be detected by gross examination, histological examination or by molecular detection (PCR, Western blotting, or the like), or imaged in-vivo using the IVIS® Imaging System (Caliper).

In an embodiment, a method for screening tissue-biased delivery of a transfection complex may include preparing a plurality of unique transfection complexes, each transfection complex having at least one test transfection compound in combination with an mRNA or a cDNA that encodes a specific transcription factor. Each unique transfection complex may be delivered either intravenously, subcutaneously, or to a tissue to a transgenic animal that expresses a reporter gene (such as, e.g., luciferase) under the control of the specific transcription factor. After a predetermined amount of time, tissues from the transgenic animal may be harvested and the expression of reporter gene in various tissues may be detected by gross examination, histological examination or by molecular detection (PCR, Western blotting, or the like). If the reporter gene is luciferase, detection may be accomplished in-vivo using the IVIS® Imaging System (Caliper).

In one non-limiting embodiment, a method for screening tissue-biased delivery of a transfection complex may include preparing a plurality of unique transfection complexes, each unique transfection complex containing at least one unique test transfection compound in combination with an mRNA or DNA molecule that encodes Cre recombinase. The plurality of unique transfection complexes may also optionally include one or more transfection enhancers, one or more helper lipids, one or more pegylated lipids or one or more targeting moieties as described above and incorporated herein. Each of the unique transfection complexes may be delivered either intravenously (for example by tail vein injection), subcutaneously or via intra-tissue injection to a transgenic mouse that expresses a reporter gene in the presence of Cre recombinase. In an exemplary embodiment, each of the unique transfection complexes may be delivered to a transgenic mouse bearing a loxP-STOP-loxP-Luciferase gene, such as, e.g. any of the 129S6(B6)-Gt(ROSA)26 transgenic mouse strains, in which the firefly luciferase gene is inserted into the Gt(ROSA)26Sor locus. In this transgenic line, the luciferase gene is blocked by a loxP-flanked STOP sequence located in between the luciferase transgene and its promoter. In the presence of Cre recombinase (i.e., in tissues to which the Cre-mRNA or DNA containing transfection complexes are delivered) the STOP sequence is excised and luciferase is expressed.

To determine which tissues Cre luciferase is expressed in (and hence to which tissues each of the unique test transfection compound is preferentially delivered), expression of the luciferase transgene may be accomplished according to any of the widely-used techniques for assessing gene expression known to the skilled artisan (such as PCR, Northern blotting, Western blotting, or the like or directly measuring luciferase activity). In some preferred embodiments, the transgewhole mount excised tissues or histologic sections may be examined, for example, using the IVIS® In Vivo

III. EXAMPLES

The invention will be further clarified by a consideration of the following examples, which are intended to be purely exemplary of the invention and not to in any way limit its scope.

Example 1. Synthesis of 2-Bromo-N-Dodecyl Acetamide

The title intermediate was synthesized according to the following general reaction scheme:

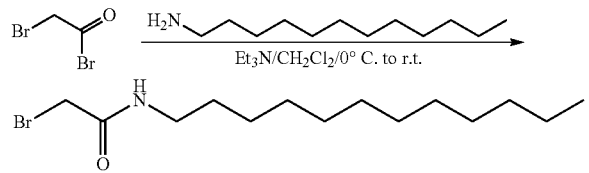

In a round bottom flask with pressure-equalizing addition funnel, to 200 mL of dichloromethane was added 1.5 g (7.431 mmol, 1.05 eq.) of bromoacetyl bromide and the mixture was stirred under nitrogen. The flask was cooled to about 0° C. using an ice bath. 1.31 g (7.077 mmol) of dodecylamine acid 0.716 (983 µL, 7.077 mmol) of triethylamine were dissolved in 100 mL of dichloromethane. This solution was transferred to the addition funnel, and bromoacetyl bromide☐ solution was slowly added within approximately 1 hour. The reaction☐ mixture was stirred for about another 1 hour at about 0° C. slowly warming to room temperature by letting the ice melt.

The resulting reaction mixture was transfer to a separatory funnel and extracted with 100 mL of saturated sodium bicarbonate solution. The aqueous layer was washed with 50 mL of dichloromethane, and the combined organic layers were washed with 100 mL of saturated sodium bicarbonate solution. Finally, the water layer was washed with 100 mL of dichloromethane. The combined organic layers were dried over sodium sulfate, filtered to remove the sodium sulfate, and the mixture was concentrated by rotary evaporator to give about 2.022 g (93.3% yield) of pure product. Molecular weight calculated: 305.14, molecular weight observed: 306.25.

Example 2. Synthesis of Tetradecyl-2-Bromoacetate

The title intermediate was synthesized according to the following general reaction scheme:

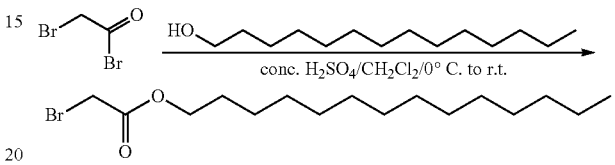

3 g (1.3 mL, 14.862 mmol, 1.05 eq.) of bromoacetyl bromide were dissolved in 50 mL of dichloromethane. The flask was cooled to about 0° C. using an ice bath. 3.03 g (14.154 mmol) of tetradecanol were dissolved in 50 mL of dichloromethane and added to the above mixture slowly via a pipettee, followed by adding about 5 drops of concentrated sulfuric acid and stirring at about 0° C. for about 30 minutes, then at room temperature overnight.

About 150 mL of saturated sodium bicarbonate solution were added and stirred rapidly for about 30 minutes. The mixture was then transferred to a separatory funnel and the organic layer is collected. The aqueous layer was washed with about 100 mL of dichloromethane. The combined organic layers were dried over sodium sulfate, filtered and concentrated to give 4.095 g (89.7% yield) of product.

No mass peak was observed. To confirm the structure a test reaction was set up as follows: 4.6 mg (0.043 mmol) of benzylamine, 17 mg (23 VaL, 0.130 mmol, 3 eq.) of N,N-Diisopropylethylamine and 22 mg (0.065 mmol, 1.5 eq.) of tetradecyl-2-bromoacetate were dissolved in 1 mL of DMF and placed in the microwave at about 160° C./200 W for 10 minutes. The resulting reaction mixture was analyzed by LCMS. Molecular weight calculated: 361.56, molecular weight observed: 362.42.

Example 3. Synthesis of Pentadecyl-4-Bromobutanoate

The title intermediate was synthesized according to the following general reaction scheme:

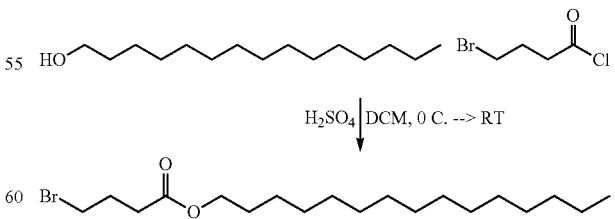

4-bromobutyl chloride (1 eq.) was dissolved in dichloromethane (50 mL) and the reaction flask was cooled to about 0° C. using an ice bath. To the above mixture, 1-pentadecanol (1 eq.) in dichloromethane (50 mL) was added slowly using a pressure-equalizing addition funnel over a period of about 30 min. To the resulting above mixture, a catalytic amount (5 drops) of concentrated sulfuric acid was added. The reaction mixture was stirred at about 0° C. for about 30 minutes and then stirred at room temperature for four hours. The reaction mixture was transferred to a separatory funnel and the organic layer was washed with saturated sodium bicarbonate (×3), water (×2), brine (×1). The organic layer was dried over sodium sulfate, filtered and concentrated to give the desired product, pentadecyl-4-bromobutanoate as colorless oil (88% yield).

No mass peak was observed. The structure of the expected product was confirmed via a test reaction: benzylamine (1 eq.), N-methylmorpholine (1 eq.), pentadecyl-4-bromobutanoate (0.9 eq.) were added to a dried heavy walled pyrex tube containing DMF (1mL). The reaction mixture was exposed to microwave irradiation (200 W) for about 10 min at about 170° C. After the irradiation, the reaction mixture was allowed to cool through an inbuilt system in the instrument until the temperature had fallen below about 30° C. The resulting reaction mixture was analyzed by LCMS. Molecular weight calculated: 403.64, molecular weight observed: 404.50.

Example 4. Synthesis of Tetradecyl 2-[3-Methylaminopropyl-(2-oxo-2-tetradecoxy-ethyl)amino]Acetate The title compound was synthesized according to the following general reaction scheme:

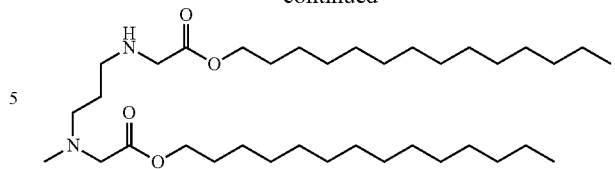

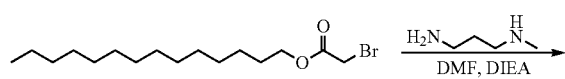

20 mg (0.227 mmol) of N-methylpropane-1,3-diamine, 160 mg (0.477 mmol, 2.1 eq.) of tetradecyl-2-bromoacetate synthesized as described in Example 2 above, and 176 mg (237 µl, 1.361 mmol, 6 eq.) of N,N-diisopropylethylamine were dissolved in 1 ml of dimethylformamide and heated to about 60° C. overnight. The resulting mixture was purified by preparative HPLC. The fractions containing the title compound were collected and characterized by LCMS. Molecular weight calculated: 596.55, molecular weight observed: 597.76.

Example 5. Synthesis of (a) 2-[2-[2-[2-[2-[bis[2-(Dodecylamino)-2-oxo-ethyl]amino]ethyl-[2-(dodecylamino)-2-oxo-ethyl]amino]ethylamino]ethyl-[2-(dodecylamino)-2-oxo-ethyl]amino]-N-dodecyl-acetamide and (b) 2-[2-[2-[2-[bis[2-(Dodecylamino)-2-oxo-ethyl]amino]ethylamino]ethylamino]ethyl-[2-(dodecylamino)-2-oxo-ethyl]amino]-N-dodecyl-acetamide The mixture of the two title compounds was synthesized according to the following general reaction scheme, showing a 4-tail title compound (a) and a 5-tail title compound (b):

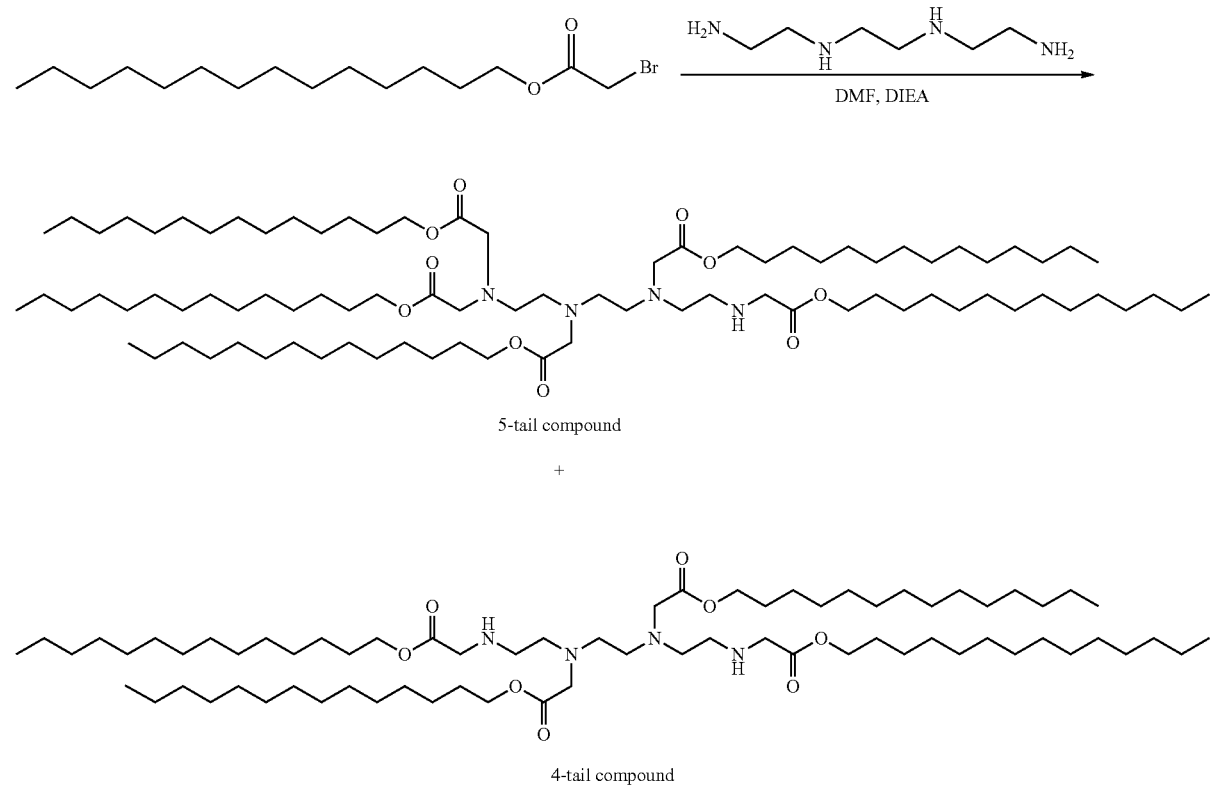

5-tail compound

+

4-tail compound 14.6 mg (0.1 mmol) of N,N'-bis(2-aminoethyl)ethane-1,2-diamine, 159 mg (0.52 mmol, 5.2 eq.) of 2-bromo-N-dodecyl acetamide obtained as described in Example 1 above, and 129 mg (174 µl, 1 mmol, 10 eq.) of N,N-diisopropylethylamine are dissolved in 1 ml DMF and heated to about 60° C. overnight. The resulting mixture is purified by preparative HPLC.

2-[2-[2-[2-[bis[2-(dodecylamino)-2-oxo-ethyl] amino]ethylamino]ethylamino]ethyl-[2-(dodecylamino)-2-oxo-ethyl] amino]-N-dodecyl-acetamide (4-tail compound shown above) and 2-[2-[2-[2-[bis[2-(dodecylamino)-2-oxo-ethyl] amino]ethyl-[2-(dodecylamino)-2-oxo-ethyl] amino]ethylamino]ethyl-[2-(dodecylamino)-2-oxo-ethyl] amino]-N-dodecyl-acetamide (5-tail compound shown above) were collected and characterized by LCMS.

For the 4-tail compound: molecular weight calculated is 1046.99, molecular weight observed was 1048.28. For the 5-tail compound: molecular weight calculated is 1272.20, molecular weight observed was 1273.50.

Example 6. Synthesis of Pentadecyl-4-Bromobutanoate

The title intermediate was synthesized according to the following general reaction scheme:

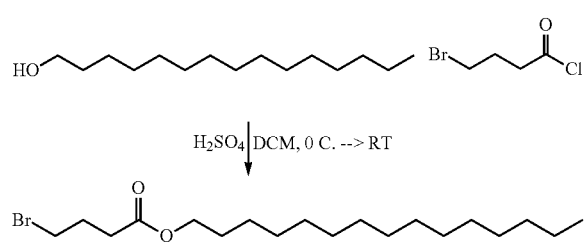

4-bromobutyl chloride (1 eq.) was dissolved in dichloromethane (50 mL) and the reaction flask was cooled to about 0° C. using an ice bath. To the above mixture, 1-pentadecanol (1 eq.) in dichloromethane (50 mL) was added slowly using a pressure-equalizing addition funnel over a period of about 30 min. To the resulting above mixture, a catalytic amount (5 drops) of concentrated sulfuric acid was added. The reaction mixture was stirred at about 0° C. for about 30 minutes and then stirred at room temperature for four hours. The reaction mixture was transferred to a separatory funnel and the organic layer was washed with saturated sodium bicarbonate (×3), water (×2), brine (×1). The organic layer was dried over sodium sulfate, filtered and concentrated to give the desired product, pentadecyl-4-bromobutanoate as colorless oil (88% yield).

No mass peak was observed. The structure of the expected product was confirmed via a test reaction: benzylamine (1 eq.), N-methylmorpholine (1 eq.), pentadecyl-4-bromobutanoate (0.9 eq.) were added to a dried heavy walled pyrex tube containing dimethylformamide (1 mL). The reaction mixture was exposed to microwave irradiation (200 W) for 10 min at 170° C. After the irradiation, the reaction mixture was allowed to cool through an inbuilt system in the instrument until the temperature had fallen below 30° C. The resulting reaction mixture was analyzed by LCMS. Molecular weight calculated: 403.64, molecular weight observed: 404.50.

Example 7. Synthesis of 4-Bromo-N-Dodecylbutanamide

The title intermediate was synthesized according to the following general reaction scheme:

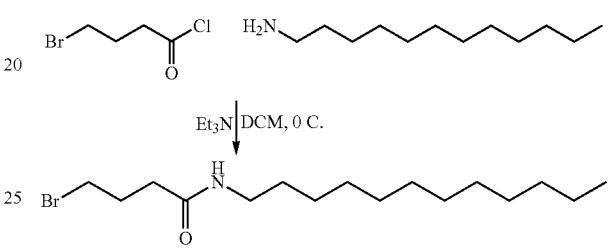

4-bromobutanoyl chloride (1.05 eq.) was added in a round bottom flask containing dichloromethane (200 mL) at about 0° C. fitted with a pressure-equalizing addition funnel and stirred under nitrogen. Separately, dodecylamine (1 eq.) and triethylamine (1 eq.) were dissolved in dichloromethane (100 mL) and the mixture was transferred to the addition funnel. This mixture was added very slowly to a round bottom flask over a period of about 60 minutes. After the completion of the addition, the reaction mixture was stirred for another 15 minutes at about 0° C. and transferred to a separatory funnel. The organic layer was washed with saturated sodium bicarbonate (×3), water (×2) and brine (×1). The organic layer was dried over sodium sulfate, filtered and concentrated to give the desired product, 4-Bromo-N-dodecylbutanamide as white solid (88.7% yield). Molecular weight calculated: 333.17, molecular weight observed: 334.31.

Example 8. Synthesis of a) Dipentadecyl 4,4'-(3-(methyl(4-oxo-4-(pentadecyloxy)butyl)amino)propylazanediyl)Dibutanoate and b) Pentadecyl 4-(methyl(3-(4-oxo-4-(pentadecyloxy)butylamino)propyl)amino)Butanoate The mixture of the two title compounds was synthesized according to the following general reaction scheme:

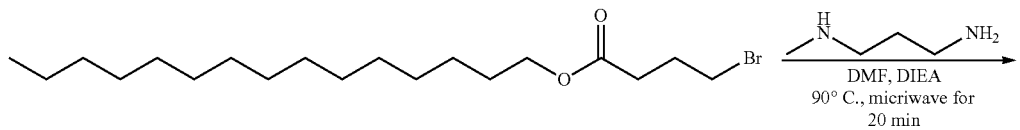

-continued

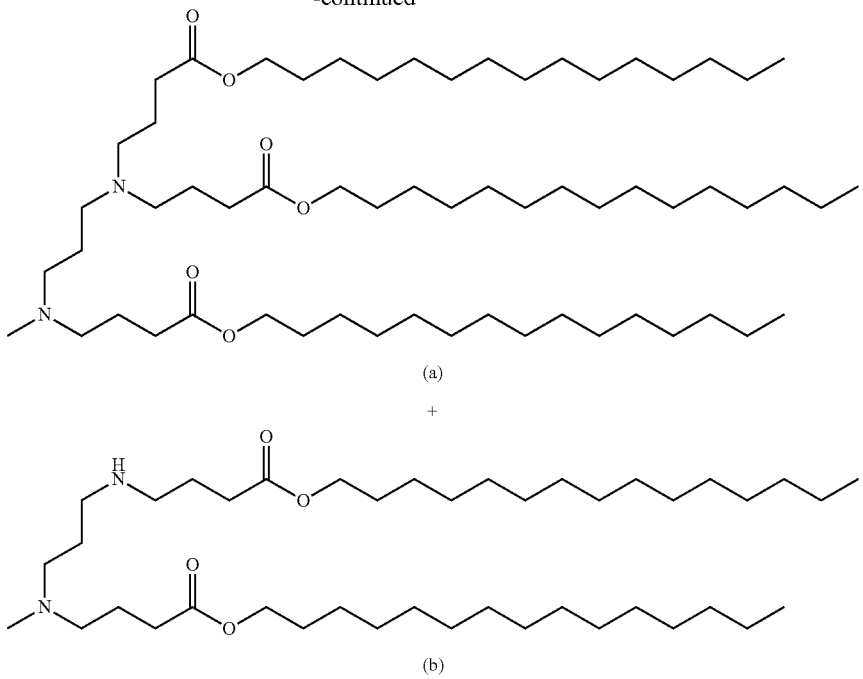

(a)

+

(b)

A dry microwave reaction synthesis vessel containing a small magnetic stir bar was charged with N1-methylpropane-1,3-diamine (42 mg, 0.48 mmole), pentadecyl-4-bromobutanoate (2.1 eq), N,N-diisopropylethyl amine (2.1 eq.) and dimethylformamide (1.0 mL). The vessel was sealed and the reaction mixture was heated up to 90° C. in a CEM microwave synthesizer. After about 20 minutes, the reaction was stopped and the vessel was allowed to cool down to about 40° C. The analytical LCMS traces of the reaction crude showed the formation of the desired products. The crude material was purified by preparative LCMS.

All the fractions containing the desired products were carefully selected and pooled. The solvent of each fraction was dried down to half of the original volume under reduced pressure followed by the addition of 1M HCl in methanol (1.0 mL). Finally, all the solvent was removed under vacuum affording the hydrochloric acid salts of the title compounds (a) and (b) shown on the reaction scheme above as white solids.

For compound (a): molecular weight calculated is 976.91, molecular weight observed was 977.91. For compound (b): molecular weight calculated is 680.64, molecular weight observed was 681.64.

Example 9. Preparation of Lipid Compositions for In Vivo Delivery

Some lipids of the present invention were formulated into lipid compositions, which also comprise cholesterol, poly (ethylene glycol) (PEG) lipids, buffers and ethanol. Animal origin-free cholesterol was purchased from Sigma-Aldrich (St Louis, Mo.), 1,2-dipalmitoyl-sn-glycero-3-phosphoethanolamine-N-[methoxy(polyethylene glycol)-2000](ammonium salt) (C16 PEG2000 PE) and 1,2-dimyristoyl-sn-glycero-3-phosphoethanolamine-N-[methoxy(polyethylene glycol)-2000] (ammonium salt) (C14 PEG2000 PE) were purchased from Avanti Lipids (Alabaster, Ala.). The RNAi was STEALTH™RNAi having 25-base-pair double-stranded RNA oligonucleotides with stabilizing chemical modifications. STEALTH™RNAi is commercially available from Invitrogen (Carlsbad, Calif.).

Dry powder lipids were re-suspended in ethanol and the cationic lipid: cholesterol and a PEG lipid were mixed at a weight ratio of 52:20:28 respectively. The lipid ethanolic mixture was mixed very rapidly in 200 mM Sodium Acetate pH 5.2 solution at a 1:4 ratio. The final formulation (i.e., the total the lipid of the invention plus PEG lipid plus cholesterol) was sterile filtered on a 0.22 μm filter and has a concentration of 15.625 mg/ml and size 50-80 nm in 50 mM Sodium acetate and 25% Ethanol (preliposomes). The formulations that were made are described in Table 1.

TABLE 1

| Lipid Formulations | | | | | |
|---|---|---|---|---|---|
| Compound of the Invention*⁾ | PEG Lipid | Helper Lipid | Buffer | Ethanol, % | Concentration, mg/ml |
| 49 | C16 PEG2000 PE | Cholesterol | 50 mM Sodium Acetate | 25 | 15.625 |
| 7 | C16 PEG2000 PE | Cholesterol | 50 mM Sodium Acetate | 25 | 15.625 |

TABLE 1-continued

| | | Lipid Formulations | | | |
|---|---|---|---|---|---|
| Compound of the Invention*) | PEG Lipid | Helper Lipid | Buffer | Ethanol, % | Concentration, mg/ml |
| 69 | C14 PEG2000 PE | Cholesterol | 50 mM Sodium Acetate | 25 | 15.625 |
| 70 | C14 PEG2000 PE | Cholesterol | 50 mM Sodium Acetate | 25 | 15.625 |
| 51 | C14 PEG2000 PE | Cholesterol | 50 mM Sodium Acetate | 25 | 15.625 |
| 52 | C14 PEG2000 PE | Cholesterol | 50 mM Sodium Acetate | 25 | 15.625 |
| 54 | C14 PEG2000 PE | Cholesterol | 50 mM Sodium Acetate | 25 | 15.625 |
| 56 | C16 PEG2000 PE | Cholesterol | 50 mM Sodium Acetate | 25 | 15.625 |
| 57 | C16 PEG2000 PE | Cholesterol | 50 mM Sodium Acetate | 25 | 15.625 |
| 73 | C16 PEG2000 PE | Cholesterol | 50 mM Sodium Acetate | 25 | 15.625 |
| 76 | C16 PEG2000 PE | Cholesterol | 50 mM Sodium Acetate | 25 | 15.625 |
| 77 | C16 PEG2000 PE | Cholesterol | 50 mM Sodium Acetate | 25 | 15.625 |

*)Numbers refer to the numbers of specific compounds of the instant invention shown above The lipoplex (siRNA preliposome complex) was prepared by mixing equal volumes of preliposome and STEALTH™RNAi solution diluted to 1.5 mg/ml in water and 25% ethanol. After mixing, the complex was incubated at about 50° C. for about 30 minutes. After incubation, the lipoplex was Dialysed for about 2 hours in 1 liter PBS 1×pH7.4 using SPECTRA/POR® FLOAT-A-LYZER® G2 8KDa. After dialysis the volume was measured and adjusted with PBS to the desired siRNA concentration. The lipoplex was incubated at about 4° C. until in vivo tail vein injection.

Mice were used at ages from 4 to 6 weeks. RNAi against Factor VII (FVII) mouse gene having the Antisense sequence 5'-AUUUGCACAGAUCAGCUGCUCAUUC-3' and the negative control Medium GC content-RNAi were complexed with pre-liposomes as previously described and tested invivo. 200 µl of lipoplexes containing FVII or CTRL RNAi in PBS were injected per 20 g mouse, by low pressure tail vein injection at a dose of 10 mg/kg and 2 mg/kg (siRNA dose). Thirty six hours after tail vein injection liver tissue and serum was collected for mRNA and protein knock down analysis respectively.

Frozen liver tissue was ground into powder and RNA was extracted using TRIZOL® PLUS RNA Purification System (Invitrogen). Total RNA (about 750 ng) for the first strand synthesis was determined using SUPERSCRIPT® III RT kit (Invitrogen) and QPCR analysis was performed using taqman assay using EXPRESS qPCR Supermix Universal (cat #11785-01K).

Factor VII serum protein level was determined as follows. Animals were anesthetized by intramuscular injection of Ketamine/xylazine/Acepromazine (75/5/1 mg/kg respectively), blood was collected by retroorbital bleed, and serum was processed to measure Factor VII protein level using a chromogenic assay (Biophen FVII, Aniara Corporation) according to manufacturers' protocols.

FIG. 1 provides a graph summarizing the relative % of Factor VII protein remaing activity, as measured by chromogenic assay, of the different lipoplex formulations in liver. Referring to the x axis, the numbers refer to the cationic lipid compounds tested, as shown in Table 1. The data demonstrate that such formulations do possess activity in vivo. No knockdown was observed when the CTRL negative control was injected in the liver.

Figure 2:
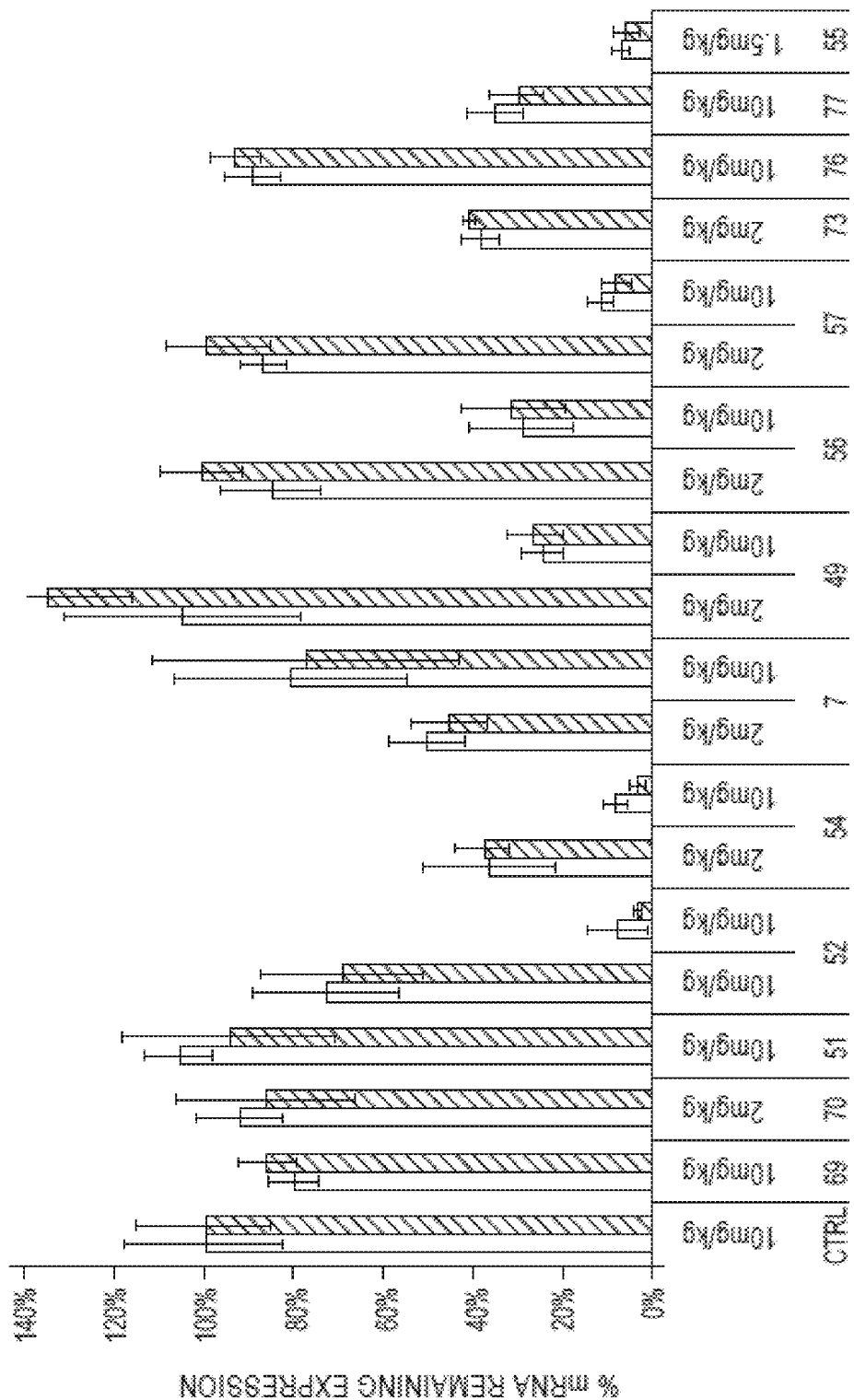
FIG. 2 shows a graph depicting some properties of a lipid composition prepared using compounds according to other embodiments of the present invention.

FIG. 2 provides a graph summarizing the relative % of mRNA Factor VII as measured by qRT-PCR using 2 Taqman assays. In each pairs of bars shown on FIG. 2, the left-hand bar referes to Taqman 29 assay and the right hand bar refers to Taqman 33 assys. The numbers along the x axis refer to the cationic lipid compounds tested, as shown in Table 1. The data demonstrate that such formulations do possess activity in vivo. No knockdown was observed when the CTRL negative control was injected in the liver.

Example 10. Preparation of Lipid Compositions

The following set of experiments were performed essentially as described above in EXAMPLE 9, with the following exceptions. The dialysis step performed after formation of the siRNA/lipoplex was not performed. Additionally, the dry powder weight ratios of the IVF 2.0, 57 NO, and 84 NO samples was 37.8:10.4:51.8, and the dry powder weight ratios of 57 OPT, 72 OPT and 84 OPT samples was 60:7:33. The formulations that were made are described in Table 2.

TABLE 2

| | | Lipid Formulations | | | |
|---|---|---|---|---|---|
| Compound of the Invention*) | PEG Lipid | Helper Lipid | Buffer | Ethanol, % | Concentration, mg/ml |
| IVF2.0 | C16 PEG2000 PE | Cholesterol | 139.5 mM Sodium Acetate | 25 | 15.625 |

TABLE 2-continued

Lipid Formulations

| Compound of the Invention*) | PEG Lipid | Helper Lipid | Buffer | Ethanol, % | Concentration, mg/ml |
|---|---|---|---|---|---|
| 57 NO (CB00396) | C16 PEG2000 PE | Cholesterol | 139.5 mM Sodium Acetate | 25 | 15.625 |
| 57 OPT (CB00396) | C14 PEG2000 PE | Cholesterol | 139.5 mM Sodium Acetate | 25 | 15.625 |
| 72 OPT (CB00401) | C14 PEG2000 PE | Cholesterol | 139.5 mM Sodium Acetate | 25 | 15.625 |
| 84 NO (CB00416) | C14 PEG2000 PE | Cholesterol | 139.5 mM Sodium Acetate | 25 | 15.625 |
| 84 OPT (CB00416) | C14 PEG2000 PE | Cholesterol | 139.5 mM Sodium Acetate | 25 | 15.625 |

Figure 3:
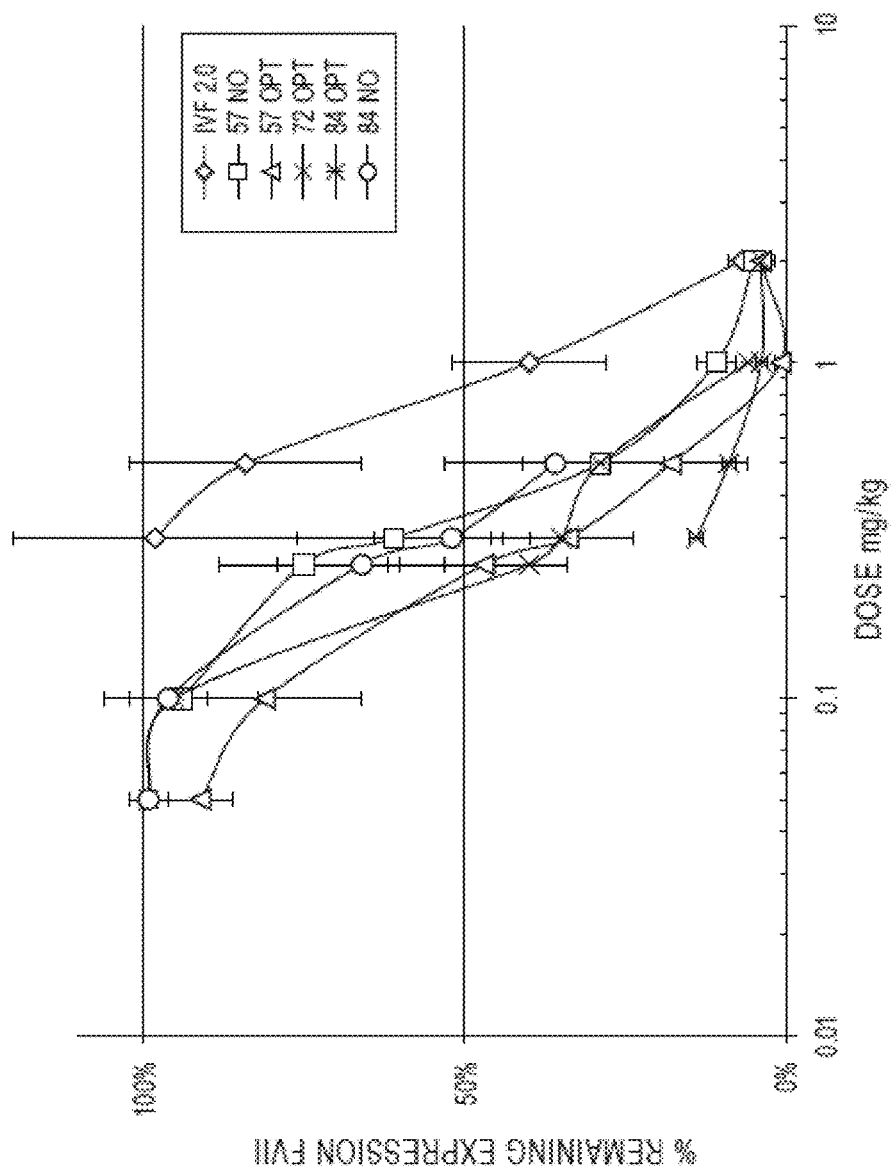
FIG. 3 shows a graph depicting some properties of a lipid composition prepared using compounds according to other embodiments of the present invention.

*)Numbers refer to the numbers of specific compounds of the instant invention shown above FIG. 3 provides a graph summarizing the relative % of Factor VII mRNA as measured by qRT-PCR as described above. The results are normalized and are expressed as a % remaining FVII expression (y axis) as a function of administered dosage (mg/kg body weight).

Example 11. Preparation of Lipid Compositions for In Vitro Delivery

Some lipids of the present invention were formulated into lipid compositions, which also comprise cholesterol or DOPE, buffers and ethanol. Animal origin-free cholesterol was purchased from Sigma-Aldrich (St Louis, Mo.) and DOPE was purchased from Avanti Lipids (Alabaster, Ala.). Silencer® Select CSNK2A1 siRNA and Silencer® Select negative control siRNA (cat #4390824 siRNA id #s3637 and cat #4390843) having the antisense sequence AAACUAUAAUCGUACAUCUGA and UUACGUCGUCGCGUCGUUATT, respectively, were resuspended with nuclease-free water to a stock concentration of 50 µM, which were further diluted to meet downstream experiments and is commercially available from Life Technologies (Carlsbad, Calif.).

For compounds 83 and 67, the dry powder lipids were re-suspended in ethanol at a final concentration of 1 mg/ml and either used as lipid alone (Compound 83) or combined with cholesterol in 1:0.5 ratio (Compound 67). The formulations tested were made as described in Table 3

TABLE 3

Lipid Formulations

| Compound of the Invention* | Helper Lipid | Ethanol, % |
|---|---|---|
| 83 | None | 100 |
| 67 | Cholesterol | 100 |

*Numbers refer to the numbers of specific compounds of the instant invention shown above Primary rat cortex neuronal cells were purchased from GIBCO (Cat. No. A10840) and maintained in Neurobasal™ medium (cat #21103-049) supplemented with 2% B-27® Serum-free (50× cat #17504-044) and 0.5 mM GlutaMAX™ (cat #35050-061). Primary rat hippocampal neuronal cells were purchased from GIBCO (Cat. No. A10841) and maintained in Neurobasal™ medium (cat #21103-049) supplemented with 2% B-27® Serum-free (50× cat #17504-044), 0.5 mM GlutaMAX™ (cat #35050-061) and 25 µM L-Glutamate (Sigma cat # G-2834). Hela cells were purchased from ATCC (ATCC # CCL-2) and maintained DMEM, high glucose, GlutaMAX™, pyruvate (cat #10569-010) supplemented with 10% fetal bovine serum, US certified, heat inactivated (cat #10082-139) without antibiotics Neuronal cells were plated in 96-well plates coated poly-d-lysine two days before transfection at 10K cells/well. Hela cells were plated in 96-well plates one day prior to transfection at 25K/well. siRNAs (3 pmol) were diluted 20 ul nuclease-free water at a final concentration of 30 nM in 1.5 mL tubes. Master mixes were made to cover all wells to be transfected for each siRNA. Lipid dilutions were prepared by pipetting 0.15, 0.3 and/or 0.6 µl/well or 0.3 ul LIPO-FECTAMINE™ RNAiMAX as a control in Opti-MEM® I in total final volume of 10 µl/well. The lipid and siRNA complexes were prepared by adding 10 ul of the lipid mixture to 20 µl of diluted siRNA. The complexes were mixed by pipetting up and down and incubated at room temperature for 10 minutes. After the 10 minute incubation, 30 µl of the complex was then added to the pre-plated cells containing 120 ul of growth medium cultured in 96-well plates containing 150 ul. After 24 hours, cells were harvested with the TaqMan® Gene Expression Cells-to-CT™ kit (cat #AM1728, Life Technologies) according to the manufacturer's protocol. After cells were lysed, reverse transcription (RT) reactions were set-up followed by real-time PCR using TaqMan Gene Expression assays for the target gene of interest (CSNK2A1 (Hs00953536_m1 for human or Rn00587582_m1for rat)) and eukaryotic 18s rRNA (4333760T) was used as the endogenous control.

Figure 4:
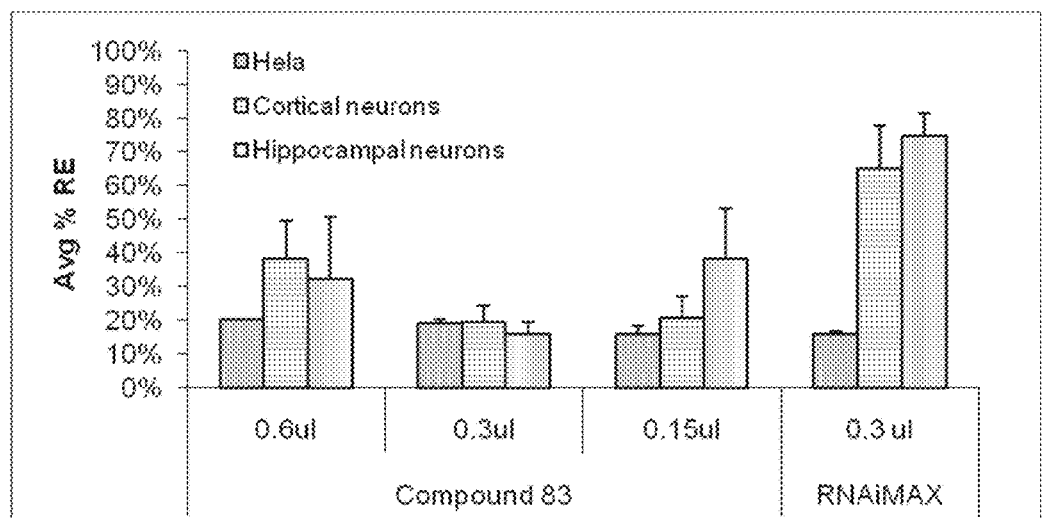
FIG. 4 shows a graph depicting some properties of a lipid composition prepared using compounds according to other embodiments of the present invention.

FIG. 4 depicts a graph summarizing the relative percent of CSNK2A1 remaining activity normalized to negative control as measured by qPCR assay of the Compound 83 lipoplex formulations in HeLa cells, rat primary cortical neurons and rat primary hippocampal neurons. Referring to the x axis, the numbers refer to the final volume of cationic lipid formulation summarized in Table 3 for each well.

Figure 5:
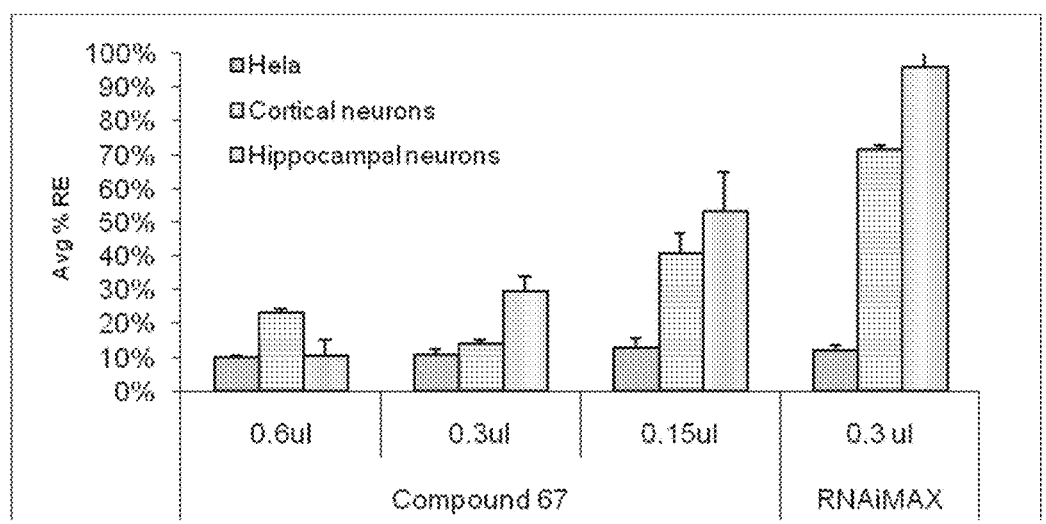
FIG. 5 shows a graph depicting some properties of a lipid composition prepared using compounds according to other embodiments of the present invention.

FIG. 5 provides a graph summarizing the relative percent of CSNK2A1 remaining activity normalized to negative control, as measured by qPCR assay of Compound 67 lipoplex formulations in Hela, primary cortical neurons and primary hippocampal neurons. Referring to the x axis, the numbers refer to the final volume of cationic lipid per well tested, as shown in Table 3. The data demonstrate that such formulations do possess activity in vitro.

The above results demonstrate that the formulation s described above are efficient at introducing siRNA molecules to various organs in animals in vivo as well as to animal and human cells cultured in vitro.

Example 12. Delivery of mRNA and Expression In Vivo

Preparation of Transfection Lipids

Cationic lipid 87 (shown above) was synthesized at Life Technologies, Carlsbad, Calif. according to methods described herein; Animal origin-free Cholesterol was purchased from Sigma-Aldrich (StLouis), 1,2-dipalmitoyl-sn-glycero-3-phosphoethanolamine-N-[methoxy(polyethylene glycol)-2000] (ammonium salt) (C16PEG)) was purchased from Avanti Lipids Alabaster. CB547, Cholesterol and C16PEG were diluted in 100% ethanol at 40° C. The lipid mixture was then mixed in 200 mM Sodium Acetate, pH 5.2 using a syringe equipped with a 27 G needle at a flow rate of 20 ml/minute. The formulation was then stored at 4° C.

Preparation of CRE mRNA

The cDNA sequence for CRE that was used in the experiments set forth below was as follow:

TTGGACCCTCGTACAGAAGCTAATACGACTCACTATATGGGCGGTAGGCG

TGTACGGTGGGAGGTCTATATAAGCAGAGCTCGCAACTTTTCTATACAAA

GTTGCTATGGGCCCAAAGAAGAAGAGAAAGGTTTCGAATTTACTGACCGT

ACACCAAAATTTGCCTGCATTACCGGTCGATGCAACGAGTGATGAGGTTC

GCAAGAACCTGATGGACATGTTCAGGGATCGCCAGGCGTTTTCTGAGCAT

ACCTGGAAAATGCTTCTGTCCGTTTGCCGGTCGTGGGCGGCATGGTGCAA

GTTGAATAACCGGAAATGGTTTCCCGCAGAACCTGAAGATGTTCGCGATT

ATCTTCTATATCTTCAGGCGCGCGGTCTGGCAGTAAAAACTATCCAGCAA

CATTTGGGCCAGCTAAACATGCTTCATCGTCGGTCCGGGCTGCCACGACC

AAGTGACAGCAATGCTGTTTCACTGG

TTATGCGGCGGATCCGAAAAGAAAACGTTGATGCCGGTGAACGTGCAAA

CAGGCTCTAGCGTTCGAACGCACTGATTTCGACCAGGTTCGTTCACTCAT

GGAAAATAGCGATCGCTGCCAGGATATACGTAATCTGGCATTTCTGGGGA

TTGCTTATAACACCCTGTTACGTATAGCCGAAATTGCCAGGATCAGGGTT

AAAGATATCT

CACGTACTGACGGTGGGAGAATGTTAATCCATATTGGCAGAACGAAAACG

CTGGTTAGCACCGCAGGTGTAGAGAAGGCACTTAGCCTGGGGGTAACTAA

ACTGGTCGAGCGATGGATTTCCGTCTCTGGTGTAGCTGATGATCCGAATA

ACTACCTGTTTTGCCGGGTCAGAAAAAATGGTGTTGCCGCGCCATCTGCC

ACCAGCCAGC

TATCAACTCGCGCCCTGGAAGGGATTTTTGAAGCAACTCATCGATTGATT

TACGGCGCTAAGGATGACTCTGGTCAGAGATACCTGGCCTGGTCTGGACA

CAGTGCCCGTGTCGGAGCCGCGCGAGATATGGCCCGCGCTGGAGTTTCAA

TACCGGAGATCATGCAAGCTGGTGGCTGGACCAATGTAAATATTGTCATG

AACTATATCCGTAACCTGGATAGTGAAACAGGGGCAATGGTGCGCCTGCT

GGAAGATGGCGATTAGACATAGCAGCAATTGGCAAGCTGCTTATATAGAA

CTTGCGGCGATTGGCA

TGCCGCTTTAAAATTTTATTTTATTTTCTTTTCTTTTCCGAATCGGATAC

ATAGCAGCAATTGGCAAGCTGCTTATATAGAACTTGCGGCGATTGGCATG

CCGCTTTAAAATTTTATTTTATTTTCTTTTCTTTTCCGAATCGGATACAT

AGCAGCAATTGGCAAGCTGCTTATATAGAACTTGCGGCGATTGGCATGCC

GCTTTAAAATTTTATTTTATTTTCTTTTCTTTTCCGAATCGGATACATAG

CAGCAATTGGCAAGCTGCTTATATAGAACTTGCGGCGATTGGCATGCCGC

TTTAAAATTTTATTTTATTTTCTTTTCTTTTCCGAATCGGATACATAGCA

GCAATTGGCAAGCTGCTTATATAGAACTTGCGGCGATTGGCATGCCGCTT

TAAAATTTTATTTTATTTTCTTTTCTTTTCCGAATCGGATACATAGCAGC

AATTGGCAAGCTGCTTATATAGAACTTGCGGCGATTGGCATGCCGCTTTA

AAATTTTATTTTATTTTCTTTTCTTTTCCGAATCGGAT

A DNA plasmid containing the cDNA sequence was synthesis (GENEART® Gene Synthesis) and cloned into a plasmid DNA vector.

Purified plasmid DNA is digested with Ase I restriction enzyme (New England Biosciences, Cat. No. R0526) according to manufacturer's protocol. The linearized DNA was purified using PureLink™ PCR purification kit (Life Technologies, Cat. No. K310001) according to manufacturer's protocol, and eluted with purified water. DNA concentration was determined by UV absorbance. The Promega RiboMAX™ Large Scale RNA production System-T7 (Cat. No. P1300) was utilized to synthesize mRNA according to manufacturer's protocol. In each reaction, 5-10 μg of linearized DNA yielded 200-250 μg of mRNA. Following synthesis, mRNA was purified using phenol:chloroform extraction followed by ethanolic precipitation. The mRNA product was resuspended in purified water and the concentration was determined. The mRNA was capped utilizing ScriptCap™ m$^7$G Capping System (Cat. No. C-SCCE0625) and ScriptCap™ 2'-O-Methyltransferase Kit (Cat. No. C-SCMT0625), both from CellScript™. The capped mRNA was polyadenylated using Epicentre® Poly(A)Polymerase Tailing Kit (Cat. No. PAP5104H). The final product is purified again via phenol:chloroform extraction followed by nucleic acid precipitation. The purified mRNA is resuspended in purified water and concentration determined. Concentration was adjusted to 3 mg/ml in water and stored at −80° C.

Preparation of Transfection Complexes Containing Lipid 87 and Cre mRNA

Concentration of mRNA synthesized in the previous step was adjusted to 0.3 mg/ml in water containing 25% ethanol. The lipoplex (mRNA preliposome complex) was prepared by mixing equal volumes of preliposome and mRNA solution. After mixing, the complex was incubated at 50° C. for 30 minutes, then dialysed for 2 hours in 1 liter phosphate buffered saline (PBS), pH 7.4 using Spectra/Por® Float-A-Lyzer® G2 8 kDa. After dialysis, the volume was measured and adjusted with PBS to the desired mRNA concentration. The lipoplex was stored at 4° C. until in vivo injection.

Intravenous Injection of Invivofectamine-547 mRNA Complex.

All procedures used in animal studies were approved by the Institutional Animal Care and Use Committee (IACUC) and were consistent with local, state and federal regulations as applicable Mice were purchased from Jackson laboratories (B6.129S4-Gt(ROSA)26Sor$^{tm3(CAG-luc)Tyj}$/J). This mouse bears a CMV driven luciferase reporter gene with a loxP-flanked STOP codon under the control of a CMV promoter. In the presence of Cre recombinase, the loxP sites recombine to excise the STOP codon, thereby allowing translation of the luciferase reporter protein.

For the lacZ experiments, mice aged from 4 to 6 weeks carrying lacZ gene (B6.129S4-Gt(ROSA)26Sor$^{tm1Sor}$/J) were purchased. Expression of lacZ was determined by qRT-PCR using standard methods. Two 200 µl of lipoplex containing mRNA CRE in PBS prepared as described above were injected per mouse by low pressure tail vein injection at a dose of 1.5 mg/kg and 0.5 mg/kg (mRNA dose). For luminescence imaging, mice received 150 mg of firefly luciferase (Biosynth AG, Staad, Switzerland) per kg body weight given i.p. After anesthesia with isoflurane gas (Abbott Laboratories, North Chicago, Ill.), the mice were placed into a Xenogen IVIS imaging station (Xenogen Corp., Alameda, Calif.) and imaged using Living Image Software (Xenogen Corporation).

Figure 6A:
FIGS. 6 A and 6B shows whole animal and whole tissue mount images depicting some properties of a lipid composition prepared using compounds according to other embodiments of the present invention.

FIG. 6A shows whole body images of mice treated with a transfection complex containing Cre mRNA and lipid 87 at 1.5 mg/kg (left), 0.5 mg/kg (middle) or PBS (right). Luciferase expression was measured using Xenogen IVIS and signal was quantified.

Figure 6B:
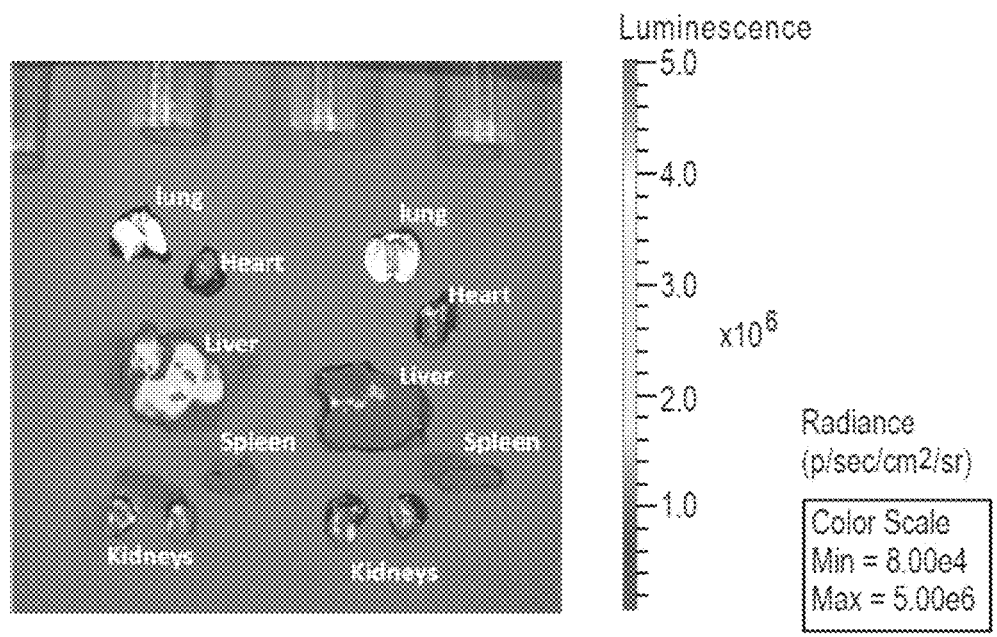
Figure 7A:
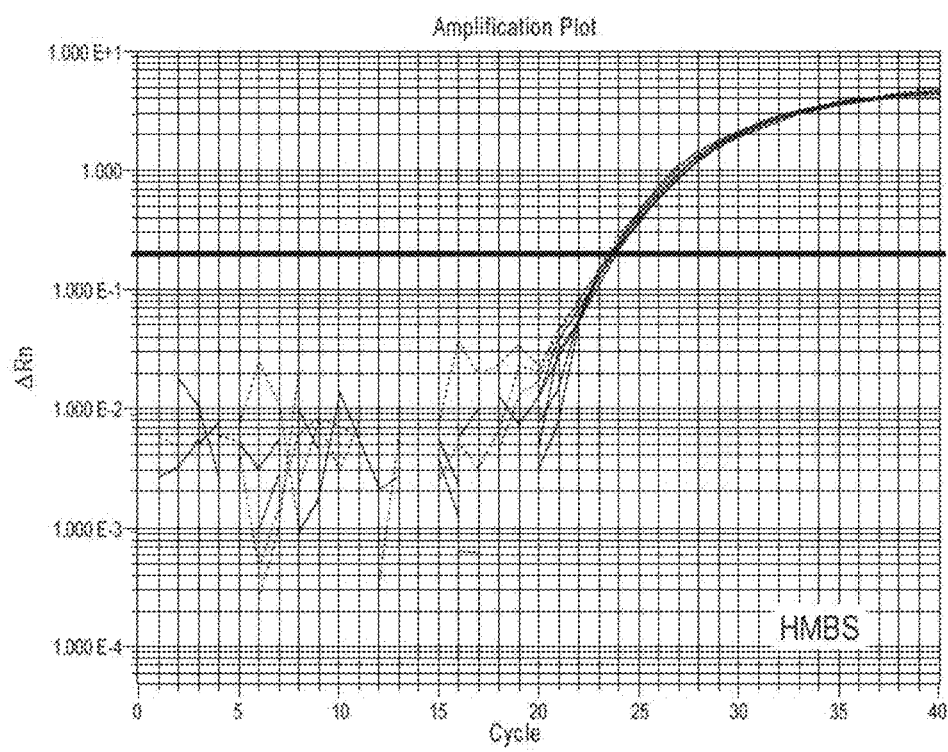
FIG. 7A-7F show graphs depicting some properties of a lipid composition prepared using compounds according to other embodiments of the present invention.
Figure 7B:
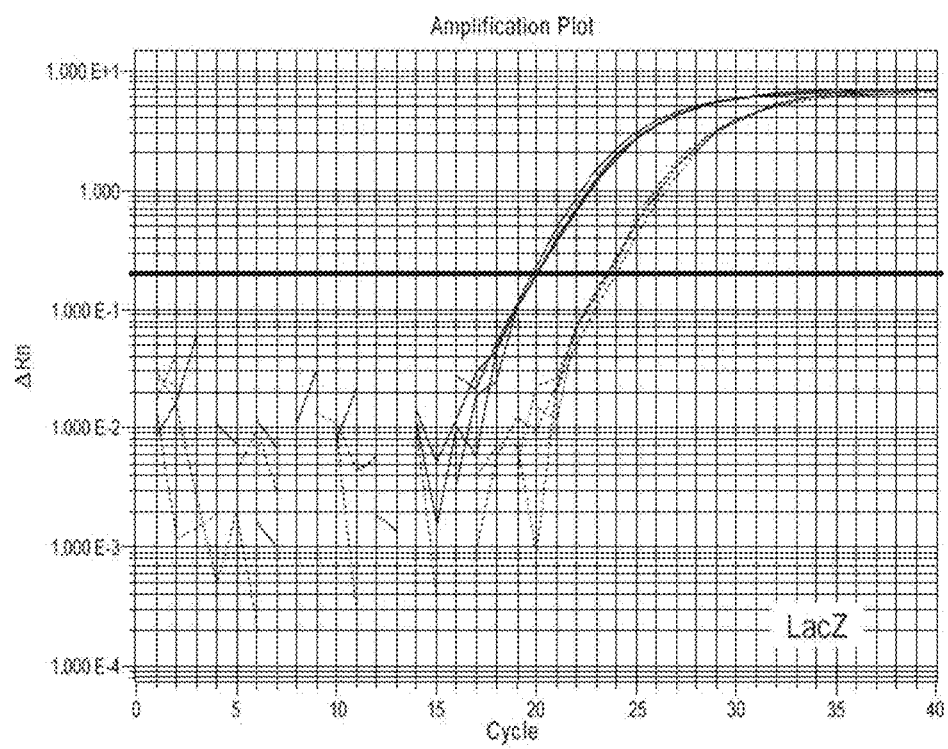
Figure 7C:
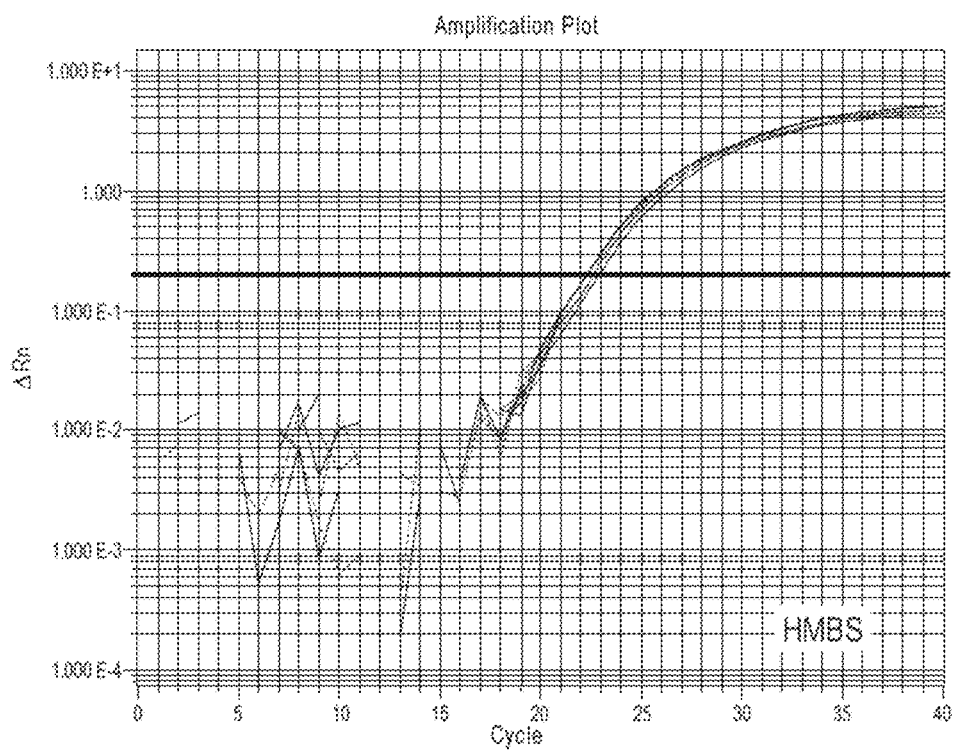
Figure 7D:
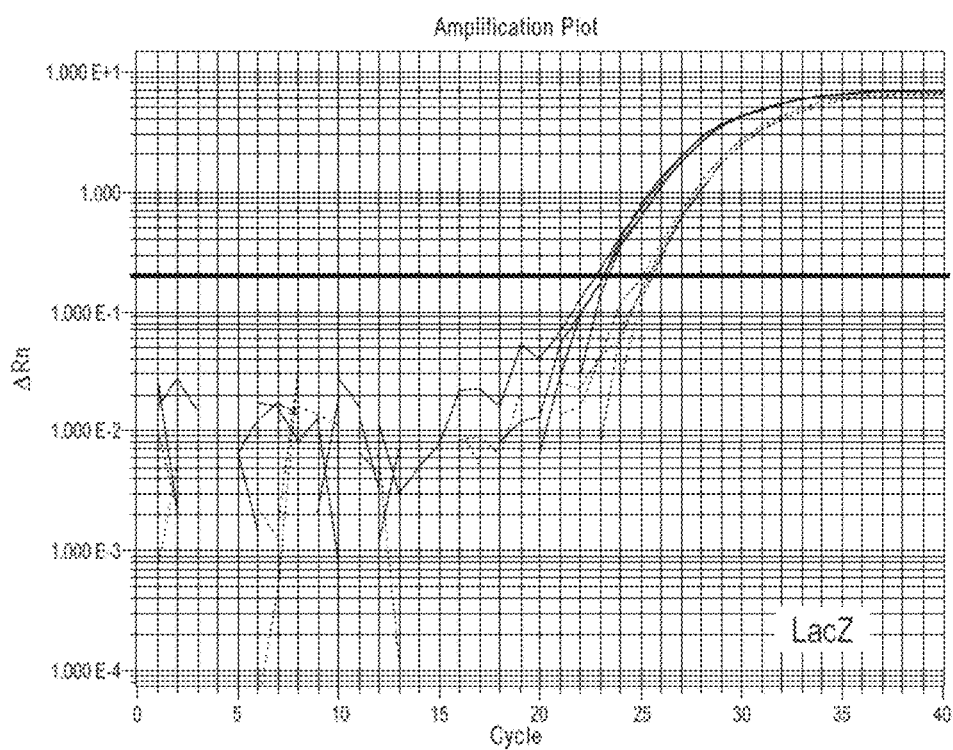
Figure 7E:
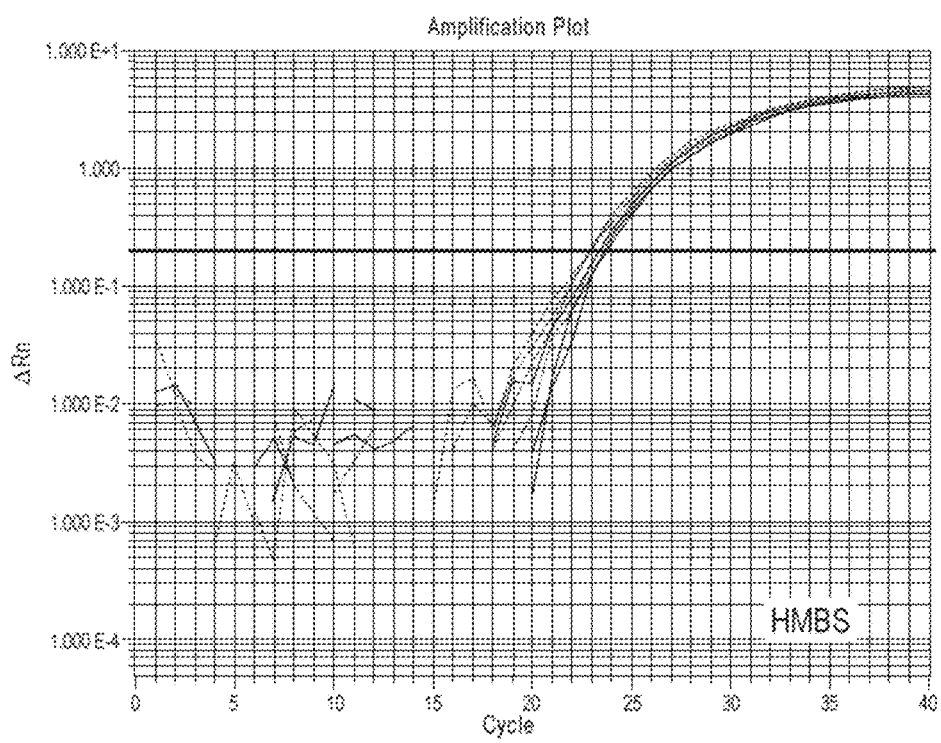
Figure 7F:
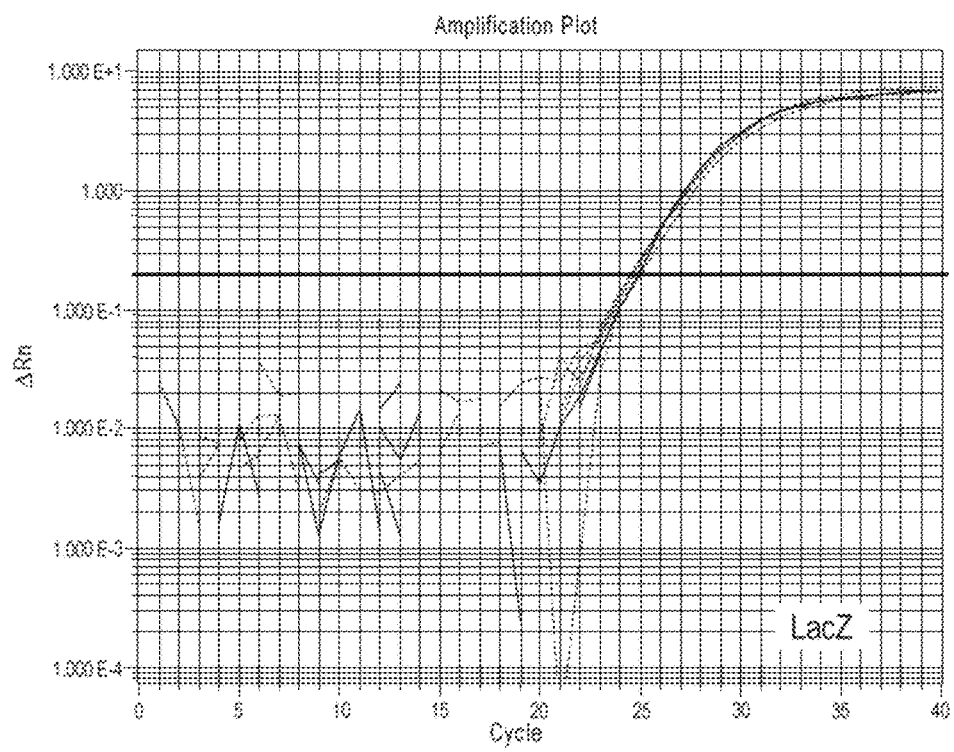

FIG. 6B shows whole mount lung, heart, spleen and liver (as indicated) organs dissected from each of the two treated mice shown in FIG. 6A. Luciferase expression measured on Xenogen IVIS. Luciferase expression was detected in Liver and Spleen. No luciferase expression was detected in PBS injected mice (FIG. 1).

FIG. 7 A-F is a graphical representation showing analysis of LacZ gene expression as measured by qRT-PCR. Mice treated with a transfection complex containing Cre mRNA and lipid 87 displayed a much stronger expression of the lacZ gene in Spleen (compare spleen control HMBS expression FIG. 7A with spleen LacZ expression FIG. 7B), Liver (compare liver control HMBS expression FIG. 7C with liver LacZ expression FIG. 7D) compared to control as determined by Cts. cDNA input was normalized using HMBS. No increase expression of lacZ was observed in Kidney (FIG. 7E and FIG. 7F).

Although only a few embodiments have been described in detail and exemplified above, those having ordinary skill in the art will clearly understand that many modifications are possible in the described embodiments without departing from the teachings thereof. All such modifications are intended to be encompassed within the following claims.

What is claimed is:

1. A chemical entity selected from the structure II and pharmaceutically acceptable salts thereof

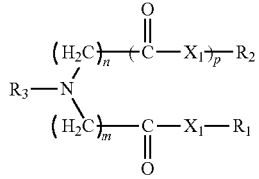
(II)

wherein each $X_1$ is independently selected from O or NH;
wherein $R_1$ is selected from substituted or unsubstituted, branched or unbranched alkyl or alkenyl groups having between 3 and about 20 carbon atoms and between 0 and about 4 double;
wherein $R_2$ is selected from H or substituted or unsubstituted, branched or unbranched alkyl or alkenyl groups having between 3 and about 20 or between about 8 and about 18 carbon atoms and between 0 and about 4 double bonds or between 0 and about 2 double bonds;
wherein p is 1 or 0, and when n=p=0, $R_2$ is H;
wherein n is 0, 1, 2, or 3;
wherein m is 1, 2, or 3;
wherein $R_3$ is selected from

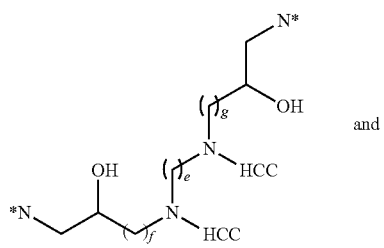
and

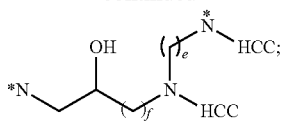

wherein "HCC" symbolizes a straight or branched alkyl, alkenyl, or alkynyl hydrocarbon chain having up to about 20 carbon atoms;

wherein each e, f, and 6 is an integer between 1 to 6;

wherein each * shows a potential point of attachment of $R_3$ to the nitrogen in structure II such that each H on any * position can be replaced to achieve the attachment to the nitrogen atom in structure II.

2. The chemical entity according to claim 1, wherein e is 4.

3. The chemical entity according to claim 2, wherein f and g are 1.

4. The chemical entity according to claim 3, wherein n and m are 2.

5. The chemical entity according to claim 3, wherein n and m are independently 1 and 3.

6. The chemical entity according to claim 3, wherein n and m are 1 or 3.

7. The chemical entity according to claim 1, wherein e is 4, wherein f and g are 1, and wherein n and m are 1, 2, or 3.

8. The chemical entity according to claim 1 selected from compounds 20, 22, 25, 26, 27, 28, 29, 30, 31, 32, 33, 34, 35, 36, 37, 38, 39, 43, 44, 48, 49, 54, 55, 56, 57, 58, 59, 60, 61, 62, 63, 64, 65, 72, 73, 76, 77, 80, 81, 82, 83, 84, 85, and 86, and pharmaceutically acceptable salts thereof:

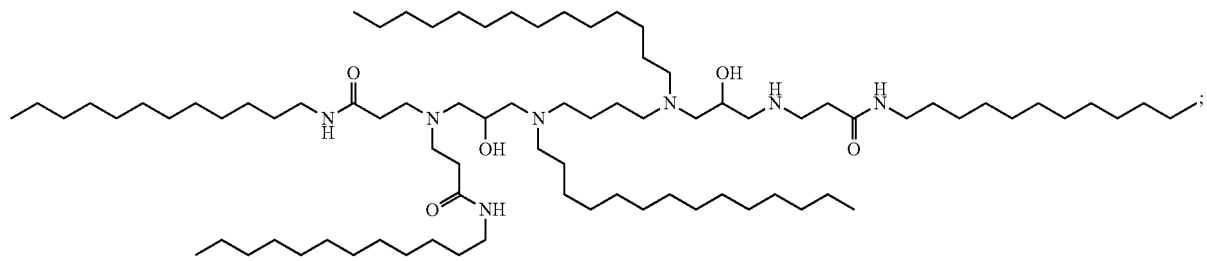

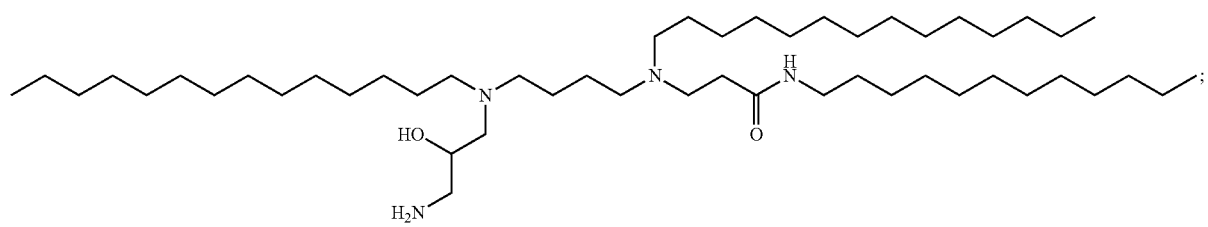

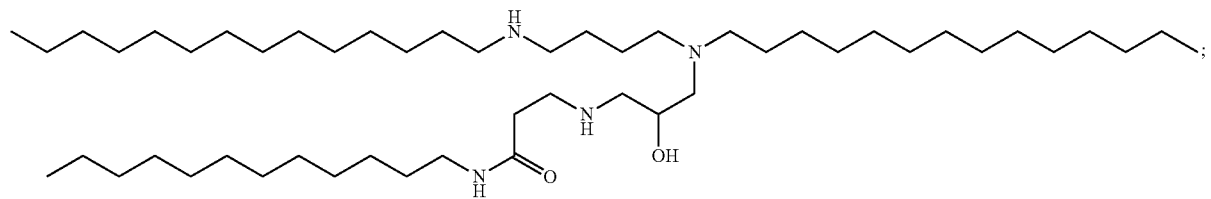
25
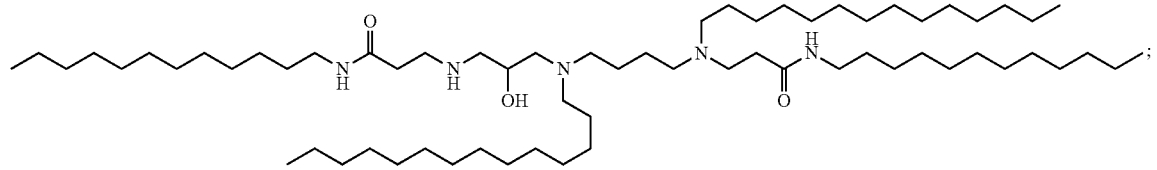
26
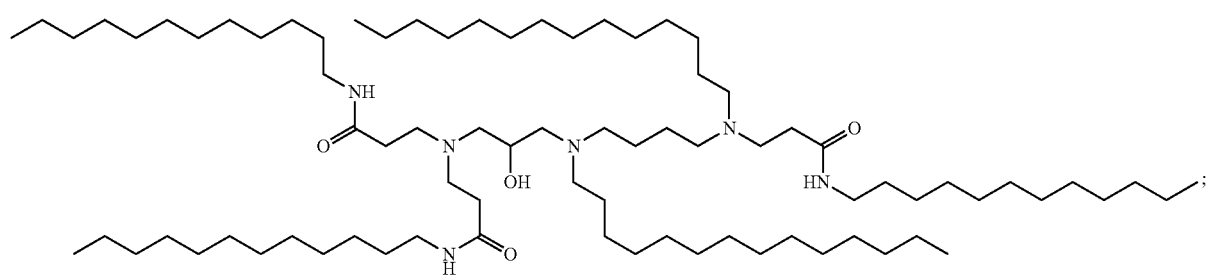
27
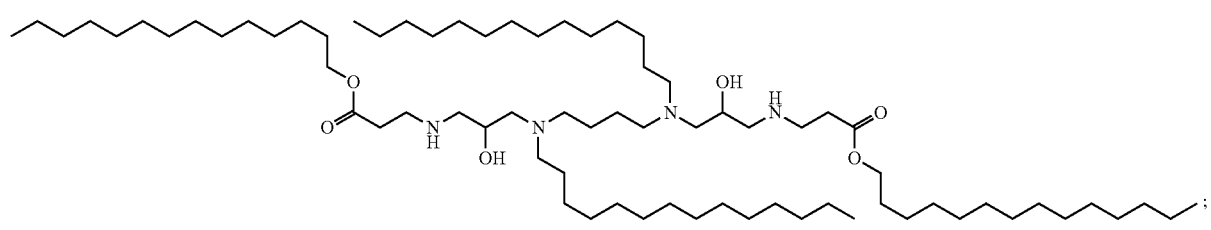
28
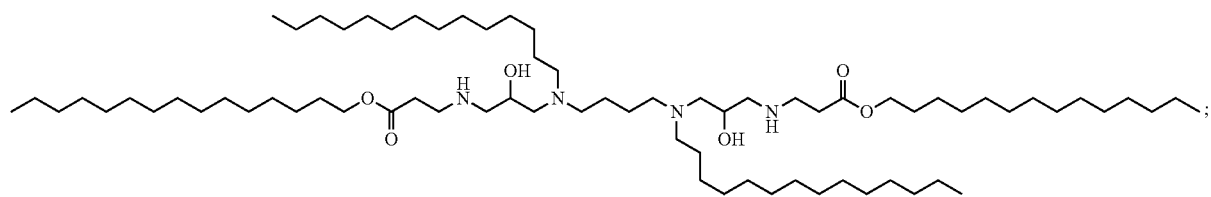
29
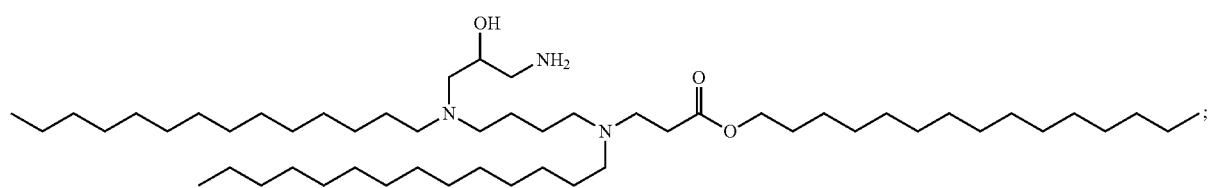
30
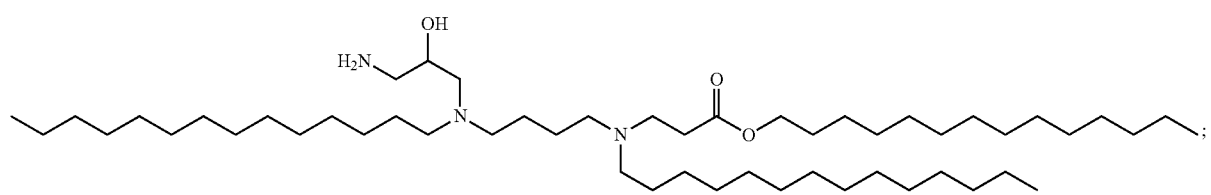
31

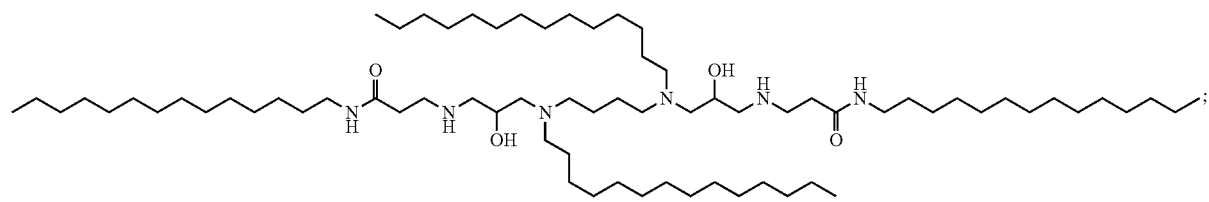
32
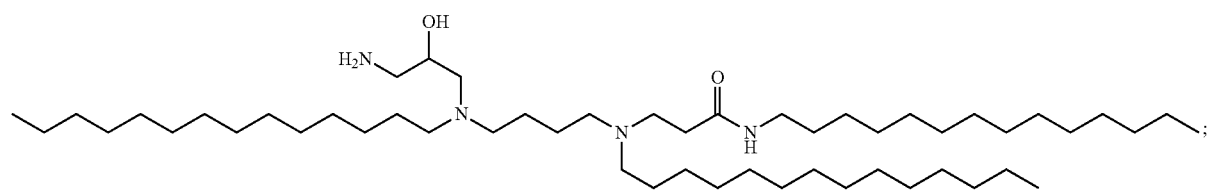
33
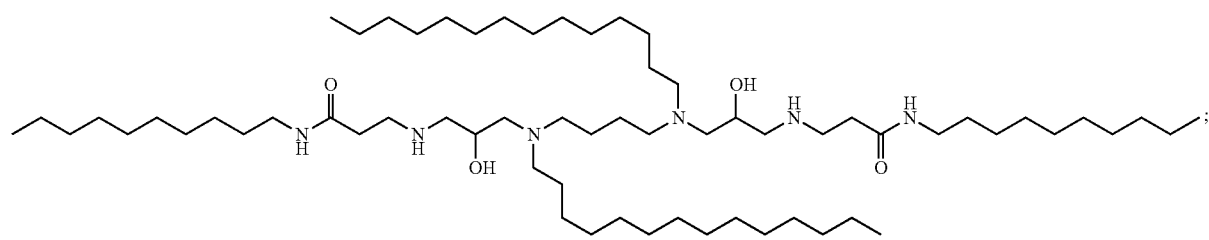
34
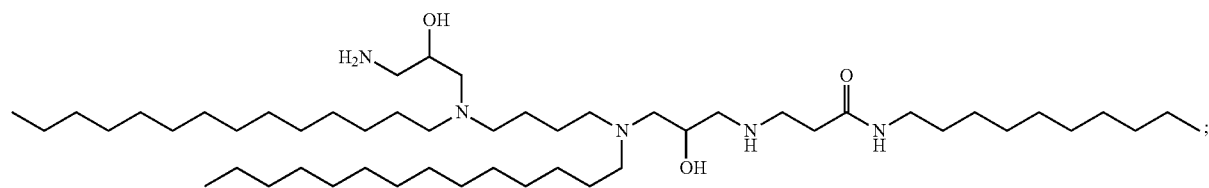
35
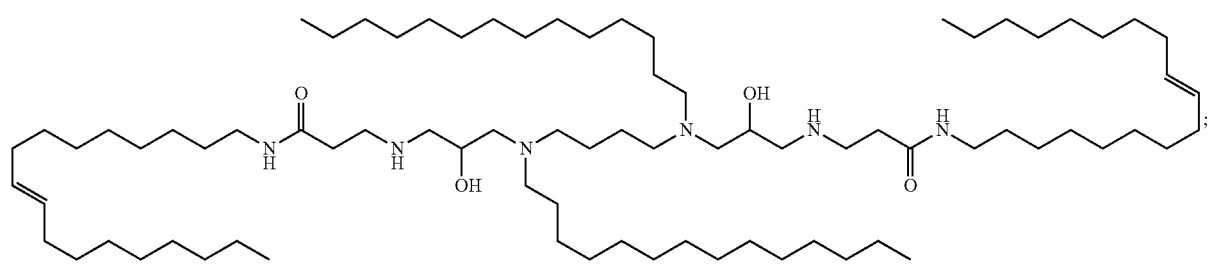
36
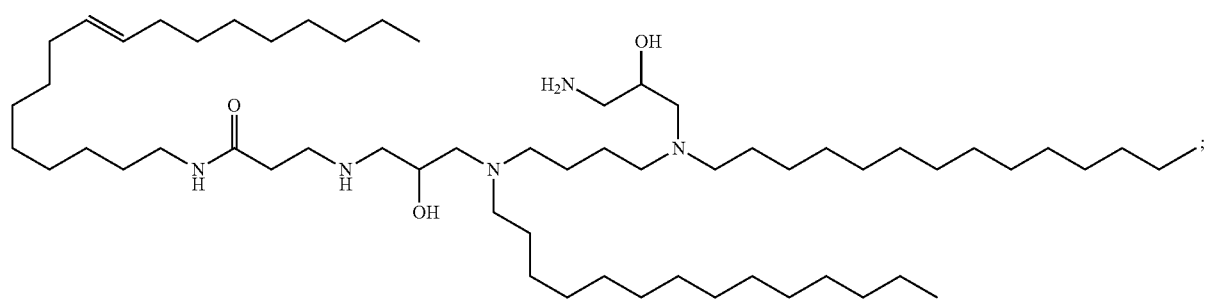
37

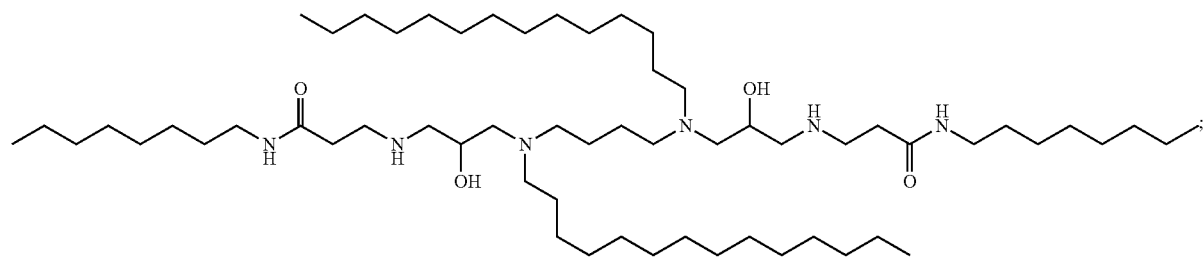
38
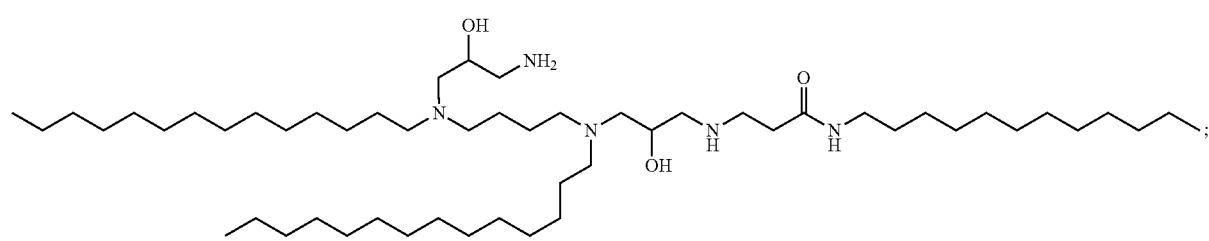
39
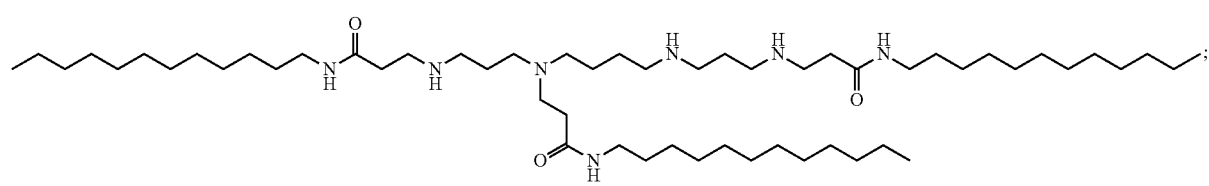
40
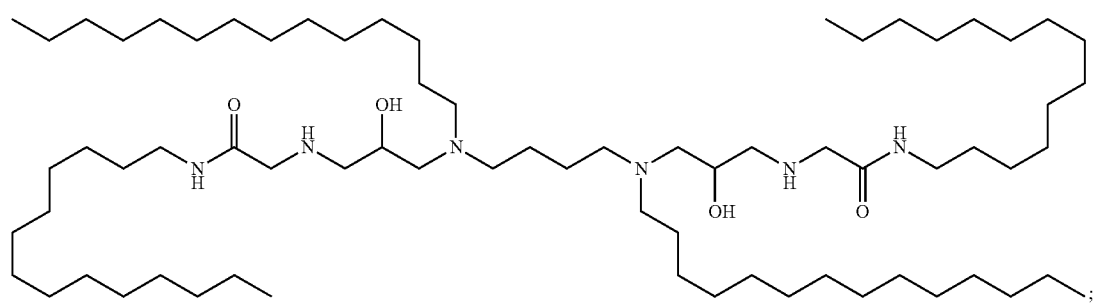
48
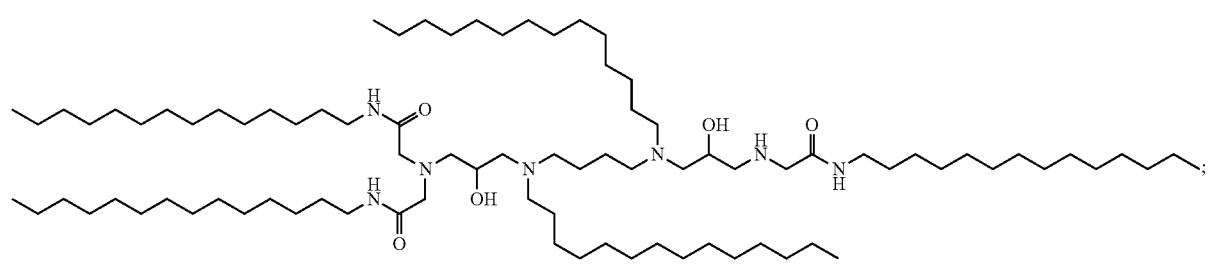
49
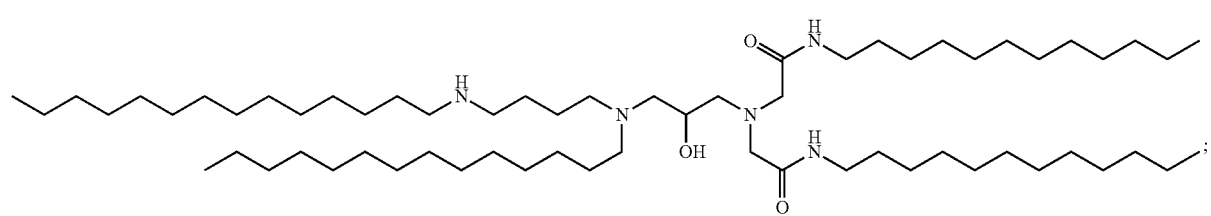
54

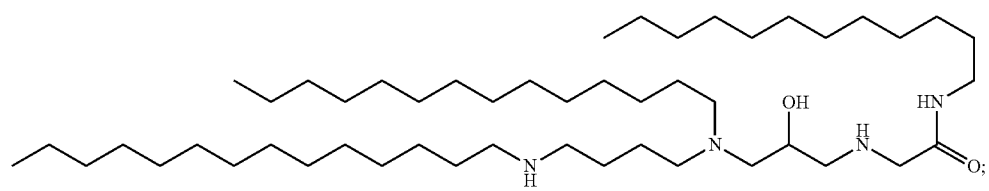
55
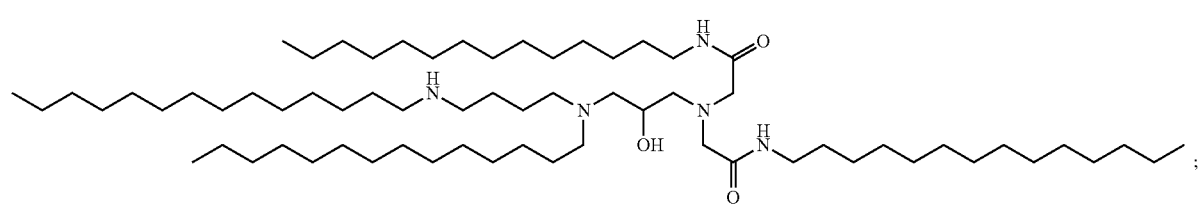
56
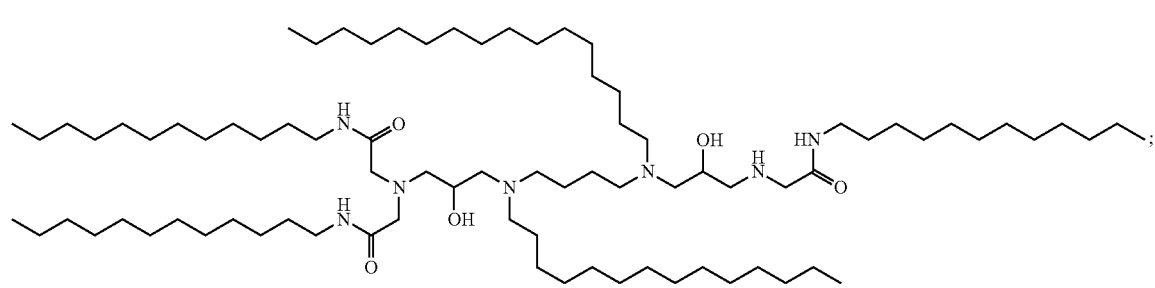
57
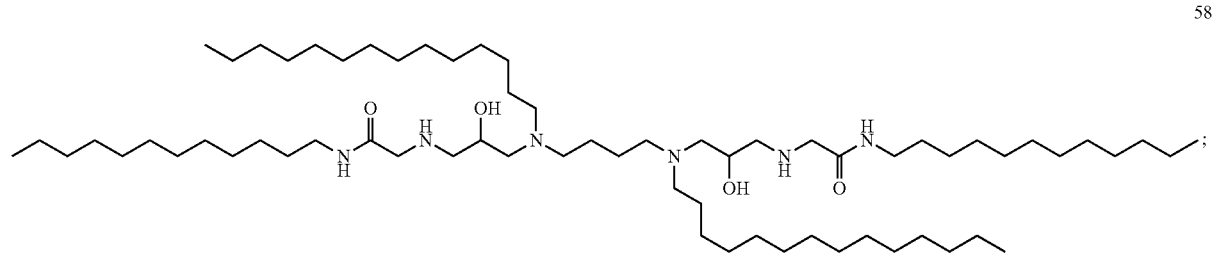
58
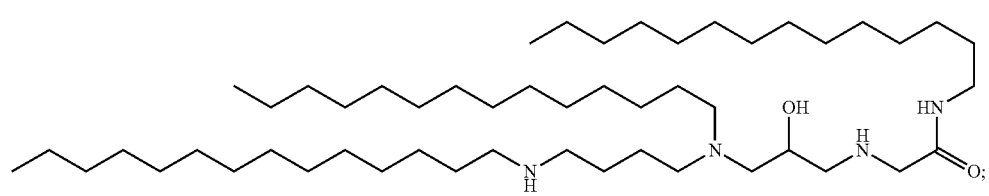
59
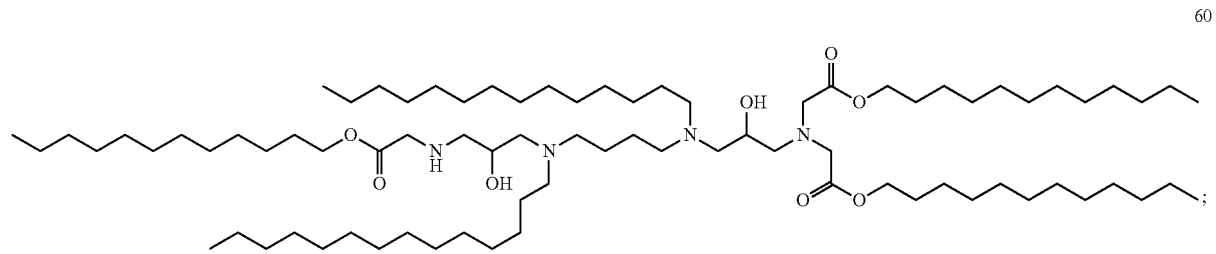
60
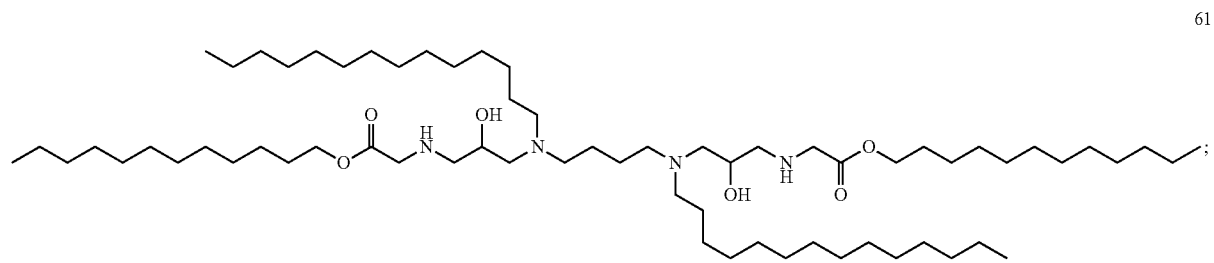
61

-continued
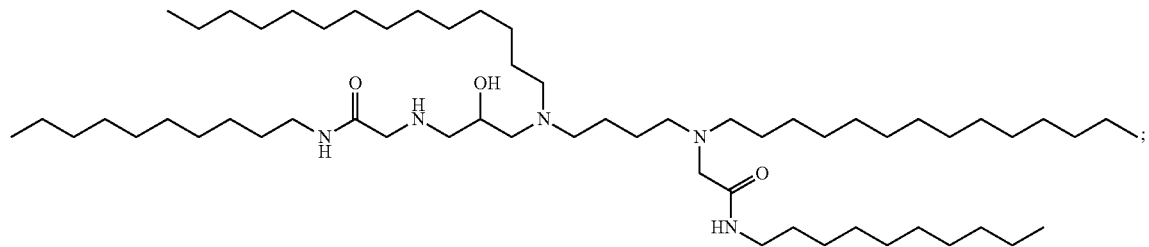
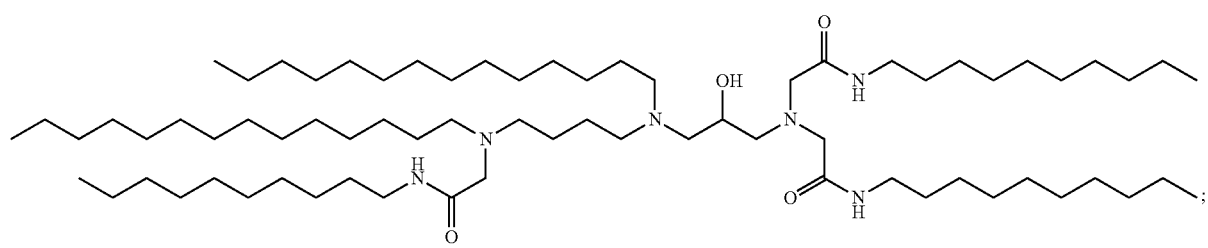
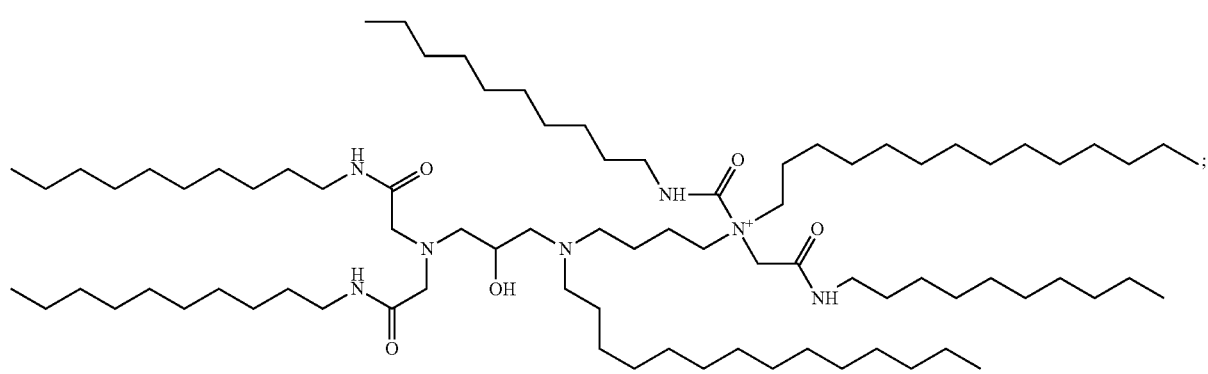
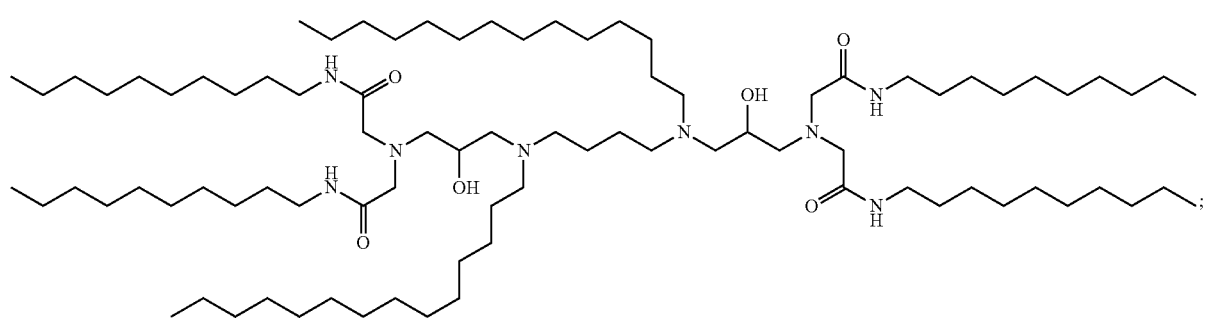
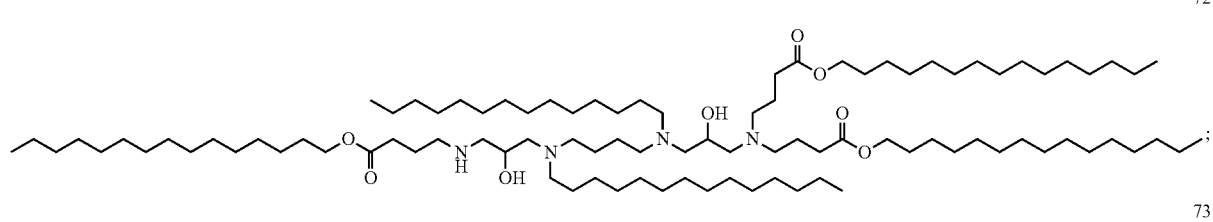
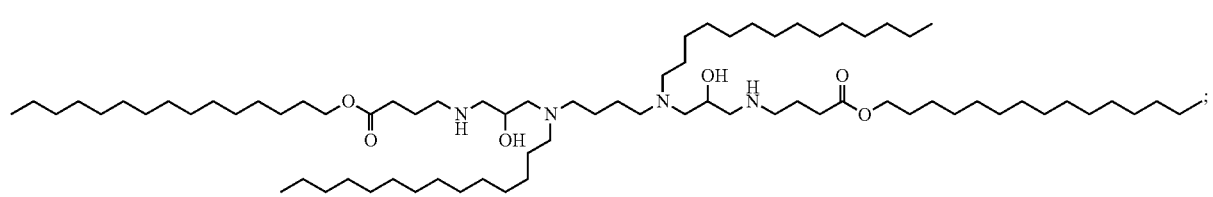

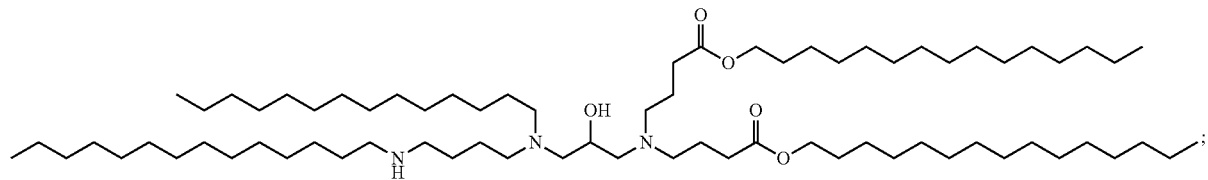
76
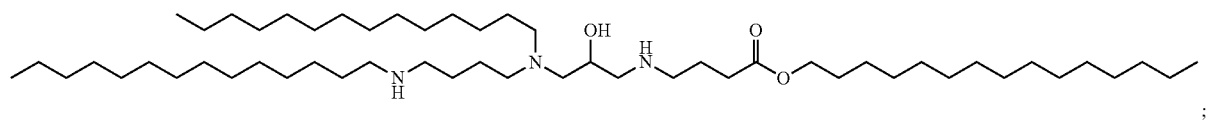
77
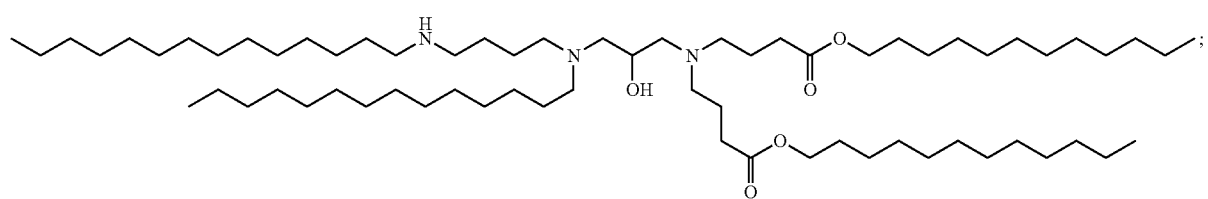
80
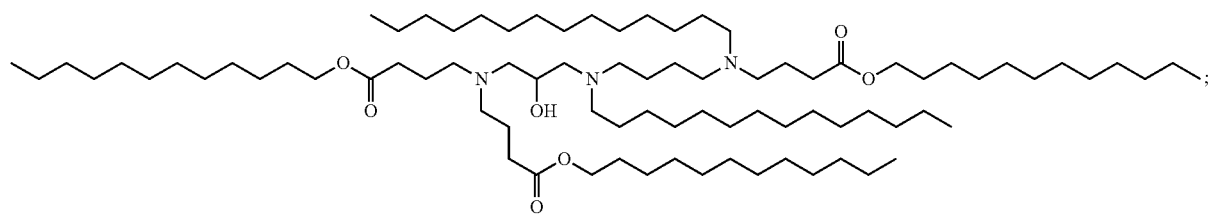
81
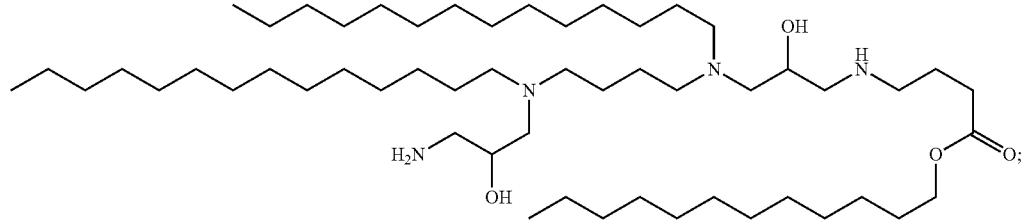
82
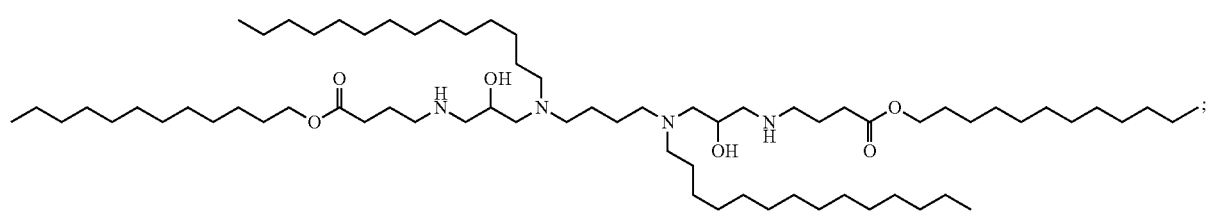
83
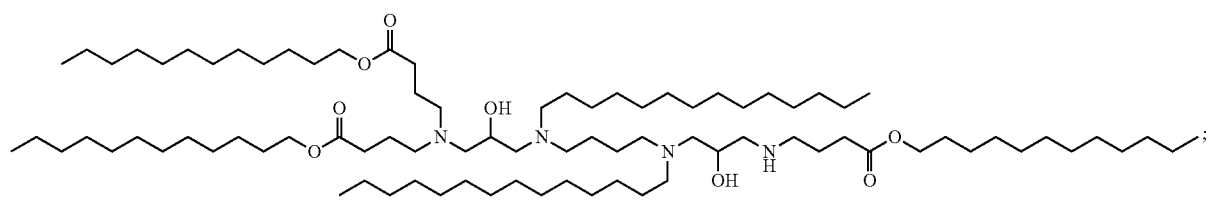
84

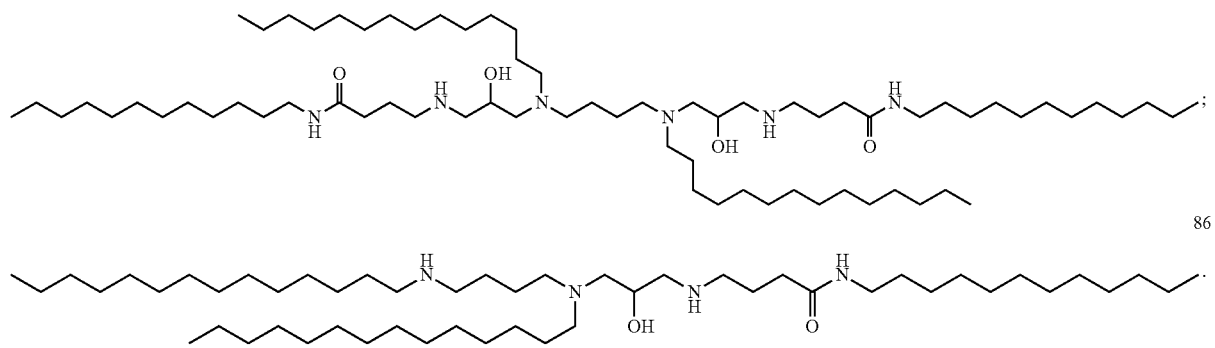

9. A transfection complex comprising a chemical entity according to claim 1.

10. The transfection complex according to claim 9, wherein e is 4, wherein f and g are 1, and wherein n and m are 1, 2, or 3.

11. The transfection complex according to claim 9, wherein the chemical entity is selected from compounds 20, 22, 25, 26, 27, 28, 29, 30, 31, 32, 33, 34, 35, 36, 37, 38, 39, 43, 44, 48, 49, 54, 55, 56, 57, 58, 59, 60, 61, 62, 63, 64, 65, 72, 73, 76, 77, 80, 81, 82, 83, 84, 85, and 86, and pharmaceutically acceptable salts thereof.

12. The transfection complex according to claim 9, further comprising at least one helper lipid.

13. The transfection complex according to claim 12, wherein the at least one helper lipid is selected from neutral and cationic lipids.

14. The transfection complex according to claim 12, wherein the at least one helper lipid is selected from 3βOH-sterols; phosphatidylcholines; phosphatidylethanolamines; lecithins; glycerol esters; sphingolipids; fatty acid esters; cerebrosides; piperazine-based cationic lipids; phosphatidylglycerols; diquaternary ammonium salts; N,N'-dicetyl saturated analogues; diphosphatidylglycerols; phosphatidylserines; Ethyl-PC; ceramides and derivatives thereof.

15. The transfection complex according to claim 12, wherein the at least one helper lipid is selected from cholesterol; DOPE (dioleoylphosphatidylethanolamine); and DOPC (Dioleoylphosphatidylcholine) or salts thereof.

16. The transfection complex according to claim 12, wherein the at least one helper lipid is selected from BMOP (N-(2-bromoethyl)-N,N-dimethyl-2,3-bis(9-octadecenyloxy)-propanaminium bromide); DDPES (Dip almitoyl-phosphatidylethanolamine 5-carboxyspermylamide); DMPE (Dimyristoylphospatidylethanolamine); CTAB:DOPE (cetyltrimethylammonium bromide (CATB) and DOPE); DMPC (dimyristoylphosphatidylcholine); DPEPC (Dipalmitoylethylphosphatidylcholine); DPPC (Dipalmitoylphosphatidylcholine); DPPC (dipalmitoylphosphatidylcholine); POPC (palmitoyloleoylphosphatidylcholine); distearoylphosphatidylcholine; cardiolipin; POPC (1-palmitoyl-2-oleoyl-sn-glycero-3-phosphocholine); DOSPER (1,3-Di-Oleoyloxy-2-(6-Carboxyspermyl)-Propylamid); DOTMA (N-[1-(2,3-dioleyloxy)propyl]-n,n,n-trimethylammoniumchloride); DDAB (didoceyl methylammonium bromide); DOTAP (N-[1-(2,3-dioleoyloxy)propyl]-N,N,N-trimethyl-ammonium methylsulfate); DOTAP.Cl, DC-chol (3,β-N,(N',N'-dimethylaminoethane)-carbamoyl] cholesterol); DOSPA (2,3-dioleoyloxy-N-[2-(sperminecarboxamidoethyl]-N,N-di-met- hyl-1-propanaminium trifluoroacetate); DOMG; DODAC; DSPC; GAP-DLRIE:DOPE (N-(3-aminopropyl)-N, N-dimethyl-2,3-bis(dodecyloxy)-1-propaniminium bromide/dioleyl phosphatidylethanolamine); DPhPE (diphytanoylphosphatidylethanolamine); DPPE (dipalmitoylphosphatidylethanolamine); dipalmiteoylphosphatidylethanolamine; O-Chol (3 beta[1-ornithinamidecarbamoyl] cholesterol); POPE (palmitoyloleoylphosphatidylethanolamine); DSPE (distearoylphosphatidylethanolamine); HexEce; TmedAce; PropAce; HexAce; N,N'-dioleyl-N,N,N',N'-tetramethyl-1,2-ethanediamine (TmedEce); N,N'-dioleyl-N,N,N',N'-tetramethyl-1,3-propanediamine (PropEce); N,N'-dioleyl-N,N,N',N'-tetramethyl-1,6-hexanediamine; phosphatidylglycerol; DOPG (dioleoylphosphatidylglycerol); DPPG (dipalmitoylphosphatidylglycerol); distearoylphosphatidylglycerol; dioleoyl- and dipalmitoylphosphatidylserine; DC-6-14 (O,O'-Ditetradecanoyl-N-(alphatrimethylammonioacetyl) diethanolamine chloride); DCPE (Dicaproylphosphtidylethanolamine); DLRIE (dilauryl oxypropyl-3-dimethylhydroxy ethylammonium bromide); DODAP (1,2-Dioleoyl-3-dimethylammonium-propane); DOGS (dioctadecylamidoglycyl carboxyspermine); DMRIE (N-[1-(2,3 dimyristyloxy)propyl]-N,N-dimethyl-N-(2-hydroxyethyl) ammonium bromide); DOEPC (Dioleoylethyl-phosphocholine); DOHME (N-[1-(2,3-dioleoyloxy)propyl]-N-[1-(2-hydroxyethyl)]-N,Ndimethylammonium iodide); DOPG (1,2-dioleoyl-sn-glycero-3-[phospho-rac-(3-lysyl(1-glycerol)).Cl); N-lauroylsarcosine; (R)-(+)-limonene; 1-deoxy-1-[dihexadecyl(methyl)ammonio]-D-xylitol; 1-deoxy-1-[methyl(ditetradecyl)ammonio]-Darabinitol; and 1-deoxy-1-[dihexadecyl(methyl)ammonio]-D-arabinitol; 1-deoxy-1[methyl(dioctadecyl)ammonio]-d-arabinitol.

17. The transfection complex according to claim 9, further comprising at least one pegylated lipid.

18. The transfection complex of claim 9, further comprising at least one bioactive agent.

19. The transfection complex of claim 18, wherein the at least one bioactive agent is selected from DNA molecules, RNA molecules, proteins, and drugs.

20. The transfection complex of claim 19, wherein the RNA molecule is selected from siRNA, shRNA, miRNA, stRNA, and mRNA.

21. The transfection complex of claim 19, wherein the at least one bioactive agent is siRNA.

22. The transfection complex of claim 19, wherein the at least one bioactive agent is mRNA.

23. The transfection complex of claim 19, wherein the at least one bioactive agent is DNA.

24. A transfection complex comprising at least one chemical entity according to claim 8 and pharmaceutically acceptable salts thereof, at least one helper lipid, optionally at least one pegylated lipid, and at least one bioactive agent selected from DNA molecules, RNA molecules, and proteins.

* * * * *

SEQUENCE LISTING

```
<160> NUMBER OF SEQ ID NOS: 4

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
auuugcacag aucagcugcu cauuc                                          25

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aaacuauaau cguacaucug a                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
uuacgucguc gcgucguuat t                                              21

<210> SEQ ID NO 4
<211> LENGTH: 1750
<212> TYPE: DNA
<213> ORGANISM: Artificial Sequence
<220> FEATURE:
```

<223> OTHER INFORMATION: Description of Artificial Sequence: Synthetic polynucleotide

<400> SEQUENCE: 4

```
ttggaccctc gtacagaagc taatacgact cactatatgg gcggtaggcg tgtacggtgg      60
gaggtctata taagcagagc tcgcaactttt tctatacaaa gttgctatgg gcccaaagaa    120
gaagagaaag gtttcgaatt tactgaccgt acaccaaaat ttgcctgcat taccggtcga    180
tgcaacgagt gatgaggttc gcaagaacct gatggacatg ttcagggatc gccaggcgtt    240
ttctgagcat acctggaaaa tgcttctgtc cgtttgccgg tcgtgggcgg catggtgcaa    300
gttgaataac cggaaatggt ttcccgcaga acctgaagat gttcgcgatt atcttctata    360
tcttcaggcg cgcggtctgg cagtaaaaac tatccagcaa catttgggcc agctaaacat    420
gcttcatcgt cggtccgggc tgccacgacc aagtgacagc aatgctgttt cactggttat    480
gcggcggatc cgaaaagaaa acgttgatgc cggtgaacgt gcaaacagg ctctagcgtt    540
cgaacgcact gatttcgacc aggttcgttc actcatggaa aatagcgatc gctgccagga    600
tatacgtaat ctggcatttc tggggattgc ttataacacc ctgttacgta tagccgaaat    660
tgccaggatc agggttaaag atatctcacg tactgacggt gggagaatgt taatccatat    720
tggcagaacg aaaacgctgg ttagcaccgc aggtgtagag aaggcactta gcctgggggt    780
aactaaactg gtcgagcgat ggatttccgt ctctggtgta gctgatgatc gaataacta    840
cctgttttgc cgggtcagaa aaaatggtgt tgccgcgcca tctgccacca gccagctatc    900
aactcgcgcc ctggaaggga tttttgaagc aactcatcga ttgatttacg gcgctaagga    960
tgactctggt cagagatacc tggcctggtc tggacacagt gcccgtgtcg gagccgcgcg   1020
agatatggcc cgcgctggag tttcaatacc ggagatcatg caagctggtg gctggaccaa   1080
tgtaaatatt gtcatgaact atatccgtaa cctggatagt gaaacagggg caatggtgcg   1140
cctgctggaa gatggcgatt agacatagca gcaattggca agctgcttat atagaacttg   1200
cggcgattgg catgccgctt taaaatttta ttttatttc ttttcttttc cgaatcggat   1260
acatagcagc aattggcaag ctgcttatat agaacttgcg gcgattggca tgccgcttta   1320
aaattttatt ttatttctt ttctttccg aatcggatac atagcagcaa ttggcaagct   1380
gcttatatag aacttgcggc gattggcatg ccgctttaaa attttatttt attttctttt   1440
cttttccgaa tcggatacat agcagcaatt ggcaagctgc ttatatagaa cttgcggcga   1500
ttggcatgcc gctttaaaat tttattttat ttcttttct tttccgaatc ggatacatag   1560
cagcaattgg caagctgctt atatagaact tgcggcgatt ggcatgccgc tttaaaattt   1620
tattttattt tcttttcttt tccgaatcgg atacatagca gcaattggca agctgcttat   1680
atagaacttg cggcgattgg catgccgctt taaaatttta ttttatttc ttttcttttc   1740
cgaatcggat                                                            1750
```